United States Patent
Shoseyov et al.

(10) Patent No.: US 12,186,449 B2
(45) Date of Patent: Jan. 7, 2025

(54) DERMAL FILLERS AND APPLICATIONS THEREOF

(71) Applicant: CollPlant Ltd., Rehovot (IL)

(72) Inventors: Oded Shoseyov, Shoham (IL); Nadav Orr, Mazkeret Batya (IL); Jasmine Seror Maknouz, Tel-Aviv (IL); Revital Zarka, Mazkeret Batya (IL)

(73) Assignee: CollPlant Ltd., Rehovot (IL)

( * ) Notice: Subject to any disclaimer, the term of this patent is extended or adjusted under 35 U.S.C. 154(b) by 0 days.

(21) Appl. No.: 18/379,190

(22) Filed: Oct. 12, 2023

(65) Prior Publication Data

US 2024/0042099 A1     Feb. 8, 2024

Related U.S. Application Data

(62) Division of application No. 17/052,216, filed as application No. PCT/IL2019/050492 on May 2, 2019, now Pat. No. 11,801,329.

(60) Provisional application No. 62/666,267, filed on May 3, 2018.

(51) Int. Cl.
| | |
|---|---|
| A61L 27/26 | (2006.01) |
| A61K 8/04 | (2006.01) |
| A61K 8/65 | (2006.01) |
| A61K 8/73 | (2006.01) |
| A61L 27/36 | (2006.01) |
| A61Q 19/08 | (2006.01) |
| C08L 5/08 | (2006.01) |

(Continued)

(52) U.S. Cl.
CPC .............. *A61L 27/26* (2013.01); *A61K 8/042* (2013.01); *A61K 8/65* (2013.01); *A61K 8/735* (2013.01); *A61L 27/3687* (2013.01); *A61Q 19/08* (2013.01); *C08L 5/08* (2013.01); *C08L 89/04* (2013.01); *C12N 15/8257* (2013.01); *A61K 2800/59* (2013.01); *A61K 2800/81* (2013.01); *A61K 2800/91* (2013.01); *A61L 2400/06* (2013.01); *A61L 2430/34* (2013.01)

(58) Field of Classification Search
None
See application file for complete search history.

(56) References Cited

U.S. PATENT DOCUMENTS

| | | |
|---|---|---|
| 3,121,049 A | 2/1964 | Nishihara et al. |
| 3,131,130 A | 4/1964 | Oneson |
| 3,314,861 A | 4/1967 | Tadahiko |

(Continued)

FOREIGN PATENT DOCUMENTS

| | | |
|---|---|---|
| DE | 102011121982 | 4/2013 |
| EP | 0067553 | 12/1982 |

(Continued)

OTHER PUBLICATIONS

Examination Report Dated Jan. 31, 2024 From the Australian Government, IP Australia Re. Application No. 2023200188. (4 Pages).

(Continued)

*Primary Examiner* — Dominic Lazaro

(57) ABSTRACT

The disclosure herein relates to photoinitiated dermal fillers, hyaluronic acid-rhCollagen double crosslinked dermal fillers and hyaluronic acid-rhCollagen semi interpenetrated network, each comprising plant-derived human collagen, as well as methods of using the same.

27 Claims, 61 Drawing Sheets
Specification includes a Sequence Listing.

(51) Int. Cl.
*C08L 89/04* (2006.01)
*C12N 15/82* (2006.01)

(56) References Cited

U.S. PATENT DOCUMENTS

| | | | |
|---|---|---|---|
| 3,530,037 A | 9/1970 | Nishihara | |
| 3,934,852 A | 1/1976 | Weber et al. | |
| 3,949,073 A | 4/1976 | Daniels et al. | |
| 4,233,360 A | 11/1980 | Luck et al. | |
| 4,424,208 A | 1/1984 | Wallace et al. | |
| 4,488,911 A | 12/1984 | Luck et al. | |
| 4,597,762 A | 7/1986 | Walter et al. | |
| 4,855,237 A | 8/1989 | Morinaga et al. | |
| 5,316,931 A | 5/1994 | Donson et al. | |
| 5,316,942 A | 5/1994 | Fink | |
| 5,523,291 A | 6/1996 | Janzen et al. | |
| 5,591,444 A | 1/1997 | Boss, Jr. | |
| 5,670,369 A | 9/1997 | Fink et al. | |
| 5,676,698 A | 10/1997 | Janzen et al. | |
| 5,716,404 A | 2/1998 | Vacanti et al. | |
| 5,814,328 A | 9/1998 | Gunasekaran | |
| 5,827,937 A | 10/1998 | Agerup | |
| 5,854,382 A | 12/1998 | Loomis | |
| 5,900,245 A | 5/1999 | Sawhney et al. | |
| 5,997,895 A | 12/1999 | Narotam et al. | |
| 6,051,248 A | 4/2000 | Sawhney et al. | |
| 6,171,610 B1 | 1/2001 | Vacanti et al. | |
| 6,217,894 B1 | 4/2001 | Sawhney et al. | |
| 6,352,710 B2 | 3/2002 | Sawhney et al. | |
| 6,531,147 B2 | 3/2003 | Sawhney et al. | |
| 6,605,294 B2 | 8/2003 | Sawhney | |
| 6,617,431 B1 | 9/2003 | Gruber et al. | |
| 6,852,330 B2 | 2/2005 | Bowman et al. | |
| 7,153,518 B2 | 12/2006 | Wironen et al. | |
| 7,238,364 B2 | 7/2007 | Sawhney et al. | |
| 7,316,822 B2 | 1/2008 | Binette et al. | |
| 7,326,571 B2 | 2/2008 | Freyman | |
| 7,427,273 B2 | 9/2008 | Mitsui | |
| 7,604,817 B2 | 10/2009 | Yi et al. | |
| 7,637,900 B2 | 12/2009 | Burgess | |
| 7,648,713 B2 | 1/2010 | Sawhney | |
| 7,685,721 B2 | 3/2010 | Adams, Jr. et al. | |
| 7,723,108 B2 | 5/2010 | Truncale et al. | |
| 7,727,537 B2 | 6/2010 | Modi | |
| 7,736,391 B2 | 6/2010 | Schwibner et al. | |
| 7,745,105 B2 | 6/2010 | Fujisato et al. | |
| 7,767,452 B2 | 8/2010 | Kleinsek | |
| 7,780,980 B2 | 8/2010 | Sawhney | |
| 7,862,831 B2 | 1/2011 | Wang et al. | |
| 7,897,165 B2 | 3/2011 | Elisseeff et al. | |
| 7,919,112 B2 | 4/2011 | Pathak et al. | |
| 7,998,202 B2 | 8/2011 | Lesh | |
| 7,998,735 B2 | 8/2011 | Morrison et al. | |
| 8,025,896 B2 | 9/2011 | Malaviya et al. | |
| 8,038,665 B2 | 10/2011 | Burgess | |
| 8,066,691 B2 | 11/2011 | Khouri | |
| 8,105,622 B2 | 1/2012 | Sawhney | |
| 8,119,398 B2 | 2/2012 | Sayre et al. | |
| 8,124,120 B2 | 2/2012 | Sadozai et al. | |
| 8,142,815 B2 | 3/2012 | Vogel et al. | |
| 8,153,591 B2 | 4/2012 | Masters et al. | |
| 8,192,487 B2 | 6/2012 | Brooks et al. | |
| 8,198,245 B2 | 6/2012 | Niklason et al. | |
| 8,338,375 B2 | 12/2012 | Schroeder et al. | |
| 8,357,129 B2 | 1/2013 | Graham et al. | |
| 8,361,501 B2 | 1/2013 | DiTizio et al. | |
| 8,415,159 B2 | 4/2013 | Ward et al. | |
| 8,425,600 B2 | 4/2013 | Maxwell | |
| 8,455,459 B2 | 6/2013 | Wortzman et al. | |
| 8,455,717 B2 | 6/2013 | Shoseyov et al. | |
| 8,512,756 B2 | 8/2013 | Voytik-Harbin et al. | |
| 8,546,142 B2 | 10/2013 | Martin et al. | |
| 8,641,775 B2 | 2/2014 | Harmon et al. | |
| 8,642,735 B2 | 2/2014 | Murray et al. | |
| 8,673,333 B2 | 3/2014 | Elisseeff et al. | |
| 8,697,059 B2 | 4/2014 | Van Epps et al. | |
| 8,702,684 B2 | 4/2014 | Bodor et al. | |
| 8,703,118 B2 | 4/2014 | Schroeder et al. | |
| 8,734,930 B2 | 5/2014 | Bennett et al. | |
| 8,758,781 B2 | 6/2014 | Ward et al. | |
| 8,759,487 B2 | 6/2014 | Shoseyov et al. | |
| 8,771,678 B2 | 7/2014 | Hedrick et al. | |
| 8,771,743 B2 | 7/2014 | Kim et al. | |
| 8,778,333 B2 | 7/2014 | Vogel et al. | |
| 8,778,909 B2 | 7/2014 | Wortzman et al. | |
| 8,865,199 B2 | 10/2014 | Coleman et al. | |
| 8,871,267 B2 | 10/2014 | Masters | |
| 8,883,182 B2 | 11/2014 | Ratcliffe et al. | |
| 8,945,624 B2 | 2/2015 | Elisseeff et al. | |
| 8,992,551 B2 | 3/2015 | Sherry et al. | |
| 8,999,933 B2 | 4/2015 | Neuberger et al. | |
| 9,074,190 B2 | 7/2015 | Yoshimura | |
| 9,101,692 B2 | 8/2015 | Bader | |
| 9,150,668 B2 | 10/2015 | Altman et al. | |
| 9,173,975 B2 | 11/2015 | Altman et al. | |
| 9,206,442 B2 | 12/2015 | Chen | |
| 9,220,807 B2 | 12/2015 | Nguyen et al. | |
| 9,248,165 B2 | 2/2016 | Han et al. | |
| 9,289,533 B2 | 3/2016 | Schussler et al. | |
| 9,315,778 B2 | 4/2016 | Voytik-Harbin et al. | |
| 9,339,369 B2 | 5/2016 | McQuillan et al. | |
| 9,415,138 B2 | 8/2016 | Yang et al. | |
| 9,441,200 B2 | 9/2016 | Rosson et al. | |
| 9,457,177 B2 | 10/2016 | Dauvister et al. | |
| 9,474,706 B2 | 10/2016 | Shin et al. | |
| 9,474,791 B2 | 10/2016 | Drunecky et al. | |
| 9,480,640 B2 | 11/2016 | Zhang | |
| 9,561,307 B2 | 2/2017 | Bosley, Jr. et al. | |
| 9,622,845 B2 | 4/2017 | Markman | |
| 9,631,176 B2 | 4/2017 | Yoshimura et al. | |
| 9,636,435 B2 | 5/2017 | Sun et al. | |
| 9,648,938 B2 | 5/2017 | Takebayashi et al. | |
| 9,662,422 B2 | 5/2017 | Pollock et al. | |
| 9,681,941 B2 | 6/2017 | Griffin et al. | |
| 9,695,398 B2 | 7/2017 | Peterson et al. | |
| 9,713,656 B2 | 7/2017 | Dufrane et al. | |
| 9,724,369 B2 | 8/2017 | Siemionow | |
| 9,744,260 B2 | 8/2017 | Nguyen et al. | |
| 9,752,138 B2 | 9/2017 | Paspaliaris et al. | |
| 9,775,886 B2 | 10/2017 | Bhatia et al. | |
| 9,782,517 B2 | 10/2017 | Pollock et al. | |
| 9,795,711 B2 | 10/2017 | Yu et al. | |
| 9,801,976 B2 | 10/2017 | Stilwell et al. | |
| 9,814,744 B2 | 11/2017 | Badylak et al. | |
| 9,814,745 B2 | 11/2017 | Wilhelmi et al. | |
| 9,821,086 B2 | 11/2017 | Yu et al. | |
| 9,867,905 B2 | 1/2018 | Voytik-Harbin et al. | |
| 9,901,440 B2 | 2/2018 | Liu et al. | |
| 9,913,705 B2 | 3/2018 | Hayzlett et al. | |
| 9,943,398 B2 | 4/2018 | Ceradini | |
| 9,950,093 B2 | 4/2018 | Zussman et al. | |
| 9,956,072 B2 | 5/2018 | Diaz et al. | |
| 9,956,317 B2 | 5/2018 | Rahimian | |
| 2002/0142391 A1 | 3/2002 | Kivirikko et al. | |
| 2002/0091251 A1 | 7/2002 | Zhao | |
| 2002/0098578 A1 | 11/2002 | Prockop et al. | |
| 2003/0096973 A1 | 5/2003 | Gruber et al. | |
| 2004/0047892 A1 | 3/2004 | Desrosiers et al. | |
| 2005/0107876 A1 | 5/2005 | Kim et al. | |
| 2005/0142161 A1 | 6/2005 | Freeman et al. | |
| 2006/0100138 A1 | 5/2006 | Olsen et al. | |
| 2006/0154365 A1 | 7/2006 | Ratcliffe et al. | |
| 2007/0053987 A1 | 3/2007 | Bayer et al. | |
| 2007/0104693 A1 | 5/2007 | Quijano et al. | |
| 2007/0104695 A1 | 5/2007 | Quijano et al. | |
| 2007/0186312 A1* | 8/2007 | Shoseyov | C12N 9/0071 |
| | | | 435/468 |
| 2008/0063677 A1 | 3/2008 | Long et al. | |
| 2008/0081362 A1 | 4/2008 | Keeley et al. | |
| 2008/0188416 A1 | 8/2008 | Bernstein | |
| 2009/0022808 A1 | 1/2009 | Champion et al. | |
| 2009/0023631 A1 | 1/2009 | Lorenc et al. | |
| 2009/0074868 A1* | 3/2009 | Elisseeff | A61K 8/8152 |
| | | | 424/78.38 |

(56) References Cited

U.S. PATENT DOCUMENTS

| | | | |
|---|---|---|---|
| 2009/0093755 A1 | 4/2009 | Schroeder et al. |
| 2009/0098214 A1 | 4/2009 | Nanbu |
| 2009/0162423 A1 | 6/2009 | Neuberger et al. |
| 2009/0204101 A1 | 8/2009 | Wortzman et al. |
| 2009/0221985 A1 | 9/2009 | Bukshpan et al. |
| 2009/0291066 A1 | 11/2009 | Pappas et al. |
| 2009/0324722 A1 | 12/2009 | Elisseeff |
| 2010/0055184 A1 | 3/2010 | Zeitels et al. |
| 2010/0119451 A1 | 5/2010 | Sawhney |
| 2010/0136070 A1 | 6/2010 | Dobak et al. |
| 2010/0316683 A1 | 12/2010 | Piron et al. |
| 2011/0002997 A1 | 1/2011 | Elisseeff et al. |
| 2011/0274666 A1 | 11/2011 | Turner et al. |
| 2011/0281946 A1 | 11/2011 | Waddon |
| 2012/0226352 A1 | 9/2012 | Becker |
| 2012/0328581 A1 | 12/2012 | Leek |
| 2013/0116188 A1 | 5/2013 | Pollock et al. |
| 2013/0116190 A1 | 5/2013 | Pollock et al. |
| 2013/0129835 A1 | 5/2013 | Pollock et al. |
| 2013/0224280 A1 | 8/2013 | Toth |
| 2013/0261606 A1 | 10/2013 | Andrew et al. |
| 2014/0005793 A1 | 1/2014 | Koford et al. |
| 2014/0052168 A1 | 2/2014 | Sawhney |
| 2014/0163678 A1 | 6/2014 | Van Epps |
| 2014/0228950 A1 | 8/2014 | Whitcup et al. |
| 2015/0030688 A1 | 1/2015 | Sell et al. |
| 2015/0150764 A1 | 6/2015 | Pinsky |
| 2015/0190517 A1 | 7/2015 | Nguyen et al. |
| 2015/0290248 A1 | 10/2015 | Peddie |
| 2015/0366976 A1 | 12/2015 | Nguyen et al. |
| 2015/0368373 A1 | 12/2015 | Turley |
| 2016/0120955 A1 | 5/2016 | Gueta et al. |
| 2016/0184440 A1 | 6/2016 | Elisseeff |
| 2016/0193384 A1 | 7/2016 | Phopase |
| 2016/0279288 A1 | 9/2016 | David et al. |
| 2016/0339185 A1 | 11/2016 | Törnsten |
| 2017/0071725 A1 | 3/2017 | Barere et al. |
| 2017/0087273 A1 | 3/2017 | Van Epps et al. |
| 2017/0224869 A1 | 8/2017 | Shah et al. |
| 2017/0258965 A1 | 9/2017 | Reichmann et al. |
| 2017/0274052 A1 | 9/2017 | Pierce |
| 2017/0296700 A1 | 10/2017 | Barrett |
| 2017/0367807 A1 | 12/2017 | Chen et al. |
| 2018/0008745 A1 | 1/2018 | Park et al. |
| 2018/0015204 A1 | 1/2018 | Pashos et al. |
| 2018/0028719 A1 | 2/2018 | Yu et al. |
| 2018/0044629 A1 | 2/2018 | Qin et al. |
| 2018/0064854 A1 | 3/2018 | Hingtgen et al. |
| 2018/0071430 A1 | 3/2018 | Nassif et al. |
| 2018/0092737 A1 | 4/2018 | Barere et al. |
| 2018/0098836 A1 | 4/2018 | Lee et al. |
| 2021/0138113 A1 | 5/2021 | Shoseyov et al. |

FOREIGN PATENT DOCUMENTS

| | | |
|---|---|---|
| EP | 0194809 | 9/1986 |
| EP | 0278667 | 8/1988 |
| EP | 0696210 | 9/1998 |
| EP | 1280562 | 12/2004 |
| EP | 1367961 | 12/2008 |
| EP | 1730264 | 11/2009 |
| EP | 1613663 | 8/2010 |
| EP | 1773416 | 12/2010 |
| EP | 2374485 | 10/2011 |
| EP | 1943336 | 4/2014 |
| EP | 2310061 | 10/2014 |
| EP | 2696908 | 3/2015 |
| EP | 1814606 | 7/2015 |
| EP | 2129406 | 8/2015 |
| EP | 2994484 | 3/2016 |
| EP | 2254608 | 5/2016 |
| EP | 2802288 | 7/2016 |
| EP | 1734894 | 8/2016 |
| EP | 3067074 | 9/2016 |
| EP | 2324813 | 10/2016 |
| EP | 1546307 | 1/2017 |
| EP | 2231061 | 1/2017 |
| EP | 2413894 | 1/2017 |
| EP | 2152329 | 2/2017 |
| EP | 3013379 | 2/2017 |
| EP | 2032629 | 3/2017 |
| EP | 2818174 | 3/2017 |
| EP | 3174566 | 6/2017 |
| EP | 3180042 | 6/2017 |
| EP | 2384189 | 9/2017 |
| EP | 2603248 | 1/2018 |
| EP | 2900288 | 1/2018 |
| EP | 2550028 | 3/2018 |
| EP | 2433492 | 4/2018 |
| EP | 2753647 | 8/2018 |
| EP | 2550027 | 3/2019 |
| EP | 3357519 | 3/2019 |
| EP | 2895217 | 10/2020 |
| EP | 3247413 | 11/2020 |
| EP | 3253417 | 6/2023 |
| ES | 2541177 | 7/2015 |
| FR | 2948286 | 1/2011 |
| FR | 3057778 | 4/2018 |
| IT | 1405781 | 1/2014 |
| JP | 63-14693 | 1/1988 |
| JP | 2008-514225 | 5/2008 |
| JP | 2009-507103 | 2/2009 |
| JP | 2015-529268 | 10/2015 |
| RU | 2526813 | 8/2014 |
| RU | 2015150447 | 5/2017 |
| UA | 53229 | 9/2010 |
| UA | 59398 | 5/2011 |
| UA | 66403 | 12/2011 |
| WO | WO 87/006261 | 10/1987 |
| WO | WO 96/029370 | 9/1996 |
| WO | WO 2004/029137 | 4/2004 |
| WO | WO 2004/96098 | 11/2004 |
| WO | WO 2005/034875 | 4/2005 |
| WO | WO 2005/035442 | 4/2005 |
| WO | WO 2006/035442 | 4/2006 |
| WO | WO 2006/036681 | 4/2006 |
| WO | WO 2007/004214 | 1/2007 |
| WO | WO 2007/032078 | 3/2007 |
| WO | WO 2008/002063 | 1/2008 |
| WO | WO 2008/072229 | 6/2008 |
| WO | WO 2008/098019 | 8/2008 |
| WO | WO 2009/017555 | 2/2009 |
| WO | WO 2009/018555 | 2/2009 |
| WO | WO 2009/053985 | 4/2009 |
| WO | WO 2010/021738 | 2/2010 |
| WO | WO 2010/021993 | 2/2010 |
| WO | WO 2010/053918 | 5/2010 |
| WO | WO 2012/004142 | 1/2012 |
| WO | WO 2012/101473 | 8/2012 |
| WO | WO 2013/067293 | 5/2013 |
| WO | WO 2013/106715 | 7/2013 |
| WO | WO 2013/112488 | 8/2013 |
| WO | WO 2014/015229 | 1/2014 |
| WO | WO 2016/057603 | 4/2016 |
| WO | WO 2016/123693 | 8/2016 |
| WO | WO 2017/118972 | 7/2017 |
| WO | WO 2017/136786 | 8/2017 |
| WO | WO 2017/217818 | 12/2017 |
| WO | WO 2018/225076 | 12/2018 |
| WO | WO 2019/211854 | 11/2019 |

OTHER PUBLICATIONS

Decision on Rejection Dated Feb. 28, 2024 From the State Intellectual Property Office of the People's Republic of China Re. Application No. 2019800402852. (10 Pages).

English Translation of Technical Examination Report Dated Feb. 27, 2024 From the Servico Publico Federal, Ministerio da Economia, Instituto Nacional da Propriedade Industrial do Brasil Re. BR 12 2023 011548 1. (8 pages).

Relatório de Exame Tecnico [Technical Examination Report] Dated Feb. 27, 2024 From the Serviço Público Federal, Ministério da

(56) References Cited

OTHER PUBLICATIONS

Economia, Instituto Nacional da Propriedade Industrial do Brasil Rc. Application No. BR 12 2023 011548 1. (5 Pages).
Summary Dated Mar. 8, 2024 of Decision on Rejection Dated Feb. 28, 2024 From the State Intellectual Property Office of the People's Republic of China Re. Application No. 2019800402852. (14 Pages).
Communication Pursuant to Article 94(3) EPC Dated May 9, 2023 From the European Patent Office Re. Application No. 19725422.0. (8 Pages).
Communication Pursuant to Article 94(3) EPC Dated Nov. 2, 09021From the European Patent Office Re. Application No. 19725422. 0. (7 Pages).
Communication Pursuant to Article 94(3) EPC Dated Aug. 10, 2022 From the European Patent Office Re. Application No. 19725422.0. (6 Pages).
Communication Pursuant to Article 94(3) EPC Dated Jan. 10, 2023 From the European Patent Office Re. Application No. 19725422.0. (4 Pages).
Examination Report Dated Oct. 1, 2021 From the Australian Government, IP Australia Re. Application No. 2019263122. (6 Pages).
Final Official Action Dated Mar. 16, 2023 from the Re. U.S. Appl. No. 17/052,216. (27 pages).
International Preliminary Report on Patentability Dated Nov. 12, 2020 From the International Bureau of WIPO Re. Application No. PCT II L2019/050492. (10 Pages).
International Search Report and the Written Opinion Dated Jul. 16, 2019 From the International Searching Authority Re. Application No. PCT/IL2019/050492. (14 Pages).
Notice of Allowance Dated Jun. 15, 2023 Together with Interview Summary Dated Jun. 6, 2023 from the Re. U.S. Appl. No. 17/052,216. (21 pages).
Notice of Reason(s) for Rejection Dated Feb. 28, 2023 From the Japan Patent Office Re. Application No. 2020-561769. (6 pages).
Notification of Office Action and Search Report Dated May 6, 2023 From the China National Intellectual Property Administration Re. Application No. 2019800402852 and Its Summary in English. (26 Pages).
Notification of Office Action and Search Report Dated Nov. 16, 2022 From the China National Intellectual Property Administration Re. Application No. 2019800402852 and Its Summary in English. (24 Pages).
Notification of Office Action and Search Report Dated Apr. 26, 2022 From the State Intellectual Property Office of the People's Republic of China Re.Application No. 2019800402852. (7 Pages).
Notification of Office Action Dated Sep. 26, 2023 From the State Intellectual Property Office of the People's Republic of China Re. Application No. 2019800402852 and Its Summary in English and Machine Translation in English. (51 Pages).
Office Action Dated Jul. 7, 2022 From the Israel Patent Office Re. Application No. 278370. (4 Pages).
Official Action Dated May 26, 2022 From the Re. U.S. Appl. No. 17/052,216. (29 Pages).
Relatorio de Busca e Parecer [Search Report and Opinion] Dated Mar. 8, 2023 From the Servico Publico Federal, Ministerio da Economia, Instituto Nacional da Propriedade Industrial do Brasil Re. Application No. BR 11 2020 022438 3 (4 Pages).
Requisition by the Examiner Dated Jun. 30, 2023 From the Innovation, Science and Economic Development Canada, Canadian Intellectual Property Office Re. Application No. 3,099,139. (5 pages).
Restriction Official Action Dated Feb. 11, 2022 From the Re. U.S. Appl. No. 17/052,216. (6 Pages).
Translation Dated Mar. 13, 2023 of Notice of Reason(s) for Rejection Dated Feb. 28, 2023 From the Japan Patent Office Re. Application No. 2020-561769. (5 pages).
Translation Dated Mar. 24, 2023 of Relatório de Busca e Parecer [Search Report and Opinion] Dated Mar. 8, 2023 From the Serviço Público Federal, Ministério da Economia, Instituto Nacional da Propriedade Industrial do Brasil Re. Application No. BR 11 2020 022438 3 (4 pages).

Alster et al. "Human-Derived and New Synthetic Injectable Materials for Soft-Tissue Augmentation: Current Status and Role in Cosmetic Surgery", Plastic and Reconstructive Surgery, 105(7): 2515-2525, Jun. 2000.
Andres et al. "Treatment of Tendinopathy: What Works, What Does Not, and What is on the Horizon", Clinical Orthopaedics and Related Research, 466(7):1539-1554, Apr. 30, 2008.
Baier Leach et al. "Photocrosslinked Hyaluronic Acid Hydrogels: Natural, Biodegradable Tissue Engineering Scaffold", Biotechnology and Bioengineering, 82(5): 578-589, Mar. 17, 2003.
Brinkman et al. "Photo-Cross-Linking of Type I Collagen Gels in the Presence of Smooth Muscle Cells: Mechanical Properties, Cell Viability, and Function", Biomacromolecules 4: 890-895, May 7, 2003.
Bulleid et al. "Recombinant Expression Systems for the Production of Collagen", Biochemical Society Transactions, 28(4): 350-353, Aug. 1, 2000.
Castrow et al. "Injectable Collagen Implant-Update", Journal of the American Academy of Dermatology, 9(6): 889-893, Dec. 1983.
Dawson et al. "A Tobacco Mosaic Virus-Hybrid Expresses and Loses an Added Gene", Virology, 172(1):, 285-292, Sep. 1989.
DeLong et al. "Sports Medicine; Update on Platelet-Rich Plasma", Current Orthopaedic Practice, 22(6), 514-523, 2011.
Di Matteo et al. "Platelet-Rich Plasma: Evidence for the Treatment of Patellar and Achilles Tendinopathy—A Systematic Review", Musculoskelet Surgery 99:1-9, Oct. 17, 2014.
Duggan et al. "Synthesis of Mucoadhesive Thiolated Gelatin Using a Two-Step Reaction Process", European Journal of Pharmaceutics and Biopharmaceutics, 91: 75-81, Apr. 2015.
Eckert et al. "DNA Polymerase Fidelity and the Polymerase Chain Reaction", Genome Research, 1: 17-24, 1991.
Elisseeff et al. "Transderma IPhotopolymerization for Ininhnally Invasive Implantation", Proceedings of the National Academy of Sciences, 96: 3104-3107, Mar. 1999.
French et al. "Bacterial Gene Inserted in an Engineered RNA Virus: Efficient Expression in Monocotyledonous Plant Cells". Science, 231 (4743): 1294-1297, Mar. 14, 1986.
Fromm et al. "Stable Transformation of Maize After Gene Transfer By Electroporation", Nature,319: 791-793, Feb. 27, 1986.
Gallie et al. "The 5' -Leader Sequence of Tobacco Mosaic Virus RNA Enhances the Expression of Foreign Gene Transcripts In Vitro and In Vivo", Nucleic Acid Research, 15(8): 3257-3273, Feb. 20, 1987.
Gaudet et al. "Characterization of Methacrylated Type-I Collagen as a Dynamic, Photoactive Hydrogel", Biointerphase, 7(1-4): 25-1-25-9, Published Online Mar. 10, 2012.
Goldman et al. "A Randomized Trial to Determine the Influence of Laser Therapy, Monopolar Radiofrequency Treatment and Intense Pulsed Light Therapy Administered Immediately after Hyaluronic Acid Gal Implantatiort", Dermatol Surgery, 33(5):535-542, May 2007.
Habeeb "Determination of Free Amino Groups in Proteins by Trinitrobenzenesulfonic Acid", Analytical Biochemistry, 14(3): 328-336, Mar. 1966.
Hare et al. "Metabolic Implications of Stress-Induced Proline Accumulation in Plants", Plant Growth Regulation, 21(2): 79-102, Feb. 1997.
Harrison et al. "Platelet Activation by Collagen Provides Sustained Release of Anabolic Cytokines", The American Journal of Sports Medicine, 39(4): 729-734, Mar. 11, 2011.
Hillel et al. "Validation of a Small Animal Model for Soft Tissue Filler Characterization", Dermatologic Surgery, 38(3): 471-478, Mar. 2012.
Horsch et al. "Leaf Disc Transformation", Plant Molecular Biology Manual, A5: 1-9: 63-71, 1988.
Hulmes et al. "Building Collagen Molecules, Fibrils, and Suprafibrillar Structures", Journal of Structural Biology, 137(1-2): 2-10, Jan. 2002.
Inkinen "Connective Tissue Formation in Wound Healing; An Experimental Study", Helsinki University Central Hospital and Division of Biochemistry, Department of Biosciences, 107P., Sep. 11, 2003.

(56) References Cited

OTHER PUBLICATIONS

Kadler "Matrix Loading: Assembly of Extracellular Matrix Collagen Fibrils during Embryogenesis", Birth Defects Research, (Part C) 72:1-11, 2004.
Kadler et al. "Collagens at a Glance", Journal of Cell Science, 120(12):1955-1958, Jun. 15, 2007.
Kaijkawa et al. "Platelet-Rich Plasma Enhances the Initial Mobilization of Circulation-Derived Cells for Tendon Healing", Journal of Cellular Physiology, 215(3): 837-845, Jan. 7, 2008.
Kaux et al. "Current Opinions on Tendinopathy", Journal of Sports, Science and Medicine, 10(2): 238-253, Jun. 1, 2011.
Kaux et al. "Effects of Platelet-Rich Plasma (PRP) on the Healing of Achilles Tendons of Rats", Wound Repair and Regeneration, 20(5): 748-756, Aug. 10, 2012.
Khan et al. Histopathology of Common Tendinopathies: Update and Implications for Clinical Management, Sports Medicine, 27(6):393-408, Nov. 27, 2012.
Khoshnoodi et al. "Molecular Recognition in the Assembly of Collagens: Terminal Noncollagenous Domains are Key Recognition Modules in the Formation of Triple Helical Protomers", Journal of Biological Chemistry, 281(50): 38117-38121,Dec. 15, 2006.
Klee et al. "Agrobacterium-Mediated Plant Transformation and its Further Applications to Plant Biology", Annual Review of Plant Physiology, 38:467-486, Jun. 1987.
Klein et al. "Factors Influencing Gene Delivery into *Zea Mays* Cells by High-Velocity Microprojectiles", Nature Biotechnology, 6: 559-563, May 1, 1988.
Kreger et al. "Polymerization and Matrix Physical Properties as Important Design Considerations for Soluble Collagen Formulations", Biopolymers, 93(8): 690-707, Mar. 16, 2010.
Maffulli et al. "Types and Epidemiology of Tendinopathy", Clinics in Sports Medicine, 22: 675-692, Oct. 1, 2003.
Majumdar et al. "Influence of Collagen Source on Fibrillar Architecture and Properties of Vitrified Collagen Membranes", Journal of Biomedical Materials Research, 104(2): 300-307, Mar. 12, 2015.
McCabe et al. "Stable Transformation of Soybean (*Glycine max*) by Particle Acceleration", Nature Biotechnology, 6(8): 923-926, Aug. 1, 1988.
Merle et al. "Hydroxylated Human Homotrimeric Collagen I in Agrobacterium Tumofaciens-Mediated Transient Expression and In Transgenic Tobacco Plant", FEBS Lettters, 515(1-3): 114-118, Mar. 5, 2002.
Moraes et al. "Platelet-Rich Therapies for Musculoskeletal Soft Tissue Injuries (Review)", Cochrane Database of Systematic Reviews, 12(CD010071): 102P., Apr. 29, 2014.
Neuhaus et al. "Plant Transformation by Microinjection Techniques", Physiologia Plantarum, 79(1): 213-217, May 1990.
Neuhaus et al. "Transgenic Rapeseed Plants Obtained by the Microinjection of DNA into Microspore-derived Embryoids", Theoretical and Applied Genetics, 75(1): 30-36, Dec. 1987.
Ohta "High-Efficiency Genetic Transformation of Maize by a Mixture of Pollen and Exogenous DNA", Proceedings of the National Academy of Sciences, 83: 715- 719, Feb. 1986.
Olsen et al. "Recombinant Collagen and Gelatin for Dn1g Delivery", Advanced Drug Delivery Review, 55(12): 1547-1567, Nov. 28, 2003.
Omlor et al. "Injection of a Polymerized Hyaluronic Acid/Collagen Hydrogel Matrix in an In Vivo Porcine Disc Degeneration Model", European Spine Journal, 21: 1700-1708, Apr. 25, 2012.
Park et al. "Photopolymerized Hyaluronic Acid-Based Hydrogels and Interpenetrating Networks", Biomaterials, 24(6): 893-900, Mar. 2003.
Potrykus "Gene Transfer To Plants: Assessment of Published Approaches and Results", Annual Review of Plant Physiolgy and Plant Molecular Biology, 42: 205-225, 1991.

Ross et al. "Laser Versus Intense Pulsed Light: Competing Technologies in Dermatology†", Lasers in Surgery and Medicine,38(4): 261-272, Apr. 4, 2006.
Ruggiero et al. "Triple Helix Assembly and Processing of Human Collagen Produced in Transgenic Tobacco Plants", FEBS Letters, 496(1): 132-136., Mar. 3, 2000.
Sanford Biolistic Plant Transformation, Physologia Plantarum, 79(1):, 206-209, May 1990.
Sashidhar "Quantitation of E-Amino Group Using Amino Acids as Reference Standards by Trinitrobenzene Sulfonic Acid; A simple Spectrophotometric Method for the Estimation of Hapten to Carrier Protein Ratio", Journal of Immunological Methods, 167(1-2): 121-127, Jan. 3, 1994.
Shilo et al. "Cutaneous Wound Healing After Treatment with Plant-Derived Human Recombinant Collagen Flowable Gel", Tissue Engineering Part A, 19(13-14): 1519-1526, Feb. 5, 2013.
Shimamoto et al. "Fertile Transgenic Rice Plants Regenerated From Transformed Protoplasts", Nature, 338(6212): 274-276,Mar. 16, 1989.
Shoseyov et al. "Human Collagen Produced in Plants; More than just another Molcule", Bioengineered, 5(1): 49-52, Aug. 9, 2013.
Shoseyov et al. "Human Recombinant Type I Collagen Produced In Plants",Tissue Engineering: Part A, 19(13-14): 1527-1533, Feb. 18, 2013.
Siegle et al. "Intradermal Implantation of Bovine Collagen: Humoral Immune Responses Associated With Clinical Reactions",Archives of Dermatology, 120(2):183-187, Feb. 1, 1984.
Stein et al. "Production of Bioactive, Post-Translationally Modified, Heterotrimeric~ Human Recombinant Type-I Collagen in Transgenic Tobacco", Biomacromo!ecules, 10(9): 2640-2645, Aug. 14, 2009.
Takamatsu et al. "Expression of Bacterial Chloramphenicol Acetyltransferase Gene in Tobacco Plants Mediated by TMV-RNA", The EMBO Journal, 6(2): 307-311, 1987.
Takamatsu et al. "Production of enkephalin in tobacco protoplasts using tobacco mosaic virus RNA vector", FEBS Ltters, 269(1): 73-76, Aug. 20, 1990.
Toriyama et al. "Transgenic Rice Plants After Direct Gene Transfer into Protoplasts", Nature Biotechnology, 6(9):1072-1074, Sep. 1, 1988.
Van Engelen et al. "pBINPLUS: An Improved Plant Transformation Vector Based on PBIN19", Transgenic Research, 4(4): 288-290, Jul. 1995.
Wang et al. "The Third Activity for Lysyl Hydroxylase 3: Galactosylation of Hydroxylysyl Residues in Collagens In Vitro", Matrix Biology, 21(7): 559-566, Nov. 2002.
Willard et al. "Plant-Derived Human Collagen Scaffolds for Skin Tissue Engineering", Tissue Engineering; Part A, 19(13,14): 1507-1518, Feb. 18, 2013.
Yaari et al. "Liquid Crystalline Human Recombinant Collagen: The Challenge and the Opportunity", Tissue Engineering; Part A, 19(13, 14 ): 1502-1506, Jan. 31, 2013.
Yaari et al. "Wet Spinning and Drawing of Human Recombinant Collagen", ACS Biomaterials Science & Engineering. 2(3): 349-360, Feb. 15, 2016.
Yuan et al. "Augmenting Tendon and Ligament Repair with Platelet-Rich Plasma (PRP)", Muscles, Ligaments, Tendons Journal, 3(3): 139-149, Aug. 11, 2013.
Zhang et al. "Platelet-Rich Plasma Releasate Promotes Differentiation of Tendon Stem Cells Into Active Tenocytes", The American Journal of Sports Medicine, 38(12): 2477-2486, Aug. 27, 2010.
Zhang et al. "Transgenic Rice Plants Produced By Electroporation-Mediated Plasmid Uptake into Protoplasts", Plant Cell Reports, 7(6 ): 379-384, Oct. 1, 1988.
Zhou et al. "Visible Light-Curable Polymers for Biomedical Applications", Science China Chemistry, 57(4): 510-521, Mar. 1, 2014.

\* cited by examiner

| Vacuole | Cytoplasm | Apoplasm |
|---|---|---|
| 2: Cole a1 (I) / Cole a2 (I) | 1: Cole a1 (I) / Cole a2 (I) | 7: Cole a1 (I) / Cole a2 (I) |
| 3: Cole a1 (I) P4Hb / Cole a2 (I) P4Ha | 5: Cole a1 (I) P4Hb / Cole a2 (I) P4Ha | 8: Cole a1 (I) P4Hb / Cole a2 (I) P4Ha |
| 4: Cole a1 (I) P4Hb / Cole a2 (I) P4Hplant | 6: Cole a1 (I) P4Hb / Cole a2 (I) P4Hplant | 9: Cole a1 (I) P4Hb / Cole a2 (I) P4Hplant |
| 10: Protease C / Protease N | 11: Protease C / Protease N | 12: Protease C / Protease N |
| 13: Cole a1 (I) P4Hb LH3 / Cole a2 (I) P4Ha | 14: Cole a1 (I) P4Hb LH3 / Cole a2 (I) P4Ha | 15: Cole a1 (I) P4Hb LH3 / Cole a2 (I) P4Ha |
| 20: P4Hb LH3 / P4Ha | | 21: P4Hb LH3 / P4Ha |

Fig. 2

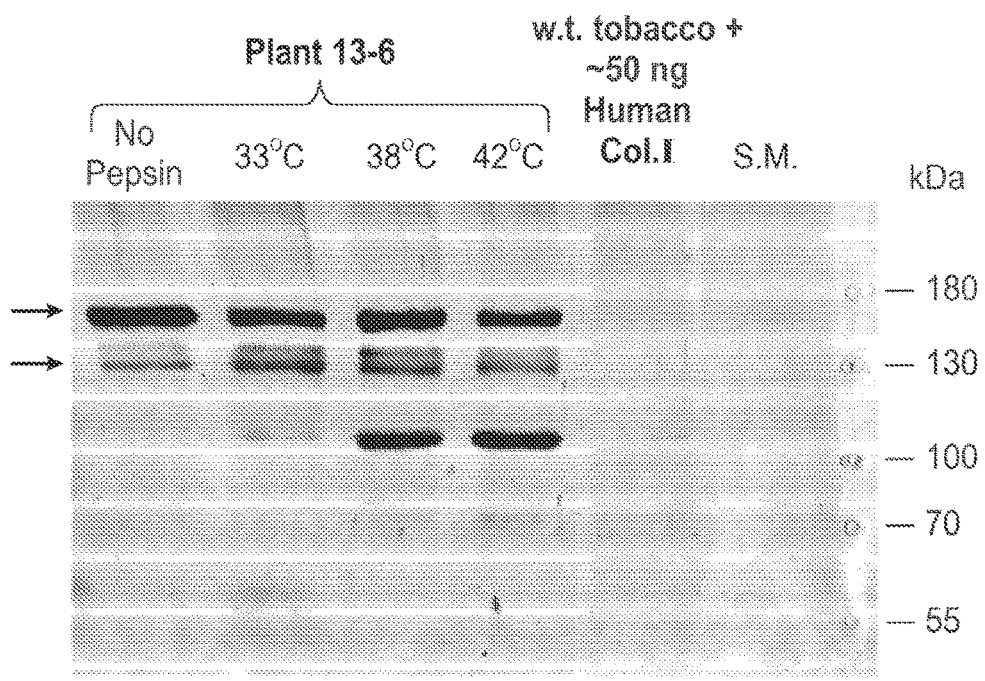
Fig. 6b
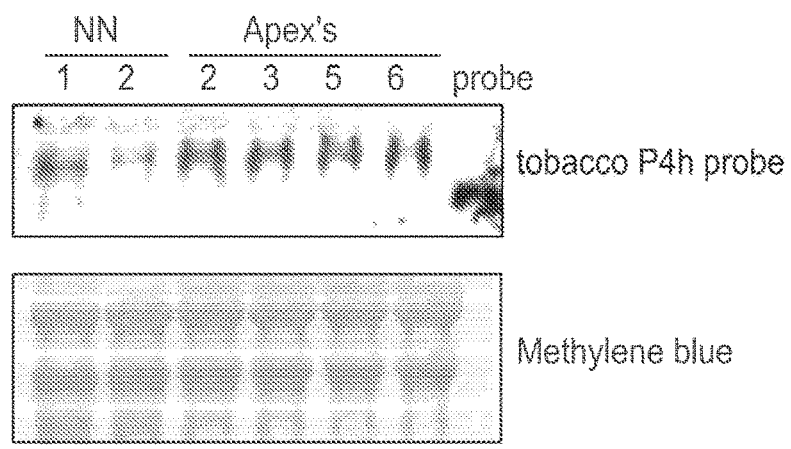
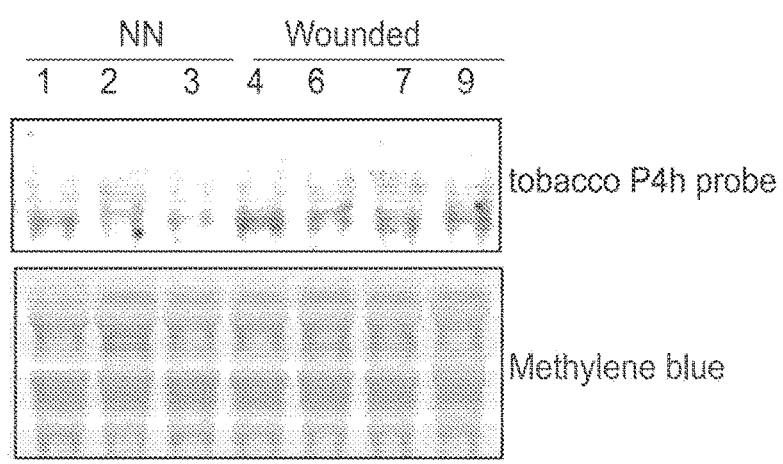
Fig. 7

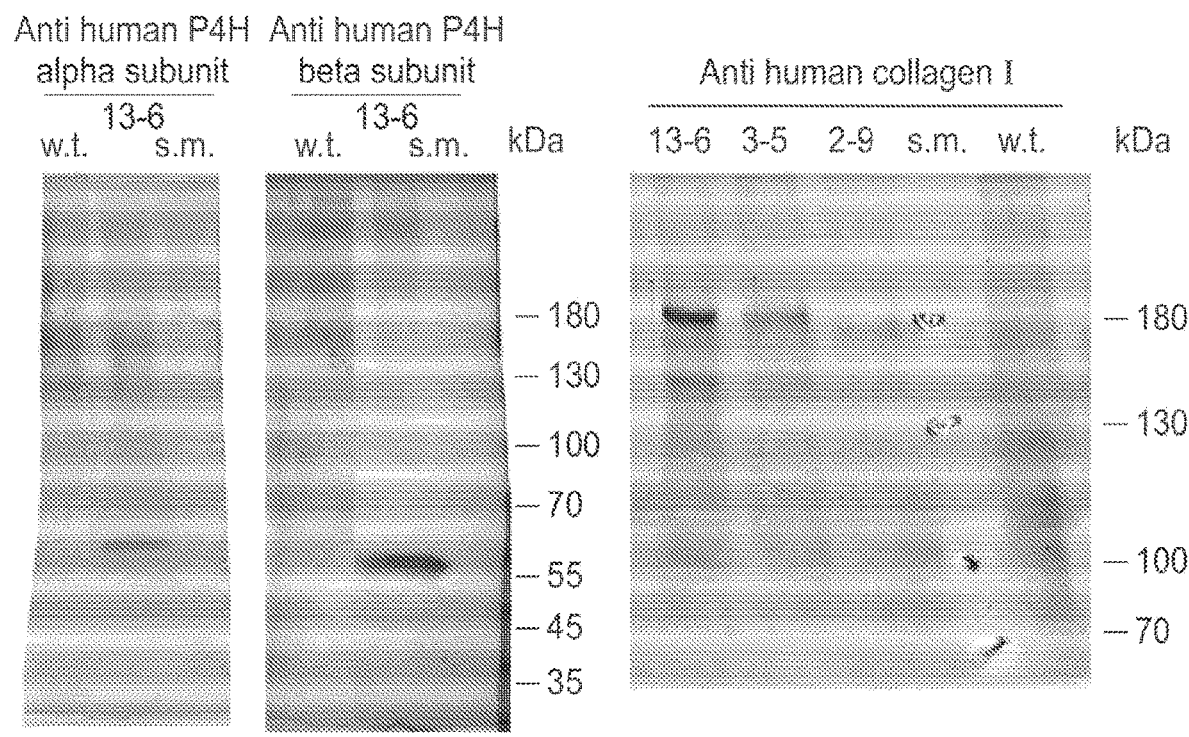
Fig. 8
Fig. 9
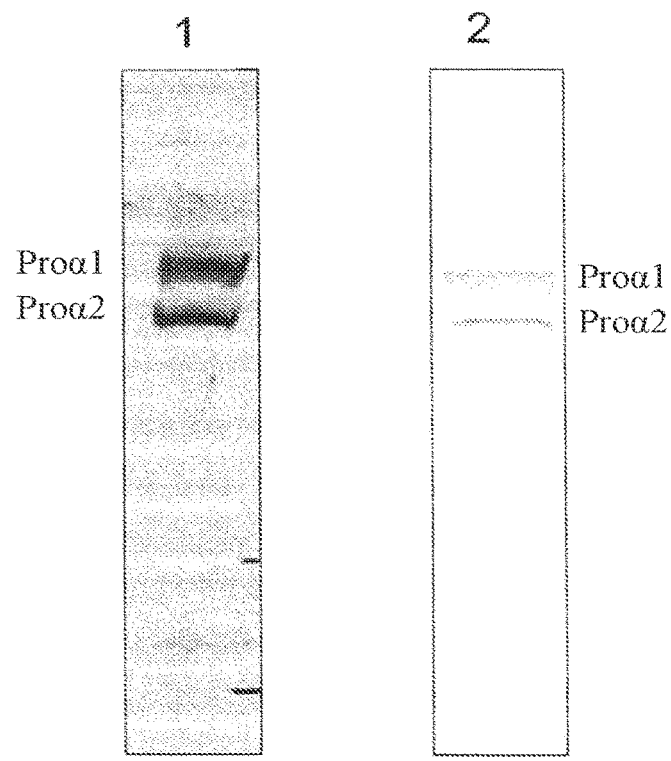

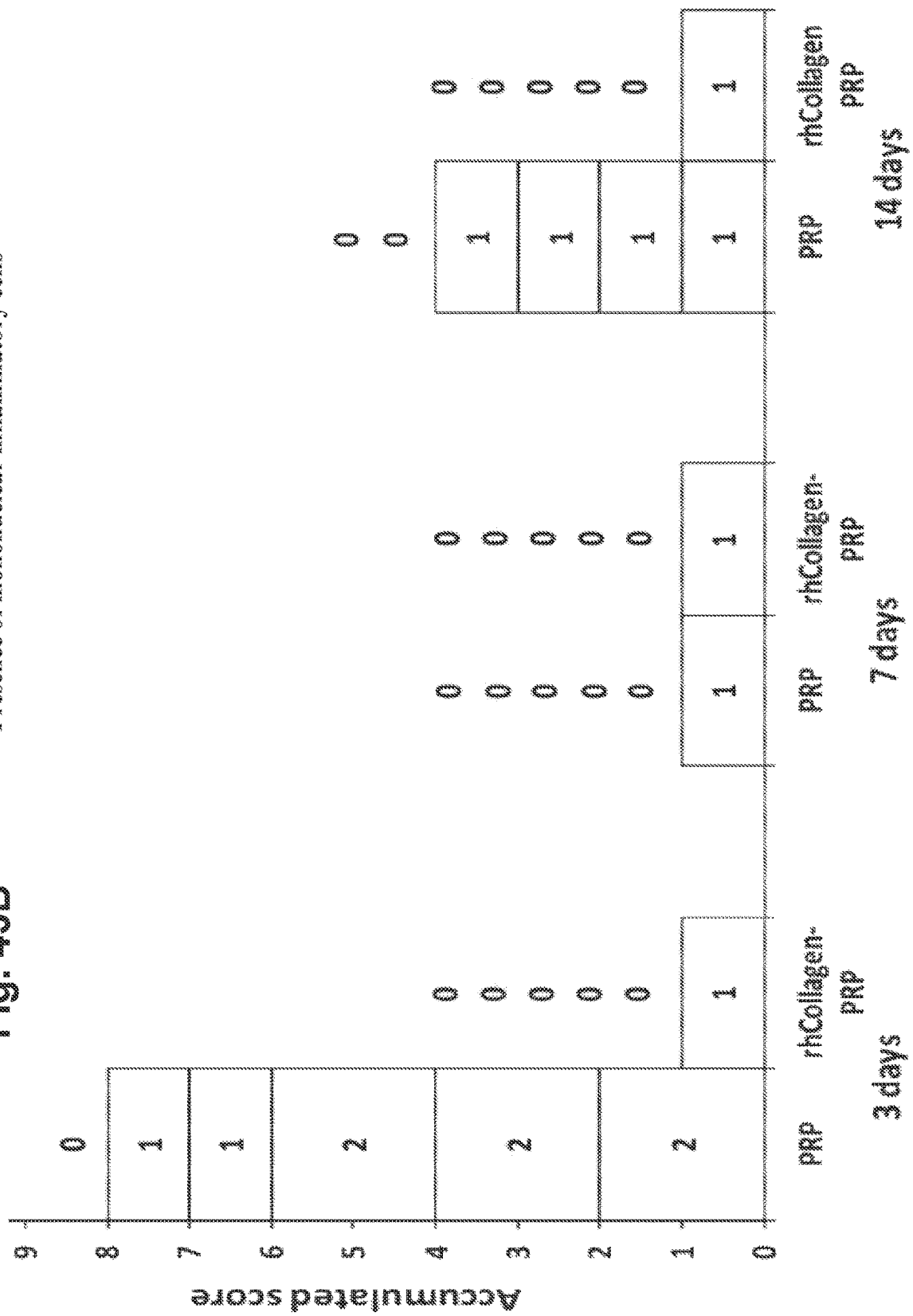

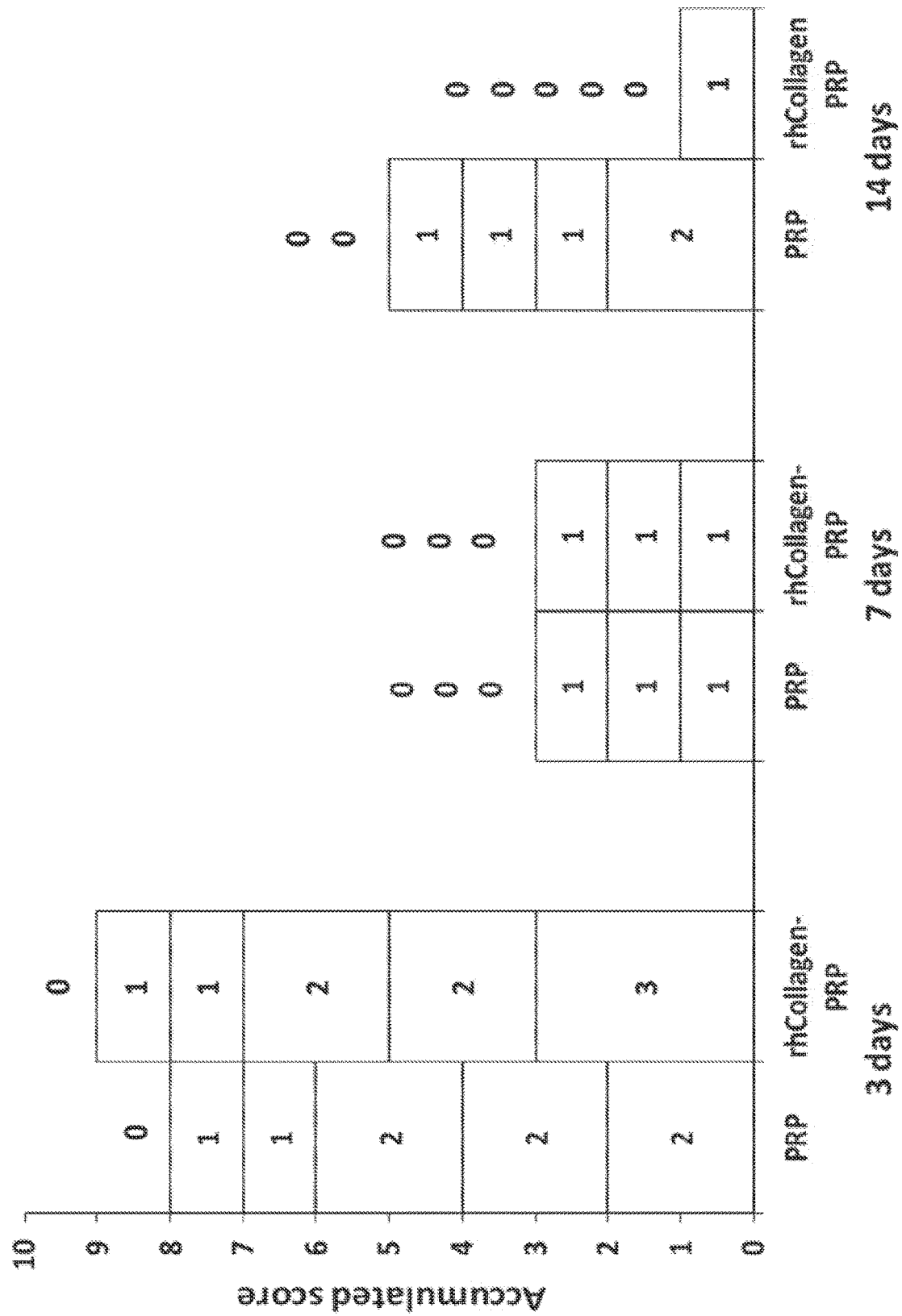

| Day 7 | bleb | Histology H&E | Histology Masson Trichrome |
|---|---|---|---|
| Formulation 2 | | | |
| Formulation 2A | | | |
| Control - commercially available | | | |

Fig. 56

SEQUENCE LISTING

```
Sequence total quantity: 42
SEQ ID NO: 1            moltype = DNA  length = 4662
FEATURE                 Location/Qualifiers
misc_feature            1..4662
                        note = Synthetic sequence containing the coding regions of
                        the vacuolar signal sequence of barley gene for Thiol
                        protease aleurain precursor fused to the human Collagen
                        alpha 1(I) chain and flanking regions
source                  1..4662
                        mol_type = other DNA
                        organism = synthetic construct
SEQUENCE: 1
gcgatgcatg taatgtcatg agccacatga tccaatggcc acaggaacgt aagaatgtag   60
atagatttga ttttgtccgt tagatagcaa acaacattat aaaaggtgtg tatcaatacg  120
aactaattca ctcattggat tcatagaagt ccattcctcc taagtatcta aaccatggct  180
cacgctcgtg ttctcctcct cgctctcgct gttttggcaa cagctgctgt ggctgtggct  240
tctagttctt cttttgctga ttcaaaccct attagacctg ttactgatag agcagcttcc  300
actttggctc aattgcaaga ggagggccag gttgagggcc aagatgagga tatccctcca  360
attacatgcg tgcaaaatgg cttgcgttac cacgataggg atgtgtggaa acctgaacct  420
tgtcgtatct gtgtgtgtga taacggcaag gtgctctgcg atgatgttat ctgcgatgag  480
acaaaaaatt gccctggcgc tgaagttcct gagggcgagt gttgccctgt gtgccctgat  540
ggttccgagt ccccaactga tcaggaaact actggcgtgg agggcccaaa aggagatact  600
ggtccacgtg gtcctagggg tccagcaggt cctccaggta gagatggtat tccaggccag  660
cctgattgc caggaccacc aggcccacct ggcccaccag gacctcctgg tcttggtgga  720
aatttcgctc cacaactctc ttatggctat gatgagaagt caacaggtgg tatttccgtt  780
ccaggtccta tgggaccatc cggaccaaga ggtctcccag gtcctccagg tgctcctgga  840
cctcaaggct ttcaaggacc tccaggcgaa ccaggagaac caggcgcttc tggaccaatg  900
ggcccaaggg gaccacctgg cccaccagga aaaaatggcg atgatggcga agctggaaag  960
cctggtcgtc ctggagagag aggtcctcct ggcccacagg gtgcaagagg cttgccagga 1020
actgctggct tgcctggaat gaagggacat aggggcttct ccggcctcga tggcgctaag 1080
ggtgatgctg gccctgctgg accaaagggc gagccaggtt ccctggaga aaacggtgct 1140
cctggacaaa tgggtcctcg tggacttcca ggagaaaggg tcgtccagg cgctccagga 1200
ccagcaggtg ctagggaaa cgatggtgca acaggcgctg ctggccctcc tggcccaact 1260
ggtcctgctg gccctccagg attcccaggc gcagttggag ctaaaggaga agcaggacca 1320
cagggcccta ggggttctga aggacctcag ggtgttagag gtgaaccagg tcctccaggc 1380
ccagctggag cagctggtcc agcaggaaat ccaggtgctg atggtcaacc tggagctaag 1440
ggcgctaatg gcgcaccagg tatcgcaggc gcaccaggtt ttcctggcgc tagaggccca 1500
agtggtcctc aaggaccagg tggaccacca ggtccaaaag gcaattctgg cgaacctggc 1560
gctccaggtt ctaaaggaga tactggtgct aaaggcgaac caggacctgt tggtgttcag 1620
ggtcctcctg gtcctgctgg agaagaagga aaaagaggtg ctcgtggaga accaggacca 1680
actggacttc ctggacctcc tggtgaacgt ggcggacctg gctcaagggg tttccctgga 1740
gctgatggag tggcaggtcc aaaaggccct gctggagaga gaggttcacc aggtccagct 1800
ggtcctaagg gctcccctgg tgaagcaggt agaccaggcg aagcaggatt gccaggccga 1860
aagggattga caggctctcc tggtagtcct ggcccagatg gaaaaacagg cccaccaggt 1920
ccagcaggac aagatggacg tccaggccca ccaggtcctc ctggagcaag gggacaagct 1980
ggcgttatgg gttttccagg acctaaaggt gctgctggag agcaggaaa ggcaggtgaa 2040
agaggattc ctggtcacc aggagcagtg ggtcctgctg gcaaagatg tgaagctgga 2100
gcacagggcc ctccaggccc tgctggccca gctggcgaac gtgagaaca aggcccagct 2160
ggtagtccag gatttcaagg attgcctggc cctgctggcc ctccaggaga agcaggaaaa 2220
cctggagaac aaggagttcc tggtgatttg ggagcacctg gaccttcagg agcacgtggt 2280
gaaagaggct tccctggcga gaggggtgtt caaggtccac caggtccaca aggacctaga 2340
ggtgctaatg gcgctcctgg caacgatgga gcaaaaggtg atgctggtgc tcctggcgca 2400
cctgaagtc agggtgctcc tggattgcaa ggaatgcctg gagagagggg tgctgctggc 2460
ttgccaggcc caaagggcga taggggtgat gctgaccaa aaggtgctga tggatcccca 2520
ggaaaagatg gagttcgtgg tcttactggc ccaatcggac ctccaggccc tgctggcgct 2580
ccaggtgata agggcgaaag tggcccaagt ggacctgctg gacctactgg tgctagaggt 2640
```

```
gcacctggtg ataggggtga acctggacca cctggtccag ctggttttgc tggtcctcct    2700
ggagctgatg gacaacctgg cgcaaagggt gaaccaggtg atgctggcgc aaagggagat    2760
gctggtccac ctggacctgc tggtccagca ggccccctg ggccaatcgg taatgttgga     2820
gcaccaggtg ctaagggagc taggggttcc gctggtccac ctggagcaac aggatttcca    2880
ggcgctgctg gtagagttgg cccaccaggc ccatccggaa acgcaggccc tcctggtcct    2940
ccaggtcctg ctggcaagga gggtggcaaa ggaccaaggg gcgaaactgg ccctgctggt    3000
agacctggcg aagttggccc tcctggacca ccaggtccag caggagaaaa aggttcccca    3060
ggagctgatg gcccagctgg tgctccagga actccaggcc ctcaaggtat tgctggacag    3120
agaggcgttg tgggactccc tggtcaaagg ggagagagag gatttccagg cttgccagga    3180
cctagtggag aacctggaaa acaaggccca tcaggcgcta gtgggagacg tggacctcct    3240
ggccctatgg gacctcctgg attggctggc ccacctggcg aatcaggtcg tgaaggcgca    3300
ccaggcgcag aaggatcacc tggaagagat ggatccctg tgctaaagg cgatcgtgga     3360
gaaactggtc cagcaggccc accaggcgca ccaggtcac ctggcgctcc aggacctgtg     3420
ggaccagctg gaaaatccgg ataggggc gagacaggcc agcaggacc agctggacct     3480
gttggccctg ctggcgctcg tggaccagca ggacctcaag gaccaagggg agataaggga    3540
gaaacaggcg aacaaggcga tagggggcatt aaggggtcata gggggtttag tggcctccag    3600
ggtcctcctg gcccacctgg atcaccagga aacagggac catctggtgc ttccggccca     3660
gctggtccaa gaggacctcc aggatcagct ggtgcacctg gaaaagatgg tcttaacgat     3720
ctcccaggac caatcggccc tcaggacct agaggaagaa caggagatgc tggccctgtt     3780
ggccctccag gacctcctgg tccaccaggt ccacctggtc ctccatcagc tggattcgat     3840
tttttcattc ttccacagcc accacaagag aaagctcacg atggcggcag atattaccgt     3900
gctgatgtg ctaacgttgt tagggataga gatttggaag tggatacaac tttgaaatcc      3960
ctctcccagc aaattgaaaa cattagatct ccagaaggtt cacgtaaaaa cccagctaga     4020
acatgtcgtg atttgaaaat gtgtcactcc gattggaaaa gtggtgaata ctggattgat     4080
ccaaatcagg gctgtaatct cgatgctatc aaagttttct gtaacatgga aacaggcgaa     4140
acatgcgttt atcctactca accttccgtg gctcagaaaa attggtacat ctcaaaaaat     4200
cctaaagata agaggcacgt ttggttcggt gaaagtatga ctgatgatt tcaatttttgag    4260
tacggcggtc aaggtagtga tccagctgat gtggctattc aactcacatt tttgcgtctt     4320
atgtccacag aggcatcaca aaacatcact taccactgca aaaacagtgt ggcttatatg     4380
gatcaacaaa caggaaacct taagaaggct cttctttttga agggctcaaa cagagatttgag   4440
attagagcag agggcaactc aaggtttact tattcagtta ctgttgatgg ctgcacttca    4500
catactggcg cttggggtaa aacagttatc gagtataaga ctacaaaaac atcaagactc    4560
ccaatcattg atgttgctcc tctcgatgtt ggcgctcctg atcaagagtt cggttttgat     4620
gtgggcccag tttgtttcct ctaatgagct cgcggccgca tc                       4662
```

SEQ ID NO: 2     moltype = DNA length = 4662
FEATURE       Location/Qualifiers
misc_feature     1..4662
          note = Synthetic sequence of the vacuolar signal sequence
          of barley gene for Thiol protease aleurain precursor fused
          to the human Collagen alpha 1(I) chain and flanking regions
source         1..4662
          mol_type = other DNA
          organism = synthetic construct
CDS          175..4644
SEQUENCE: 2

```
gcgatgcatg taatgtcatg agccacatga tccaatggcc acaggaacgt aagaatgtag      60
atagatttga ttttgtccgt tagatagcaa acaacattat aaaaggtgtg tatcaatacg     120
aactaattca ctcattggat tcatagaagt ccattcctcc taagtatcta aaccatggct     180
cacgctcgtg ttctcctcct cgctctcgct gttttggcaa cagctgctgt ggctgtggct     240
tctagtttctt cttttgctga ttcaaaccct attagacctc ttactgatag agcagcttcc    300
actttggctc aattgcaaga ggagggccag gttgagggcc aagatgagga tatccctcca     360
attacatgcg tgcaaaatgg cttgcgttac cacgataggg atgtgtgaa acctgaacct     420
tgtcgtatct gtgtgtgtga taacggcaag gtgctctgcg atgatgttat ctgcgatgag     480
acaaaaaatt gccctggcgc tgaagttcct gagggcgagt gttgccctgt gtgccctgat     540
ggttccgagt ccccaactga tcaggaaact actggcgtgg agggcccaaa aggagatact     600
ggtccacgtg gtcctagggg tccagcaggt cctccaggta gagatggtat tccaggccag     660
cctggattgc caggaccacc aggcccacct ggcccaccag gacctcctgg tcttggtgga     720
aatttcgctc cacaactctc ttatgctat gatgagaagt caacaggtgg taatttccgtt     780
ccaggtccta tgggaccatc cggaccaaga ggtctcccag gtcctccagg tgctcctgga    840
cctcaaggct ttcaaggacc tccaggcgaa ccaggagaac caggcgcttc tggaccaatg    900
ggcccaaggg gaccacctgg cccaccagga aaaaatggcg atgatggcga agctggaaag    960
cctggtcgtc ctggagagag aggtcctcct ggcccacagg gtgcaagagg cttgccagga    1020
actgctggct gcctggaat gaagggacat aggggcttct ccggcctcga tggcgctaag    1080
ggtgatgctg gccctgctgg accaaggggc gagccaggtt ccctggaga aacggtgct     1140
cctggacaaa tgggtcctcg tggacttcca ggagaaaggg gtcgtccagg cgctccagga    1200
ccagcaggtg ctaggggaaa cgatggtgca acaggcgctg ctggccctcc tggcccaact    1260
ggtcctgctg gccctccagg attcccaggc gcagttggag ctaaaggaga agcaggacca    1320
cagggcccta ggggttctga aggacctcag ggtgttaggg gtgaaccagg tcctccaggc    1380
ccagctggag cagctggtcc agcaggaaat ccaggtgctg atggtcaacc tggagctaag    1440
ggcgctaatg gcgcaccagg tatcgcaggc gcaccaggtt ttcctggcgc tagaggccca    1500
agtggtcctc aaggaccagg tggaccacca ggtccaaaag caattctgg cgaacctggc    1560
gctccaggtt ctaaaggaga tactggtgct aaggcgaac caggaccagt tggtgttcag    1620
ggtcctcctg gtcctgctgg agaagaagga accaggacca aggcaggacca    1680
actggacttc ctggacctcc tggtgaacgt ggcggaccctg gctcaagggg tttcctggaa    1740
gctgatggag tggcaggtcc aaaaggccct gctggagaga ggttcacc aggtccagct    1800
ggtcctaagg gctcccctgg tgaagcaggt agaccaggcg aagcaggatt gccaggcgca    1860
aagggattga caggctctcc tggtagtcct ggccagatg aaaaacagg cccaccaggt    1920
ccagcaggac aagatggacg tccaggccca ccaggtcctc tggagcaag gggacaagct    1980
```

```
ggcgttatgg gttttccagg acctaaaggt gctgctggag agccaggaaa ggcaggtgaa   2040
agaggagttc ctggtccacc aggagcagtg ggtcctgctg gcaaagatgg tgaagctgga   2100
gcacagggcc ctccaggccc tgctggccca gctggcgaac gtggagaaca aggcccagct   2160
ggtagtccag gatttcaagg attgcctggc cctgctggcc ctccaggaga gcaggaaaa    2220
cctggagaac aaggagttcc tggtgatttg ggagcacctg gacctbcagg agcacgtgtt   2280
gaaagaggct tccctggcga gaggggtgtt caaggtccac caggtccagc aggacctaga   2340
ggtgctaatg gcgctcctgg caacgatgga gcaaaggtg atgctggtgc tcctggcgca    2400
cctggaagtc agggtgctcc tggattgcaa ggaatgcctg gagagagggg tgctgctggc   2460
ttgccaggcc caaagggcga taggggtgat gctggaccaa aaggtgctga tggatcccca   2520
ggaaaagatg gagttcgtgg tcttactggc ccaatcggac ctccaggccc tgctggcgct   2580
ccaggtgata agggcgaaag tggcccaagt ggacctgctg gacctactgg tgctagaggt   2640
gcacctggtg ataggggtga acctggacca cctggtccag ctggttttgc tggtcctcct   2700
ggagctgatg acaacctggg cgcaaagggt gaaccaggtg atgctggcgc aaagggagat   2760
ggtccccac ctggacctgc tggtccagca ggccccctgg ggcaatggta taatgttgga    2820
gcaccaggtg ctaagggagc taggggtccg gctggtccac ctggagcaac aggatttcca   2880
ggcgctgctg gtagagttgg cccaccaggc ccatccggaa acgcaggccc tcctggtcct   2940
ccaggtcctg ctggcaagga gggtggcaaa ggaccaaggg gcgaaactgg ccctgctggt   3000
agacctggcg aagttggccc tcctggacca ccaggtccag caggagaaaa aggttcccca   3060
ggagctgatg gcccagctgg tgctccagga actccaggcc ctcaaggtat tgctggacag   3120
agaggcgttg tgggactccc tggtcaaagg ggagagagag gatttccagg cttgccagga   3180
cctagtggag aacctggaaa acaaggccca tcaggcgcta gtgagagcg tggacctcct    3240
ggccctatgg gacctcctgg attggctggc gcacctgctg gaaggcgca aggcatcacc    3300
ccaggcgcag aaggatcacc tggaagagat ggatccctg tgctaaagg cgatcgtgga    3360
gaaactggtc cagcaggccc accaggcgca ccaggtgcac ctggcgctcc aggacctgtg   3420
ggaccagctg gaaaatccgg agatagggc gagacaggcc cagcaggacc agctggacct   3480
gttggccctg ctggcgctcg tggaccagca ggacctcaag gaccaaggg agataaggga    3540
gaaacaggcg aacaaggcga taggggcatt aagggtcata ggggttttag tggcctccaa   3600
ggtcctcctg gcccacctgg atcaccagga gaacagggac catctggtgc ttccggccca   3660
gctggtccaa gaggacctcc aggatcagct ggtgcacctg aaaagatgg tcttaacggt    3720
ctcccaggac aatcggccc tcaggacct agaggaagaa ggagatgc tggccctgtt     3780
ggccctccag gacctcctgg tccaccaggt ccacctggtc ctccatcagc tggattcgat   3840
tttcatttc ttccacagcc accacaagag aaagctcacg atggcggcag atattaccgt   3900
gctgatgatg ctaacgttgt tagggataga gatttggaag tggatacaac tttgaaatcc   3960
ctctcccagc aaattgaaaa cattagatct ccagaaggtt ccgtaaaaa cccagctaga   4020
acatgtcgtg atttgaaaat gtgtcactcc gattgaaaa gtgtaaata ctggattgat    4080
ccaaatcagg gctgtaatct cgatgctatc aaagttttct gtaacatgga aacaggcgaa   4140
acatgcgttt atcctactca accttccgtg gctcagaaaa attggtacat ctcaaaaaat   4200
cctaaagata agaggcacgt ttggttcggt gaaagtatga ctgatggatt tcaatttgag   4260
tacggcggtc aagtagtga tccagctgat gtggctattc aactcacatt tttgcgtctt   4320
atgtccacag aggcatcaca aaacatcact taccactgca aaaacagtgt ggcttatatg   4380
gatcaacaaa caggaaacct taagaaggct cttcttttga agggctcaaa cgagattgag   4440
attagagcag agggcaactc aaggtttact tattcagtta ctgttgatgg ctgcacttca   4500
catactggcg cttggggtaa aacagttatc gagtataaaa ctacaaaaac atcaagactc   4560
ccaatcattg atgttgctcc tctcgatgtt ggcgctcctg atcaagagtt cggttttgat   4620
gtgggcccag tttgtttcct ctaatgagct cgcggccgca tc                     4662
```

SEQ ID NO: 3        moltype = AA   length = 1489
FEATURE              Location/Qualifiers
REGION               1..1489
                      note = Synthetic Construct
source               1..1489
                      mol_type = protein
                      organism = synthetic construct
SEQUENCE: 3
```
MAHARVLLLA LAVLATAAVA VASSSSFADS NPIRPVTDRA ASTLAQLQEE GQVEGQDEDI     60
PPITCVQNGL RYHDRDVWKP EPCRICVCDN GKVLCDDVIC DETKNCPGAE VPEGECCPVC   120
PDGSESPTDQ ETTGVEGPKG DTGPRGPRGP AGPPGRDGIP GQPGLPGPPG PPGPPGPPGL   180
GGNFAPQLSY GYDEKSTGGI SVPGPMGPSG PRGLPGPPGA PGPQGFQGPP GEPGEPGASG   240
PMGPRGPPGP PGKNGDDGEA GKPGRPGERG PPGPQGARGL PGTAGLPGMK GHRGFSGLDG   300
AKGDAGPAGP KGEPGSPGEN GAPGQMGPRG LPGERGRPGA PGPAGARGND GATGAAGPPG   360
PTGPAGPPGF PGAVGAKGEA GPQGPRGSEG PQGVRGEPGP PGPAGAAGPA GNPGADGQPG   420
AKGANGAPGI AGAPGFPGAR GPSGPQGPGG PPGPKGNSGE PGAPGSKGDT GAKGEPGPVG   480
VQGPPGPAGE EGKRGARGEP GPTGLPGPPG ERGGPGSRGF PGADGVAGPK GPAGERGSPG   540
PAGPKGSPGE AGRPGEAGLP GAKGLTGSPG SPGPDGKTGP PGPAGQDGRP GPPGPPGARG   600
QAGVMGFPGP KGAAGEPGKA GERGVPGPPG AVGPAGKDGE AGAQGPPGPA GPAGERGEQG   660
PAGSPGFQGL PGPAGPPGEA GKPGEQGVPG DLGAPGPSGA RGERGFPGER GVQGPPGPAG   720
PRGANGAPGN DGAKGDAGAP GAPGSQGAPG LQGMPGERGA AGLPGPKGDR GDAGPKGADG   780
SPGKDGVRGL TGPIGPPGPA GAPGDKGESG PSGPAGPTGA RGPAGPDRGEP PGPPGPAGFAG   840
PPGADGQPGA KGEPGDAGAK GDAGPPGPAG PAGPPGPIGN VGAPGAKGAR GSAGPPGATG   900
FPGAAGRVGP PGPSGNAGPP GPPGPAGKEG KGPRGETGP AGRPGEVGPP GPPGPAGEKG   960
SPGADGPAGA PGTPGPQGIA GQRGVVGLPG QRGERGFPGL PGPSGEPGKQ GPSGASGERG  1020
PPGPMGPPGL AGPPGESGRE GAPGAEGSPG RDGSPGAKGD RGETGPAGPP GAPGAPGAPG  1080
PVGPAGKSGD RGETGPAGPA GPVGPAGARG PAGPGKGETGEQGDR GIKGHRGFSG  1140
LQGPPGPPGS PGEQGPSGAS GPAGPRGPPG SAGAPGKDGL NGLPGIPGPP GPRGRTGDAG  1200
PVGPPGPPGP PGPPGPPSAG FDFSFLPQPP QEKAHDGGRY YRADDANVVR DRDLEVDTTL  1260
KSLSQQIENI RSPEGSRKNP ARTCRDLKMC HSDWKSGEYW IDPNQGCNLD AIKVFCNMET  1320
GETCVYPTQP SVAQKNWYIS KNPKDKRHVW FGESMTDGFQ FEYGGQGSDP ADVAIQLTFL  1380
RLMSTEASQN ITYHCKNSVA YMDQQTGNLK KALLLKGSNE IEIRAEGNSR FTYSVTVDGC  1440
TSHTGAWGKT VIEYKTTKTS RLPIIDVAPL DVGAPDQEFG FDVGPVCFL               1489
```

SEQ ID NO: 4            moltype = DNA  length = 4362
FEATURE                 Location/Qualifiers
misc_feature            1..4362
                        note = Synthetic sequence containing the coding regions of
                        the vacuolar signal sequence of barley gene for Thiol
                        protease aleurain precursor fused to the human Collagen
                        alpha 2(I) chain and flanking regions
source                  1..4362
                        mol_type = other DNA
                        organism = synthetic construct
SEQUENCE: 4
gcgatgcatg taatgtcatg agccacatga tccaatggcc acaggaacgt aagaatgtag    60
atagatttga ttttgtccgt tagatagcaa acaacattat aaaaggtgtg tatcaatacg   120
aactaattca ctcattggat tcatagaagt ccattcctcc taagtatcta aaccatggct   180
cacgctcgtg ttctcctcct cgctctcgct gttttggcaa cagctgctgt ggctgtggct   240
tcaagttcta gttttgctga ttccaaccca attcgtccag ttactgatag agcagcttcc   300
actttggctc aattgcttca agaagaaact gtgaggaagg gccctgctgg cgataggggc   360
cctaggggcg aaaggggtcc accaggacct ccaggcaggg atggcgaaga tggtccaact   420
ggccctcctg gacctcctgg ccctccaggg ccacccggct gggcggaaaa cttcgcagct   480
caatacgatg gcaagggtgt tggtcttggt cctggtccta tgggcttgat gggacctaga   540
ggcccacctg gtgctgctgg tgctcctgga ccacaggggt ttcagggacc agctggctgg   600
ccaggagagc caggccaaac aggaccagct ggtgcaaggg gacctgctgg acctcctgga   660
aaagctggtg aagatggtca cccaggcaaa ccaggacgtc ctggcgaaag aggtgttgtt   720
ggaccacaag gcgctagggg atttccaggt cacctggat tgccaggttt aagggcatt    780
cgtggtcata acgcctcga tggattgaag ggacagcctg gcgcacctgg cgttaagggt   840
gaacctggag caccaggtga aaacggtact cctggccaga ctggtgcaag aggactccca   900
ggtgaaaggg gtagagttgg tgctcctgga cctgctggag ctaggggtag tgatggtagt   960
gttggtcctg tgggccctgc tggtccaatc ggttccgctg gccacctgg attcccaggc  1020
gctccaggac ctaaaggaga aatcggtgct gtgggtaacg caggtcctac tggtccagca  1080
ggtcctcgtg gagaagtggg attgccagga cttctggtc cagtgggccc tccaggcaac  1140
cctggagcta acggcttgac aggagctaaa ggcgcagcag gactcctgg agtggctggc  1200
gcaccaggat tgcctggtcc aagggggtatc ccaggccctg ttggcgcagc tggagctact  1260
ggtgcacgtg gacttgttgg cgaaccaggc cctgctggat caaaggcga gtctggaaat  1320
aagggagaac ctggttcgc tggacctcaa gtcctcctg gaccttctgg agaagaggca  1380
aaaggggac caaatggcga ggctggatca gcaggtccac caggaccacc tggacttcgt  1440
ggatcccctg gtagtagagg acttccaggc gctgatggta gagcaggcgt tatgggacca  1500
ccaggaagta gaggagcatc cggtccagca ggagttaggg gtcctaacgg agatgctggt  1560
agaccaggtg aaccaggtct tatgggccca aggggcctcc caggtagtcc aggaaatatc  1620
ggccctgctg gaaaagaagg ccctgttgga cttccaggta ttgatggacg tcctggccct  1680
attggcccag caggtgcaag aggagaacct ggcaatattg gatttccagg accaaagggt  1740
ccaacaggcg atcctggaaa aaatggagat aagggtcatg ctggattggc aggcgcaagg  1800
ggcgctcctg gtcagatgg aaacaacggc gcacaggtc cacctggcc tcagggtgtt  1860
caaggcggaa aaggcgaaca aggcccagct ggaccaccag gctttcaagg cttgccagga  1920
ccaagtggtc cagcaggtga agttggcaag ccaggcgagc gtggacttca tggcgagttt  1980
ggactccctg gaccagcagg accaagggg gaaagaggcc ctcctggaga gagtggcgct  2040
gctggaccaa caggcccaat cggtagtaga ggtcctagtg gacctccagg cccagatgga  2100
aataagggtg aaccaggagt tgtgggcgct gttggaacag ctggtcctc aggaccatca  2160
ggactcccag cgagagagg cgctgctggg attcctggag aaaaggtga aaaggcgaa  2220
cctggcctcc gtggcgaaat cggaaatcct ggacgtgatg gtgctcgtgg tgcacacggc  2280
gctgtgaggc ctcaggccc tgctggtgct actggtgata gaggagagcc tggccgagct  2340
ggcccagcag gtcctgctgg cccaagggt agtcctggtg aaagaggcga agttggacct  2400
gctgcccta acggctttgc tggcctgct ggagcagcag gtcaacctgg cgctaaaggt  2460
gaaaggggcg aaaggggccc aaaaggtgaa atggcgttg tgggaccaac tggtccagtg  2520
ggcgcagcgg gacctgctgg tccaaatgga ccaccaggt agaaggagat  2580
ggtggaccct caggaatgac aggtttccca ggtgctgctg gtagaacagg acctcctggt  2640
cctagtggta tttctggtcc accaggacca ccaggtcctg ctggaaaaga aggattgagg  2700
ggtccacgtg gtgatcaagg accagtggc agaactggtg aagttggcgc agtgggacca  2760
cctggttttg ctgagaaaa gggccttct ggagaggcag gaacagctgg tcctcctgt  2820
acacctggac ctcaaggact tttgggtgca cctggtattc tcggattgcc aggaagtagg  2880
ggcgaacgtg gacttcctgg cgtggcagga gcagttggag aacctggccc tctcggaatc  2940
gcaggcccac caggcgcaag aggaccacca ggagctgttg atcaccagg cgtgaatggt  3000
gcacctggcg aggctggtcg tgatggaaac ccaggaaatg atgcccacc aggaagagat  3060
ggtcaaccag acacaaagg cgagagggc tacccgaac atattgccgc agttggtgat  3120
gctggcgcac caggcccaca cggtccagtt ggaccagcag gaaaacacgg taatcgtggc  3180
gaaacaggcc cttcaggccc agtgggacct gctggtgctg ttggcccaag gaccatct  3240
ggacctcaag gcattagagg cgataaggga gagcctggcg aaaaggacc tagaggcttg  3300
cctggtttta aggacacaa cggtctccaa ggacttccag gtatcgctgg tcatcatgga  3360
gatcagggtg ctcctggatc agtgggtcca gcaggtccta gagggccagc aggcccttcc  3420
ggtccagcag gaaaggatgg acgtactggc caccctggaa ctgtgggccc tgctggaatt  3480
agaggtcctc aaggtcatca gggccctgct ggccctccag tccaccagg tcctccaggc  3540
ccaccagag tttcaggtgg tggttacgat tttggtatg atggtgattt taccgtgct  3600
gatcaaccta gaagtgctcc ttctctccgt cctaaagatt atgaagttga tgctactttg  3660
aaatcactta acaaccagat tgagactctt ctcacccagt gggatcaag aaagaatccca  3720
gcacgtacat gccgtgatct cagacttagt cacccagagt ggtcaagtgg ctattattgg  3780
attgatccta atcagggttg tacaatggag gctatcaaag tttactgtga ttttccaact  3840
ggagagacat gtattagggc acaacctgag aacattccag ctaaaattg gtatcgttcc  3900
tctaaagata agaaacatgt ttggctcgga gagactatta cgctggttc tcagttcgag  3960
tataatgttg agggcgttac ttctaaagag atggcaactc agctcgcttt tatgagattg  4020

```
ctcgctaact acgcatccca aaacatcact tatcactgca aaaattccat tgcatatatg  4080
gatgaggaga caggaaattt gaagaaagca gttattctcc aaggtagtaa cgatgttgag  4140
cttgtggctg agggaaatag tagattcact tacacagttt tggtggatgg atgctcaaag  4200
aaaactaatg agtggggcaa gacaatcatt gagtacaaga caaataagcc ttctaggctc  4260
ccatttctcg atattgcacc tcttgatatc ggaggagctg atcacgagtt ttttgttgat  4320
atcggacctg tttgttttaa gtaatgagct cgcggccgca tc                    4362
```

| | | |
|---|---|---|
| SEQ ID NO: 5 | moltype = DNA   length = 4362 | |
| FEATURE | Location/Qualifiers | |
| misc_feature | 1..4362 | |
| | note = Synthetic sequence of the vacuolar signal sequence of barley gene for Thiol protease aleurain precursor fused to the human Collagen alpha 2(I) chain and flanking regions | |
| source | 1..4362 | |
| | mol_type = other DNA | |
| | organism = synthetic construct | |
| CDS | 175..4344 | |

SEQUENCE: 5

```
gcgatgcatg taatgtcatg agccacatga tccaatggcc acaggaacgt aagaatgtag   60
atagatttga ttttgtccgt tagatagcaa acaacattat aaaaggtgtg tatcaatacg  120
aactaattca ctcattggat tcatagaagt ccattcctcc taagtatcta aaccatggct  180
cacgctcgtg ttctcctcct cgctctcgct gttttgccaa cagctgctgt ggctgtggct  240
tcaagttcta gttttgctga ttccaaccca attcgtccag ttactgatag agcagcttcc  300
actttggctc aattgcttca agaagaaact gtgaggaagg gccctgctgg cgatagggc   360
cctaggggcg aaaggggtcc accaggacct ccaggcaggg atggcgaaga tggtccaact  420
ggccctcctg gacctcctgg ccctccaggg ccacccggct tgggcggaaa cttcgcagct  480
caatacgatg gcaagggtgt tggtcttggt cctggtccta tgggcttgat gggacctaga  540
ggcccacctg gtgctgctgg tgctcctgga ccacagggtt ttcagggacc agctggcgag  600
ccaggagagc caggccaaac aggaccagct ggtgcaaggg gacctgctgg acctcctgga  660
aaagctggtg aagatggtca cccaggcaaa ccaggacgtc ctggcgaaag aggtgttgtt  720
ggaccacaag gcgctagggg atttccaggt acacctggat tgccaggttt taagggcatt  780
cgtggtcata acgcctcga tggattgaag ggacagcctg gcgcacctgg cgttaagggt  840
gaacctggag caccaggtga aaacggtact cctggccaga ctggtgcaag aggactccca  900
ggtgaaaggg gtagagttgg tgctcctgga cctgctggag ctaggggtag tgatggtagt  960
gttggtcctg tgggccctgc tggtccaatc ggttccgctg gcccacctgg attcccaggc 1020
gctccaggac ctaaaggaga aatcggtgct gtgggtaacg caggtcctac tggtccagca 1080
ggtcctcgtg gagaagtggg attgccagga ctttctggtc cagtgggccc tccaggcaac 1140
cctggagcta acggcttgac aggagctaaa ggcgcagcag gactccctgg agtggctggc 1200
gcaccaggat tgcctggtcc aaggggtatc ccaggccgtc ttggcgcagc tggagctact 1260
ggtgcacgtg gacttgttgg cgaaccaggc cctgctggat caaaaggcga gtctggaaat 1320
aagggagaac ctggttctgc tggacctcaa ggtcctcctg gacttctgg agaagaagga 1380
aaagggggac caaatggcga ggctggatca gcaggtccac caggaccacc tggacttcgt 1440
ggatcccctg gtagtagagg acttccaggc gctgatggta gagcaggcgt tatgggacca 1500
ccaggaagta gaggagcatc cggtccagca ggagttaggg gtcctaacgg agatgctggt 1560
agaccaggtg aaccaggtct tatgggccca aggggcctcc caggtagtcc aggaaatatc 1620
ggccctgctg aaaagaagg ccctgttgga cttccaggta ttgatggacg tcctggccct 1680
attggcccag caggtgcaag aggagaacct ggcaatattg gatttccagg accaaagggt 1740
ccaacaggcg atcctggaaa aaatggagat aagggtcatg ctggattggc aggcgcaagg 1800
ggcgctcctg gtccagatgg aaacaacggc gcaggggtc cacctggccc tcagggtgtt 1860
caaggcggaa aaggcgaaca aggcccagct ggaccaccag gctttcaagg cttgccagga 1920
ccaagtggtc cagcaggtga agttggcaag ccaggcgagc gtggacttca tggcgagttt 1980
ggactccctg gaccagcagg accaaggggg gaaagaggcc ctcctggaga gagtggcgct 2040
gctggaccaa caggccccaat cggtagtaga ggtcctagtg gacctccagg cccagatgga 2100
aataagggta accaggagt tgtgggcgct gttggaacag ctggtccttc aggaccatca 2160
ggactcccag gcgagagagg cgctgctggc attcctggag gaaaaggtga aaaaggcgaa 2220
cctggcctcc gtggcgaaat cggaaatcct ggacgtgatg gtgctcgtgg tgcacacgtg 2280
gctgtgggcg ctcaggccc tgctggtgct actggtgata gaggagagc tggcgcagct 2340
ggcccagcag gtcctgctgg cccaaggggt agtcctggt aaagaggcga agttggacct 2400
gctggcccta acggctttgc tggcccgct ggagcagcag gtcaacctgg cgctcaaagt 2460
gaaaggggcg gaaagggccc aaaaggtgaa aatggcgtg tgggaccaac tggtccagtg 2520
ggcgcagctg gacctgctgg tccaaatgga ccaccaggac cagcaggtag tagaggagat 2580
ggtgaccctc caggaatgac aggttttcca ggtgctgctg gtagaacagg acctcctggt 2640
cctagtggta tttctggtcc accaggacca ccaggtcctg ctggaaaaga aggattgagg 2700
ggtccacgtg gtgatcaagg accagtgggc agaactggca agttggccgc agtggaccaa 2760
cctggttttg ctggagaaaa gggccttct ggagaggcag gaacagctgg tcctcctggt 2820
acacctggac tcaaggact tttgggtgca cctggtattc tcgattgcc aggaagtagg 2880
ggcgaacgtg gacttcctgg cgtggcagga gcagttggaa aacctggccc tctcggaatc 2940
gcaggccac caggcgcaag aggaccacca ggagctgttg gatcaccagg cgtgaatggt 3000
gcacctggcg aggctggtcg tgatggaaac ccaggaaatg atggcccacc aggaagagat 3060
ggtcaacctg gacacaaagg cgagagggc tacccaggaa atattggcc agttggtgct 3120
gctggcgcac caggcccaca cggtccagtt ggaccagcag aaaacacgg taatcgtggc 3180
gaaacaggcc cttcagggcc agtgggacct gctggtgctg ttggcccaag gaccatct 3240
ggacctcaag gcattagagg cgataaggga gagcctggcg aaaaaggacc tagaggcttg 3300
cctggttta aaggacacaa cggtctccaa gaccttgctg catcatgga  3360
gatcagggtg ctcctggatc agtgggtcca gcaggtccta gaggcccagc aggcccttcc 3420
ggtccagcag gaaaggatgg acgtactggc caccctggaa ctgtgggccc tgctggaatt 3480
agaggtcctc aaggtcatca gggccctgct ggccctccag gtccaccagg tcctccaggc 3540
ccaccaggag tttcaggtgg tggttacgat tttggttacg atggtgattt ttaccgtgct 3600
gatcaaccta aagtgctccc ttctctccgt cctaaagatt atgaagttga tgctactttg 3660
```

-continued

```
aaatcactta acaaccagat tgagactctt ctcacacctg agggatcaag aaagaatcca  3720
gcacgtacat gccgtgatct cagacttagt cacccagagt ggtcaagtgg ctattattgg  3780
attgatccta atcagggttg tacaatggag gctatcaaag tttactgtga ttttccaact  3840
ggagagacat gtattagggc acaacctgag aacattccag ctaaaaattg gtatcgttcc  3900
tctaaagata agaaacatgt ttggctcgga gagactatta acgctggttc tcagttcgag  3960
tataatgttg agggcgttac ttctaaagag atggcaactc agctcgcttt tatgagattg  4020
ctcgctaact acgcatccca aaacatcact tatcactgca aaaattccat tgcatatatg  4080
gatgaggaga caggaaattt gaagaaagca gttattctcc aaggtagtaa cgatgttgag  4140
cttgtggctg agggaaatag tagattcact tacacagttt tggtggatgg atgctcaaag  4200
aaaactaatg agtggggcaa gacaatcatt gagtacaaga caaataagcc ttctaggctc  4260
ccatttctcg atattgcacc tcttgatatc ggaggagctg atcacgagtt ttttgttgat  4320
atcggacctg tttgttttaa gtaatgagct cgcggccgca tc                     4362

SEQ ID NO: 6          moltype = AA  length = 1389
FEATURE               Location/Qualifiers
REGION                1..1389
                      note = Synthetic Construct
source                1..1389
                      mol_type = protein
                      organism = synthetic construct
SEQUENCE: 6
MAHARVLLLA LAVLATAAVA VASSSSFADS NPIRPVTDRA ASTLAQLLQE ETVRKGPAGD   60
RGPRGERGPP GPPGRDGEDG PTGPPGPPGP GPPPGLGGNF AAQYDKGVG LGPGPMGLMG   120
PRGPPGAAGA PGPQGFQGPA GEPGEPGQTG PAGARGPAGP PGKAGEDGHP GKPGRPGERG  180
VVGPQGARGF PGTPGLPGFK GIRGHNGLDG LKGQPGAPGV KGEPGAPGEN GTPGQTGARG  240
LPGERGRVGA PGPAGARGSD GSVGPVGPAG PIGSAGPPGF PGPAGPPKGEI GAVGNAGPTG  300
PAGPRGEVGL PGLSGPVGPP GNPGANGLTG AKGAAGLPGV AGAPGLPGPR GIPGPVGAAG  360
ATGARGLVGE PGPAGSKGES GNKGEPGSAG PQGPPGPSGE EGKRGPNGEA GSAGPPGPPG  420
LRGSPGSRGL PGADGRAGVM GPPGSRGASG PAGVRGPNGD AGRPGEPGLM GPRGLPGSPG  480
NIGPAGKEGP VGLPGIDGRP GPIGPAGARG EPGNIGFPGP KGPTGDPGKN GDKGHAGLAG  540
ARGAPGPDGN NGAQGPPGPQ GVQGGKGEQG PAGPPGFQGL PGPSGPAGEV GKPGERGLHG  600
EFGLPGPAGP RGERGPPGES GAAGPTGPIG SRGPSGPPGP DGNKGEPGVV GAVGTAGPSG  660
PSGLPGERGA AGIPGGKGEK GEPGLRGEIG NPGRDGARGA HGAVGAPGPA GATGDRGEAG  720
AAGPAGPAGP RGSPGERGEV GPAGPNGFAG PAGAAGQPGA KGERGGKGPK GENGVVGPTG  780
PVGAAGPAGP NGPPGPAGSR GDGGPPGMTG FPGAAGRTGP PGPSGISGPP GPPGPAGKEG  840
LRGPRGDQGP VGRTGEVGAV GPPGPAGEKG PSGEAGTAGP PGTPGPQGLL GAPGILGLPG  900
SRGERGLPGV AGAVGEPGPL GIAGPPGARG PPGAVGSPGV NGAPGEAGRD GNPGNDGPPG  960
RDGQPGHKGE RGYPGNIGPV GAAGAPGPHG PVGPAGKHGN RGETGPSGPV PGAGAVGPRG  1020
PSGPQGIRGD KGEPGEKGPR GLPGFKGHNG LQGLPGIAGH HGDQGAPGSV GPAGPRGPAG  1080
PSGPAGKDGR TGHPGTVGPA GIRGPQGHQG PAGPPGPPGP PGPPGVSGGG YDFGYDGDFY  1140
RADQPRSAPS LRPKDYEVDA TLKSLNNQIE TLLTPEGSRK NPARTCRDLR LSHPEWSSGY  1200
YWIDPNQGCT MEAIKVYCDF PTGETCIRAQ PENIPAKNWY RSSKDKKHVW LGETINAGSQ  1260
FEYNVEGVTS KEMATQLAFM RLLANYASQN ITYHCKNSIA YMDEETGNLK KAVILQGSND  1320
VELVAEGNSR FTYTVLVDGC SKKTNEWGKT IIEYKTNKPS RLPFLDIAPL DIGGADHEFF  1380
VDIGPVCFK                                                          1389

SEQ ID NO: 7          moltype = DNA  length = 127
FEATURE               Location/Qualifiers
misc_feature          1..127
                      note = Synthetic sequence containing the coding region of
                        the appoplast signal of Arabidopsis thaliana
                        endo-1,4-beta-glucanase and flanking regions
source                1..127
                      mol_type = other DNA
                      organism = synthetic construct
SEQUENCE: 7
gccatggcta ggaagtcttt gattttccca gtgattcttc ttgctgtgct tcttttctct   60
ccacctattt actctgctgg acacgattat agggatgctc ttaggaagtc atctatggct  120
caattgc                                                            127

SEQ ID NO: 8          moltype = DNA  length = 127
FEATURE               Location/Qualifiers
misc_feature          1..127
                      note = Synthetic sequence of the appoplast signal of
                        Arabidopsis thaliana endo-1,4-beta-glucanase and flanking
                        regions
source                1..127
                      mol_type = other DNA
                      organism = synthetic construct
CDS                   10..120
SEQUENCE: 8
gccatggcta ggaagtcttt gattttccca gtgattcttc ttgctgtgct tcttttctct   60
ccacctattt actctgctgg acacgattat agggatgctc ttaggaagtc atctatggct  120
caattgc                                                            127

SEQ ID NO: 9          moltype = AA  length = 37
FEATURE               Location/Qualifiers
REGION                1..37
                      note = Synthetic Construct
```

| | | |
|---|---|---|
| source | 1..37 | |
| | mol_type = protein | |
| | organism = synthetic construct | |
| SEQUENCE: 9 | | |
| RKSLIFPVIL LAVLLFSPPI YSAGHDYRDA LRKSSMA | | 37 |

| | | |
|---|---|---|
| SEQ ID NO: 10 | moltype = DNA   length = 1037 | |
| FEATURE | Location/Qualifiers | |
| misc_feature | 1..1037 | |
| | note = Chrysanthemum rbcS1 promoter and 5′ UTR | |
| source | 1..1037 | |
| | mol_type = other DNA | |
| | organism = synthetic construct | |
| SEQUENCE: 10 | | |
| aaatggcgcg ccaagcttag acaaacaccc cttgttatac aaagaatttc gctttacaaa | | 60 |
| atcaaattcg agaaaataat atatgcacta aataagatca ttcggatcca atctaaccaa | | 120 |
| ttacgatacg ctttgggtac acttgatttt tgtttcagta gttacatata tcttgtttta | | 180 |
| tatgctatct ttaaggatct tcactcaaag actatttgtt gatgttcttg atggggctcg | | 240 |
| gaagatttga tatgatacac tctaatcttt aggagatacc agccaggatt atattcagta | | 300 |
| agacaatcaa attttacgtg ttcaaactcg ttatcttttc atttaatgga tgagccagaa | | 360 |
| tctctataga atgattgcaa tcgagaatat gttcggccga tatcccttg ttggcttcaa | | 420 |
| tattctacat atcacacaag aatcgaccgt attgtaccct ctttccataa aggaacacac | | 480 |
| agtatgcaga tgcttttttc ccacatgcag taacataggt attcaaaaat ggctaaaaga | | 540 |
| agttggataa caaattgaca actatttcca tttctgttat ataaatttca caacacacaa | | 600 |
| aagcccgtaa tcaagagtct gcccatgtac gaaataactt ctattatttg gtattgggcc | | 660 |
| taagcccagc tcagagtacg tgggggtacc acatatagga aggtaacaaa atactgcaag | | 720 |
| atagccccat aacgtaccag cctctcctta ccacgaagag ataagatata agacccaccc | | 780 |
| tgccacgtgt cacatcgtca tggtggttaa tgataaggga ttacatcctt ctatgtttgt | | 840 |
| ggacatgatg catgtaatgt catgagccac atgatccaat ggccacagga acgtaagaat | | 900 |
| gtagatagat ttgattttgt ccgttagata gcaaacaaca ttataaaagg tgtgatcaa | | 960 |
| tacgaactaa ttcactcatt ggattcatag aagtccattc ctcctaagta tctaaacata | | 1020 |
| tgcaattgtc gactaaa | | 1037 |

| | | |
|---|---|---|
| SEQ ID NO: 11 | moltype = DNA   length = 975 | |
| FEATURE | Location/Qualifiers | |
| misc_feature | 1..975 | |
| | note = Chrysanthemum rbcS1 3′UTR and terminator | |
| source | 1..975 | |
| | mol_type = other DNA | |
| | organism = synthetic construct | |
| SEQUENCE: 11 | | |
| aaaaggatcc gcggccgcat aagttttact atttaccaag acttttgaat attaaccttc | | 60 |
| ttgtaacgag tcggttaaat ttgattgttt agggttttgt attatttttt tttggtctttt | | 120 |
| taattcatca ctttaattcc ctaattgtct gttcatttcg ttgtttgttt ccggatcgat | | 180 |
| aatgaaatgt aagagatatc atatataaat aataaattgt cgtttcatat ttgcaatctt | | 240 |
| tttttacaaa ccttttaatta attgtatgta tgacatttc tcttgttat attagggga | | 300 |
| aataagtta aataaaagta caaaataaac tacagtacat cgtactgaat aaattaccta | | 360 |
| gccaaaaagt acacctttcc atatacttcc tacatgaagg cattttcaac attttcaaat | | 420 |
| aaggaatgct acaaccgcat aataacatcc acaatttttt ttataaaata acatgtcaga | | 480 |
| cagtgattga aagattttat tatagtttcg ttatcttctt ttctcattaa gcgaatcact | | 540 |
| acctaacacg tcattttgtg aaatattttt tgaatgtttt tatatagttg tagcattcct | | 600 |
| cttttcaaat tagggtttgt ttgagatagc atttcagccg gttcatacaa cttaaaagca | | 660 |
| tactctaatg ctggaaaaaa gactaaaaaa tcttgtaagt tagcgcagaa tattgaccca | | 720 |
| aattatatac acacatgacc ccatatagag actaattaca cttttaacca ctaataatta | | 780 |
| ttactgtatt ataacatcta ctaattaaac ttgtgagttt ttgctagaat tattatcata | | 840 |
| tatactaaaa ggcaggaacg caaacattgc cccggtactg tagcaactac ggtagacgca | | 900 |
| ttaattgtct atagtggacg cattaattaa ccaaaaccgc ctctttcccc ttcttcttga | | 960 |
| agcttgagct cttttt | | 975 |

| | | |
|---|---|---|
| SEQ ID NO: 12 | moltype = DNA   length = 1633 | |
| FEATURE | Location/Qualifiers | |
| misc_feature | 1..1633 | |
| | note = Synthetic sequence containing the coding regions of the vacuolar signal sequence of barley gene for Thiol protease aleurain precursor fused to the human Prolyl 4-hydroxylase beta subunit and flanking regions | |
| source | 1..1633 | |
| | mol_type = other DNA | |
| | organism = synthetic construct | |
| SEQUENCE: 12 | | |
| ctcgagtaaa ccatggctca tgctagggtt ttgcttttgg ctcttgctgt tcttgctact | | 60 |
| gctgctgttg ctgtggcttc ttcttcatct ttcgctgatt ctaacccaat taggccagtg | | 120 |
| actgatagag ctgcttctac tcttgctcaa ttggtcgaca tggatgctcc agaagaggag | | 180 |
| gatcacgttc ttgtcttag gaagtctaac ttcgctgaag tctctgctgc tcacaagtac | | 240 |
| cttcttgtgg agttttatgc tccttggtgc ggacattgca aagctcttgc tccagagtat | | 300 |
| gctaaggctc tggaaagtt gaaggctgag ggatctgaaa ttaggcttgc taaagtggat | | 360 |
| gctactgagg agtctgatct tgctcaacag tacggagtta gggatacccc aactattaag | | 420 |
| ttcttcagga acggagatac tgcttctcca aggagtatac tgctggaag ggaggctgat | | 480 |
| gatattgtga actggcttaa gaagagaact ggaccagctc tactactcct tccagatgga | | 540 |

-continued

```
gctgctgctg aatctcttgt ggagtcatct gaggtggcag tgattggatt cttcaaggat    600
gtggagtctg attctgctaa gcagttcctt caagctgctg aggctattga tgatattcca    660
ttcggaatta cttctaactc tgatgtgttc tctaagtacc agcttgataa ggatggagtg    720
gtgcttttca agaaattcga tgagggaagg aacaatttcg agggagaggt gacaaaggag    780
aaccttcttg atttcattaa gcacaaccag cttccacttg tgattgagtt cactgagcag    840
actgctccaa agattttcgg aggagagatt aagactcaca ttcttctttt ccttccaaag    900
tctgtgtctg attacgatgg aaagttgtct aacttcaaga ctgctgctga gtctttcaag    960
ggaaagattc ttttcatttt cattgattct gatcacactg ataaccagag gattcttgag   1020
ttcttcggac ttaagaagga agagtgccca gctgttaggc ttattactct tgaggaggag   1080
atgactaagt acaagccaga gtctgaagaa cttactgctg agaggattac tgagttctgc   1140
cacagattcc ttgagggaaa gattaagcca caccttatgt ctcaagagct tccagaggat   1200
tgggataagc agccagttaa ggtgttggtg ggtaaaaact cgaggatgt ggctttcgat    1260
gagaagaaga acgtgttcgt ggagttctac gcaccttggt gtggtcactg taagcagctt   1320
gctccaattt gggataagtt gggagagact tacaaggatc agagaaacat tgtgattgct   1380
aagatggatt ctactgctaa cgaggtggag gctgttaagg ttcactcttt cccaactttg   1440
aagttcttcc cagcttctgc tgataggact gtgattgatt acaacggaga aaggactctt   1500
gatggattca agaagttcct tgagtctgga ggacaagatg gagctggaga tgatgatgat   1560
cttgaggatt tggaagaagc tgaggagcca gatatggagg aggatgatga tcagaaggct   1620
gtgtgatgag ctc                                                      1633

SEQ ID NO: 13        moltype = AA  length = 537
FEATURE              Location/Qualifiers
REGION               1..537
                     note = Synthetic sequence containing the vacuolar signal
                     sequence of barley gene for Thiol protease aleurain
                     precursor fused to the human Prolyl 4-hydroxylase beta
                     subunit and flanking regions
source               1..537
                     mol_type = protein
                     organism = synthetic construct
SEQUENCE: 13
MAHARVLLLA LAVLATAAVA VASSSSFADS NPIRPVTDRA ASTLAQLVDM DAPEEEDHVL     60
VLRKSNFAEA LAAHKYLLVE FYAPWCGHCK ALAPEYAKAA GKLKAEGSEI RLAKVDATEE    120
SDLAQQYGVR GYPTIKFFRN GDTASPKEYT AGREADDIVN WLKKRTGPAA TTLPDGAAAE    180
SLVESSEVAV IGFFKDVESD SAKQFLQAAE AIDDIPFGIT SNSDVFSKYQ LDKDGVVLFK    240
KFDEGRNNFE GEVTKENLLD FIKHNQLPLV IEFTEQTAPK IFGGEIKTHI LLFLPKSVSD    300
YDGKLSNFKT AAESFKGKIL FIFIDSDHTD NQRILEFFGL KKEECPAVRL ITLEEEMTKY    360
KPESEELTAE RITEFCHRFL EGKIKPHLMS QELPEDWDKQ PVKVLVGKNF EDVAFDEKKN    420
VFVEFYAPWC GHCKQLAPIW DKLGETYKDH ENIVIAKMDS TANEVEAVKV HSFPTLKFFP    480
ASADRTVIDY NGERTLDGFK KFLESGGQDG AGDDDDLEDL EEAEEPDMEE DDDQKAV      537

SEQ ID NO: 14        moltype = DNA  length = 1723
FEATURE              Location/Qualifiers
misc_feature         1..1723
                     note = Synthetic sequence containing the coding regions of
                     the vacuolar signal sequence of barley gene for Thiol
                     protease aleurain precursor fused to the human Prolyl
                     4-hydroxylase alpha-1 subunit and flanking regions
source               1..1723
                     mol_type = other DNA
                     organism = synthetic construct
SEQUENCE: 14
ctcgagtaaa ccatggctca tgctagggtt ttgcttttgg ctcttgctgt tcttgctact     60
gctgctgttg ctgtggcttc ttcttcatct ttcgctgatt ctaacccaat taggccagtg    120
actgatagag ctgcttctac tcttgctcaa ttggtcgaca tgcacccagg attcttcact    180
tctattggac agatgactga tcttattcac actgagaagg atcttgtgac ttctcttaag    240
gattacatta aggctgagga ggataagttg gagcagatta agagtgggc tgagaagttg    300
gataggctta cttctactgc tacaaaagat ccagagggat tcgttggtca tccagtgaac    360
gctttcaagt tgatgaagag gcttaacact gagtggagtg agcttgagaa ccttgtgctt    420
aaggatatgt ctgatggatt catttctaac cttactattc acgagcagta cttcccaaat    480
gatgaggatc aagtgggagc tgctaaggct cttcttaggc ttcaggatac ttacaacctt    540
gatactgata caatttctaa gggaaaccct ccaggagtta gcacaagtc tttccttact    600
gctgaggatt gcttcgagct tggaaaggtt gcatacactg aggctgatta ctaccacact    660
gagctttgga tggaacaagc tcttaggcaa cttgatggaga gatttc tactattgat    720
aaggtgtcag tgcttgatta ccttcttttac gctgtgtacc agcagggtga tcttgataag    780
gctcttttgc ttactaagaa gttcttgag cttgatccag aacatcagag ggctaacgga    840
aaccttaagt acttcgagta cattatggct aaggaaaagg atgtgaacaa gtctgcttct    900
gatgatcagt ctgatcaaaa agactactcc aagaagaagg gagtggctgt tgattatctt    960
cctgagaggc agaagtatga gatgttgtgt aggggaggag gtattaagat gactccaagg   1020
aggcagaaga gagttgttct caggtatcac gatggaaca ggaacccaaa gttcattctt   1080
gctccagcta gcaagaaga tgagtgggat aagccaagga ttattaggtt ccacgatatt   1140
atttctgatg ctgagattga gattgtgaag gatcttctg agccaagact tagggaggct   1200
actatttcta acactattac tggtgatctt gagactgtgc actacaggat tgttaagtct   1260
gcttggcttg ctgatacga gaaccagtg gtgctaggag ttaacatgag gatcaggat   1320
cttactggac ttgatgtgtc tactgctgag gagcttcaag ttgctaacta cggagttgga   1380
ggacaatatg agccacactt cgatttcgct aggaaggatg agccagatgc ttttaaggag   1440
cttgaactg gaaacaggat tgcacttgg cttttctaca tgtctgatgt ttctgctgga   1500
ggagctactg ttttcccaga agtgggagct ctgtttggc aaagaaggg aactgctgtg   1560
ttctggtaca acctttcgc ttctggagag ggagattact ctactaggca tgctgcttgc   1620
```

```
ccagttcttg ttggaaacaa gtgggtgtca aacaagtggc ttcatgagag gggacaagag   1680
tttagaaggc catgcactct ttctgagctt gagtgatgag ctc                    1723
```

| | | |
|---|---|---|
| SEQ ID NO: 15 | moltype = AA   length = 567 | |
| FEATURE | Location/Qualifiers | |
| REGION | 1..567 | |
| | note = Synthetic sequence containing the vacuolar signal sequence of barley gene for Thiol protease aleurain precursor fused to the human Prolyl 4-hydroxylase alpha-1 subunit and flanking regions | |
| source | 1..567 | |
| | mol_type = protein | |
| | organism = synthetic construct | |

SEQUENCE: 15
```
MAHARVLLLA LAVLATAAVA VASSSSFADS NPIRPVTDRA ASTLAQLVDM HPGFFTSIGQ   60
MTDLIHTEKD LVTSLKDYIK AEEDKLEQIK KWAEKLDRLT STATKDPEGF VGHPVNAFKL  120
MKRLNTEWSE LENLVLKDMS DGFISNLTIQ RQYFPNDEDQ VGAAKALLRL QDTYNLDTDT  180
ISKGNLPGVK HKSFLTAEDC FELGKVAYTE ADYYHTELWM EQALRQLDEG EISTIDKVSV  240
LDYLSYAVYQ QGDLDKALLL TKKLLELDPE HQRANGNLKY FEYIMAKEKD VNKSASDDQS  300
DQKTTPKKKG VAVDYLPERQ KYEMLCRGEG IKMTPRRQKK LFCRYHDGNR NPKFILAPAK  360
QEDEWDKPRI IRFHDIISDA EIEIVKDLAK PRLRRATISN PITGDLETVH YRISKSAWLS  420
GYENPVVSRI NMRIQDLTGL DVSTAEELQV ANYGVGGQYE PHFDFARKDE PDAFKELGTG  480
NRIATWLFYM SDVSAGGATV FPEVGASVWP KKGTAVFWYN LFASGEGDYS TRHAACPVLV  540
GNKWVSNKWL HERGQEFRRP CTLSELE                                      567
```

| | | |
|---|---|---|
| SEQ ID NO: 16 | moltype = DNA   length = 928 | |
| FEATURE | Location/Qualifiers | |
| misc_feature | 1..928 | |
| | note = Synthetic sequence containing the coding regions of the vacuolar signal sequence of barley gene for Thiol protease aleurain precursor fused to the plant Prolyl 4-hydroxylase Plant and flanking regions | |
| source | 1..928 | |
| | mol_type = other DNA | |
| | organism = synthetic construct | |

SEQUENCE: 16
```
ctcgagtaaa ccatggctca tgctagggtt ttgcttttgg ctcttgctgt tcttgctact   60
gctgctgttg ctgtggcttc ttcttcatct ttcgctgatt ctaacccaat taggccagtg  120
actgatagag ctgcttctac tcttgctcaa ttggtcgaca tgcttggtat tctttctctt  180
ccaaacgcta acaggaactc ttctaagact aacgatctta ctaacattgt gaggaagtct  240
gagacttctt ctggagatga ggagggaaat ggagaaagat gggtggaagt gatttcttgg  300
gagccaaggg ctgttgttta ccacaacttc cttactaatg aggagtgcga gcaccttatt  360
tctcttgcta agccatctat ggtagatgct actgtggtga tgagaaaaac tggaggatct  420
aaggattcaa gagtgaggac ttcatctggt actttcctta ggaggggaca tgatgaagtt  480
gtggaagtta ttgagaagag gatttctgat ttcactttca ttccagtgga gaacggagaa  540
ggacttcaag ttcttcacta ccaagtggga caaaagtacg agccacacta cgattacttc  600
cttgatgagt tcaacactaa gaacggagga cagaggattg ctactgtgct tatgtacctt  660
tctgatgtgg atgatggagg agagactgtt tttccagctg ctaggggaaa catttctgct  720
gttccttggt ggaacgagct ttctaagtgt ggaaaggagg gactttctgt gcttccaaag  780
aaaagggatg ctcttcttt ctggaacatg aggccagatg cttctcttga tccatcttct  840
cttcatggag gatgcccagt tgttaaggga aacaagtggc catctactaa gtggttccac  900
gtgcacgagt tcaaggtgta atgagctc                                     928
```

| | | |
|---|---|---|
| SEQ ID NO: 17 | moltype = AA   length = 302 | |
| FEATURE | Location/Qualifiers | |
| REGION | 1..302 | |
| | note = Synthetic sequence containing the vacuolar signal sequence of barley gene for Thiol protease aleurain precursor fused to the plant Prolyl 4-hydroxylase Plant and flanking regions | |
| source | 1..302 | |
| | mol_type = protein | |
| | organism = synthetic construct | |

SEQUENCE: 17
```
MAHARVLLLA LAVLATAAVA VASSSSFADS NPIRPVTDRA ASTLAQLVDM LGILSLPNAN   60
RNSSKTNDLT NIVRKSETSS GDEEGNGERW VEVISWEPRA VVYHNFLTNE ECEHLISLAK  120
PSMVKSTVVD EKTGGSKDSR VRTSSGTFLR RGHDEVVEVI EKRISDFTFI PVENGEGLQV  180
LHYQVGQKYE PHYDYFLDEF NTKNGGQRIA TVLMYLSDVD DGGETVFPAA RGNISAVPWW  240
NELSKCGKEG LSVLPKKRDA LLFWNMRPDA SLDPSSLHGG CPVVKGNKWS STKWFHVHEF  300
KV                                                                302
```

| | | |
|---|---|---|
| SEQ ID NO: 18 | moltype = DNA   length = 2689 | |
| FEATURE | Location/Qualifiers | |
| misc_feature | 1..2689 | |
| | note = Synthetic sequence containing the coding regions of the human Procollagen C-proteinase and flanking regions | |
| source | 1..2689 | |
| | mol_type = other DNA | |
| | organism = synthetic construct | |

-continued

```
SEQUENCE: 18
agatctatcg atgcatgcca tggtaccgcg ccatggctca attggctgca acatcaaggc   60
ctgaaagagt ttggccagat ggtgttattc ctttcgttat tggtggaaac tttactggat  120
ctcagagagc agttttttaga caagctatga gacattggga aaagcacact tgtgtgacat  180
tccttgaaag gactgatgaa gattcttata ttgtgttcac ataccgtcca tgtggatgct  240
gctcatatgt tggtagaagg ggaggaggtc cacaagcaat ttctattgga aaaaactgcg  300
ataagttcgg aattgtggtg catgaattgg gacatgttgt tggtttctgg cacgaacaca  360
caaggccaga tagggatagg cacgtgtcta ttgtgaggga aaacattcag ccaggtcaag  420
agtacaattt tcttaagatg gaacctcaag aggtggaatc tctcggagag acttacgact  480
tcgactccat catgcactac gcaaggaata cttttcagcag gggcatcttc ttggatacca  540
ttgtgcctaa gtacgaggtg aacgcgttaa agccacctat tggtcaaagg actaggctct  600
ctaagggtga tattgcacag gctaggaagc tctacaaatg tccagcatgc ggagaaactc  660
ttcaggattc cactggcaac ttctcatctc cagagtaccc aaacggatac tctgctcata  720
tgcactgtgt ttggaggatc tcagtgactc ctggagagaa gatcatcctc aacttcactt  780
ccctcgatct ctatcgttct aggctctgtt ggtacgacta tgtggaagtg agagatggct  840
tctgagagaaa ggctccactt agaggaaggt tctgcggatc taaacttcct gagccaatcg  900
tgtctactga ttccagattg tgggtggagt tcaggtcctc ttctaattgg gttggcaagg  960
gctttttttgc tgtgtacgag gctatttgtg gcggcgacgt gaaaaaggac tacggacata 1020
ttcaaagtcc aaattcccca gatgattacc gtccttcaaa agtgtgtatt tggaggattc 1080
aagtgagtga gggtttccat gttggattga cattccaatc tttcgaaatt gagagacacg 1140
attcatgcgc atacgattat ttggaagtga gagatggaca ctctgaatct tctacactta 1200
tggaaggta ctgcggttta gagaaactg atgatattaa gtctacttct agtaggtttgt 1260
ggcttaaatt tgtgtcagat ggttctatta acaaggctgg tttcgcagtg aacttcttca 1320
aggaagtgga tgaatgctca agacctaaca gaggaggatg tgagcaaaga tgccttaaca 1380
ctttgggaag ttacaagtgt tcttgcgatc ctggatacga gttggctcct gataagaaa 1440
gatgcgaagc tgcttgcggt ggttttttga caaaattgaa cggatctatt acttctcctg 1500
gatggccaaa agagtaccca cctaataaga attgcatttg gcagcttgtt gcacctactc 1560
agtaccgtat tcattgcaa tcgattttt tcgagactga gggtaatgat gtgtgcaagt 1620
acgatttcgt ggaagtgaga tcaggtctta ctgctgatag taaattgcac ggaaagttct 1680
gcggatctga aaaaccagaa gtgattacat cacagtacaa caatatgagg gtggagttca 1740
aatctgataa tactgtttct aaaaaaggtt ttaaggcaca tttcttttct gataaggacg 1800
agtgctctaa agataatggt ggttgccagc aggattgcgt gaacacattc ggttcatatg 1860
agtgccaatg ccgtagtgga tttgttcttc acgataacaa acatgattgc aaagaggcag 1920
gttgcgatca caaggtgaca tctacttcag gtactatcac atctccaaac tggcctgata 1980
agtatccttc aaaaaaagaa tgtacatggg caatttcttc tacaccaggt cataggtta 2040
agttgacatt catggagatg gatattgaga gtcaaccaga gtgcgcttat gatcatcttg 2100
aggtgttcga tggaagggat gctaaggctc tgttcttgg tagattctgt ggtagtaaaa 2160
agccagaacc agtgcttgca acaggatcta ggatgttcct tagattctac tctgataact 2220
cagttcagag gaaaggattc caagctagtc acgcaactga atgcggtgga caagttagag 2280
cagatgttaa gactaaggat cttttactcac acgcacagtt cggagataac aactaccctg 2340
gaggagttga ttgcgagtgg gttattgtgg ctgaagaggg atacggagtt gagcttgttt 2400
tccagacatt cgaggtggag gaggaaactg attgcggtta cgattatatg gaacttttgt 2460
atggatacga tagtactgct ccaagacttg gaaggtattg tggtagtggt ccaccagaag 2520
aggtgtactc agctggagat agtgttcttg ttaagttcca cagtgatgat acaattacta 2580
agaagggat ccatccttaga tatacttcaa ctaagtttca ggatactctt cattctagga 2640
agtaatgagc tcgcggccgc atccaagctt ctgcagacgc gtcgacgtc 2689

SEQ ID NO: 19           moltype = AA   length = 870
FEATURE                 Location/Qualifiers
REGION                  1..870
                        note = Synthetic sequence containing the human Procollagen
                        C-proteinase and flanking regions
source                  1..870
                        mol_type = protein
                        organism = synthetic construct
SEQUENCE: 19
MAQLAATSRP ERVWPDGVIP FVIGGNFTGS QRAVFRQAMR HWEKHTCVTF LERTDEDSYI   60
VFTYRPCGCC SYVGRRGGGP QAISIGKNCD KFGIVVHELG HVVGFWHEHT RPDRDRHVSI  120
VRENIQPGQE YNFLKMEPQE VESLGETYDF DSIMHYARNT FSRGIFLDTI VPKYEVNGVK  180
PPIGQRTRLS KGDIAQARKL YKCPACGETL QDSTGNFSSP EYPNGYSAHM HCVWRISVTP  240
GEKIILNFTS LDLYRSRLCW YDYVEVRDGF WRKAPLRGRF CGSKLPEPIV STDSRLWVEF  300
RSSSNWVGKG FFAVYEAICG GDVKKDYGHI QSPNYPDDYR PSKVCIWRIQ VSEGFHVGLT  360
FQSFEIERHD SCAYDYLEVR DGHSESSTLI GRYCGYEKPD DIKSTSSRLW LKFVSDGSIN  420
KAGFAVNFFK EVDECSRPNR GGCEQRCLNT LGSYKCSCDP GYELAPDKRR CEAACGGFLT  480
KLNGSITSPG WPKEYPPNKN CIWQLVAPTQ YRISLQFDFF ETEGNDVCKY DFVEVRSGLT  540
ADSKLHGKFC GSEKPEVITS QYNNMRVEFK SDNTVSKKGF KAHFFSDKDE CSKDNGGCQQ  600
DCVNTFGSYE CQCRSGFVLH DNKHDCKEAG CDHKVTSTSG TITSPNWPDK YPSKKECTWA  660
ISSTPGHRVK LTFMEMDIES QPECAYDHLE VFDGRDAKAP VLGRFCGSKK PEPVLATGSR  720
MFLRFYSDNS VQRKGFQASH ATECGGQVRA DVKTKDLYSH AQFGDNNYPG GVDCEWVIVA  780
EEGYGVELVF QTFEVEEETD CGYDYMELFD GYDSTAPRLG RYCGSGPPEE VYSAGDSVLV  840
KFHSDDTITK KGFHLRYTST KFQDTLHSRK                                   870

SEQ ID NO: 20           moltype = DNA   length = 2912
FEATURE                 Location/Qualifiers
misc_feature            1..2912
                        note = Synthetic sequence containing the coding regions of
                        the human Procollagen I N-proteinase and flanking regions
source                  1..2912
                        mol_type = other DNA
```

```
                        organism = synthetic construct
SEQUENCE: 20
gcgccatggc tcaattgagg agaagggcta ggagacacgc agctgatgat gattacaaca   60
ttgaagtttt gcttggtgtt gatgatagtg tggtgcaatt ccacggaaaa gagcatgttc  120
agaaatatct tttgacactt atgaatattg tgaacgaaca ctaccatgat gagtctttgg  180
gagcacacat taacgtggtt cttgtgagga ttattcttct ttcatacggt aaatctatgt  240
cacttattga gattggaaac ccttctcagt ctcttgagaa tgtgtgcaga tgggcatacc  300
ttcaacagaa gcctgatact ggacacgatg agtatcacga tcacgctatt ttccttacaa  360
ggcaggattt cggtccaagt ggaatgcaag atatgctcc tgttactggt atgtgccacc  420
ctgttaggtc ttgtacactt aaccacgagg atggttttc atctgctttc gtggtggcc  480
atgagacagg tcatgttttg gaatggaac atgatggaca gggtaataga tgtggagatg  540
aagtgagact tggttcaatt atggctcctc ttgttcaagc tgcttttcat aggttccact  600
ggagtaggtg ttcacagcaa gagttgagta gataccttca ttcttacgat tgcttgcttg  660
atgatccatt tgctcatgat tggccagctt tgcctcaact tcctggattg cactactcta  720
tgaacgagca gtgcagattt gatttcggtc ttggttacat gatgtgcaca gctttcagga  780
ctttcgatcc atgcaaacag ttgtggtgtt cacacccaga taaccatat ttctgtaaaa  840
caaaaaaagg tccaccactt gatggtacta tgtgcgcacc tggaaagcac tgcttcaagg  900
gacactgcat ttggcttact cctgatattc ttaaaaggga tggatcatgg ggagcttggt  960
ctccattcgg aagttgctca agaacttgcg gaacaggtgt taagtttaga actaggcagt 1020
gcgataatcc acaccctgct aatggtggta gaacttgctc tggactttgct tacgattttc 1080
agttgtgttc taggcaagat tgccctgata gtcttgctga ttttagagaa gagcaatgta 1140
gacagtggga tctttacttt gagcacggcg acgctcagca ccactggctt ccacacgagt 1200
atagagatgc aaaagaaagg tgtcaccttt attgcgagag tagagagact ggagaggtgg 1260
tgtcaatgaa gagaatggtg cacgatggta caaggtgttc ttataaggat gcattctctt 1320
tgtgtgtgag gggagattgc aggaaagtgg gttgtgatgg agtgattgga tctagtaagc 1380
aagaagataa gtgcggagtg tgcggaggag ataactctca ttgcaaggtt gtgaaaggaa 1440
cttttacaag atcaccaaaa aaacacggtt acattaagat gttcgaaatt cctgctggaa 1500
caaggcattt gcttattcag gaagtggatg caacatctca ccacttggca gtgaaaaacc 1560
ttgagactgg aaaattcatt ttgaacgagg agaacgatgt tgatgcatct agtaagactt 1620
tcattgcaat gggtgttgaa tgggagtata gggatgaagg tgaaggggaa acacttcaaa 1680
caatgggtcc tcttcatgga acaattactg tgttggtgat tccagtggga gatacaaggg 1740
tgtcattgac atacaagtat atgattcacg aggatagtct taacgttgat gataacaacg 1800
ttttggaaga agattctgtg gtttacgagt gggctcttaa gaaatggtca ccttgctcta 1860
agccatgtgg aggaagtcag ttcactaa gtaggttg taggaggagg cttgatcata 1920
agatggttca tagggattt tgcgcagcac ttagtaagcc aaaggcaatt aggagggctt 1980
gtaaccctca agaatgctca caaccagttt gggtgacagg agagtgggag ccatgttcac 2040
aaacatgcgg aagaactgga atgcaagtta gatcagttag atgcattcaa cctcttcatg 2100
ataacactac aagaagtgtg cacgcaaaac actgtaacga tgctaggcca gagagtagaa 2160
gagcttgctc tagggaactt tgccctggta gatggagggc aggaccttgg gctcagtgct 2220
ctgtgacatg tggaaacggt actcaggaaa gacctgttcc atgtagaact gctgatgata 2280
gtttcggaat tgtcaggag gaaaggccag aaacagctag gacttgtaga cttggacctt 2340
gtcctaggaa tatttctgat cctagtaaaa aatcatacgt ggtgcaatgg ttgagtaggc 2400
cagatccaga ttcaccaatt aggaagattt cttcaaaagg acactgccag gtgataaga 2460
gtattttctg cagaatgaa gttcttagta ggtactgttc tattccaggt ataacaaac 2520
tttcttgtaa gagttgcaac ttgtataaca atcttactaa cgtggagggt agaattgaac 2580
ctccaccagg aaagcacaac gatattgatg tgtttatgcc tactcttcct gtgccaacag 2640
ttgcaatgga agttagacct tctccatcta tccacttgga gtgccactt aatgcatcaa 2700
gtactaacgc tactgaggat cacccagaga ctaacgcagt tgatgagcct tataagattc 2760
acggacttga ggatgaggtt cagccaccaa accttattcc taggaggcca agtccttacg 2820
aaaaaactag aaatcagagg attcaggagc ttattgatga gatgaggaaa aaggagatgc 2880
ttggaaagtt ctaatgagct cgcggccgca tc                              2912

SEQ ID NO: 21          moltype = AA   length = 962
FEATURE                Location/Qualifiers
REGION                 1..962
                       note = Synthetic sequence containing the human Procollagen
                       I N-proteinase and flanking regions
source                 1..962
                       mol_type = protein
                       organism = synthetic construct
SEQUENCE: 21
MAQLRRRARR HAADDDYNIE VLLGVDDSVV QFHGKEHVQK YLLTLMNIVN EIYHDESLGA   60
HINVVLVRII LLSYGKSMSL IEIGNPSQSL ENVCRWAYLQ QKPDTGHDEY HDHAIFLTRQ  120
DFGPSGMQGY APVTGMCHPV RSCTLNHEDG FSSAFVVAHE TGHVLGMEHD GQGNRCGDEV  180
RLGSIMAPLV QAAFHRFHWS RCSQQELSRY LHSYDCLLDD PFAHDWPALP QLPGLHYSMN  240
EQCRFDFGLG YMMCTAFRTF DPCKQLWCSH PDNPYFCKTK KGPPLDGTMC APGKHCFKGH  300
CIWLTPDILK RDGSWGAWSP FGSCSRTCGT GVKFRTRQCD NPHPANGGRT CSGLAYDFQL  360
CSRQDCPDSL ADFREEQCRQ WDLYFEHGDA QHHWLPHEHR DAKERCHLYC ESRETGEVVS  420
MKRMVHDGTR CSYKDAFSLC VRGDCRKVGC DGVIGSSKQE DKCGVCGGDN SHCKVVKGTF  480
TRSPKKHGYI KMFEIPAGAR HLLIQEVDAT SHHLAVKNLE TGKFILNEEN DVDASSKTFI  540
AMGVEWEYRD EDGRETLQTM GPLHGTITVL VIPVGDTRVS LTYKYMIHED SLNVDDNNVL  600
EEDSVVYEWA LKKWSPCSKP CGGGSQFTKY GCRRRLDHKM VHRGFCAALS KPKAIRRACN  660
PQECSQPVWV TGEWEPCSQT CGRTGMQVSR VRCIQPLHDN TTRSVHAKHC NDARPESRRA  720
CSRELCPGRW RAGPWSQCSV TCGNGTQERP VPCRTADDSF GICQEERPET ARTCRLGPCP  780
RNISDPSKKS YVVQWLSRPD PDSPIRKISS KGHCQGDKSI FCRMEVLSRY CSIPGYNKLS  840
CKSCNLYNNL TNVEGRIEPP PGKHNDIDVF MPTLPVPTVA MEVRPSPSTP LEVPLNASST  900
NATEDHPETN AVDEPYKIHG LEDEVQPPNL IPRRPSPYEK TRNQRIQELI DEMRKKEMLG  960
KF                                                                962
```

```
SEQ ID NO: 22              moltype = DNA   length = 2888
FEATURE                    Location/Qualifiers
misc_feature               1..2888
                           note = Synthetic sequence containing the coding regions of
                             the vacuolar signal sequence of barley gene for Thiol
                             protease aleurain precursor fused to the human Lysyl
                             hydroxylase 3 and flanking regions
source                     1..2888
                           mol_type = other DNA
                           organism = synthetic construct
SEQUENCE: 22
gcgaattcgc tagctatcac tgaaaagaca gcaagacaat ggtgtctcga tgcaccagaa   60
ccacatcttt gcagcagatg tgaagcagcc agagtggtcc acaagacgca ctcagaaaag  120
gcatcttcta ccgacacaga aaaagacaac cacagctcat catccaacat gtagactgtc  180
gttatgcgtc ggctgaagat aagactgacc ccaggccagc actaaagaag aataatgca   240
agtggtccta gctccacttt agctttaata attatgtttc attattattc tctgcttttg  300
ctctctatat aaagagcttg tattttcatt tgaaggcaga ggcgaacaca cacacagaac  360
ctccctgctt acaaaccaga tcttaaacca tggctcacgc tagggtttg cttcttgctc   420
ttgctgttct tgctactgct gctgttgctg tggcttcttc aagttctttc gctgattcta  480
acccaattag gccagtgact gatagagctg cttctactct tgctcaattg agatctatgt  540
ctgatagacc aaggggaagg gatccagtta atccagaaga gttgcttgtg attactgtgg  600
ctactgctga gactgaagga tacctttagat tccttaggag tgctgagtgc ttcaactaca  660
ctgtgaggac tcttggactt ggagaagaat ggaggggagg agatgttgct agaactgttg  720
gaggaggaca gaaagtgaga tggcttaaga aagagatgga gaagtacgct gatagggagg  780
atatgattat tatgttcgtg gattcttacg atgtgattct tgctggatct ccaactgagc  840
ttttgaagaa attcgttcag tctgatctta ggcttctttt ctctgctgag tcttttttgt  900
ggccagaatg gggacttgct gagcaatatc cagaagttgg aactggaaag agattcctta  960
actctggagg attcattgga ttcgctacta ctattcacca gattgtgagg cagtggaagt 1020
acaaggatga cgatgatgat cagcttttct acactaggct ttaccttgat ccaggactta 1080
gggagaagtt gtctctcaac cttgatcaca agtctagaat tttccagaac cttaacggtg 1140
ctcttgatga ggttgtgctt aagttcgata ggaacagagt gaggattagg aacgtggctt 1200
acgatactct tccattgtg gtgcatggaa acggaccaac aaaaactccag cttaactacc  1260
ttggaaacta cgttccaaac ggatggactc agaaggagg atgtggattc tgcaatcagg  1320
ataggagaac tcttccagga ggacaaccac caccaagagt tttccttgct gtgttcgttg  1380
aacagccaac tccattcctt ccaagattcc ttcagagatc tcttcttttg gattacccac  1440
cagataggggt gacactttc cttcacaaca acgaggttt ccacgagcca cacattgctg   1500
attcttggcc acagcttcag gatcatttct ctgctgtgaa gttggttggt ccagaagaag  1560
ctctttctcc aggagaagct agggatatgg ctatggattt gtgcaggcag gatccagagt  1620
gcgagttcta cttctctctt gatgctgatg ctgtgcttac taaccttcag actcttagga  1680
ttcttattga ggagaacagg aaagtgattg ctccaatgct ttctaggcac ggaaaagttgt 1740
ggtctaattt ctggggtgct cttttctcctg atgagtacta cgctagatca gaggactacg  1800
tggagcttgt tcagagaaag agagtgggag tttgaacgt tccttatatt tctcaggctt    1860
acgtgattag gggagatact cttaggatgg agcttccaca gagggatgtt ttctctgat   1920
ctgatactga tccagatatg gctttctgca agtctttcag ggataaggga atttttcctt   1980
accttctaa ccagcatgag ttcggaagat tgcttgctac ttcaagatac gatactgagc   2040
accttcatcc tgatctttgg cagatttcg ataacccagt ggattggaag gagcagtaca   2100
ttcacgagaa ctactctagg gctcttgaag gagaaggaat tgtgggacaa ccatgcccag   2160
atgtttactg gttcccactt ctttctgagc aaatgtgcga tgagcttgtt gctgagatgt   2220
agcattacgg acaatggagt ggaggtagac atgaggattc taggcttgct ggaggatacg   2280
agaacgttcc aactgtggat attcacatga agcaagtggg atacgaggat caatggcttc   2340
agcttcttag gacttatgtg ggaccaatga ctgagtctct tttcccagga taccacacta   2400
aggctagggc tgttatgaac ttcgttgtga ggtatcgtcc agatgagcaa ccatctctta   2460
ggccacacca cgattcttct acttttcactc ttaacgtggc tcttaaccac aagggacttg    2520
attatgaggg aggaggatgc cgtttcctta gatacgattg cgtgatttct tcaccaagaa   2580
agggatgggc tcttcttcat ccaggaaggc ttactcatta ccacgaggga cttccaacta   2640
cttggggaac tagatatatt atggtgtctt tcgtggatcc atgactgctt taatgagata   2700
tgcgagacgc ctatgatcgc atgatatttg cttttcaattc tgttgtgcac gttgtaaaaa   2760
acctgagcat gtgtagctca gatccttacc gccggtttcg gttcattcta atgaatatat   2820
cacccgttac tatcgtattt ttatgaataa tattctccgt tcaatttact gattgtccag   2880
aattcgcg                                                           2888

SEQ ID NO: 23              moltype = AA   length = 764
FEATURE                    Location/Qualifiers
REGION                     1..764
                           note = Synthetic sequence containing the vacuolar signal
                             sequence of barley gene for Thiol protease aleurain
                             precursor fused to the human Lysyl hydroxylase 3 and
                             flanking regions
source                     1..764
                           mol_type = protein
                           organism = synthetic construct
SEQUENCE: 23
MAHARVLLLA LAVLATAAVA VASSSSFADS NPIRPVTDRA ASTLAQLRSM SDRPRGRDPV    60
NPEKLLVITV ATAETEGYLR FLRSAEFFNY TVRTLGLGEE WRGGDVARTV GGGQKVRWLK   120
KEMEKYADRE DMIIMFVDSY DVILAGSPTE LLKKFVQSGS RLLFSAESFC WPEWGLAEQY   180
PEVGTGKRFL NSGGFIGFAT TIHQIVRQWK YKDDDDDQLF YTRLYLDPGL REKLSLNLDH   240
KSRIFQNLNG ALDEVVLKFD RNRVRIRNVA YDTLPIVVHG NGPTKLQLNY LGNYVPNGWT   300
PEGGCGFCNQ DRRTLPGGQP PPRVFLAVFV EQPTPFLPRF LQRLLLLDYP PDRVTLFLHN   360
NEVFHEPHIA DSWPQLQDHF SAVKLVGPEE ALSPGEARDM AMDLCRQDPE CEFYFSLDAD   420
```

```
AVLTNLQTLR ILIEENRKVI APMLSRHGKL WSNFWGALSP DEYYARSEDY VELVQRKRVG    480
VWNVPYISQA YVIRGDTLRM ELPQRDVFSG SDTDPDMAFC KSFRDKGIFL HLSNQHEFGR    540
LLATSRYDTE HLHPDLWQIF DNPVDWKEQY IHENYSRALE GEGIVEQPCP DVYWFPLLSE    600
QMCDELVAEM EHYGQWSGGR HEDSRLAGGY ENVPTVDIHM KQVGYEDQWL QLLRTYVGPM    660
TESLFPGYHT KARAVMNFVV RYRPDEQPSL RPHHDSSTFT LNVALNHKGL DYEGGGCRFL    720
RYDCVISSPR KGWALLHPGR LTHYHEGLPT TWGTRYIMVS FVDP                    764

SEQ ID NO: 24           moltype = AA  length = 45
FEATURE                 Location/Qualifiers
REGION                  1..45
                        note = Vacuole signal sequence of barley gene for Thiol
                         protease aleurain precursor
source                  1..45
                        mol_type = protein
                        organism = synthetic construct
SEQUENCE: 24
MAHARVLLLA LAVLATAAVA VASSSSFADS NPIRPVTDRA ASTLA                    45

SEQ ID NO: 25           moltype = DNA  length = 24
FEATURE                 Location/Qualifiers
misc_feature            1..24
                        note = Single strand DNA oligonucleotide
source                  1..24
                        mol_type = other DNA
                        organism = synthetic construct
SEQUENCE: 25
atcaccagga gaacagggac catc                                           24

SEQ ID NO: 26           moltype = DNA  length = 29
FEATURE                 Location/Qualifiers
misc_feature            1..29
                        note = Single strand DNA oligonucleotide
source                  1..29
                        mol_type = other DNA
                        organism = synthetic construct
SEQUENCE: 26
tccacttcca aatctctatc cctaacaac                                      29

SEQ ID NO: 27           moltype = DNA  length = 23
FEATURE                 Location/Qualifiers
misc_feature            1..23
                        note = Single strand DNA oligonucleotide
source                  1..23
                        mol_type = other DNA
                        organism = synthetic construct
SEQUENCE: 27
aggcattaga ggcgataagg gag                                            23

SEQ ID NO: 28           moltype = DNA  length = 27
FEATURE                 Location/Qualifiers
misc_feature            1..27
                        note = Single strand DNA oligonucleotide
source                  1..27
                        mol_type = other DNA
                        organism = synthetic construct
SEQUENCE: 28
tcaatccaat aatagccact tgaccac                                        27

SEQ ID NO: 29           moltype = DNA  length = 102
FEATURE                 Location/Qualifiers
misc_feature            1..102
                        note = pBINPLUS multiple cloning site
source                  1..102
                        mol_type = other DNA
                        organism = synthetic construct
SEQUENCE: 29
atgaccatga ttacgccaag ctggcgcgcc aagcttgcat gcctgcaggt cgactctaga    60
ggatccccgg gtaccgagct cgaattctta attaacaatt ca                      102

SEQ ID NO: 30           moltype = AA  length = 1464
FEATURE                 Location/Qualifiers
source                  1..1464
                        mol_type = protein
                        organism = Homo sapiens
SEQUENCE: 30
MFSFVDLRLL LLLAATALLT HGQEEGQVEG QDEDIPPITC VQNGLRYHDR DVWKPEPCRI    60
CVCDNGKVLC DDVICDETKN CPGAEVPEGE CCPVCPDGSE SPTDQETTGV EGPKGDTGPR    120
GPRGPAGPPG RDGIPGQPGL PGPPGPPGPP GPPGLGGNFA PQLSYGYDEK STGGISVPGP    180
MGPSGPRGLP GPPGAPGPQG FQGPPGEPGE PGASGPMGPR GPPGPPGKNG DDGEAGKPGR    240
```

```
PGERGPPGPQ GARGLPGTAG LPGMKGHRGF SGLDGAKGDA GPAGPKGEPG SPGENGAPGQ    300
MGPRGLPGER GRPGAPGPAG ARGNDGATGA AGPGPGPTGPA GPPGFPGAVG AKGEAGPQGP   360
RGSEGPQGVR GEPGPPGPAG AAGPAGNPGA DGQPGAKGAN GAPGIAGAPG FPGARGPSGP    420
QGPGGPPGPK GNSGEPGAPG SKGDTGAKGE PGPVGVQGPP GPAGEEGKRG ARGEPGPTGL    480
PGPPGERGGP GSRGFPGADG VAGPKGPAGE RGSPGPAGPK GPAGEGRPG EAGLPGAKGL     540
TGSPGSPGPD GKTGPPGPAG QDGRPGPPGP PGARGQAGVM GFPGPKGAAG EPGKAGERGV    600
PGPPGAVGPA GKDGEAGAQG PPGPAGPAGE RGEQGPAGSP GFQGLPGPAG PPGEAGKPGE    660
QGVPGDLGAP GPSGARGERG FPGERGVQGP PGPAGPRGAN GAPGNDGAKG DAGAPGAPGS    720
QGAPGLQGMP GERGAAGLPG PKGDRGDAGP KGADGSPGKD GVRGLTGPIG PPGPAGAPGD    780
KGESGPSGPA GPTGARGAPG DRGEPGPPGP AGFAGPPGAD GQPGAKGEPG DAGAKGDAGP    840
PGPAGPAGPP GPIGNVGAPG AKGARGSAGP PGATGFPGAA GRVGPPGPSG NAGPPGPPGP    900
AGKEGGKGPR GETGPAGRPG EVGPPGPPGP AGEKGSPGAD GPAGAPGTPG PQGIAGQRGV    960
VGLPGQRGER GFPGLPGPSG EPGKQGPSGA SGERGPPGPM GPPGLAGPPG ESGREGAPGA   1020
EGSPGRDGSP GAKGDRGETG PAGPPGAPGA PGAGPGVGPA GKSGDRGETG PAGPAGPVGP   1080
VGARGPAGPQ GPRGDKGETG EQGDRGIKGH RGFSGLQGPP GPPGSPGEQG PSGASGPAGP   1140
RGPPGSAGAP GKDGLNGLPG PIGPPGPRGR TGDAGPVGPP GPPGPPGPPG PPSAGFDFSF   1200
LPQPPQEKAH DGGRYYRADD ANVVRDRDLE VDTTLKSLSQ QIENIRSPEG SRKNPARTCR   1260
DLKMCHSDWK SGEYWIDPNQ GCNLDAIKVF CNMETGETCV YPTQPSVAQK NWYISKNPKD   1320
KRHVWFGESM TDGFQFEYGG QGSDPADVAI QLTFLRLMST EASQNITYHC KNSVAYMDQQ   1380
TGNLKKALLL QGSNEIEIRA EGNSRFTYSV TVDGCTSHTG AWGKTVIEYK TTKTSRLPII   1440
DVAPLDVGAP DQEFGFDVGP VCFL                                         1464

SEQ ID NO: 31           moltype = AA   length = 1366
FEATURE                 Location/Qualifiers
source                  1..1366
                        mol_type = protein
                        organism = Homo sapiens
SEQUENCE: 31
MLSFVDTRTL LLLAVTLCLA TCQSLQEETV RKGPAGDRGP RGERGPPGPP GRDGEDGPTG     60
PPGPPGPPGP PGLGGNFAAQ YDGKGVGLGP GPMGLMGPRG PPGAAGAPGP QGFQGPAGEP    120
GEPGQTGPAG ARGPAGPPGK AGEDGHPGKP GRPGERGVVG PQGARGFPGT PGLPGFKGIR    180
GHNGLDGLKG QPGAPGVKGE PGAPGENGTP GQTGARGLPG ERGRVGAPGP AGARGSDGSV    240
GPVGPAGPIG SAGPPGFPGA PGPKGEIGAV GNAGPAGPAG PRGEVGLPGL SGPVGPPGNP    300
GANGLTGAKG AAGLPGVAGA PGLPGPRGIP GPVGAAGATG ARGLVGEPGP AGSKGESGNK    360
GEPGSAGPQG PPGPSGEEGK RGPNGEAGSA GPPGPPGLRG SPGSRGLPGA DGRAGVMGPP    420
GSRGASGPAG VRGPNGDAGR PGEPGLMGPR GLPGSPGNIG PAGKEGPVGL PGIDGRPGPI    480
GPAGARGEPG NIGFPGPKGP TGDPGKNGDK GHAGLAGARG APGPDGNNGA QGPPGPQGVQ    540
GGKGEQGPAG PPGFQGLPGP SGPAGEVGKP GERGLHGEFG PLGPAGPRGE RGPPGESGAA    600
GPTGPIGSRG PSGPPGPDGN KGEPGVVGAV GTAGPSGPSG LPGERGAAGI PGGKGEKGEP    660
GLRGEIGNPG RDGARGAPGA VGAPGPAGAT GDRGEAGAAG PAGPAGPRGS PGERGEVGPA    720
GPNGFAGPAG AAGQPGAKGE RGAKGPKGEN GVVGPTGPVG AAGPAGPNGP PGPAGSRGDG    780
GPPGMTGFPG AAGRTGPPGP SGISGPPGPP GPAGKEGLRG PRGDQGPVGR TGEVGAVGPP    840
GFAGEKGPSG EAGTAGPPGT PGPQGLLGAP GILGLPGSRG ERGLPGVAGA VGEPGPLGIA    900
GPPGARGPPG AVGSPGVNGA PGEAGRDGNP GNDGPPGRDG QPGHKGERGY PGNIGPVGAA    960
GAPGPHGPVG PAGKHGNRGE TGPSGPVGPA GAVGPRGPSG PQGIRGDKGE PGEKGPRGLP   1020
GLKGHNGLQG LPGIAGHHGD QGAPGSVGPA GPRGPAGPSG PAGKDGRTGH PGTVGPAGIR   1080
GPQGHQGPAG PPGPPGPGPP PGVSGGGYDF GYDGDFYRAD QPRSAPSLRP KDYEVDATLK   1140
SLNNQIETLL TPEGSRKNPA RTCRDLRLSH PEWSSGYYWI DPNQGCTMDA IKVYCDFSTG   1200
ETCIRAQPEN IPAKNWYRSS KDKKHVWLGE TINAGSQFEY NVEGVTSKEM ATQLAFMRLL   1260
ANYASQNITY HCKNSIAYMD EETGNLKKAV ILQGSNDVEL VAEGNSRFTY TVLVDGCSKK   1320
TNEWGKTIIE YKTNKPSRLP FLDIAPLDIG GADQEFFVDI GPVCFK                 1366

SEQ ID NO: 32           moltype = DNA   length = 5927
FEATURE                 Location/Qualifiers
source                  1..5927
                        mol_type = genomic DNA
                        organism = Homo sapiens
SEQUENCE: 32
tcgtcggagc agacgggagt ttctcctcgg ggtcggagca ggaggcacgc ggagtgtgag     60
gccacgcatg agcggacgct aaccccctcc ccagccacaa agagtctaca tgtctagggt    120
ctagacatgt tcagctttgt ggacctccgg ctcctgctcc tcttagcggc caccgccctc    180
ctgacgcacg gccaagagga aggccaagtc gagggccaag acgaagacat cccaccaatc    240
acctgcgtac agaacggcct caggtaccat gaccgagacg tgtggaaacc cgagccctgc    300
cggatctgcg tctgcgatga cggcaaggtg ttgtgcgatg acgtgatctg tgacgagacc    360
aagaactgcc ccggcgccga agtccccgag ggcgagtgct gtcccgtctg ccccgacggc    420
tcagagtcac ccaccgacca agaaaccacc ggcgtcgagg gacccaaggg agacactggc    480
ccccgaggcc aaggggaccc gcaggcccc cctggccgag atggcatccc tggacagcct    540
ggacttcccg gaccccccgg accccccgga cctcccggac cccctggcct cggaggaaac    600
tttgctcccc agctgtctta tggctatgat gagaaataca cggagaatga ttccgtgcct    660
ggccccatgg gtccctctgg tcctcgtggt ctccctggcc ccctggtgc acctggtccc    720
caaggcttcc aaggtccccc tggtgagcct ggcgagcctg agcttcagg tccccatgggt    780
ccccgaggtc cccaggtcc cctggaaag aatggagatg atggggaagc tggaaaacct    840
ggtcgtcctg gtgagcgtgg gcctcctggg cctcaggtg ctcaggatt gcccggaaca    900
gctggctgct gtgaatgaa gggacacaga ggtttcagtg gtttggatgg tgcaaggga   960
gatgctggtc ctgctggtcc taagggtgag cctggcagcc ctggtgaaaa tggagctcct  1020
ggtcagatgg gccccgtggg cctgctggt gagagaggtc gcctggagc cctggccct    1080
gctggtgctc gtggaaatga tggtgctact ggtgctgccg gcccctggg tccaccggc   1140
cccgctggtc tcctggctt cccggtgct gttggtgcta gggtgaagc tggtcccaa    1200
gggccccgag gctctgaagg tcccaggg gtgcgtggt agcctggcc cctggcct     1260
```

```
gctggtgctg ctggccctgc tggaaaccct ggtgctgatg gacagcctgg tgctaaaggt  1320
gccaatggtg ctcctggtat tgctggtgct cctggcttcc ctggtgcccg aggcccctct  1380
ggaccccagg gccccggcgg ccctcctggt cccaagggta acagcggtga acctggtgct  1440
cctggcagca aggagacac tggtgctaag ggagagcctg ccctgttgg tgttcaagga  1500
cccctggcc ctgctggaga ggaaggaaag cgaggagctg gaggtgaacc cggacccact  1560
ggcctgcccg gacccctgg cgagcgtggt ggacctggta gccgtggttt ccctggcgca  1620
gatggtgttg ctggtcccaa gggtcccgct ggtgaacgtg gttctcctgg ccctgctggc  1680
cccaaaggat ctcctggtga agctggtcgt cccggtgaag ctggtctgcc tggtgccaag  1740
ggtctgactg gaagcccgg cagccctggt cctgatggca aaactggccc cctggtccc  1800
gccggtcaag atggtcgccc cggaccccca ggcccacctg gtgcccgtgg tcaggctggt  1860
gtgatgggat tccctggacc taaaggtgct gctggagagc ccgcaaggc tggagagcga  1920
ggtgttccg gaccccctgg cgctgtcggt cctgctggca agatggaga ggctggagct  1980
cagggacccc ctggccctgc tggtcccgct ggcgagagag gtgaacaagg ccctgctggc  2040
tcccccggat tccagggtct ccctggtcct gctggtcctc caggtgaagc aggcaaacct  2100
ggtgaacagg gtgttcctgg agaccttggc gcccctggcc cctctggagc aagaggcgag  2160
agaggtttcc ctggcgagcg tggtgtgcaa ggtccccctg gtcctgctgg tccccgaggg  2220
gccaacggtg ctcccggcaa cgatggtgct aagggtgatg ctggtgcccc tggagctccc  2280
ggtagccagg gcgcccctgg ccttcaggga atgcctggca acgtggtgc agctggtctt  2340
ccagggccta agggtgacag aggtgatgct ggtcccaaag gtgctgatgg ctctcctggc  2400
aaagatggcg tccgtggtct gactggcccc attggtcctc ctggccctgc tggtgcccct  2460
ggtgacaagg gtgaaagtgg tcccagcggc cctgctggtc ccactggagc tcgtggtgcc  2520
cccggagacc gtggtgagcc tggtccccc tggtcccggc gctttgctgg ccccccctgg  2580
gctgacggcc aacctggtgc taaggccgaa cctggtgatg ctggtgctaa aggcgatgtc  2640
ggtccccctg gccctgccgg accgctgga ccccctggcc ccattggtaa tgttggtgct  2700
cctggagcca aggtgctcg cggcagcgct ggtccccctg gtgctactgg tttccctggt  2760
gctgctggcc gagtcggtcc tcctggcccc tctggaaatg ctggaccctc tggcctcct  2820
ggtcctgctg gcaaagaagg cggcaaaggt cccgtggtg agactggccc tgctggacgt  2880
cctggtgaag ttggtccccc tggtcccct ggccctgctg gcgagaaagg atccctggt  2940
gctgatggtc ctgctggtgc tcctggtact cccgggcctc aaggtattgc tggacagcgt  3000
ggtgtggtcg gcctgcctgg tcagagagga gagagggct tccctggtct tcctggcccc  3060
tctctggaac ctggcaaaca aggtccctct ggagcaagtg gtgaacgtgg tccccctggg  3120
cccatgggcc ccctggatt ggctggaccc cctggtgaat ctggacgtga ggggctcct  3180
ggtgccgaag gttcccctgg acgagacggt tctcctggcg ccaagggtga ccgtggtgag  3240
accggccccg ctggaccccc tggtgctcct ggtgctctg gtgcccctgg ccccgttggc  3300
cctgctggca agagtggtga tcgtggtgag actggtcctg ctggtcccgc cggtcctgct  3360
ggccctgttg gcgcccgtgg ccccgccgga ccccaaggcc ccgtggtga caagggtgag  3420
acaggcgaac agggcgacag aggcataaag ggtcaccgtg gcttctctgg cctccagggt  3480
cccccctggc ctcctggctc tcctggtgaa caaggtccct ctggagcctc tggtcctgct  3540
ggtccccgag gtccccctgg ctctgtggt gctcctggca aagatggact caacggtctc  3600
cctggcccca ttgggccccc tggtcctcgc ggtcgcactg gtgatgctgg tcctgttggt  3660
cccccggcc ctcctggacc tcctggtccc ctggtcctc ccagcgctgg tttcgacttc  3720
agcttcctgc cccagccacc tcaagagaag gctcacgatg tggccgcta ctaccgggct  3780
gatgatgcca atgtggttcg tgaccgtgac ctcgaggtgg acaccaccct caagagcctg  3840
agccagcaga tcgagaacat ccggagccca gagggcagcc gcaagaaccc cgcccgcacc  3900
tgccgtgacc tcaagatgtg ccactctgac tggaagagtg gagagtactg gattgacccc  3960
aaccaaggct gcaacctgga tgccatcaaa gtcttctgca acatggagac tggtgagacc  4020
tgcgtgtacc ccactcagcc cagtgtggcc cagaagaact ggtacatcag caagaacccc  4080
aaggacaaga ggcatgtctg gttcggcgag agcatgaccg atggattcca gttcgagtat  4140
ggcggccagg gctccgaccc tgccgatgtg gccatccagc tgaccttcct cgcctgatg  4200
tccaccgagg cctcccagaa catcacctac cactgcaaga cagcgtggc ctacatggac  4260
cagcaggctg gcaacctcaa gaaggccctg tcctccaagg gctccaacga gatcgagatc  4320
cgcgccgagg gcaacagccg cttcacctac agcgtcactg tcgatggctg cacgagtcac  4380
accggagcct ggggcaagac agtgattgaa tacaaaacca ccaagacctc ccgcctgccc  4440
atcatcgatg tggccccctt ggacgttggt gcccagacc aggaattcgg cttcgacgtt  4500
ggccctgtct gcttcctgta aactccctcc atcccaacct ggctccctcc cacccaacca  4560
actttccccc caacccgaa acagacaagc aacccaaact gaaccccctc aaaagccaaa  4620
aaatgggaga caatttcaca tggactttgg aaaatatttt tttccttcgc attcatctct  4680
caaacttagt ttttatcttt gaccaaccga acatgaccaa aaaccaaaag tgcattcaac  4740
cttaccaaaa aaaaaaaaaa aaaagaata aataataac ttttaaaaaa aggaagcttg  4800
gtccacttgc ttgaagaccc atgcgggggt aagtcccttt ctgccccgttg ggcttatgaa  4860
accccaatgc tgcccttct gctccttct ccacacccc cttggggcct cccctccact  4920
ccttcccaaa tctgtctccc cagaagacac aggaaacaat gtattgtctg cccagcaatc  4980
aaaggcaatg ctcaaacacc caagtggccc ccaccctcag cccgctcctg cccgcccagc  5040
accccaggcc cctgggggac ctgggggtct cagactgcca aagaagcctt ggcatctgcc  5100
gctcccatgg ctcttgcaac atctcccctt cgttttgag ggggtcatgc cggggagcc  5160
accagcccct cactgggttc ggaggagagt caggaagggc cacgacaaag cagaaacatc  5220
ggatttgggg aacgcgtgtc aatcccttgt gccgcagggc tgggcgggag agactgttct  5280
gttccttgtg taactgtgtt gctgaaagac taccgcgtte ttgtcttgat gtgtcaccgg  5340
gcaactgcc tggggcagg gatggggca gggtggaagc ggctccccat tttataccaa  5400
aggtgctaca tctatgtgat gggtggggtg ggagggaat cactggtgct atagaaattg  5460
agatgccccc ccaggccagc aaatgttcct ttttgttcaa agtctatttt tattccttga  5520
tatttttctt ttttttttt ttttttgtg gatgggact tgtgaatttt ctaaaggtg  5580
ctatttaaca tgggaggaga gcgtgtgcgg ctccagccca gccgctgct cactttccac  5640
cctctctcca cctgcctctg cgtttctcagg cctctgctct ccgacctctc tcctctgaaa  5700
cctcctcca cagctgcagc ccatcctccc ggctccctcc tagtctgtcc tgcgtcctct  5760
gtccccgggt tcagagaca acttcccaaa gcacaaagca gttttcccc ctaggggtgg  5820
gaggaagcaa aagactctgt acctattttg tatgtgtata ataatttgag atgttttaa  5880
ttatttgat tgctggaata aagcatgtgg aaatgaccca aacataa         5927
```

| SEQ ID NO: 33 | moltype = DNA length = 5411 |
|---|---|
| FEATURE | Location/Qualifiers |
| source | 1..5411 |
| | mol_type = genomic DNA |
| | organism = Homo sapiens |

SEQUENCE: 33

```
gtgtcccata gtgtttccaa acttggaaag ggcgggggag ggcgggagga tgcggagggc    60
ggaggtatgc agacaacgag tcagagtttc cccttgaaag cctcaaaagt gtccacgtcc   120
tcaaaaagaa tggaaccaat ttaagaagcc agccccgtgg ccacgtccct tcccccattc   180
gctccctcct ctgcgccccc gcaggctcct cccagctgtg gctgcccggg ccccagccc   240
cagccctccc attggtggag gcccttttgg aggcaccta gggccaggga aacttttgcc   300
gtataaatag ggcagatccg ggctttatta ttttagcacc acggcagcag gaggtttcgg   360
ctaagttgga ggtactggcc acgactgcat gcccgcgccc gccaggtgat acctccgccg   420
gtgacccagg ggctctgcga cacaaggagt ctgcatgtct aagtgctaga catgctcagc   480
tttgtggata cgcggacttt gttgctgctt gcagtaacct tatgcctagc aacatgccaa   540
tctttacaag aggaaactgt aagaaagggc ccagccggag atagaggacc acgtggagaa   600
aggggtccac caggcccccc aggcagagat ggtgaagatg tcccacagg ccctcctggt    660
ccacctggtc ctcctggccc ccctggtctc ggtgggaact ttgctgctca gtatgatgga   720
aaaggagttg gacttggccc tggaccaatg ggcttaatgg gacctagagg cccacctggt   780
gcagctggag ccccaggccc tcaaggtttc caaggacctg ctggtgagcc tggtgaacct   840
ggtcaaactg gtcctgcagg tgctcgtggt ccagctggcc ctcctggcaa ggctggtgaa   900
gatggtcacc ctggaaaacc cggacgacct ggtgagagga gagttgttgg accacagggt   960
gctcgtggtt tccctggaac tcctggactt cctggcttca aaggcattag ggacacaat   1020
ggtctgatg gattgaaggg acagcccggt gctcctggtg tgaagggtga acctggtgcc  1080
cctggtgaaa atgaactcc aggtcaaaca ggagcccgtg ggcttcctgg tgagagagga  1140
cgtgttggtg cccctggcca agctggtgcc cgtggcagtg atggaagtgt gggtcccgtg  1200
ggtcctgctg gtcccattgg gtctgctggc cctccaggct tcccaggtgc ccctggcccc  1260
aagggtgaaa ttggagctgt tggtaacgct ggtcctgctg gtcccgccgg tccccgtggt  1320
gaagtgggtc ttccaggcct ctccggcccc gttggacctc ctggtaatcc tggagcaaac  1380
ggccttactg gtgccaaggg tgctgctgga ctccccggcc ttgctgggac tccccggctc  1440
cctggacccc gcggtattcc tggcctgttg ggtgctgccg gtgctactgg tgccagagga  1500
cttgttggtg agcctggtcc agctggctca aaggagaga gcggtaacaa gggtgagccc  1560
ggctctgctg ggccccaagg tcctcctggt cccagtggtg aagaaggaaa gagaggccct  1620
aatgggaag ctggatctgc cggccctcca ggacctgctg ggctgagagg tagtcctggt  1680
tctcgtggtc ttcctggagc tgatggcaga cctggcgtca tgggccctcc tggtagtcgt  1740
ggtcaaagtg gccctgctgg agtccgagga cctaatggag atgctggtcg ccctgggag  1800
cctggtctca tgggacccag aggtcttcct ggttcccctg gaaatatcgg ccccgctgga  1860
aaagaaggtc ctgtcggcct cccctggcatc gacggcaggc ctggcccaat tgggccagct  1920
ggagcagag gagagcctgg caacattgga ttccctggca ccaaaggccc cactggtgat  1980
cctggcaaaa acggtgataa aggtcatgct ggtcttgctg gtgctcgggg tgctccaggt  2040
cctgatggaa acaatggtgc tcagggacct cctggaccac agggtgttca aggtggaaaa  2100
ggtgaacagg gtccccctgg tcctccaggc ttcaggggtc tgcctggccc ctcaggtccc  2160
gctggtgaag ttggcaaacc aggagaaaag ggtctccatg gtgatttggg tctccctggt  2220
cctgctggtc aagagggga acgcggtccc caggtgagaa gtggtgctgc cggtcctact  2280
ggtcctattg gaagccgagg tccttctgga cccccagggc ctgatggaaa caagggtgaa  2340
cctggtgtgt tggtgctgt gggcactgct ggtccatctg gtcctagtgg actcccagga  2400
gagaggggtg ctgctggcat acctggagcc aagggagaaa agggtgaacc tggtctcaga  2460
ggtgaaattg gtaaccctgg cagagatggt gctcgtggtg ctcctggtgc tgtaggtgcc  2520
cctggtcctg ctggagccac aggtgaccgg ggcgaagctg gggctgctgg tcctgctggt  2580
cctgctggtc ctcggggaag ccctggtgaa cgtggtgagg tcggtcctgc tggccccaat  2640
ggatttgctg gtcctgctgg tgctgctggt caacctggta ctaaaggaaa agaggaagcc  2700
aaagggccta agggtgaaaa cggtgttgtt ggtcccacag gccccgttgg agctgctggc  2760
ccagctggtc caaatggtcc cccggtcct gctggaagtc gtggtgatgg aggccccct   2820
ggtatgactg gtttccctgg tgctgctgga cggactggtc ccccaggacc ctctggtatt  2880
tctggccctc ctggtcccc tggtcctgct gggaaagaag ggcttcgtgg tcctcgtggt  2940
gaccaaggtc cagttggccg aactggagaa gtaggtgcag ttggtccccc tggcttcgt  3000
ggtgagaagg gtccctctgg agaggctggt actgctggac ctcctggcac tccaggtcct  3060
cagggtcttc ttggtgctcc tggtattctg ggtctccctg gctcgagagg tgaacgtggt  3120
ctaccaggtg ttgctggtgc tgtgggtgaa cctggtcctc ttggcattgc cggccctcct  3180
ggggcccgtg gtcctcctgg tgctgtgggt agtcctggtg tcaacggtgc tcctggtgaa  3240
gctggtcgtg atggcaaccc tgggaacgat ggtcccccag gtcgcgatgg tcaacccgga  3300
cacaaggag agcgcggtta ccctggcaat attggtcccg ttggtgctgc aggtgcacct  3360
ggtcctcatg gccccgtggg tcctgctggc aaacatgaa accgtggtga aactggtcct  3420
tctggtcctg ttggtcctgc tggtgctgtt ggccaagtc gtctagtgg cccacaggaa  3480
attcgtggcg ataagggaga gcccggtgaa aaggggccca gggtcttcc tggcttaaag  3540
ggacacaatg gattgcaagg tctgcctggt atcgctggtc accatggtga tcaaggtgct  3600
cctggctccg tgggtcctgc tggtcctagg ggccctgctg tccttctgg ccctgctgga  3660
aaagatggtc tgcactggaca tcctggtaca gttggacctg ctggcattcg aggccctcag  3720
ggtcaccaag gccctgctgg tcccccaggt ccctctggac ctctgaca tccaggttga  3780
agcggtggtg gttatgactt tggttacgat ggagacttct acagggctga ccagcctcgc  3840
tcagcacctt ctctcagacc caaggactat gaagttgatg ctactctgaa gtctctcaac  3900
aaccagattg agacccttct tactcctgaa ggctctagaa agaaccccagc tcgcacatgc  3960
cgtgacttga gactcagcca cccagagtgg agcagtggtt actactggat tgaccctaac  4020
caaggatgca tatggatgc tatcaaagta tactctgatc cgaaacctgt  4080
atccgggcca aacctgaaaa catcccagc aagaactggt ataggagctc caaggacaag  4140
aaacacgtct ggctaggaga aactatcaat gctggcagcc agtttgaata taatgtgaaa  4200
ggagtgactt ccaaggaaat ggctacccaa cttgccttca tgcgcctgct ggccaactat  4260
gcctctcaga acatcaccta ccactgcaag aacagcattg catacatgga tgaggagact  4320
ggcaacctga aaaaggctgt cattctacag ggctctaatg atgttgaact tgtttctgag  4380
```

```
ggcaacagca ggttcactta cactgttctt gtagatggct gctctaaaaa gacaaatgaa    4440
tggggaaaga caatcattga atacaaaaca aataagccat cacgcctgcc cttccttgat    4500
attgcacctt tggacatcgg tggtgctgac caggaattct ttgtggacat tggcccagtc    4560
tgtttcaaat aaatgaactc aatctaaatt aaaaaagaaa gaaatttgaa aaaactttct    4620
ctttgccatt tcttcttctt ctttttaac tgaaagctga atccttccat ttcttctgca    4680
catctacttg cttaaattgt gggcaaaaga gaaaagaag gattgatcag agcattgtgc     4740
aatacagttt cattaactcc ttccccgct ccccaaaaa tttgaattt ttttcaaca       4800
ctcttacacc tgttatggaa aatgtcaacc tttgtaagaa aaccaaaata aaaattgaaa    4860
aataaaaacc ataaacatt gcaccacttg tggcttttga atatcttcca cagagggaag    4920
tttaaaaccc aaacttccaa aggtttaaac tacctcaaaa cactttccca tgagtgtgat   4980
ccacattgtt aggtgctgac ctagacagag atgaactgag gtcctgttt tgttttgttc   5040
ataatacaaa ggtgctaatt aatagtattt cagatacttg aagaatgttg atggtgctag   5100
aagaatttga gaagaaatac tcctgtattg agttgtatcg tgtggtgtat tttttaaaaa   5160
atttgattta gcattcatat tttccatctt attcccaatt aaaagtatgc agattatttg    5220
cccaaatctt cttcagattc agcatttgtt ctttgccagt ctcattttca tcttcttcca    5280
tggttccaca gaagctttgt ttcttgggca agcagaaaaa ttaaattgta cctattttgt   5340
atatgtgaga tgtttaaata aattgtgaaa aaatgaaat aaagcatgtt tggttttcca    5400
aaagaacata t                                                         5411

SEQ ID NO: 34           moltype = DNA  length = 1633
FEATURE                 Location/Qualifiers
misc_feature            1..1633
                        note = Synthetic sequence containing the coding regions of
                        the vascular signal sequence of barley gene for Thiol
                        protease aleurain precursor fused to the human Prolyl
                        4-hydroxylase beta subunit and flanking regions
source                  1..1633
                        mol_type = other DNA
                        organism = synthetic construct
SEQUENCE: 34
ctcgagtaaa ccatggctca tgctagggtt ttgcttttgg ctcttgctgt tcttgctact    60
gctgctgttg ctgtggcttc ttcttcatct ttcgctgatt ctaacccaat taggccagtg    120
actgatagag ctgcttctac tcttgctcaa ttggtcgaca tggatgctcc agaagaggag    180
gatcacgttc ttgtgcttag gaagtctaac ttcgctgaag ctcttgctgc tcacaagtac    240
cttcttgtgg agttttatgc tccttggtgc ggacattgca aagctcttgc tccagatat    300
gctaaggctg ctggaaagtt gaaggctgag ggatctgaaa ttaggcttgc taaagtggat    360
gctactgagg agtctgatct tgctcaacag tacggagtta ggggataccc aactattaag    420
ttcttcagga acggagatac tgcttctcca aaggagtata ctgctggaag ggaggctgat    480
gatattgtga actggcttaa gaagagaact ggaccagctg ctactactct tccagatgga    540
gctgctgctg aatctcttgt ggagtcatct gaggtggcag tgattggatt cttcaaggat    600
gtggagtctg attctgctaa gcagttcctt caagctgctg aggctattga tgatattcca    660
ttcggaatta cttctaactc tgatgtgttc tctaagtacc agcttgataa ggatggagtg    720
gtgcttttca gagaattcga tgaggaaagg aacaattcga ggagagtga gacaaaggga    780
aaccttcttg atttcattaa gcacaaccag cttccacttg tgattgagtt cactgagcag    840
actgctccaa agattttcgg aggagagatt aagactcaca ttcttctttt ccttccaaag    900
tctgtgtctg attacgatgg aaagttgtct aacttcaaga ctgctgctga gtcttcaag    960
ggaaagattc ttttcatttt cattgattct gatcacactg ataaccagag gattcttgag    1020
ttcttcggac ttaagaagga agagtgccca gctgttaggc ttattactct tgaggaggag    1080
atgactaagt acaagccaga gtctgaagaa cttactgctg agaggattac tgagttctgc    1140
cacagattcc ttgagggaaa gattaagcca caccttatgt ctcaagagct tccagaggat    1200
tgggataagt agccagttaa ggtgttggtg ggtaaaaact tcgaggatgt ggcttttcgat   1260
gagaagaaga acgtgttcgt ggagttctac gcaccttggt gtggtcactg taagcagctt    1320
gctccaattt gggataagtt gggagagact tacaaggatc acgagaacat tgtgattgct    1380
aagatggatt ctactgctaa cgaggtggag gctgttaagg ttcactcttt cccaactttg    1440
aagttcttcc cagcttctgc tgataggact gtgattgatt acaacggaga aaggactctt    1500
gatggattca gaagttcct tgagtctgga ggacaagtgg aagctggaga tgatgatctt    1560
cttgaggatt tggaagaagc tgaggagcca gatatggagg aggatgatga tcagaaggct    1620
gtgtgatgag ctc                                                       1633

SEQ ID NO: 35           moltype = DNA  length = 1723
FEATURE                 Location/Qualifiers
misc_feature            1..1723
                        note = Synthetic sequence containing the coding regions of
                        the vascular signal sequence of barley gene for Thiol
                        protease aleurain precursor fused to the human Prolyl
                        4-hydroxylase alpha-1 subunit and flanking regions
source                  1..1723
                        mol_type = other DNA
                        organism = synthetic construct
SEQUENCE: 35
ctcgagtaaa ccatggctca tgctagggtt ttgcttttgg ctcttgctgt tcttgctact    60
gctgctgttg ctgtggcttc ttcttcatct ttcgctgatt ctaacccaat taggccagtg    120
actgatagag ctgcttctac tcttgctcaa ttggtcgaca tgcacccagg attcttcact    180
tctattggac agatgactga tcttattcac actgagaagg atctgtgac ttctcttaag    240
gattacatta aggctgagga ggataagttg gagcagatta agaagtgggc tgagaagttg    300
gataggctta cttctactgc tacaaaagat ccagagggat cgttggtca tccagtgaac    360
gctttcaagt tgatgaagag gcttaacact gagtggagtg agcttgagaa ccttgtgctt    420
aaggatatgt ctgatggatt catttctaac cttactattc agaggcagta cttcccaaat    480
gatgaggatc aagtgggagc tgctaaggct cttcttagc ttcaggatac ttacaaccct    540
```

```
gatactgata caatttctaa gggaaacctt ccaggagtta agcacaagtc tttccttact    600
gctgaggatt gcttcgagct tggaaaggtt gcatacactg aggctgatta ctaccacact    660
gagctttgga tggaacaagc tcttaggcaa cttgatgagg gagagatttc tactattgat    720
aaggtgtcag tgcttgatta cctttcttac gctgtgtacc agcagggtga tcttgataag    780
gctcttttgc ttactaagaa gttgcttgag cttgatccag aacatcagag ggctaacgga    840
aaccttaagt acttcgagta cattatggct aaggaaaagg atgtgaacaa gtctgcttct    900
gatgatcagt ctgatcaaaa gactactcca aggaagaagg gagtggctgt tgattatctt    960
cctgagaggc agaagtatga gatgttgtgt aggggagagg gtattaagat gactccaagg   1020
aggcagaaga agttgttctg caggtatcac gatggaaaca ggaacccaaa gttcattctt   1080
gctccagcta agcaagaaga tgagtgggat aagccaagga ttattaggtt ccacgatatt   1140
atttctgatg ctgagattga gattgtgaag gatcttgcta agccaagact taggagggct   1200
actatttcta accctattac tggtgatctt gagactgtgc actacaggat ttctaagtct   1260
gcttggcttt ctggatacga gaacccagtg tgtctctagga ttaacatgag gattcaggat   1320
cttactggac ttgatgtgtc tactgctgag gagcttcaag ttgctaacta cggagttgga   1380
ggacaatatg agccacactt cgatttcgct aggaaggatg agccagatgc tttttaaggag   1440
cttggaactg gaaacaggat tgctacttgg cttttctaca tgtctgatgt ttctgctgga   1500
ggagctactg ttttcccaga agtgggagct tctgtttggc caaagaaggg aactgctgtg   1560
ttctggataca acctttcgc ttctggagag ggagattact ttctaggcca tgctgcttgc   1620
ccagttcttg ttggaaacaa gtgggtgtca aacaagtggc ttcatgagag gggacaagag   1680
tttagaaggc catgcactct ttctgagctt gagtgatgag ctc                      1723

SEQ ID NO: 36            moltype = AA    length = 1489
FEATURE                  Location/Qualifiers
source                   1..1489
                         mol_type = protein
                         organism = Homo sapiens
SEQUENCE: 36
MAHARVLLLA LAVLATAAVA VASSSSFADS NPIRPVTDRA ASTLAQLQEE GQVEGQDEDI     60
PPITCVQNGL RYHDRDVWKP EPCRICVCDN GKVLCDDVIC DETKNCPGAE VPEGECCPVC    120
PDGSESPTDQ ETTGVEGPKG DTGPRGPRGP AGPPGRDGIP GQPGLPGPPG PPGPPGPPGL    180
GGNFAPQLSY GYDEKSTGGI SVPGPMGPSG PRGLPGPPGA PGPQGFQGPP GEPGEPGASG    240
PMGPRGPPGP PGKNGDDGEA GKPGRPGERG PPGPQGARGL PGTAGLPGMK GHRGFSGLDG    300
AKGDAGPAGP KGEPGSPGEN GAPGQMGPRG LPGERGRPGA PGPAGARGND GATGAAGPPG    360
PTGPAGPPGF PGAVGAKGEA GPQGPRGSEG PQGVRGEPGP PGPAGAAGPA GNPGADGAPG    420
AKGANGAPGI AGAPGFPGAR GPSGPQGPGG PPGPKGNSGE PGAPGSKGDT GAKGEPGPVG    480
VQGPPGPAGE EGKRGARGEP GPTGLPGPPG ERGGPGSRGF PGADGVAGPK GPAGERGSPG    540
PAGPKGSPGE AGRPGEAGLP GAKGLTGSPG SPGPDGKTGP PGPAGQDGRP GPPGPPGARG    600
QAGVMGFPGP KGAAGEPGKA GERGVPGPPG AVGPAGKDGE AGAQGPPGPA GPAGERGEQG    660
PAGSPGFQGL PGPAGPPGEA GKPGEQGVPG DLGAPGPSGA RGERGFPGER GVQGPPGPAG    720
PRGANGAPGN DGAKGDAGAP GAPGSQGAPG LQGMPGERGA AGLPGPKGDR GDAGPKGADG    780
SPGKDGVRGL TGPIGPPGPA GAPGDKGESG PSGPAGPTGA RGAPGDRGEP GPPGPAGFAG    840
PPGADGQPGA KGEPGDAGAK GDAGPPGPAG PAGPPGPIGN VGAPGAKGAR GSAGPPGATG    900
FPGAAGRVGP PGPSGNAGPP GPPGPAGKEG GKGPRGETGP AGRPGEVGPP GPPGPAGEKG    960
SPGADGPAGA PGTPGPQGIA GQRGVVGLPG QRGERGFPGL PGPSGEPGKQ GPSGASGERG   1020
PPGPMGPPGL AGPPGESGRE GAPGAEGSPG RDGSPGAKGD RGETGPAGPP GAPGAPGAPG   1080
PVGPAGKSGD RGETGPAGPA GPVGPAGARG PAGPQGPRGD KGETGEQGDR GIKGHRGFSG   1140
LQGPPGPPGS PGEQGPSGAS GPAGPRGPPG SAGAPGDKGL NGLPGPIGPP GPRGRTGDAG   1200
PVGPPGPPGP PGPPGPPSAG FDFSFLPQPP QEKAHDGGRY YRADDANVVR DRDLEVDTTL   1260
KSLSQQIENI RSPEGSRKNP ARTCRDLKMC HSDWKSGEYW IDPNQGCNLD AIKVFCNMET   1320
GETCVYPTQP SVAQKNWYIS KNPKDKRHVW FGESMTDFGQ FEYGGQGSDP ADVAIQLTFL   1380
RLMSTEASQN ITYHCKNSVA YMDQQTGNLK KALLLKGSNE IEIRAEGNSR FTYSVTVDGC   1440
TSHTGAWGKT VIEYKTTKTS RLPIIDVAPL DVGAPDQEFG FDVGPVCFL               1489

SEQ ID NO: 37            moltype = AA    length = 1389
FEATURE                  Location/Qualifiers
source                   1..1389
                         mol_type = protein
                         organism = Homo sapiens
SEQUENCE: 37
MAHARVLLLA LAVLATAAVA VASSSSFADS NPIRPVTDRA ASTLAQLLQE ETVRKGPAGD     60
RGPRGERGPP GPPGRDGEDG PTGPPGPPGP PGPPGLGGNF AAQYDGKGVG LGPGPMGLMG    120
PRGPPGAAGA PGPQGFQGPA GEPGEPGQTG PAGARGPAGP PGKAGEDGHP GKPGRPGERG    180
VVGPQGARGF PGTPGLPGFK GIRGHNGLDG LKGQPGAPGV KGEPGAPGEN GTPGQTGARG    240
LPGERGRVGA PGPAGARGSD GSVGPVGPAG PIGSAGPPGF PGAPGPKGEI GAVGNAGPTG    300
PAGPRGEVGL PGLSGPVGPP GNPGANGLTG AKGAAGLPGV AGAPGLPGPR GIPGPVGAAG    360
ATGARGLVGE PGPAGSKGES GNKGEPGSAG PQGPPGPSGE EGKRGPNGEA GSAGPPGPPG    420
LRGSPGSRGL PGADGRAGVM GPPGSRGASG PAGVRGPNGD AGRPGEPGLM GPRGLPGSPG    480
NIGPAGKEGP VGLPGIDGRP GPIGPAGARG GPIGPAGARG KGPTGDPGKN GDKGHAGLAG    540
ARGAPGPDGN NGAQGPPGPQ GVQGGKGEQG PAGPPGFQGL PGPSGPAGEV GKPGERGLHG    600
EFGLPGPAGP RGERGPPGES GAAGPTGPIG SRGPSGPPGP DGNKGEPGVV GAVGTAGPSG    660
PSGLPGERGA AGIPGGKGEK GEPGLRGEIG NPGRDGARGA HGAVGAPGPA GATGDRGEAG    720
AAGPAGPAGP RGSPGERGEV GPAGPNGFAG PAGAAGQPGA KGERGGKGPK GENGVVGPTG    780
PVGAAGPAGP NGPPGAGSR GDGGPPGMTG FPGAAGRTGP PGPSGISGPP GPPGPAGKEG    840
LRGPRGDQGP VGRTGEVGAV GPPGFAGEKG PSGEAGTAGP PGTPGPQGLL GAPGILGLPG    900
SRGERGLPGV AGAVGEPGPL GIAGPPGARG PPGAVGSPGV NGAPGEAGRD GNPGNDGPPG    960
RDGQPGHKGE RGYPGNIGPV GAAGAPGPHG PVGPAGKHGN RGETGPSGPV GPAGAVGPRG   1020
PSGPQGIRGD KGEPGEKGPR GLPGFKGHNG LQGLPGIAGH HGDQGAPGSV GPAGPRGPAG   1080
PSGPAGKDGR TGHPGTVGPA GIRGPQGHQG PAGPPGPPGP PGPPGVSGGG YDFGYDGDFY   1140
RADQPRSAPS LRPKDYEVDA TLKSLNNQIE TLLTPEGSRK NPARTCRDLR LSHPEWSSGY   1200
```

```
YWIDPNQGCT MEAIKVYCDF PTGETCIRAQ PENIPAKNWY RSSKDKKHVW LGETINAGSQ   1260
FEYNVEGVTS KEMATQLAFM RLLANYASQN ITYHCKNSIA YMDEETGNLK KAVILQGSND   1320
VELVAEGNSR FTYTVLVDGC SKKTNEWGKT IIEYKTNKPS RLPFLDIAPL DIGGADHEFF   1380
VDIGPVCFK                                                          1389

SEQ ID NO: 38           moltype = DNA   length = 2888
FEATURE                 Location/Qualifiers
misc_feature            1..2888
                        note = Synthetic sequence containing the coding regions of
                          the vascular signal sequence of barley gene for Thiol
                          protease aleurain precursor fused to the human Lysyl
                          hydroxylase 3 and flanking regions
source                  1..2888
                        mol_type = other DNA
                        organism = synthetic construct
SEQUENCE: 38
gcgaattcgc tagctatcac tgaaaagaca gcaagacaat ggtgtctcga tgcaccagaa   60
ccacatcttt gcagcagatg tgaagcagcc agagtggtcc acaagacgca ctcagaaaag   120
gcatcttcta ccgacacaga aaaagacaac cacagctcat catccaacat gtagactgtc   180
gttatgcgtc ggctgaagat aagactgacc ccaggccagc actaaagaag aaataatgca   240
agtggtccta gctccacttt agctttaata attatgtttc attattattc tctgcttttg   300
ctctctatat aaagagcttg tattttcatt tgaaggcaga ggcaaacaca cacacagaac   360
ctccctgctt acaaaccaga tcttaaacca tggctcacgc tagggttttg cttcttgctc   420
ttgctgttct tgctactgct gctgttgctg tggcttcttc aagttctttc gctgattcta   480
acccaattag gccagtgact gatagagctg cttctactct tgctcaattg agatctatgt   540
ctgatagacc aaggggaagg gatccagtta atccagagaa gtgcttgtg attactgtgg   600
ctactgctga gactgaagga taccttagat tccttaggag tgctgagttc ttcaactaca   660
ctgtgaggac tcttggactt ggagaagaat ggagggagg agatgttgct agaactgttg   720
gaggaggaca gaaagtgaga tggcttaaga agagatggaa gaagtacgct ataggggagg   780
atatgattat tatgttcgtg gattcttacg atgtgatttc tgctgatct ccaactgagc   840
tttgaagaa attcgttcag tctggatcta ggcttctttt ctctgctgag tctttttgtt   900
ggccagaatg gggacttgct gagcaatatc cagaagtggg aactggaaag agattccta   960
actctggagg attcattgga ttcgctacta ctattcacca gattgtgagg cagtggaagt   1020
acaaggatga cgatgatgat cagctttct cacactaggc ttaccttgat ccaggactta   1080
gggagaagtt gtctcttaac cttgatcaca agtctaggat tttcagaac cttaacggtg   1140
ctcttgatga ggttgtgctt aagttcgata ggaacagagt gaggattagg aacgtggctt   1200
acgatactct tccattgtg gtgcatgaa acggaccaac aaaactccag cttaactacc   1260
ttgggaaacta cgttccaaac ggatggactc cagaaggagg atgtggattc tgcaatcagg   1320
ataggagaac tcttccagga ggacaaccac caccaagagt tttccttgct gtgttcgttg   1380
aacagccaac tccattcctt ccaagattcc ttcagaggct tcttcttttg gattacccac   1440
cagatagggt gacacttttc cttcacaaca acgaggtttt ccacgagcca cacattgctg   1500
attcttggcc acagcttcag gatcatttct ctgctgtgaa gttggttggt ccagaagaag   1560
ctctttctcc aggagaagct agggatatgg ctatgatt gtgcaggcag gatccagagc   1620
gcgagttcta cttctctctt gatgctgatg ctgtgcttac taaccttcag actcttagga   1680
ttcttattga ggagaacagg aaagtgattg ctccaatgct ttctaggcac ggaaagttgt   1740
ggtctaattt ctggggtgct ctttctcctg atgagtacta cgctagatca gaggactacg   1800
tggagcttgt tcagagaaag agagtgggag tttggaacgt tccttatatt tctcaggctt   1860
acgtgattag gggagatact cttaggatgg agcttccaca gagggatgtt ttctctggat   1920
ctgatactga tccagatatg gctttctgca agtctttcag ggataaggga attttccttc   1980
accttcta ccagcatgag ttcggaagat tgcttgctac ttcaagatac gatactgagc   2040
accttcatcc tgatctttgg cagatttct ataaccagt ggattggaag gagcagtaca   2100
ttcacgagaa ctactctagg gctcttgaag gagaaggaat tgtggagcaa ccatgccag   2160
atgtttactg gttcccactt ctttctgagc aaatgtgcga tgagcttgtt gctgagatgg   2220
agcattacgg acaatggagt ggaggtagac atgaggattc taggcttgct ggaggatacg   2280
agaacgttcc aactgtggat attcacatga agcaagtggg atacgaggat caatggcttc   2340
agcttcttag gacttatgtg ggaccaatga ctgagtctct ttcccagga taccacacta   2400
aggctagggc tgttataga ttcgttgtga ggatcgtcc agatgagcaa ccatctctta   2460
ggccacacca cgattcttct actttcactc ttaacgtggc tcttaaccac aagggacttg   2520
attatgaggg aggaggatgc cgtttccta gatacgagga cgtgatttct tcaccaagaa   2580
agggatggc tcttcttcat ccaggaaggc ttactcatta ccacgaggga cttccaacta   2640
cttgggaac tagatatatt atggtgtctt tcgtggatcc atgactgctt taatgagata   2700
tgcgagacgc ctatgatcgc atgatattg ctttcaattc tgttgtgcac gttgtaaaaa   2760
acctgagcat gtgtagctca gatccttacc gccggtttcg gttcattcta atgaatatat   2820
cacccgttac tatcgtattt ttatgaataa tattctccgt tcaatttact gattgtccag   2880
aattcgcg                                                            2888

SEQ ID NO: 39           moltype = DNA   length = 2689
FEATURE                 Location/Qualifiers
misc_feature            1..2689
                        note = Synthetic sequence containing the coding regions of
                          the human Procollagen C-proteinase and flanking regions
source                  1..2689
                        mol_type = other DNA
                        organism = synthetic construct
SEQUENCE: 39
agatctatcg atgcatgcca tggtaccgcg ccatggctca attggctgca acatcaaggc   60
ctgaaagagt ttggccagat ggtgttattc cttcgttat tggtggaaac tttactggat   120
ctcagagagc agtttttaga caagctatga cattggga aaagcacact tgtgtgacat   180
tccttgaaag gactgatgaa gattcttata ttgtgttcac ataccgtcca tgtggatgct   240
```

```
gctcatatgt tggtagaagg ggaggaggtc cacaagcaat ttctattgga aaaaactgcg   300
ataagttcgg aattgtggtg catgaattgg gacatgttgt tggtttctgg cacgaacaca   360
caaggccaga tagggatagg cacgtgtcta ttgtgaggga aaacattcag ccaggtcaag   420
agtacaattt tcttaagatg gaacctcaag aggtggaatc tctcggagag acttacgact   480
tcgactccat catgcactac gcaaggaata ctttcagcag gggcatcttc ttggatacca   540
ttgtgcctaa gtacgaggtg aacggcgtta agccacctat tggtcaaagg actaggctct   600
ctaagggtga tattgcacag gctaggaagc tctacaaatg tccagcatgc ggagaaactc   660
ttcaggattc cactggcaac ttctcatctc cagagtaccc aaacggatac tctgctcata   720
tgcactgtgt ttggaggatc tcagtgactc ctggagagaa gatcatcctc aacttcactt   780
ccctcgatct ctatcgttct aggctctgtt ggtacgacta tgtgaagtg agagatggct    840
tctggagaaa ggctccactt agaggaaggt tctgcggatc taaacttcct gagccaatcg   900
tgtctactga ttccagattg tgggtggagt tcaggtcctc ttctaattgg gttggcaagg   960
gcttttttgc tgtgtacgag gctatttgtg gcggcgacgt gaaaaaggac tacggacata  1020
ttcaaagtcc aaattaccca gatgattacc gtccttcaaa agtgtgtatt tggaggattc  1080
aagtgagtga gggtttccat gttggattga cattccaatc tttcgaaatt gagagacacg  1140
attcatgcgc atacgattat ttggaagtga gagatggaca ctctgaatct tctacactta  1200
ttggaaggta ctgcggttat gagaaacctg atgatattaa gtctacttct agtaggttgt  1260
ggcttaaatt tgtgtcagat ggttctatta acaaggctgg tttcgcagtg aacttcttca  1320
aggaagtgga tgaatgctca agacctaaca gaggaggatg tgagcaaaga tgccttaaca  1380
ctttgggaag ttacaagtgt tcttgcgatc ctggatacga gttggctcct gataagagaa  1440
gatgcgaagc tgcttgcggt ggtttttga caaaattgaa cggatctatt acttctcctg   1500
gatggccaaa agagtaccca cctaataaga attgcatttg gcagctttgt gcacctactc  1560
agtaccgtat ttcattgcaa ttcgattttt tcgagactga gggtaatgat gtgtgcaagt  1620
acgatttcgt ggaagtgaga tcaggtctta ctgctgatag taaattgcac ggaaagttct  1680
gcggatctga aaaaccagaa gtgattacat cacagtacaa caatatgagg gtggagttca  1740
aatctgataa tactgtttct aaaaaaggtt ttaaggcaca tttcttttct gataaggacg  1800
agtgctctaa agataatggt ggttgccagc aggattgcgt gaacacattc ggttcatatg  1860
agtgccaatg ccgtagtgga tttgttcttc acgataacaa acatgattgc aaagaggcag  1920
gttgcgatca caaggtgaca tctacttcag gtactatcac atctccaaac tggcctgata  1980
agtatccttc aaaaaaagaa tgtacatggg caatttcttc tacaccaggt cataggggtta  2040
agttgacatt catggagatg gatattgaga gtcaaccaga gtgcgcttat gatcatcttg  2100
aggtgttcga tggaagggat gctaaggctc tgttcttgg tagattctgt ggtagtaaaa  2160
agccagaacc agtgcttgca acaggatcta ggatgttcct tagattctac tctgataact  2220
cagttcagag gaaaggattc caagctagtc acgcaactga atgcggtgga caagttagag  2280
cagatgttaa gactaaggat ctttactcac acgcacagtt cggagataac aactaccctg  2340
gaggagttga ttgcgagtgg gttattgtgg ctgaagaggg atacggagtt gagcttgttt  2400
tccagacatt cgaggtggag gaggaaactg attgcggtta cgattatatg gaactttttg  2460
atggatacga tagtactgct ccaagacttg gaaggtattg tggtagtggt ccaccagaag  2520
aggtgtactc agctggagat agtgtttcttg ttaagttcca cagtgatgat acaattacta  2580
agaagggatt ccatcttaga tatacttcaa ctaagtttca ggatactctt cattctagga  2640
agtaatgagc tcgcggccgc atccaagctt ctgcagacgc gtcgacgtc               2689
```

| SEQ ID NO: 40 | molytpe = DNA  length = 2912 |
|---|---|
| FEATURE | Location/Qualifiers |
| misc_feature | 1..2912 |
| | note = Synthetic sequence containing the coding regions of the human Procollagen I N-proteinase and flanking regions |
| source | 1..2912 |
| | mol_type = other DNA |
| | organism = synthetic construct |

SEQUENCE: 40

```
gcgccatggc tcaattgagg agaagggcta ggagacacgc agctgatgat gattacaaca    60
ttgaagtttt gcttggtgtt gatgatagtg tggtgcaatt ccacggaaaa gagcatgttc   120
agaaatatct tttgacactt atgaatattg tgaacgaaat ctaccatgat gagtctttgg   180
gagcacacat taacgtggtt cttgtgagga ttattcttct ttcatccggt aaatctatgt   240
cacttattga gattggaaac ccttctcagt ctccttgaaga tgtgtgcaga tgggcatacc   300
ttcaacagaa gcctgatact ggacacgatg agtatcacga tcacgctatt ttccttacaa   360
ggcaggattt cggtccaagt ggaatgcaag gatatgctcc tgttactggt atgtgccacc   420
ctgttaggtc ttgtacactt aaccacgagg atggttttc atctgctttc gtggtggcatg   480
atgagacagg tcatgttttg ggaatggaac atgatggaca gggtaataga tgtggagatg   540
aagtgagact tggttcaatt atggctcctc ttgttcaagc tgcttttcat aggttccact   600
ggagtaggtg ttcacagcaa gagttgagta gatacttca ttcttacgat tgcttgcttg    660
atgatccatt tgctcatgat tggccagctt tgcctcaact tcctggattg cactactcta   720
tgaacgagca gtgcagattt gattctgtc ttggttacat gatgtgcaca gctttcagga   780
ctttcgatcc atgcaaacag ttgtggtgtt cacaccaga taacccatat ttctgtaaaa   840
caaaaaaagg tccaccactt gatggtacta tgtgcgcacc tggaaagcac tgcttcaagg   900
gacactgcat ttggcttact cctgatattc ttaaagggga tggatcatgg ggagcttggt   960
ctccattcgg aagttgctca agaacttgcg gaacaggtgt taagtttaga actaggcagt  1020
gcgataatcc acaccctgct aatggtggta gaacttgctc tggacttgct tacgatttc   1080
agttgtgttc taggcaagat tgccctgata gtcttgctga ttttagagaa gagcaatgta  1140
gacagtggga tctttacttt gagcacgcg acgctcagca ccactggctt ccacacgagc  1200
atagagatgc aaaagaaagg tgtcaccttt attgcgagag tagagagact ggagaggtgg  1260
tgtcaatgaa gagaatggtg cacgatggta caaggtgttc ttataaggat gcattctctt  1320
tgtgtgtgag gggagattgc aggaaagtgg gttgtatgga gttatttgga tctagtaagc  1380
aagaagataa gtgcggagtg tgcggaggag ataactctca ttgcaaggtt gtgaaggaa   1440
cttttacaag atcaccaaaa aaacacggtt acattaagat gttcgaaatt cctgctggag  1500
caaggcattt gcttattcag gaagtggatg caacatctca ccacttggca gtgaaaaacc  1560
ttgagactgg aaaaattcatt ttgaacgagg agaacgatgt tgatgcatct agtaagactt  1620
tcattgcaat gggtgttgaa tgggagtata gggatgagga tggaagggaa acacttcaaa  1680
```

```
caatgggtcc tcttcatgga acaattactg tgttggtgat tccagtggga gatacaaggg   1740
tgtcattgac atacaagtat atgattcacg aggatagtct taacgttgat gataacaacg   1800
ttttggaaga agattctgtg gtttacgagt gggctcttaa gaaatggtca ccttgctcta   1860
agccatgtgg tggaggaagt cagttcacta agtatggttg taggaggagg cttgatcata   1920
agatggttca taggggattt tgcgcagcac ttagtaagcc aaaggcaatt aggagggctt   1980
gtaaccctca agaatgctca caaccagttt gggtgacagg agagtgggag ccatgttcac   2040
aaacatgcgg aagaactgga atgcaagtta gatcagttag atgcattcaa cctcttcatg   2100
ataacactac aagaagtgtg cacgcaaaac actgtaacga tgctaggcca gagagtagaa   2160
gagcttgctc tagggaactt tgccctggta gatggagggc aggaccttgg agtcagtgct   2220
ctgtgacatg tggaaacggt actcaggaaa gacctgttcc atgtagaact gctgatgata   2280
gtttcggaat ttgtcaggag gaaaggccag aaacagctag gacttgtaga cttgaccttt   2340
gtcctaggaa tatttctgat cctagtaaaa aatcatacgt ggtgcaatgg ttgagtaggc   2400
cagatccaga ttcaccaatt aggaagattt cttcaaaagg acactgccag ggtgataaga   2460
gtattttctg cagaatggaa gttcttagta ggtactgttc tattccaggt tataacaacg   2520
tttcttgtaa gagttgcaac ttgtataaca atcttactaa cgtggagggt agaattgaac   2580
ctccaccagg aaagcacaac gatattgatg tgtttatgcc tactcttcct gtgccaacag   2640
ttgcaatgga agttagacct tctccatcta ctccacttga ggtgccactt aatgcatcaa   2700
gtactaacgc tactgaggat cacccagaga ctaacgcagt tgatgagcct tataagattc   2760
acggacttga ggatgaggtt cagccaccaa accttattcc taggaggcca agtccttacg   2820
aaaaaactag aaatcagagg attcaggagc ttattgatga gatgaggaaa aaggagatgc   2880
ttggaaagtt ctaatgagct cgcggccgca tc                                 2912

SEQ ID NO: 41          moltype = DNA   length = 4467
FEATURE                Location/Qualifiers
source                 1..4467
                       mol_type = genomic DNA
                       organism = Homo sapiens
SEQUENCE: 41
atggctcacg ctcgtgttct cctcctcgct ctcgctgttt tggcaacagc tgctgtggct     60
gtggcttcta gttcttcttt tgctgattca aaccctatta gacctgttac tgatagagca    120
gcttccactt tggctcaatt gcaagaggag ggccaggttg agggccaaga tgaggatatc    180
cctccaatta catgcgtgca aaatggcttg cgttaccacg atagggatgt gtggaaacct    240
gaaccttgtc gtatctgtgt gtgtgataac ggcaaggtgc tctgcgatga tgttatctgc    300
gatgagacaa aaaattgccc tggcgctgaa gttcctgagg gcgagtgttg ccctgtgtgc    360
cctgatggtt ccgagtcccc aactgatcag gaaactactg gcgtggaggg cccaaaagga    420
gatactggtc cacgtggtcc taggggtcca gcaggtcctc caggtagaga tggtattcca    480
ggccagcctg gattgccagg accaccaggc ccacctggcc caccaggacc tcctggtctt    540
ggtggaaatt tcgctccaca actctcttat ggctatgatg agaagtcaac aggtggtatt    600
tccgttccag gtcctatggg accatccgga ccaagaggtc cccaggtcc tccaggtgct    660
cctggacctc aaggctttca aggacctcca ggcgaaccag agaaccagg cgcttctgga    720
ccaatgggcc caaggggacc acctggccca ccaggaaaaa atggcgatga tggcgaagct    780
ggaaagcctg gtcgtcctgg agagagaggt cctcctggcc cacagggtgc aagaggcttg    840
gcaggaactg ctggcttgcc tggaatgaag ggacatagg gcttctccgg cctcgatggt    900
gctaagggtg atgctggccc tgctggacca aagggcgagc caggttcccc tggagaaaac    960
ggtgctcctg gacaaatggg tcctgtggga cttccaggag aaaggggtcg tccaggcgct   1020
ccaggaccag caggtgctag gggaaacgat ggtgcaacag gcgctgctgg ccctcctggc   1080
ccaactgctc ctgctggccc tccaggattc ccaggctgga ttggagctaa aggagaagca   1140
ggaccacagg gccctagggg ttctgaagga cctcagggtg ttagaggtga accaggtcct   1200
ccaggcccag ctggagcagc tggtccagca ggaaatccag gtgctgatgg tcaacctgga   1260
gctaagggc ctaatggcgc accaggtatc gcaggcgcac caggttttcc tggcgctaga   1320
ggcccaggtg gtcctcaagg acaggtggaa ccaccaggtc caaaaggcaa ttctggcgaa   1380
cctggcgctc caggttctaa aggagatact ggtgctaaag gcgaaccagg acctgttggt   1440
gttcaggtc ctcctggtcc tgctggagaa aaggaaaaa gaggtgctcg tggagaacca   1500
ggaccaactg gacttcctgg acctcctggt gaacgtggcg gacctggctc aaggggtttc   1560
cctgagagctg atggagtgg aggtccaaaa ggccctgtcg gagagaggt tcaccaggt   1620
ccagctggtc ctaagggctc ccctggtgaa gcaggtagac aggcgaagc aggattgcca   1680
ggcgcaaagg gattgacagg ctctcctggt agtcctggcc cagatggaaa acaggcccca   1740
ccaggtccag caggacaaga tggacgtcca ggcccaccag gtcctcctgg agcaagggga   1800
caagctggcg ttatgggttt tccaggacct aaaggtgctg ctggagagca aggaaaggca   1860
ggtgaaagag gagttcctgg tccaccagga gcagtgggtc ctgctggcaa agatggtgaa   1920
gctggagcac agggccctcc aggccctgct ggccagctg cgaacgtgg agaacaaggc   1980
ccagctggta gtccaggatt caaggattgc ctggccctg ctggccctcc aggagaagca   2040
ggaaaacctg gagaacaagg agttcctggt gatttgggaa cacctggacc ttcaggagca   2100
cgtggtgaaa gagcttccc tggcgagagg ggtgttcaag gtccaccagg tccagcagga   2160
cctagaggtg ctaatggcgc tcctggcaac gatggagcaa aaggtgatgc tggtgctcct   2220
ggcgcacctg gaagtcaggg tgctcctgga ttgcaaggaa tgcctggaga gggggtgct   2280
gctggcttgc caggcccaaa gggcgatagg ggtgatgctg accaaaagg tgctgatgga   2340
tccccaggaa aagatggagt tcgtggtctt actggcccaa tcgaccttcc aggccctgct   2400
gggcgctcca gtgataaggg cgaaagtggc ccaagtggac ctgctgaac tactggtgct   2460
agaggtgcac ctggtgatag gggtgaacct ggaccacctg gtccagctgg ttttgctggt   2520
cctcctggaa ctgatggaca acctggcgca aaggtgaac caggtgatgc tggcgcaaag   2580
ggagatgctg gtccacctgg acctgctggt ccagcaggcc ccctgggcc aatcggtaat   2640
gttggagcac aggtgctaa gggagctagg ggttccgctg gtccaccgg agcaacagga   2700
tttccaggag ctgtggctag agttggccca caggccgat ccggaaacgc aggccctcct   2760
ggtcctccag gtcctgctgg caaggagggt ggcaaaggca aggggcga aactggccct   2820
gctggtagac ctgcgaagt tggccctcct ggaccaccag gtccagcagg agaaaaaggt   2880
tccccaggag ctgatggccc agctggtgct ccaggaactc aggccctca aggtattgct   2940
ggacagagag gcgttgtggg actccctggt caaggggag agaggatt tccaggcttg   3000
ccaggaccta gtggagaacc tggaaaacaa ggcccatcag cgctagtgg agagcgtgga   3060
```

```
cctcctggcc ctatgggacc tcctggattg gctggcccac ctggcgaatc aggtcgtgaa  3120
ggcgcaccag gcgcagaagg atcacctgga agagatggat cccctggtgc taaaggcgat  3180
cgtggagaaa ctggtccagc aggcccacca ggcgcaccag gtgcacctgg cgctccagga  3240
cctgtgggac cagctggaaa atccggagat aggggcgaga caggcccagc aggaccagct  3300
ggacctgttg gccctgctgg cgctcgtgga ccagcaggac ctcaaggacc aaggggagat  3360
aaggaagaaa caggcgaaca aggcgatagg ggcattaagg gtcataggg  ttttagtggc  3420
ctccagggtc ctcctggccc acctggatca ccaggagaac agggaccatc tggtgcttcc  3480
ggcccagctg gtccaagagg acctccagga tcagctggtg cacctggaaa agatggtctt  3540
aacggtctcc caggaccaat cggccctcca ggacctagag gaagaacagg agatgctggc  3600
cctgttggcc ctccaggacc tcctggtcca ccaggtccac ctggtcctcc atcagctgga  3660
ttcgattttt catttcttcc acagccacca caagagaaag ctcacgatgg cggcagatat  3720
taccgtgctg atgatgctaa cgttgttagg gatagagatt tggaagtgga tacaactttg  3780
aaatccctct cccagcaaat tgaaaacatt agatctccag aaggttcacg taaaaaccca  3840
gctagaacat gtcgtgattt gaaaatgtgt cactccagat ggaaaagtgg tgaatactgg  3900
attgatccaa atcagggctg taatctcgat gctatcaaag ttttctgtaa catggaaaca  3960
ggcgaaacat gcgtttatcc tactcaacct tccgtggctc agaaaaattg gtacatctca  4020
aaaaatccta agataagag  gcacgtttgg ttcggtgaaa gtatgactga tggatttcaa  4080
tttgagtacg gcggtcaagg tagtgatcca gctgatgtgg ctattcaact cacattttg   4140
cgtcttatgt ccacagaggc atcacaaaac atcacttacc actgcaaaaa cagtgtggct  4200
tatatggatc aacaaacagg aaaccttaag aaggctcttc ttttgaaggg ctcaaacgag  4260
attgagatta gagcagaggg caactcaagg tttacttatt cagttactgt tgatggctgc  4320
acttcacata ctggcgcttg gggtaaaaca gttatcgagt ataagactac aaaaaacatca 4380
agactcccaa tcattgatgt tgctcctctc gatgttggcg ctcctgatca agagttcggt  4440
tttgatgtgg gcccagtttg tttcctc                                       4467

SEQ ID NO: 42         moltype = DNA   length = 4167
FEATURE               Location/Qualifiers
source                1..4167
                      mol_type = genomic DNA
                      organism = Homo sapiens
SEQUENCE: 42
atggctcacg ctcgtgttct cctcctcgct ctcgctgttt tggcaacagc tgctgtggct    60
gtggcttcaa gttctagttt tgctgattcc aacccaattc gtccagttac tgatagagca   120
gcttccactt tggctcaatt gcttcaagaa gaaactgtga ggaagggccc tgctggcgat   180
aggggcccta ggggcgaaag gggtccacca ggacctccag gcaggcggtgg cgaagatgat  240
ccaactggcc ctcctggacc tcctggccct ccagggccac ccggcttggg cggaaacttc   300
gcagctcaat acgatggcaa gggtgttggt cttggtcctg gtcctatggg cttgatggga   360
cctagaggcc cacctggtgc tgctggtgct cctggaccac agggttttca gggaccagct   420
ggcgagccag gagagccagg ccaaacagga ccagctggtg caagggggacc tgctggacct   480
cctgaaaaag ctggtgaaga tggtcaccca ggcaaaccag gacgtcctgg cgaaagaggt   540
gttgttggac cacaaggcgc tagggggattt ccaggtacac ctggattgcc aggttttaag   600
ggcattcgtg gtcataacgg cctcgatgga ttgaaggac  agcctggcgc acctggcgtt   660
aagggtgaac ctggagcacc aggtgaaaac ggtactcgtg gccagactgg tgcaagagga   720
ctccaggtg  aaaggggtag agttggtgct cctggacctg ctggagctag gggtagtgat   780
ggtagtgttg tcctgtgggg ccctgctggt ccaatcggtt ccgctggccc acctggattc   840
ccaggcgctc caggacctaa aggagaaatc ggtgctgtgg taacgcagg tcctactggt   900
ccagcaggtc ctcgtggaga agtgggattg ccaggactt  ctggtccagt gggccctcca   960
ggcaacccctg gagctaacgg cttgacagga gctaaaggcg cagcaggact ccctggagtg  1020
gctggcgcac caggattgcc tggtccaagg ggtatcccag gcctgttgg cgcagctgga  1080
gctactggtg cacgtggact tgttggcgaa ccaggccctg ctggatcaaa aggcgagtct  1140
ggaaataagg gagaacctgg ttctgctgga cctcaaggtc ctcctggaac ttctggagaa  1200
gaaggaaaaa gggaccaaa  tggcgaggct ggatcagcag gtccaccagg accacctgga  1260
cttcgtggat cccctggtag taggagactt ccaggcgctg atggtagagc aggcgttatg  1320
ggaccaccag gaagtagagg agcatccggt ccagcaggag ttaggggtcc taacggagat  1380
gctggtagac caggtgaacc aggtcttatg ggcccaaggg gcctcccagg tagtccagga  1440
aatatcggcc ctgctggaaa agaaggcccc gttggacttc caggtattga tggacgtcct  1500
ggccctattg gccagcagg  tgcaagagga gaacctggca atattggatt tccaggacca  1560
aagggtccaa caggcgatcc tggaaaaaat ggagataagg gtcatgctgg attggcaggc  1620
gcaaggggcg ctcctggtcc agatggaaac aacggcgcac agggtccacc tggccctcag  1680
ggtgttcaag gcggaaaagg cgaacaaggc ccagctggac caccaggctt tcaaggcttg  1740
ccaggaccaa gtggtccagc aggtgaagtt ggcaagccag cgagcgtgg  acttcatggc  1800
gagtttggac tccctggacc agcaggacca aggggtgaaa gaggccctcc tggagagagt  1860
ggcgctgctg gaccaacagg cccaatcggt agtagaggtc ctagtggacc tccaggccca  1920
gatggaaata agggtgaaga agagttgtg  ggcgctgtgg tccttcagga ccagcgatgg  1980
ccatcaggac tccaggcgaa gagaggcgct gctggcattc tgaggaaaa  aggtgaaaaa  2040
ggcgaacctg gcctccgtgg cgaaatcgga atcctggac  gtgatggtgc tcgtggtgca  2100
cacggcgctg tgggcgctcc aggccctgct ggtgctactg gtgatagagg agaggctggc  2160
gcagctggcc cagcaggtcc tgctggccca agggtagtc  ctggtgaaaa aggcgaagtt  2220
ggacctgctg gccctaacgg ctttgctggc cctgctggaa cagcaggtca acctggcgct  2280
aaaggtgaaa gggcggaaa  gggcccaaaa ggtgaaaatg gcgttgtggg accaactggt  2340
ccagtggggcg cagctggacc tgctggtcca aatggaccac aggaccagcag aggtagtaga  2400
ggagatggtg gacctccagg aatgacaggt tttccaggtg ctgctggtag aacaggacct  2460
cctggtccta gtgtatttc  tggtccacca ggaccaccag gtcctgctgg aaaagaagga  2520
ttgagggtcg gagctgctga tcaaggcaca gtgggcaaga ctggtgaagt tggcgcaggt  2580
ggaccacctg gttttgctgg agaaaaggc  ccttctggag aggcaggaac agctggtcct  2640
cctggtacac ctgacctcga aggacttttt ggtgcacctg gtattctcgg attgccagga  2700
agtgggggcg aacgtggact tcctggcgtg gcaggagcag ttgagaacc  tggccctctc  2760
ggaatcgcag gccaccagg  cgcaagagga ccaccggag  ctgttggatc accaggcgtg  2820
aatggtgcac ctggcgaggc tggtcgtgat ggaaacccag gaaatgatgg cccaccagga  2880
```

```
agagatggtc aacctggaca caaaggcgag aggggctacc caggaaatat tggcccagtt 2940
ggtgctgctg gcgcaccagg cccacacggt ccagttggac cagcaggaaa acacggtaat 3000
cgtggcgaaa caggcccttc aggcccagtg ggacctgctg gtgctgttgg cccaagagga 3060
ccatctggac ctcaaggcat tagaggcgat aagggagagc ctggcgaaaa aggacctaga 3120
ggcttgcctg gttttaaagg acacaacggt ctccaaggac ttccaggtat cgctggtcat 3180
catggagatc agggtgctcc tggatcagtg ggtccagcag gtcctagagg cccagcaggc 3240
ccttccggtc cagcaggaaa ggatggacgt actggccacc ctggaactgt gggccctgct 3300
ggaattagag gtcctcaagg tcatcagggc cctgctggcc ctccaggtcc accaggtcct 3360
ccaggcccac caggagtttc aggtggtggt tacgattttg gttacgatgg tgatttttac 3420
cgtgctgatc aacctagaag tgctccttct ctccgtccta aagattatga agttgatgct 3480
actttgaaat cacttaacaa ccagattgag actcttctca cacctgaggg atcaagaaag 3540
aatccagcac gtacatgccg tgatctcaga cttagtcacc cagagtggtc aagtggctat 3600
tattggattg atcctaatca gggttgtaca atggaggcta tcaaagttta ctgtgattt 3660
ccaactggag agacatgtat tagggcacaa cctgagaaca ttccagctaa aaattggtat 3720
cgttcctcta aagataagaa acatgtttgg ctcggagaga ctattaacgc tggttctcag 3780
ttcgagtata atgttgaggg cgttacttct aaagagatgg caactcagct cgcttttatg 3840
agattgctcg ctaactacgc atcccaaaac atcacttatc actgcaaaaa ttccattgca 3900
tatatggatg aggagacagg aaatttgaag aaagcagtta ttctccaagg tagtaacgat 3960
gttgagcttg tggctgaggg aaatagtaga ttcacttaca cagttttggt ggatggatgc 4020
tcaaagaaaa ctaatgagtg gggcaagaca atcattgagt acaagacaaa taagccttct 4080
aggctcccat ttctcgatat tgcacctctt gatatcggag gagctgatca cgagtttttt 4140
gttgatatcg gacctgtttg tttttaag                                     4167
```

DERMAL FILLERS AND APPLICATIONS THEREOF

RELATED APPLICATIONS

This application is a division of U.S. patent application Ser. No. 17/052,216 filed on Nov. 2, 2020, which is a National Phase of PCT Patent Application No. PCT/IL2019/050492 having the International Filing Date of May 2, 2019, which claims the benefit of priority of U.S. Provisional Patent Application No. 62/666,267 filed on May 3, 2018, which is hereby incorporated by reference in its entirety.

SEQUENCE LISTING STATEMENT

The XML file, entitled 97405SequenceListing.xml, created on Oct. 3, 2023, comprising 130,323 bytes, submitted concurrently with the filing of this application is incorporated herein by reference.

FIELD OF DISCLOSURE

Disclosed herein are photoinitiated and double cross-linked dermal fillers comprising plant-derived human collagen, and cellular growth promoting scaffolds, as well as methods of using the dermal fillers in some instances, for soft tissue augmentation.

BACKGROUND

Collagens are the main proteins responsible for the structural integrity of vertebrates and many other multicellular organisms. Collagen comprises the main component of connective tissue and is the most abundant protein in mammals, comprising approximately 30% of the protein found in the body. Loss or deterioration of collagen can occur as the result of aging or injury (Olsen et al, Adv Drug Deliv Rev. 2003 Nov. 28; 55(12):1547-67).

One common aspect of aging is the development of lines, fine lines, or wrinkles. Treatments involving the use of tissue-extracted collagen have been used to reduce or eliminate lines, fine lines, or wrinkles. Similar treatments have been used to reduce scars.

Collagen is also a component of tendons. Tendinopathy, a common injury usually associated with sports and physical activities, is associated with degeneration and disordered arrangement of the tendon's collagen fibers. Healing of injured tendons requires an orchestrated activity of specific cells and an extended presence of relevant growth factors (GFs) at the vicinity of the injury. Tendinopathy is nowadays the leading reason for consultation for a musculoskeletal complaint (Kaux et al. (January 2011) J. Sport. Sci. Med. January:238-253). Tendinopathy refers to a variety of painful conditions that develop in and around tendons and ligaments which are likely arising from an imbalance between pathological changes due to tendon overuse and the consequent regenerative responses (Andres et al. (2008) Clin. Orthop. Relat. Res. 466:1539-1554). Tendinopathy is associated with degeneration and disordered arrangement of collagen (Maffulli et al. (2003) Clin. Sport. Med. 22:675-692), sometimes associated with fibers micro tears, increase in vascularity and presence of a mild inflammation (Khan et al. (1999) Sport. Med. 27(6):393-408). Clinically, it is characterized by onset of tendon stiffness, activity-related pain, decrease in functionality and sometimes localized swelling (Kaux 2011; Andres 2008). Collagen fibers present unequal and irregular crimping, loosening, and increased waviness instead of the normal tight, parallel, bundled appearance (Mafulli 2003). As the population remains active at older ages, the incidence rate of tendon injuries is expected to rise in the coming decades. A wide variety of treatments for tendinopathy are available, including physiotherapy, pharmacological treatments and combination thereof, however, clinical results are not satisfactory, and recurrence of symptoms is common (Kaux 2011). Injection of autologous platelet rich plasma (PRP) for the treatment of tendinopathy received wide attention in the last decades (Delong et al. (2016) Curr. Orthpaedic Pract. 22:514-523; Kaux et al. (2012) Wound Repair Regen. 20:748-756; Yuan et al. (2013) Muscles. Ligaments Tendons J. 3(3):139-49; Di Matteo et al. (2015) Musculoskelet. Surg. 99(1):1-9). PRP is the plasma fraction of blood containing high concentration of platelets. Upon injection to the injured site, platelets release various types of growth factors (GFs) which are thought to promote the healing process. Among the PRP-associated GFs vasculo-endothelial growth factor (VEGF), transforming beta growth factor (TGF-beta), platelet derived growth factor (PDGF), platelet derived epidermal growth factor (PDEGF), fibroblast growth factors (bFGF), epidermal growth factors (EGF) and hepatocyte growth factors (HGF) have been reported (Delong 2016; Yuan 2013; Harrison et al. (2011) Am. J. Sports Med. 39(4):729-734). Many in vitro studies and in vivo models show that PRP treatments enhance collagen expression and extracellular matrix production, stimulate angiogenesis and increase cell migration, differentiation and proliferation, thus supporting the healing of tendon injuries (Yuan 2013; Kajikawa et al. (2008) J. Cell. Physiol. 215(3):837-845; Zhang et al. (2010) Am. J. Sports Med. 38(12):2477-2486). However, clear clinical evidences of the efficacy of PRP treatment is limited (Delong 2016; Yuan 2013; Moraes et al. (2014)).

Collagen serves as the predominant component and primary structural-mechanical determinant of most tissue extra cellular matrix (ECM) [see, for example, Kadler K. Birth Defects Res C Embryo Today. 2004; 72:1-11; Kadler K E, Baldock C, Bella J, Boot-Handford R P. J Cell Sci. 2007; 120:1955-1958.; Kreger S T. Biopolymers. 2010 93(8): 690-707]. Tropocollagen typically consists of three left-handed helices (usually two identical helices and a third distinct helix) of procollagen joining to form a right-handed triple-helical tropocollagen, resulting on the formation of fibrils.

The conformation and most of the properties of native collagen are determined by the triple helix domain which composes more than 95% of the molecule. This domain consists of three alpha chains, each containing approximately 1,000 amino acids, wrapped in a rope-like fashion to form a tight, triple helix structure. The triple helix is wound in such a way that peptide bonds linking adjacent amino acids are buried within the interior of the molecule, such that the collagen molecules are resistant to attack by proteases, such as pepsin.

Type I collagen represents the prototypical fibrillar collagen and is the major collagen type in most tissues, including bone, tendon, skin, aorta, and lung. Type I collagen fibers provide for great tensile strength and limited extensibility. The most abundant molecular form of type I collagen is a heterotrimer composed of two different alpha chains [alpha 1(I)]$_2$ and alpha 2(I) (Inkinen, Connective Tissue Formation in Wound Healing an Experimental Study, Academic Dissertation, September 2003. University of Helsinki, Faculty of Science, Department of Biosciences, Division of Biochemistry).

In all of the fibrillar collagen molecules, the three polypeptide chains are constructed from a repeating Gly-X-Y triplet, where X and Y can be any amino acid but are frequently the imino acids proline and hydroxyproline. Collagen is particularly rich in glycine, proline, and hydroxyproline amino acid residues, and the protein sequence of a strand of collagen often has a repeating amino acid sequence. Procollagen is modified by the addition of hydroxyl groups on proline and lysine residues. These hydroxylation reactions are catalyzed, respectively, by prolyl-4-hydroxylase and lysyl-hydroxylase. Hydroxyl groups on the lysine residues are then glycosylated, and the triple helix is subsequently formed.

An important feature of fibril-forming collagens is that they are synthesized as precursor procollagens containing globular N- and C-terminal extension propeptides. The biosynthesis of procollagen is a complex process involving a number of different post-translational modifications including proline and lysine hydroxylation, N-linked and O-linked glycosylation and both intra- and inter-chain disulphide-bond formation. The enzymes carrying out these modifications act in a coordinated fashion to ensure the folding and assembly of a correctly aligned and thermally stable triple-helical molecule.

The triconstituent polypeptide chains are assembled within the rough endoplasmic reticulum (RER) to form procollagen. As the polypeptide chain is co-translationally translocated across the membrane of the endoplasmic reticulum (ER), prolyl-4-hydroxylase (P4H)-dependent hydroxylation of proline and lysine residues occurs within the Gly-X-Y repeat region. The stability of the final triple-helical structure of collagen is highly dependent on the P4H-mediated hydroxylation of collagen chains. Lysyl hydroxylase (LH, EC 1.14.11.4), galactosyltransferase (EC 2.4.1.50) and glucosyltransferase (EC 2.4.1.66) are enzymes involved in posttranslational modifications of collagens. They sequentially modify lysyl residues in specific positions to hydroxylysyl, galactosylhydroxylysyl and glucosylgalactosyl hydroxylysyl residues. These structures are unique to collagens and essential for their functional activity (Wang et al. (2002) Matrix Biology, 21(7): 559-566). A single human enzyme, lysyl hydroxylase 3 (LH3) can catalyze all three consecutive steps in hydroxylysine linked carbohydrate formation (Wang et al. (2002) Matrix Biology, 21(7): 559-566). Once the polypeptide chain is fully translocated into the lumen of the endoplasmic reticulum the three pro-alpha chains then associate via their C-propeptides to form a trimeric molecule where the Gly-X-Y repeat region forms a nucleation point at its C-terminal end, ensuring correct alignment of the chains. The Gly-X-Y region then folds in a C-to-N direction to form a triple helix (Khoshnoodi et al. (2006) J. Biol. Chem. 281:38117-38121).

The temporal relationship between polypeptide chain modification and triple-helix formation is crucial as hydroxylation of proline residues is required to ensure stability of the triple helix at body temperature, once formed, the triple helix no longer serves as a substrate for the hydroxylation enzyme. The C-propeptides (and to a lesser extent the N-propeptides) keep the procollagen soluble during its passage out of the cell (Bulleid et al. (2000) Biochem. Socy. Transact., 28(4): 350-353). Following or during secretion of procollagen molecules into the extracellular matrix, propeptides are removed by procollagen N- and C-proteinases, thereby triggering spontaneous self-assembly of collagen molecules into fibrils (Hulmes, 2002, J. Struct. Biol. January-February; 137(1-2):2-10). Removal of the propeptides by procollagen N- and C-proteinases lowers the solubility of procollagen by >10000-fold and is necessary to initiate the self-assembly of collagen into fibers at 37° C. Crucial to this assembly process are the short telopeptides which are the non-triple-helical remnants of the N- and C-terminal propeptides remaining after digestion with N/C proteinases. These peptides act to ensure correct covalent registration of the collagen molecules within the fibril structure and lower the critical concentration for self-assembly (Bulleid et al. (2000) Biochem. Socy. Transact., 28(4): 350-353) through their cross-linkable aldehydes.

Native collagen is generally present in connective tissue as telopeptide-containing collagen molecules packed side by side in the form of fibrils. Each longitudinal course is composed of molecules aligned in end-to-end dispositions with slight longitudinal spaces staggered relative to the next successive laterally adjacent longitudinal course. In this way, gaps are generated between facing end regions of successive molecules in a given longitudinal course and bound by the staggered sides of the molecules in the parallel longitudinal courses laterally adjacent thereto.

Dispersal and solubilization of native animal collagen can be achieved using various proteolytic enzymes which disrupt the intermolecular bonds and remove the immunogenic non-helical telopeptides without affecting the basic, rigid triple-helical structure which imparts the desired characteristics of collagen (see U.S. Pat. Nos. 3,934,852; 3,121,049; 3,131,130; 3,314,861; 3,530,037; 3,949,073; 4,233,360 and 4,488,911 for general methods for preparing purified soluble collagen). The resulting soluble atelocollagen can be subsequently purified by repeated precipitation at low pH and high ionic strength, followed by washing and re-solublization at low pH. Nevertheless, the soluble preparation is typically contaminated with crosslinked collagen chains which decrease the homogeneity of the protein preparation.

Due to its unique characteristics and diverse profile in human body functions, collagen has been selected from a variety of biocompatible materials for use in tissue repair to support structural integrity, induce cellular infiltration and promote tissue regeneration. Among the 5 major collagen types, Type I collagen is the most abundant form of collagen in the human body.

Type I collagen can self-assemble into a fibrillar hydrogel capable of supporting tissue cells through bioactive adhesion sites. Addition of methacrylate groups to the collagen creates collagen methacrylate (CMA), which is more resistant to degradation (Gaudet et al. Biointerphases (2012) 7:25-33). Thiolation of collagen can improve cohesion and mucoadhesion and affects swelling ability (Duggan et al., Eur. J. Pharm. Biopharm. (April 2015) 91:75-81).

Collagen's unique properties have contributed to its use in regenerative medicine products. Collagen provides biomaterials with characteristics necessary for a myriad of applications including pharmaceutical (haemostatic compresses, sponges, healing dressings), medical (prostheses such as cardiac valves, tendons and ligaments, skin substitutes, filling agents), odontological (gum implants/gum disease) and cosmetic (additive, anti-wrinkling agent, microcontainer for perfumed substances). The collagen-based products manufactured in all of the aforementioned markets require vast amounts of raw collagen materials for their production.

Human and animal-derived collagens, such as from cadaver or animal sources (bovine, porcine, or equine), and collagen-based products have been used for application, injection, implantation, and oral ingestion. Uses include pre-molding into desired shapes for repair or partial replacement of damaged bone or cartilage structures, injections into damaged joints, and injections as dermal fillers.

The use of animal-derived collagen (including human-derived collagen) is problematic due to the possible risks of contamination by non-conventional infectious agents. While the risks raised by bacterial or viral contamination can be fully controlled, prions are less containable and present considerable health risks. These infectious agents which appear to have a protein-like nature, are involved in the development of degenerative animal encephalopathy (sheep trembling disease, bovine spongiform encephalopathy) and human encephalopathy (Creutzfeld-Jacob disease, Gerstmann-Straussler syndrome, and kuru disease). Other diseases (e.g., acquired immune deficiency syndrome [AIDS], hepatitis, rabies, some cancers) may also be transmitted to the recipient. Due to the lengthy time before onset of the encephalopathies and some of the other diseases, formal controls are difficult to conduct. (See generally, Castrow et al. (1983) J. Am. Acad. Dermatol. 9(6):889-93; Siegle et al. (1984) Arch. Dermatol. 120(2):183-187.)

Moreover, in some patients, treatment with human or animal collagen triggers cellular or humoral immune responses, including allergies. In addition, the quality of the collagen generally decreases with the age of the source cadaver or organism or may decrease subject to other factors. In addition, the extraction process causes significant structural damage which compromises its biological and mechanical functions (Stein et al. (2009) Biomacromolecules 10(9):2640-2645; Shilo et al. (2013) Tissue Eng. Part A 19(13-14):1519-1526; Shoseyov et al. (2013) Tiss. Eng. Part A 19(13-14):1527).

Plants expressing collagen chains are known in the art (see, e.g., WO 2005/035442; U.S. Pat. No. 6,617,431; US Publ. 2002/0098578; US Publ. 2002/0142391; Merle et al. (2002) FEBS Letters 515: 114-118; Ruggiero et al. (Mar. 3, 2000) FEBS Lett. 469(1):132-6). Although such plants can be used to produce collagen chains as well as collagen, such chains are incorrectly hydroxylated and thus self-assembly thereof, whether in planta or not, leads to collagen which is inherently unstable. For example, although plants are capable of synthesizing hydroxyproline-containing proteins the prolyl hydroxylase that is responsible for synthesis of hydroxyproline in plant cells exhibits relatively loose substrate sequence specificity as compared with mammalian P4H and thus, production of collagen containing hydroxyproline only in the Y position of Gly-X-Y triplets requires plant co-expression of collagen and P4H genes (Olsen et al. (2003) Adv. Drug Deliv. Rev., 55(12): 1547-1567).

Processing of animal-derived "insoluble collagen" with plant-derived proteases, such as ficin and/or papain, is also known in the art (U.S. Pat. Nos. 4,597,762, 5,670,369, 5,316,942, 5,997,895 and 5,814,328).

An attempt to produce human collagens that rely on the hydroxylation machinery naturally present in plants resulted in collagen that is poor in proline hydroxylation (Merle et al. (2002) FEBS Letters 515: 114-118). Such collagen melts or loses its triple helical structure at temperatures below 30° C. Co-expression of collagen and prolyl-hydroxylase results with stable hydroxylated collagen that is biologically relevant for applications at body temperatures (Merle et al. (2002) FEBS Letters 515: 114-118).

Hydroxylysins of a human collagen expressed in tobacco form less than 2% of the hydroxylysins found in a bovine collagen (0.04% of residues/1.88% of residues). This suggests that plant endogenic Lysyl hydroxylase is unable to sufficiently hydroxylate lysines in collagen.

Recent developments in technology have resulted in the development of a system for the purification of naïve human Type I collagen (rhCollagen) (COLLPLANT™, Israel; also available at SIGMA-ALDRICH®, St. Louis, MO, USA) by introducing into tobacco plants, five human genes encoding heterotrimeric type I collagen [see, for example, Stein H. (2009) Biomacromolecules 10:2640-5; Yaari et al. (2013) Tiss. Eng. Part A 19(13/14): 1502-1506; Willard et al. (2013) Tiss. Eng. Part A 19(13/14): 1507-1518; Shilo et al. (2013) Tiss. Eng. Part A 19(13/14): 1519-1526; Shoseyov et al. (2013) Tissue Eng. Part A 19:1527-1533; and Shoseyov et al. (January/February 2014) Bioengineered 5:1, 1-4]. The protein is purified to homogeneity through a cost-effective industrial process taking advantage of collagen's unique properties. See also WO 2006/035442, WO 2009/053985, and patents and patent applications deriving therefrom, all of which are incorporated by reference as if fully set forth herein.

Compared with tissue-extracted collagen, which can become partially denatured and be stripped of cell binding domains, plant-derived human collagen Type I has a more consistent structure and a greater number of cell binding domains (Shoseyov et al. (January/February 2014) Bioengineered 5:1, 1-4; Majumdar et al. (2015) J. Biomed. Mater. Res. Part B: Appl. Biomater. 104B: 300-307). rhCollagen can form functional three-dimensional (3D) matrices and scaffolding, with applications in additive manufacturing (AM), a process in which a 3D object is manufactured in a layerwise manner utilizing a computer model of the objects, via 3D bio-printing. Moreover, rhCollagen generally lacks the immunogenicity and disease transfer problems of tissue-extracted collagen.

Methods of producing collagen in a plant by expressing at least one type of a collagen alpha chain and enabling its accumulation in a subcellular compartment devoid of endogenous P4H activity are available (U.S. Pat. No. 8,455,717), as are methods of generating atelocollagen from a non-animal cell-derived human telopeptide-comprising collagen via treatment with a protease (U.S. Pat. No. 8,759,487).

Type I collagen and rhCollagen are considered candidates for use as a major component of a building material in 3D-bioprinting. Scaffolding of various types has been used for cosmetic and other reconstructive applications.

In addition, there has been an increase in the use of dermal fillers for soft tissue augmentation, e.g., the reduction of wrinkles. One possible method for the use of dermal fillers includes injection of a polymerizable dermal filler material into the desired area, followed by the contouring or molding of the filler into the desired conformation. Polymerization and cross-linking of the material by one of various methods can transform the monomers in the injected material to form polymers and chains, which can form networks, retaining the desired molded conformation. There are a number of methods to form polymers and to crosslink polymers. One method involves light-reactive reagents and light-induced reactions which create reactive species in a monomer solution. See, e.g., U.S. Pat. Nos. 9,795,711; 8,945,624; 6,352, 710; and US Publ. 2009/0324722, as well as Elisseeff et al. (March 1999) Proc. Natl. Acad. Sci. USA 96: 3104-3107.

However, at least some of these approaches continue to focus on tissue-derived collagens or non-collagen polymers (e.g., poly(vinyl alcohol), hyaluronic acid, or polyethylene glycol). Moreover, the use of tissue extracted collagen is limited due to its sensitivity to temperature and ionic strength which drives spontaneous gel formation at temperatures higher than 20° C., under physiological conditions [see, for example, PureCol, Advanced BioMatrix, Inc.]. The typical temperature-dependent formation of gel of tissue extracted-collagens hampers significantly the precise fluidity. Keeping the collagens at low temperature until application is a possible solution for this phenomenon but implies a serious technical limitation. Another solution is the use of gelatin, the denatured form of collagen which does not become gel-like under these conditions. However, gelatin lacks the genuine tissue and cell interactions of native collagen and thus crucial biological functions are lost. Moreover, the viscosity makes it more difficult to be injected under the dermis using fine-gauge needles and also makes it more difficult to spread and mold it into smaller cavities.

Thus, there is a demand for, and it would be highly desirable and advantageous to have, improved injectable dermal fillers with tunable rheological and mechanical properties, and methods and uses thereof.

SUMMARY

Disclosed herein in one aspect is a double crosslinked dermal filler comprising:
(a) a plant-derived human collagen; and
(b) a crosslinked hyaluronic acid;
wherein the plant-derived human collagen is crosslinked to the crosslinked hyaluronic acid.

In a related aspect, the plant-derived human collagen comprises
(a) type 1 recombinant human collagen (rhCollagen); or
(b) the crosslinked hyaluronic acid comprises crosslinked and non-crosslinked hyaluronic acid; or
(c) a combination thereof.

In a related aspect, the crosslinker linking the crosslinked hyaluronic acid differs from the crosslinker linking the plant-derived human collagen with the crosslinked hyaluronic acid; or the ratio of crosslinked hyaluronic acid to the plant-derived human collagen comprises a range between 4:1 to 1:2; or a combination thereof. In a further related aspect, the crosslinker crosslinking hyaluronic acid and the crosslinker crosslinking the plant-derived human collagen are independently selected from 1, 4-butanediol diglycidyl ether (BBDE), 1-[3-(Dimethylamino)propyl]-3-ethylcarbodiimide methiodide (EDC), N,N'-dicyclohexylcarbodiimide (DCC), N,N'-diisopropylcarbodiimide (DIC).

Disclosed herein in one aspect, is a method of preparing a double crosslinked dermal filler comprising plant-derived human collagen crosslinked to crosslinked hyaluronic acid, comprising the steps of
(a) crosslinking hyaluronic acid;
(b) neutralizing the crosslinked hyaluronic acid;
(c) neutralizing the plant-derived human collagen;
(d) mixing the neutralized crosslinked hyaluronic acid with the neutralized plant-derived human collagen;
(e) addition of lower molecular weight hyaluronic acid (MW HA);
(f) crosslinking the mix of crosslinked hyaluronic acid and plant-derived human collagen; and
(g) dialyzing double crosslinked crosslinked hyaluronic acid-plant-derived human collagen dermal filler.

In a related aspect, the plant-derived human collagen comprises type 1 recombinant human collagen (rhCollagen); or the crosslinker linking the crosslinked hyaluronic acid of step (a_ differs from the crosslinker linking the plant-derived human collagen with the crosslinked hyaluronic acid of step (e); or a combination thereof. In a related aspect, the ratio of crosslinked hyaluronic acid to the plant-derived human collagen comprises a range between 4:1 to 1:2; or the crosslinker crosslinking hyaluronic acid and the crosslinker crosslinking the plant-derived human collagen are independently selected from 1, 4-butanediol diglycidyl ether (BBDE), 1-[3-(Dimethylamino)propyl]-3-ethylcarbodiimide methiodide (EDC), N,N'-dicyclohexylcarbodiimide (DCC), N,N'-diisopropylcarbodiimide (DIC); or a combination thereof.

In addition, disclosed herein in one aspect, is a method of filling a tissue space under an epidermis comprising:
(a) introducing a polymerizable solution into the tissue space, wherein the polymerizable solution comprises:
(i) a cross-linkable, plant-derived human collagen;
(ii) a hyaluronic acid (HA) or modified derivative thereof, a poly(vinyl alcohol) (PVA) or modified derivative thereof, a polyethylene glycol (PEG) or modified derivative thereof, oxidized cellulose (OC) or a modified derivate thereof, polymethylmethacrylate (PMMA) microspheres or a modified derivative thereof, tricalcium phosphate (TCP) or a modified derivative thereof, calcium hydroxylapatite (CaHA) or a modified derivative thereof, carboxymethylcellulose or a modified derivative thereof, crystalline nanocellulose (CNC) or a modified derivative thereof, or a combination thereof; and
(iii) a photoinitiator; and
(b) applying light to the surface of the epidermis superficial to said space to induce polymerization.

In a related aspect, the polymerizable solution components are introduced into the tissue space independently at about the same location and about the same time, wherein the cross-linkable, plant-derived human collagen and the photoinitiator are introduced together and independently from said hyaluronic acid (HA) or modified derivative thereof, said poly(vinyl alcohol) (PVA) or modified derivative thereof, said polyethylene glycol (PEG) or modified derivative thereof, oxidized cellulose (OC) or said modified derivate thereof, polymethylmethacrylate (PMMA) microspheres or said modified derivative thereof, tricalcium phosphate (TCP) or said modified derivative thereof, calcium hydroxylapatite (CaHA) or said modified derivative thereof, carboxymethylcellulose or said modified derivative thereof, crystalline nanocellulose (CNC) or said modified derivative thereof, or said combination thereof, are introduced into the tissue space independently at about the same time. In another related aspect, the method further includes a step of molding or sculpting the polymerizable solution or the components of the polymerizable solution, into a desired configuration in the tissue space, wherein said step is concomitant with, or subsequent to, the step of applying light.

In another related aspect, the polymerizable solution components are introduced into the tissue space together as a mixture, wherein the cross-linkable, plant-derived human collagen and the photoinitiator are introduced together with said hyaluronic acid (HA) or modified derivative thereof, or said poly(vinyl alcohol) (PVA) or modified derivative thereof, or said polyethylene glycol (PEG) or modified derivative thereof, or said oxidized cellulose (OC) or said modified derivate thereof, or said polymethylmethacrylate (PMMA) microspheres or said modified derivative thereof, or said tricalcium phosphate (TCP) or said modified derivative thereof, or said calcium hydroxylapatite (CaHA) or said modified derivative thereof, or said carboxymethylcellulose or said modified derivative thereof, or said crystalline nanocellulose (CNC) or said modified derivative thereof, or a combination thereof.

In another related aspect, the polymerizable solution components are introduced into the tissue space independent from one another, wherein the cross-linkable, plant-derived human collagen and the photoinitiator are introduced together and independently from said hyaluronic acid (HA) or modified derivative thereof, or said poly(vinyl alcohol)

(PVA) or modified derivative thereof, or said polyethylene glycol (PEG) or modified derivative thereof, or said oxidized cellulose (OC) or said modified derivate thereof, or said polymethylmethacrylate (PMMA) microspheres or said modified derivative thereof, or said tricalcium phosphate (TCP) or said modified derivative thereof, or said calcium hydroxylapatite (CaHA) or said modified derivative thereof, or said carboxymethylcellulose or said modified derivative thereof, or said crystalline nanocellulose (CNC) or said modified derivative thereof, or said combination thereof.

In another related aspect, following introduction into the tissue space, the method further includes a step of molding or sculpting the polymerizable solution or the components of the polymerizable solution, into a desired configuration in the tissue space, wherein said step is concomitant with, or subsequent to, the step of applying light.

In another related aspect, the method is non-therapeutic, and the molding or sculpting step reduces lines, folds, fine lines, wrinkles, or scars, or a combination thereof.

In another related aspect,
(a) the cross-linkable, plant-derived human collagen is methacrylated or thiolated type 1 human recombinant collagen (rhcollagen); or
(b) the modified derivative of hyaluronic acid (HA), poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, or crystalline nanocellulose (CNC) comprises a methacrylated or thiolated derivative; or
(c) the hyaluronic acid (HA), poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, or crystalline nanocellulose (CNC) comprises a crosslinked hyaluronic acid (HA), crosslinked poly(vinyl alcohol) (PVA), crosslinked polyethylene glycol (PEG), crosslinked oxidized cellulose (OC), crosslinked polymethylmethacrylate (PMMA) microspheres, crosslinked tricalcium phosphate (TCP), crosslinked calcium hydroxylapatite (CaHA), crosslinked carboxymethylcellulose, or crosslinked crystalline nanocellulose (CNC); or
(d) a combination of (a) and (b), or (a) and (c).

In a further related aspect, when MA-rhCollagen is selected, and hyaluronic acid or a derivative thereof, or crosslinked hyaluronic acid is selected, the ratio of HA to MA-rhCollagen is 1:1, 2:1, 3:1, 4:1, 5:1, 6:1, 1:2, 1:3, 1:4, 1:5, 1:6, or 0:1.

Disclosed herein, in one aspect is a method of filling a tissue space under an epidermis comprising introducing a double crosslinked dermal filler into the tissue space, wherein the double crosslinked dermal filler comprises:
(a) a plant-derived human collagen; and
(b) a crosslinked hyaluronic acid (HA) or modified crosslinked derivative thereof, a crosslinked poly(vinyl alcohol) (PVA) or modified crosslinked derivative thereof, a crosslinked polyethylene glycol (PEG) or modified crosslinked derivative thereof, crosslinked oxidized cellulose (OC) or a modified crosslinked derivate thereof, crosslinked polymethylmethacrylate (PMMA) microspheres or a modified crosslinked derivative thereof, crosslinked tricalcium phosphate (TCP) or a modified crosslinked derivative thereof, crosslinked calcium hydroxylapatite (CaHA) or a modified crosslinked derivative thereof, crosslinked carboxymethylcellulose or a modified crosslinked derivative thereof, crosslinked crystalline nanocellulose (CNC) or a modified crosslinked derivative thereof, or a combination thereof;

wherein the plant-derive human collagen is crosslinked to the crosslinked crosslinked hyaluronic acid (HA) or modified crosslinked derivative thereof, a crosslinked poly(vinyl alcohol) (PVA) or modified crosslinked derivative thereof, a crosslinked polyethylene glycol (PEG) or modified crosslinked derivative thereof, crosslinked oxidized cellulose (OC) or a modified crosslinked derivate thereof, crosslinked polymethylmethacrylate (PMMA) microspheres or a modified crosslinked derivative thereof, crosslinked tricalcium phosphate (TCP) or a modified crosslinked derivative thereof, crosslinked calcium hydroxylapatite (CaHA) or a modified crosslinked derivative thereof, crosslinked carboxymethylcellulose or a modified crosslinked derivative thereof, crosslinked crystalline nanocellulose (CNC) or a modified crosslinked derivative thereof.

In a related aspect, the plant-derived human collagen is type 1 human recombinant collagen (rhcollagen), or an MA or Thiolated derivative thereof; or the modified derivative of hyaluronic acid (HA), poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, or crystalline nanocellulose (CNC) comprises a methacrylated or thiolated derivative; or a combination thereof.

In another related aspect, when crosslinked HA is selected, the ratio of crosslinked HA to the plant-derived human collagen is 1:1, 2:1, 3:1, 4:1, 5:1, 6:1, 1:2, 1:3, 1:4, 1:5, 1:6, or 0:1.

In a related aspect, the method is non-therapeutic, and reduces lines, folds, fine lines, wrinkles, or scars, or a combination thereof.

Disclosed herein in one aspect, is a polymerizable or non-polymerizable solution for use for tissue augmentation, wherein
(a) the polymerizable solution comprises a cross-linkable, plant-derived human collagen and a photoinitiator to induce polymerization prior to, on concomitant with, application of visible light, or
(b) the non-polymerizable solution comprises a double crosslinked dermal filler comprising a plant-derived human collagen, and a crosslinked hyaluronic acid or a crosslinked PVA, or a crosslinked PGE, or a crosslinked OC, wherein the plant-derived human collagen is crosslinked to the crosslinked hyaluronic acid or crosslinked PVA, or a crosslinked PGE, or a crosslinked OC;
and said use comprises injecting said polymerizable or non-polymerizable solution into a tissue space under an epidermis, followed by molding or sculpting the polymerizable or non-polymerizable solution into a desired configuration to reduce lines, folds, fine lines, wrinkles, or scars.

In a related aspect, the cross-linkable, plant-derived human collagen is methacrylated or thiolated; or the polymerizable solution further comprises a hyaluronic acid (HA) or a modified derivative thereof or a photopolymerizable modified derivative thereof, a poly(vinyl alcohol) (PVA) or a modified derivative thereof or a photopolymerizable modified derivative thereof, a polyethylene glycol (PEG) or a modified derivative thereof or a photopolymerizable modified derivative thereof, polymethylmethacrylate (PMMA) microspheres or a modified derivative thereof or a photopolymerizable modified derivative thereof, tricalcium phosphate (TCP) or a modified derivative thereof or a photopolymerizable modified derivative thereof, calcium a hydroxylapatite (CaHA) or a modified derivative thereof or a photopolymerizable modified derivative thereof, a carboxymethylcellulose or a modified derivative thereof or a photopolymerizable modified derivative thereof, a crystalline nanocellulose (CNC) or a modified derivative thereof or a photopolymerizable modified derivative thereof, or a combination thereof, wherein optionally the derivative thereof comprises a methacrylated or thiolated derivative; or a combination thereof.

In another related aspect, the tissue augmentation is required as a result of any medical or dental (gum implants/gum disease) condition. In a further related aspect, the tissue augmentation reduces lines, folds, fine lines, wrinkles, or scars, or a combination thereof.

Disclosed herein in one aspect, is a method of inducing a cellular growth promoting scaffold in a tissue space under an epidermis comprising introducing a solution into the tissue space, the solution comprising:
(a) a plant-derived human collagen; and
(b) at least one growth factor or source thereof;
wherein said method promotes healing or replacement of a collagen-comprising tissue.

In a related aspect, the plant-derived collagen comprises type 1 recombinant human collagen (rhCollagen); or the source of the at least one growth factor comprises a plasma or a platelet-rich plasma; or the collagen-comprising tissue comprises skin; or any combination thereof.

In another aspect, the method is non-therapeutic and the cellular growth promoting scaffold fills in tissue space reducing lines, folds, fine lines, wrinkles, or scars, or a combination thereof.

Disclosed herein in one aspect, is a solution for use inducing a cellular growth promoting scaffold, the solution comprising a plant-derived human collagen and at least one growth factor or source thereof, wherein the use comprises injecting said solution into a tissue space under an epidermis and wherein said use is for promoting healing or replacement due to degradation or injury of a collagen-comprising skin tissue.

In a related aspect, the plant-derived collagen comprises type 1 recombinant human collagen (rhCollagen); or the source of the at least one growth factor comprises a plasma or a platelet-rich plasma; or the collagen-comprising tissue comprises skin; or any combination thereof.

In another related aspect, the rhCollagen comprises a methacrylate or thiol derivative thereof.

In a related aspect, the solution used in the method further comprises a hyaluronic acid (HA) or modified derivative thereof, a poly(vinyl alcohol) (PVA) or modified derivative thereof, a polyethylene glycol (PEG) or modified derivative thereof, oxidized cellulose (OC) or a modified derivate thereof, polymethylmethacrylate (PMMA) microspheres or a modified derivative thereof, tricalcium phosphate (TCP) or a modified derivative thereof, calcium hydroxylapatite (CaHA) or a modified derivative thereof, carboxymethylcellulose or a modified derivative thereof, crystalline nanocellulose (CNC) or a modified derivative thereof, or a combination thereof, and a photoinitiator to induce polymerization prior to, on concomitant with, application of visible light; or a crosslinked hyaluronic acid or a crosslinked PVA, or a crosslinked PGE, or a crosslinked OC, wherein the plant-derived human collagen is crosslinked to the crosslinked hyaluronic acid or crosslinked PVA, or a crosslinked PGE, or a crosslinked OC.

In a related aspect, the method is non-therapeutic and the cellular growth promoting scaffold fills in tissue space reducing lines, folds, fine lines, wrinkles, or scars, or a combination thereof.

Disclosed herein is a solution for use inducing a cellular growth promoting scaffold, the solution comprising a plant-derived human collagen and at least one growth factor or source thereof, wherein the use comprises injecting said solution into a tissue space under an epidermis and wherein said use is for promoting healing or replacement due to degradation or injury of a collagen-comprising tissue.

In a related aspect, the source of the at least one growth factor comprises a plasma or a platelet-rich plasma; or the plant-derived collagen comprises type 1 recombinant human collagen (rhCollagen); or the collagen-comprising tissue comprises skin; or a combination thereof.

In another related aspect, the solution for use further comprises a hyaluronic acid (HA) or modified derivative thereof, a poly(vinyl alcohol) (PVA) or modified derivative thereof, a polyethylene glycol (PEG) or modified derivative thereof, oxidized cellulose (OC) or a modified derivate thereof, polymethylmethacrylate (PMMA) microspheres or a modified derivative thereof, tricalcium phosphate (TCP) or a modified derivative thereof, calcium hydroxylapatite (CaHA) or a modified derivative thereof, carboxymethylcellulose or a modified derivative thereof, crystalline nanocellulose (CNC) or a modified derivative thereof, or a combination thereof, and a photoinitiator to induce polymerization prior to, on concomitant with, application of visible light; or a crosslinked hyaluronic acid or a crosslinked PVA, or a crosslinked PGE, or a crosslinked OC, wherein the plant-derived human collagen is crosslinked to the crosslinked hyaluronic acid or crosslinked PVA, or a crosslinked PGE, or a crosslinked OC.

Disclosed herein in one aspect, is a method of filling a tissue space under an epidermis comprising: (a) introducing a polymerizable solution into the tissue space, wherein the polymerizable solution comprises: (i) a cross-linkable, plant-derived human collagen; and (ii) a photoinitiator; and applying light to the surface of the epidermis superficial to said space to induce polymerization.

In a related aspect, the polymerizable solution further includes a step of molding or sculpting the polymerizable solution into a desired configuration in the tissue space, wherein said step is concomitant with, or subsequent to, the step of applying light.

In another related aspect, the method is non-therapeutic, and the molding or sculpting step reduces lines, folds, fine lines, wrinkles, or scars, or a combination thereof.

In another related aspect, the cross-linkable, plant-derived human collagen is methacrylated or thiolated type 1 human recombinant collagen (rhcollagen).

Other objects, features and advantages of the present invention will become clear from the following description and drawings.

BRIEF DESCRIPTION OF THE DRAWINGS

FIG. 1a shows a cloning scheme of type I collagen alpha I chain or type II collagen alpha 2 chain into a plant expression vector in accordance with some embodiments of the present invention; FIG. 1B shows a cloning scheme of the enzyme prolyl-4-hydroxylase (P4H) into a plant expression vector in accordance with some embodiments of the present invention; FIG. 1c shows a cloning scheme proteinase C or proteinase N into a plant expression vector in accordance with some embodiments of the present invention; FIG. 1d shows a cloning scheme of Lysyl hydroxylase 3 (LH3) into a plant expression vector in accordance with some embodiments of the present invention.

FIG. 2 illustrates various co-transformations approaches used previously. Each expression cassette is represented by the short name of the coding sequence. The coding sequences are specified in Table 1. Each co-transformation was performed by two pBINPLUS binary vectors. Each rectangle represents a single pBINPLUS vector carrying one, two or three expression cassettes. Promoter and terminators are specified in Example 1.

FIGS. 6a and 6b illustrate collagen triple helix assembly and thermal stability as qualified previously by heat treatment and Trypsin or Pepsin digestion. In FIG. 6a, total soluble protein from tobacco 2-9 (expressing only col alpha1 and no P4H) and 3-5 (expressing both col alpha 1+2 and human P4H alpha and beta subunits) were subjected to heat treatment (15 minutes in 38° C. or 43° C.) followed by Trypsin digestion (20 minutes at room temperature [RT]) and tested with anti-Collagen I antibody in a Western blot procedure. Positive controls were samples of 500 ng human collagen I+total soluble proteins of w.t. tobacco. In FIG. 6b, total soluble proteins were extracted from transgenic tobacco 13-6 (expressing collagen I alpha 1 and alpha 2 chains—pointed by arrows, human P4H alpha and beta subunits and human LH3) and subjected to heat treatment (20 minutes in 33° C., 38° C., or 42° C.), immediately cooled on ice to prevent reassembly of triple helix and incubated with pepsin for 30 minutes in room temperature (about 22° C.) followed by testing with anti-Collagen I antibody ((#AB745 from Chemicon Inc.) in a standard Western blot procedure. Positive control was sample of 50 ng human collagen I (#CC050 from Chemicon Inc., extracted from human placenta by pepsin digestion) which was added to total soluble proteins extracted from wild-type (w.t., wt) tobacco.

FIG. 7 illustrates previous Northern blot analysis conducted on wild type tobacco. Blots were probed with tobacco P4H cDNA.

FIG. 8 is a previous Western blot analysis of transgenic plants generated by co-transformations 2, 3 and 13. Total soluble protein was extracted from tobacco co-transformants and tested with anti-human P4H alpha and beta and anti-Collagen I antibodies.

FIG. 9 is a previous Western blot analysis of (lane 1) cross breeding vacuolar targeted plants A (2-300+20-279) grown under normal light regimen; and 13-652 vacuolar targeted plants grown for 8 days in the dark. All plants express exogenous col1, col2, P4H-alpha and P4H-beta as well as LH3 (PCR validated).

FIG. 33A shows the upstream isolation and processing of procollagen and collagen (steps A-H). FIGS. 33B-33C show two phases of downstream processing (respectively, steps I-M and steps N-P & Z).

FIGS. 43A-43C show histopathological scoring of Achilles tendons in a rat model of tendinopathy treated with PRP or rhCollagen/PRP matrix. (A) Mature fibrosis, (B) presence of mononuclear inflammatory cells and (C) presence of immature granulation tissue.

FIG. 56 presents representative histology images at day 7 following subcutaneous injection of Formulations 2, 2A, and control (commercially available dermal filler) into the back of Sprague Dawley rats. In each case, the arrow points to an enhanced inflammation reaction in Formulations 2 and 2A (not severe) indicating initiation of tissue regeneration.

DETAILED DESCRIPTION

Figure 1A:
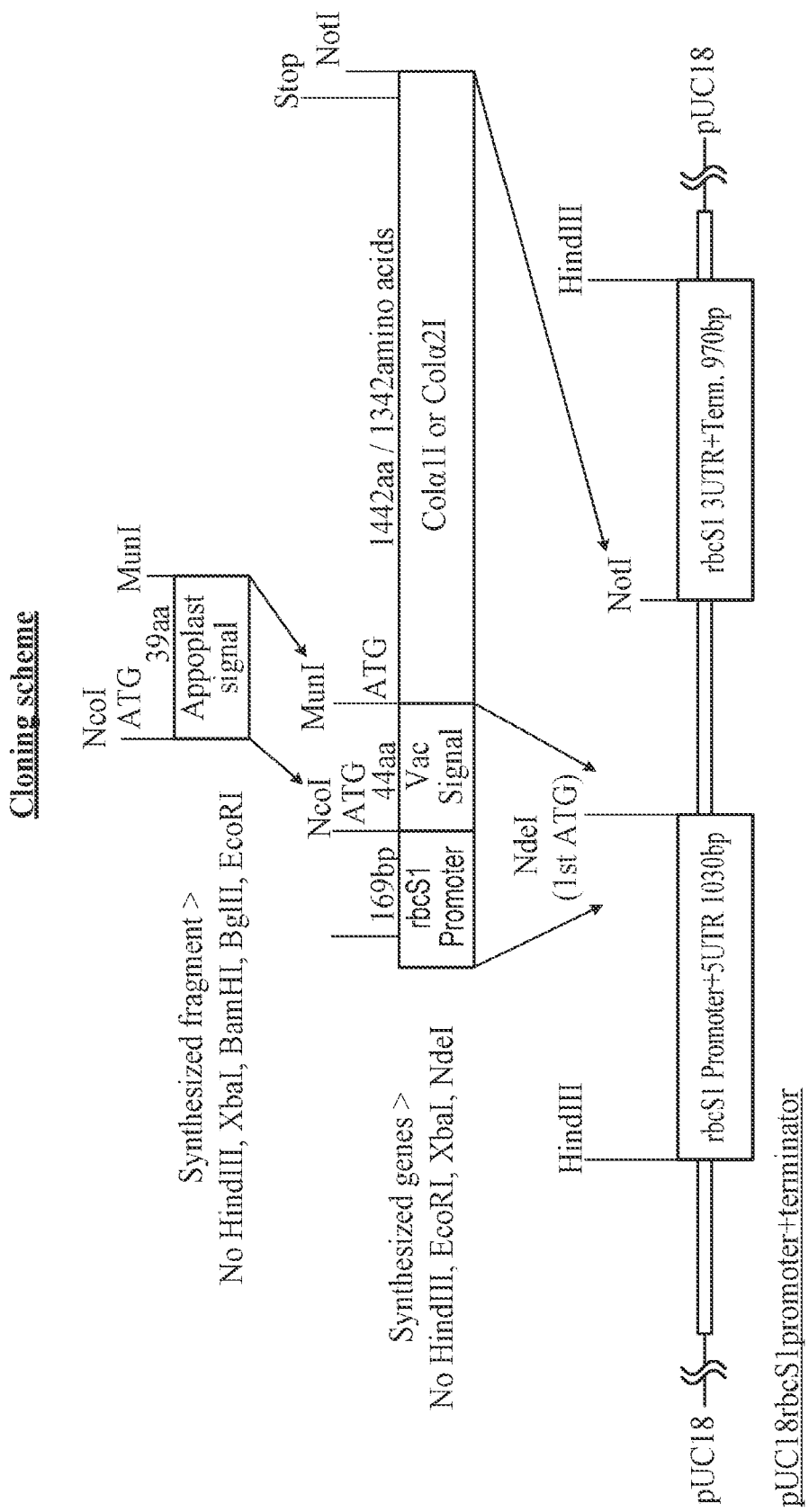
FIGS. 1a-1d illustrate construction of various expression cassettes and vectors previously used to transform test plants. All of the coding sequences synthesized as a part of the study were optimized for expression in tobacco.

Disclosed herein are photoinitiated dermal fillers and double crosslinked dermal fillers, and cellular growth promoting scaffolds, and methods of using the same, for example but not limited to, for soft tissue augmentation.

Collagen-producing plants can be used to produce collagen chains as well as collagen, but such chains are incorrectly hydroxylated and thus self-assembly thereof, whether in planta or not, leads to collagen which is inherently unstable in contrast to the plant-derived human collagen of the present application.

While reducing the present polymerizable and double crosslinked solutions, and methods of use, to practice, the practitioners have devised a plant expression approach which ensures correct hydroxylation of collagen chains and thus enables in-planta production of collagen which closely mimics the characteristics (e.g. molecular structure, temperature stability, cellular interactions) of human type I collagen.

In one aspect, disclosed herein is a method of filling a tissue space under an epidermis comprising:
(a) introducing a polymerizable solution into the tissue space, the polymerizable solution comprising:
  (i) a cross-linkable, plant-derived human collagen; and
  (ii) a photoinitiator; and
(b) applying light to the surface of the epidermis superficial to said space to induce polymerization.

In a particular embodiment, the method further comprises, prior to, or concomitant with, the step of applying light, molding or sculpting the polymerizable solution into a desired configuration in the tissue space. In another particular embodiment, the molding or sculpting step reduces lines, folds, fine lines, wrinkles, or scars.

In yet another particular embodiment, the polymer solution further comprises a filler comprising a hyaluronic acid (HA) or a modified derivative thereof, a poly(vinyl alcohol) (PVA) or a modified derivative thereof, polyethylene glycol (PEG) or a modified derivative thereof, oxidized cellulose (OC) or a modified derivative thereof, or a combination thereof. In one particular embodiment, the isolated plant-derived human collagen is optionally formulated, such as with hyaluronic acid (HA), poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, crystalline nanocellulose (CNC) or a combination thereof.

Modified derivatives include, but are not limited to, photopolymerizable versions of, e.g., HA, PVA, PEG, or OC. Modifications include, but are not limited to, methacrylation or thiolation. In yet another particular embodiment, the light source is selected from light-emitting diode (LED), laser, xenon lamp, and the like.

In some embodiments, in formulations disclosed herein methacrylate rhCollagen crosslinks under illumination conditions only to itself. In some embodiments, in formulations disclosed herein methacrylate rhCollagen crosslinks under illumination conditions to thiolated rhCollagen. In some embodiments, in formulations disclosed herein methacrylate rhCollagen crosslinks under illumination conditions to any MA/thiolated additive. In some embodiments, in formulations disclosed herein methacrylate rhCollagen crosslinks under illumination conditions to methacrylated HA. In some embodiments, in formulations disclosed herein methacrylate rhCollagen crosslinks under illumination conditions to thiolated HA. In some embodiments, in formulations disclosed herein methacrylate rhCollagen crosslinks under illumination conditions to methacrylated PVA. In some embodiments, in formulations disclosed herein methacrylate rhCollagen crosslinks under illumination conditions to thiolated PVA. In some embodiments, in formulations disclosed herein methacrylate rhCollagen crosslinks under illumination conditions to methacrylated PEG. In some embodiments, in formulations disclosed herein methacrylate rhCollagen crosslinks under illumination conditions to thiolated PEG. In some embodiments, in formulations disclosed herein methacrylate rhCollagen crosslinks under illumination conditions to methacrylated OC. In some embodiments, in formulations disclosed herein methacrylate rhCollagen crosslinks under illumination conditions to thiolated OC.

A skilled artisan would appreciate that a photocurable formulation is actually a semi IPN before curing and becomes an IPN (interpenetrated network) after curing. An IPN may encompass two entangled networks, each one crosslinked to itself and not crosslinked to the other.

In some embodiments, crosslinked formulation includes a ratio of non-modified rhCollagen to tune the stiffness following crosslinking (with light) without reducing the final total amount of rhCollagen, as non modified rhCollagen cannot crosslink under illumination, therefore does not enhance the final stiffness. Methacrylated HA may also be added to this final formulation.

Figure 49:
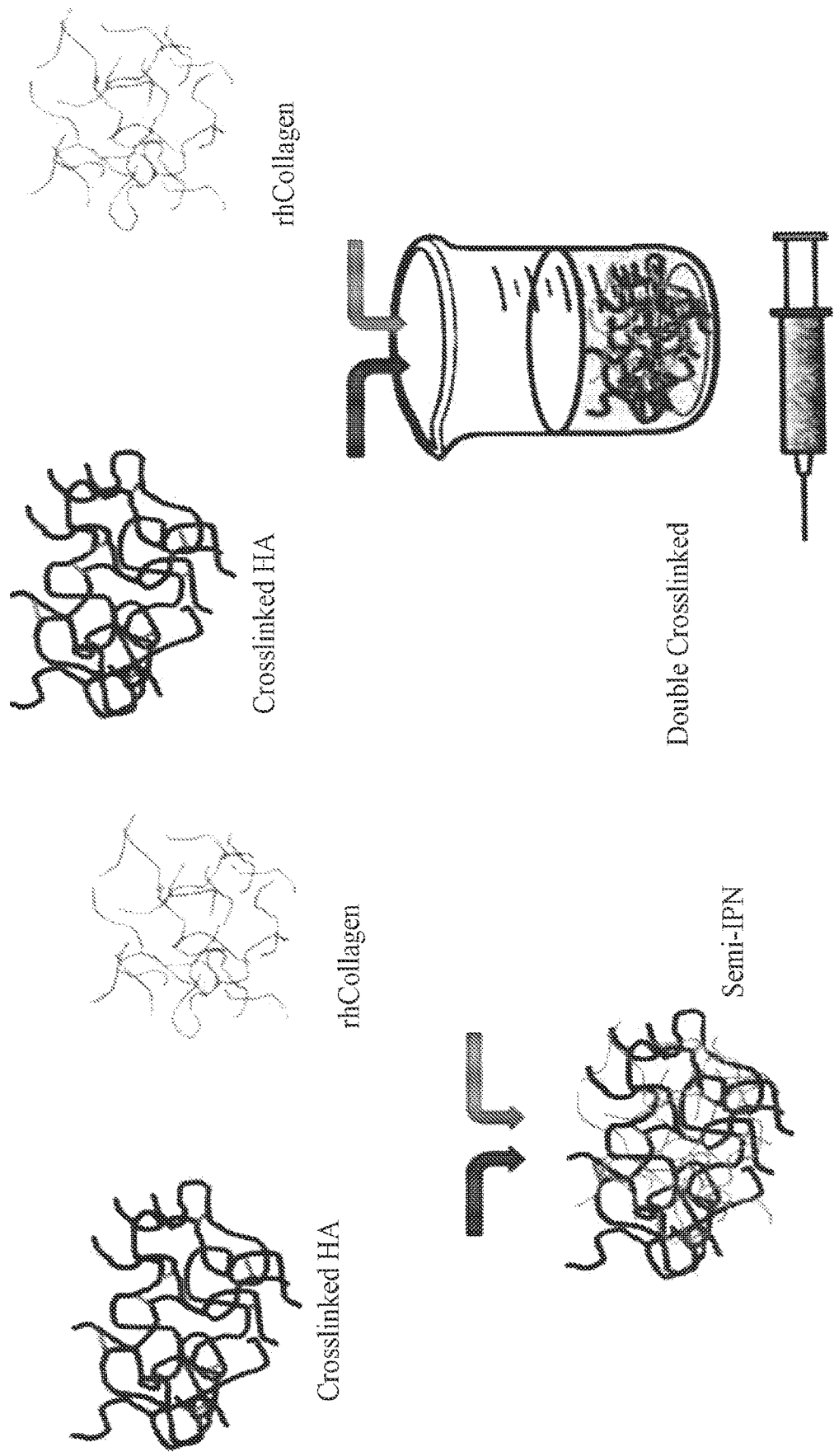
FIG. 49 shows two examples of Dermal Filler components. On the left-side is a schematic of a semi-interpenetrated dermal filler comprising crosslinked hyaluronic acid (HA) and rhCollagen. On the right-side is a schematic of the double crosslinked dermal filler comprising crosslinked hyaluronic acid and rhCollagen, wherein the crosslinked HA is further crosslinked to the rhCollagen. Light grey bars indicate the HA-crosslinker, blackstrands represent the HA, the rhcollagen is represented as thin grey strands, and the second crosslinker, cross linking crosslinked HA with rhCollagen, as black circles.

In some embodiments, the HA or MA-HA may be crossedlinked to itself using a crosslinker, for example but not limited to BDDE, as described in Example 23. In some embodiments, the crosslinker crosslinking HA or MA-HA comprises Divinyl Sulfone (DVS) or glutaraldehyde. In certain embodiments, the BDDE crosslinked HA or MA-HA is not further crosslinked to rhCollagen or MA-rhCollagen, creating what is called an interpenetrated network (FIG. 49 left-hand side).

In still another particular embodiment, the plant-derived collagen comprises rhCollagen. In another particular embodiment, the plant-derived collagen is obtained from a genetically modified plant. In another particular embodiment, the genetically modified plant is a genetically modified plant selected from the group consisting of tobacco, maize, alfalfa, rice, potato, soybean, tomato, wheat, barley, canola, carrot, and cotton. In particular, the genetically modified plant is a tobacco plant.

In still another particular embodiment, the genetically modified plant comprises an expressible sequence of at least one gene sequence of human deoxyribonucleic acid (DNA) selected from the group consisting of: COL1, COL2, P4H-alpha, P4H-beta, and LH3. In another particular embodiment, the plant-derived human collagen comprises at least modified one human collagen alpha-1 chain as set forth in SEQ ID NO: 3 and as expressed in the genetically modified plant; and at least one modified human collagen alpha-2 chain as set forth in SEQ ID NO: 6 and as expressed in the same genetically modified plant; and wherein the genetically modified plant further expresses an exogenous prolyl-4-hydroxylase (P4H). In another particular embodiment, the method further comprises expressing an exogenous polypeptide selected from the group consisting of lysyl hydroxylase (LH), protease N, and protease C. In yet another particular embodiment, the human collagen alpha-1 chain is encoded by a sequence as set forth in SEQ ID NO: 1. In another particular embodiment, the human collagen alpha-2 chain is encoded by a sequence as set further in SEQ ID NO: 4.

In still another embodiment, the exogenous P4H is a mammalian P4H. In particular, the exogenous P4H is a human P4H. In yet another embodiment, the method further comprises targeting the human collagen alpha-1 to a vacuole of the plant or the genetically modified plant and digesting it with ficin. In yet another embodiment, the method further comprises targeting the human collagen alpha-2 to a vacuole of the plant or the genetically modified plant and digesting it with ficin.

In still another embodiment, the plant-derived human collagen is atelocollagen. In another embodiment, the plant-derived human collagen is atelocollagen having an amino acid (AA) sequence derived from SEQ ID NO: 1 and SEQ ID NO: 4. Atelocollagen is derived by enzymatic digestion (e.g., with ficin) of procollagen, which is the product of SEQ ID NO: 1 and SEQ ID NO: 4.

In yet another embodiment, the photoinitiator induces polymerization of the polymerizable solution in response to visible light. In particular, the visible light has a wavelength of 390-800 nm. In particular, the photoinitiator is selected from the group consisting of Eosyn Y+triethanolamine, riboflavin, and the like.

In another embodiment, the photoinitiator induces polymerization of the polymerizable solution in response to ultraviolet (uv) light. In particular, the photoinitiator is selected from the group consisting of lithium phenyl-2,4,6-trimethylbenzoylphosphinate (LAP) or 1-[4 2-hydroxy-1-[4-(2-hydroxyethoxy)phenyl]-2-methylpropan-1-one (IRGACURE® 2959).

In another embodiment, the photoinitiator induces polymerization of the polymerizable solution in response to infrared light.

In still another embodiment, the polymerizable solution is introduced into the tissue space via a hollow needle or cannula in the range of 27 gauge to 33 gauge.

In still another embodiment, the polymerizable solution in the tissue space is molded or sculpted into the desired configuration via manual massage. In another embodiment, the polymerizable solution in the tissue space is molded or sculpted into the desired configuration using a molding or sculpting implement.

In still another embodiment, the polymerizable solution in the tissue space is essentially non-gellable at room temperature. In another embodiment, the polymerizable solution in the tissue space is essentially non-gellable at 37° C. In yet another embodiment, the polymerizable solution comprising the plant-derived human collagen has a reduced viscosity at room temperature in comparison with an analogous polymerizable solution comprising a tissue-extracted human or animal-derived collagen, for example but not limited to bovine or procine or equine collagen in the same concentration and formulation. In another embodiment, the polymerizable solution comprising the plant-derived human collagen has a reduced viscosity at 37° C. in comparison with an analogous polymerizable solution comprising a tissue-extracted human or animal-derived collagen in the same concentration and formulation.

As used throughout, the term "animal-derived collagen" may encompass bovine or procine or equine collagen or rat tail collagen and is in contrast to human derived collagen.

In still another embodiment, the polymerizable solution comprising the plant-derived human collagen is introduced into the tissue space with a reduced force at room temperature as compared with an analogous polymerizable solution comprising a tissue-extracted human or animal-derived collagen in the same concentration and formulation. In still another embodiment, the polymerizable solution comprising the plant-derived human collagen is introduced into the tissue space with a reduced force at 37° C. as compared with an analogous polymerizable solution comprising a tissued-extracted human or animal-derived collagen in the same concentration and formulation.

In another aspect, disclosed herein is a use of a polymerizable solution injected into a tissue space under an epidermis to reduce lines, folds, fine lines, wrinkles, or scars, the polymerizable solution comprising a methacrylated or thiolated cross-linkable, plant-derived human collagen and a photoinitiator to induce polymerization prior to, on concomitant with, application of visible light, and molding or sculpting the polymerizable solution into a desired configuration to reduce lines, folds, fine lines, wrinkles, or scars. In a particular embodiment, the polymer solution further comprises a filler comprising a hyaluronic acid (HA) or a modified derivative thereof, a poly(vinyl alcohol) (PVA) or a modified derivative thereof, polyethylene glycol (PEG) or a modified derivative thereof, oxidized cellulose (OC) or a modified derivative thereof, polymethylmethacrylate (PMMA) microspheres or a modified derivative thereof, tricalcium phosphate (TCP) or a modified derivative thereof, calcium hydroxylapatite (CaHA) or a modified derivative thereof, carboxymethylcellulose or a modified derivative thereof, crystalline nanocellulose (CNC) or a modified derivative thereof, or a combination of any of these.

Modified derivatives include, but are not limited to, photopolymerizable versions of, e.g., HA, PVA, PEG, OC, PMMA, TCP, CaHA, carboxymethylcellulose, or CNC. Modifications include, but are not limited to, methacrylation or thiolation.

In another aspect, disclosed herein is a method of filling a tissue space under an epidermis comprising:
  (a) introducing a polymerizable solution into the tissue space, the polymerizable solution comprising a cross-linkable, plant-derived human collagen.

The instant technology relates, in part, to cosmetic and medical collagen-based polymerizable fillers that form a moldable composition, polymerizable on photoactivation with a light source, such as a visible light source. The polymerizable filler comprises a cross-linkable, plant-derived human collagen along with a photoinitiator.

The present technology of interest has the advantage of permitting in situ formation of a custom, contoured dermal filler or implant, typically without invasive surgical intervention or general anesthesia. Generally, the collagen-based polymerizable solution is introduced into a tissue space under the skin (that is, under the epidermis), and polymerization is induced by exposure to visible light applied to the skin surface, that is, from outside of the body or outside of the skin, or to the epidermis.

The in situ polymerization methods provide cosmetic and medical corrective and/or enhancement procedures using a polymerizable solution comprising a polymer component capable of forming an insoluble crosslinked crosslinking network on activation with a visible light source.

In some embodiments, a dermal filler or cellular growth promoting scaffold disclosed herein is for cosmetic use. In some embodiments, a dermal filler or cellular growth promoting scaffold disclosed herein is for medical corrective use. In some embodiments, a dermal filler or cellular growth promoting scaffold disclosed herein is for use in an enhancement procedure, for example but not limited to tissue augmentation. In some embodiments, a double crosslinked dermal filler disclosed herein is for cosmetic use. In some embodiments, a double crosslinked dermal filler disclosed herein is for medical corrective use. In some embodiments, a double crosslinked dermal filler disclosed herein is required as a result of a medical or or dental (gum implants/gum disease) condition. In some embodiments, a double crosslinked dermal filler disclosed herein is required as a result of a medical condition requiring skin augmentation. In some embodiments, a double crosslinked dermal filler disclosed herein is for use in an enhancement procedure, for example but not limited to tissue augmentation. In some embodiments, a photocurable dermal filler disclosed herein is for cosmetic use. In some embodiments, a photocurable dermal filler disclosed herein is for medical corrective use. In some embodiments, a photocurable dermal filler disclosed herein is required as a result of a medical or or dental (gum implants/gum disease) condition. In some embodiments, a photocurable dermal filler disclosed herein is required as a result of a medical condition requiring skin augmentation. In some embodiments, a photocurable dermal filler disclosed herein is for use in an enhancement procedure, for example but not limited to tissue augmentation. In some embodiments, a cellular growth promoting scaffold disclosed herein is for cosmetic use. In some embodiments, a cellular growth promoting scaffold disclosed herein is for medical corrective use. In some embodiments, a cellular growth promoting scaffold dermal filler disclosed herein is required as a result of a medical or or dental (gum implants/gum disease) condition. In some embodiments, a cellular growth promoting scaffold dermal filler disclosed herein is required as a result of a medical condition requiring skin augmentation. In some embodiments, medical corrective use includes treating tendinitis. In some embodiments, a cellular growth promoting scaffold disclosed herein is for use in an enhancement procedure, for example but not limited to tissue augmentation.

In some embodiments, tissue augmentation is of a skin tissue.

In some embodiments, use of the dermal fillers including cellular growth promoting scaffolds disclosed herein is in a human. In some embodiments, use of the dermal fillers including cellular growth promoting scaffolds disclosed herein in a human reduces lines, folds, fine lines, wrinkles, or scars, or any combination thereof. In some embodiments, the reduction of lines, folds, fine lines, wrinkles, or scars, or any combination thereof is for cosmetic purposes. In some embodiments, the reduction of lines, folds, fine lines, wrinkles, or scars, or any combination thereof is for cosmetic purposes. In some embodiments, use of the dermal fillers including cellular growth promoting scaffolds disclosed herein in a human augments tissue, for example but not limited to, epidermal or dermal tissue. In some embodiments, tissue augmentation is for cosmetic purposes. In some embodiments, tissue augmentation is for medical treatment. In some embodiments, tissue augmentation is part of an enhancement procedure. In some embodiments, tissue augmentation is part of a skin enhancement procedure.

In some embodiments, tissue augmentation is required as a result of any medical or dental (gum disease/gum implants) condition.

In certain embodiments, a dermal filler for use described herein comprises an interpenetrated (IPN) network or a semi-interpenetrated (Semi-IPN) network, in which the different components may be crosslinked to themselves but are not crosslinked to each other. In some embodiments, an IPN or semi-IPN dermal filler comprises rhCollagen and a filler, such as hyaluronic acid (HA), poly(vinyl alcohol) (PVA), polyethylene glycol (PEG), oxidized cellulose (OC), or a derivative thereof, or a combination thereof. In some embodiments, an IPN or semi-IPN comprises rhCollagen and a crosslinked HA. In some embodiments, an IPN or semi-IPN comprises a rhCollagen derivative, for example but not limited to a methacrylated rhCollagen or a thiol rhCollagen and or a derivative of a filler, for example but not limited to a methacrylated HA, PVA, PEG, or OC, or a thiolated HA, PVA, PEG, or OC, or a combination thereof.

In some embodiments, an IPN or Semi-IPN network or a double crosslinked network comprising a dermal filler comprises a ratio of filler, for example but not limited to HA, PVA, PEG, or OC to rhCollagen of 1:1, 2:1, 3:1, 4:1, 5:1, 6:1, 1:2, 1:3, 1:4, 1:5, 1:6, or 0:1. In some embodiments, an IPN or Semi-IPN network comprising a dermal filler comprises a ratio of MA-filler, for example but not limited to HA, PVA, PEG, or OC to rhCollagen is 1:1, 2:1, 3:1, 4:1, 5:1, 6:1, 1:2, 1:3, 1:4, 1:5, 1:6, or 0:1. In some embodiments, an IPN or Semi-IPN network comprising a dermal filler comprises a ratio of filler, for example but not limited to HA, PVA, PEG, or OC to MA-rhCollagen is 1:1, 2:1, 3:1, 4:1, 5:1, 6:1, 1:2, 1:3, 1:4, 1:5, 1:6, or 0:1. In some embodiments, an IPN or Semi-IPN network comprising a dermal filler comprises a ratio of MA-filler to MA-rhCollagen is 1:1, 2:1, 3:1, 4:1, 5:1, 6:1, 1:2, 1:3, 1:4, 1:5, 1:6, or 0:1.

In some embodiments, an IPN or Semi-IPN or double crosslinked network comprising a dermal filler comprises a ratio of HA to rhCollagen of 1:1, 2:1, 3:1, 4:1, 5:1, 6:1, 1:2, 1:3, 1:4, 1:5, 1:6, or 0:1. In some embodiments, an IPN or Semi-IPN or double crosslinked network comprising a dermal filler comprises a ratio of MA-HA to rhCollagen is 1:1, 2:1, 3:1, 4:1, 5:1, 6:1, 1:2, 1:3, 1:4, 1:5, 1:6, or 0:1. In some embodiments, an IPN or Semi-IPN network comprising a dermal filler comprises a ratio of HA to MA-rhCollagen is 1:1, 2:1, 3:1, 4:1, 5:1, 6:1, 1:2, 1:3, 1:4, 1:5, 1:6, or 0:1. In some embodiments, an IPN or Semi-IPN network comprising a dermal filler comprises a ratio of MA-HA to MA-rhCollagen is 1:1, 2:1, 3:1, 4:1, 5:1, 6:1, 1:2, 1:3, 1:4, 1:5, 1:6, or 0:1.

In some embodiments, an IPN or Semi-IPN or double crosslinked network comprising a dermal filler comprises a ratio of filler to rhCollagen of 1:1, 2:1, 3:1, 4:1, 5:1, 6:1, 1:2, 1:3, 1:4, 1:5, 1:6, or 0:1. In some embodiments, an IPN or Semi-IPN or double crosslinked network comprising a dermal filler comprises a ratio of MA-HA, or MA-PVA, or MA-PEG, or MA-OC to rhCollagen is 1:1, 2:1, 3:1, 4:1, 5:1, 6:1, 1:2, 1:3, 1:4, 1:5, 1:6, or 0:1. In some embodiments, an IPN or Semi-IPN network comprising a dermal filler comprises a ratio of MA-HA, or MA-PVA, or MA-PEG, or MA-OC to MA-rhCollagen is 1:1, 2:1, 3:1, 4:1, 5:1, 6:1, 1:2, 1:3, 1:4, 1:5, 1:6, or 0:1. In some embodiments, an IPN or Semi-IPN network comprising a dermal filler comprises a ratio of MA-HA, or MA-PVA, or MA-PEG, or MA-OC to MA-rhCollagen is 1:1, 2:1, 3:1, 4:1, 5:1, 6:1, 1:2, 1:3, 1:4, 1:5, 1:6, or 0:1.

In some embodiments, an IPN or Semi-IPN network comprising a dermal filler or a double crosslinked dermal filler comprises a cellular growth promoting scaffold.

In certain embodiments, a dermal filler for use described herein comprises an photocurable dermal filler, in which at least one of the component, for example but not limited to rhCollagen comprises a methacrylate-rhCollagen derivative or a thiol-rhCollagen derivative. In some embodiments, a curable dermal filler comprises rhCollagen and a filler, such as hyaluronic acid (HA), poly(vinyl alcohol) (PVA), polyethylene glycol (PEG), oxidized cellulose (OC), or a derivative thereof, or a combination thereof. In some embodiments, photocurable dermal filler comprises MA-rhCollagen and a HA or a derivative thereof. In some embodiments, photocurable dermal filled comprises a rhCollagen derivative, for example but not limited to a methacrylated rhCollagen or a thiol rhCollagen and or a derivative of a filler, for example but not limited to a methacrylated HA, PVA, PEG, or OC, or a thiolated HA, PVA, PEG, or OC, or a combination thereof.

In some embodiments, photocurable dermal filler comprises a ratio of filler, for example but not limited to HA, PVA, PEG, or OC, or a derivative thereof, to rhCollagen of 1:1, 2:1, 3:1, 4:1, 5:1, 6:1, 1:2, 1:3, 1:4, 1:5, 1:6, or 0:1. In some embodiments, a photocurable dermal filler comprises a ratio of filler, for example but not limited to HA, PVA, PEG, or OC, or a derivative thereof, to MA-rhCollagen of 1:1, 2:1, 3:1, 4:1, 5:1, 6:1, 1:2, 1:3, 1:4, 1:5, 1:6, or 0:1. In some embodiments, a photocurable dermal filler comprises a ratio of filler, for example but not limited to HA, PVA, PEG, or OC to Thiol-rhCollagen is 1:1, 2:1, 3:1, 4:1, 5:1, 6:1, 1:2, 1:3, 1:4, 1:5, 1:6, or 0:1. In some embodiments, a photocurable dermal filler comprises a ratio of MA-filler to MA-rhCollagen is 1:1, 2:1, 3:1, 4:1, 5:1, 6:1, 1:2, 1:3, 1:4, 1:5, 1:6, or 0:1.

In some embodiments, a photocurable dermal filler comprises a ratio of HA to MA-rhCollagen of 1:1, 2:1, 3:1, 4:1, 5:1, 6:1, 1:2, 1:3, 1:4, 1:5, 1:6, or 0:1, 1:3, 1:4, 1:5, or 0:1. In some embodiments, a photocurable dermal filler comprises a ratio of MA-HA to MA-rhCollagen is 1:1, 2:1, 3:1, 4:1, 5:1, 6:1, 1:2, 1:3, 1:4, 1:5, 1:6, or 0:1. In some embodiments, a photocurable dermal filler comprises a ratio of PVA, PEG, or OC to MA-rhCollagen is 1:1, 2:1, 3:1, 4:1, 5:1, 6:1, 1:2, 1:3, 1:4, 1:5, 1:6, or 0:1. In some embodiments, a photocurable dermal filler comprises a ratio of MA-PVA, MA-HA-, or OC to MA-rhCollagen is 1:1, 2:1, 3:1, 4:1, 5:1, 6:1, 1:2, 1:3, 1:4, 1:5, 1:6, or 0:1. In some embodiments, the HA components of a photocurable dermal filler comprises a crosslinked HA or a crosslinked MA-HA.

Throughout this application, various embodiments of dermal fillers and their uses, may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1:1 to 6:1 should be considered to have specifically disclosed sub ranges such as from 1.1:1, 1.2:1, 1.3:1 to 5.9:1, from 1:1.1 to 1:1.9, etc., as well as individual numbers within that range and fractions thereof, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

For example, the instant disclosure provides a dermal filler that for a tissue space under an epidermis comprising a cross-linkable, plant-derived human collagen, either alone or together with a filler, such as hyaluronic acid (HA), poly(vinyl alcohol) (PVA), polyethylene glycol (PEG), oxidized cellulose (OC), or a combination thereof, which may be crosslinked, to provide a dermal filler that forms a water insoluble, crosslinked polymer preparation in situ on visible light activation in the presence of a photoinitiator. In some embodiments, the collagen is methacrylated or thiolated.

In some embodiments, the dermal filler provide for uses described herein forms an IPN or semi-IPN network. In some embodiments, the dermal filler provide for uses described herein forms a double crosslinked network.

In certain embodiments, a double crosslinked dermal filler provided for uses described herein comprises rhCollagen that is crosslinked to a crosslinked filler, such as crosslinked hyaluronic acid (HA), crosslinked poly(vinyl alcohol) (PVA), crosslinked polyethylene glycol (PEG), or crosslinked oxidized cellulose (OC), or a crosslinked derivative thereof, or a combination thereof. In certain embodiments, a double crosslinked dermal filler provided for uses described herein comprises rhCollagen that is further crosslinked to methacrylated or thiolated-crosslinked filler, such as HA, PVA, PEG, or OC.

In certain embodiments, in a double crosslinked dermal filler, the ratio of crosslinked filler to rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of MA-filler to rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of crosslinked filler to MA-rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of MA-filler to MA-rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of thiolated-filler to rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of crosslinked filler to thiolated-rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of thiolated-filler to thiolated-rhCollagen is 1:1, 2:1, 3:1, 4:1, 5:1, 6:1, 1:2, 1:3, 1:4, 1:5, 1:6, or 0:1.

In certain embodiments, in a double crosslinked dermal filler, crosslinked HA or crosslinked MA-HA is further crosslinked to rhCollagen or methacrylated rhCollagen or thiol rhCollagen, resulting in a double crosslinked dermal filler. In certain embodiments, in a double crosslinked dermal filler, the ratio of crosslinked HA to rhCollagen or methacrylated rhCollagen or thiol rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of crosslinked MA-HA to rhCollagen or methacrylated rhCollagen or thiol rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of crosslinked MA-HA to rhCollagen or methacrylated rhCollagen or thiol rhCollagen is 1:1, 2:1, 3:1, 4:1, 5:1, 6:1, 1:2, 1:3, 1:4, 1:5, 1:6, or 0:1.

In certain embodiments, in a double crosslinked dermal filler, crosslinked PVA, PEG, or OC or crosslinked MA-PVA, MA-PEG, or MA-OC is further crosslinked to rhCollagen or methacrylated rhCollagen, resulting in a double crosslinked dermal filler. In certain embodiments, in a double crosslinked dermal filler, the ratio of crosslinked PVA, PEG, or OC to rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of crosslinked MA-PVA, MA-PEG, or MA-OC to rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of crosslinked PVA, PEG, or OC to MA-rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of crosslinked MA-PVA, MA-PEG, or MA-OC to MArhCollagen or thiol rhCollagen is 1:1, 2:1, 3:1, 4:1, 5:1, 6:1, 1:2, 1:3, 1:4, 1:5, 1:6, or 0:1.

In certain embodiments, in a double crosslinked dermal filler, crosslinked thiol-PVA, thiol-PEG, or thiol-OC is further crosslinked to rhCollagen or methacrylated rhCollagen, resulting in a double crosslinked dermal filler. In certain embodiments, in a double crosslinked dermal filler, the ratio of crosslinked thiol-PVA, thiol-PEG, or thiol-OC to rhCollagen is 1:1, 2:1, 3:1, 4:1, 5:1, 6:1, 1:2, 1:3, 1:4, 1:5, 1:6, or 0:1. In certain embodiments, in a double crosslinked dermal filler, the ratio of crosslinked thiol-PVA, thiol-PEG, or thiol-OC to MArhCollagen or thiol rhCollagen is 1:1, 2:1, 3:1, 4:1, 5:1, 6:1, 1:2, 1:3, 1:4, 1:5, 1:6, or 0:1.

In some embodiments, any water-soluble coupling agent may be used that can crosslink hyaluronic acid to collagen. Some non-limiting examples of a coupling agent include carbodiimides such as N,N'-dicyclohexylcarbodiimide (DCC), N,N'-diisopropylcarbodiimide (DIC), or 1-ethyl-3-(3-dimethylaminopropyl)carbodiimide (EDC), etc. Carbodiimide coupling agents may facilitate ester or amide bond formation without becoming part of the linkage. In other words, an ester bond or an amide bond may comprise atoms from a carboxylate group from one of hyaluronic acid or collagen, and a hydroxyl group or an amine group from the other. However, other coupling agents that become part of the crosslinking group may be used. The concentration of a coupling agent may vary. In some embodiments, a coupling agent may be present at about 2 mM to about 150 mM, about 2 mM to about 50 mM, about 20 mM to about 100 mM, or about 50 mM. In some embodiments, the coupling agent is EDC that is present at a concentration of about 20 mM to about 100 mM, about 2 mM to about 50 mM, or about 50 mM. In some embodiments, the coupling agent is EDC that is present at an amount of EDC equal to 10 to 100-fold the number of free amines in the rhcollagen. In some embodiments, the coupling agent is EDC that is present at an amount of EDC equal to 50-fold the number of free amines in the rhcollagen. Increasing the carbodiimide concentration up to about 50 mM may result in a crosslinked macromolecular matrix with greater hydrogel stiffness and/or less swelling.

A skilled artisan would appreciate that a dermal filler comprising double crosslinking, wherein the filler is crosslinked to itself and then also crosslinked to the rhCollagen, is distinct from a dermal filler that comprises direct cross linking of collagen and HA using a single type of cross linker in a single reaction. The properties of such dermal fillers differ.

By way of example, the present polymerizable solution can be used to block or fill various lumens and voids just below a skin surface. Thus, the instant technology provides a method of tissue augmentation in a host, such as a human patient, wherein said polymerizable solution of interest is introduced at a site of interest using methods known in the art, such as injecting the polymerizable solution at or in a tissue site in need of augmentation and once applied, exposing the overlying body surface to a visible light to cause polymerization of the deposited polymerizable solution.

"Augmentation" means the repair, prevention or alleviation of defects, particularly defects due to loss or absence of tissue, by providing, augmenting, or replacing such tissue with a polymer or network or interest. Augmentation is also meant to include supplementation of a natural structure or feature, that is, a building of adding to an existing body part, for example, to increase the size thereof, such as lips, nose, breast, ears, portions of organs, chin, cheeks and so on. Thus, tissue augmentation can include the filling or reduction of lines, folds, wrinkles, scars, minor facial depressions, cleft lips, superficial wrinkles and the like, such as, in or on the face, neck, hands, feet, fingers, and toes; the correction of minor deformities due to aging or disease, including in the hands and feet, fingers and toes; the augmentation of the vocal cords or glottis to rehabilitate speech; the dermal filling of sleep lines and expression lines; the replacement of dermal and subcutaneous tissue lost due to aging; the augmentation of lips; the filling of wrinkles and the orbital groove around the eye; the augmentation of the breast; the augmentation of the chin; the augmentation of the cheek and/or nose; the filling of indentations in soft tissue, dermal or subcutaneous, due to, e.g., overzealous liposuction or other trauma; the filling of acne or traumatic scars and rhytids; the filling of nasolabial lines, nasoglabellar lines and infraoral lines and so on.

The polymerizable solution of interest, in some embodiments, encompasses a polymerizable solution which has a viscosity suitable for ready extrusion through a delivery means, such as a fine surgical needle (e.g., needles having a gauge of at least 27 gauge, at least 33 gauge or finer) at the temperature of use. Thus, a solution that is, "injectable" is one having a texture and viscosity which permits flow through a suitable delivery device, such as, a surgical needle, other surgical instrument, or other delivery means such as an equipment used in endoscopic or percutaneous discectomy procedures. The polymerizable solution of interest thus is injectable through a suitable applicator, such as a catheter, a cannula, a needle, a syringe, tubular apparatus and so on, as known in the art.

Once injected into the tissue space, the polymerizable solution can be manipulated, massaged, molded, or sculpted into the desired contours in the tissue space, typically after photoinitiation of polymerization has been triggered. In one embodiment, the manipulation, massage, molding, or sculpting takes place during the gelation process. The polymerizable, polymerizing, or partially polymerized solution can be shaped by external manipulation, using, for example, a shaping means, such as, a surgical depressor or other tool or instrument with a flat or curved surface, fingers, the palm, a knuckle and so on.

Surprisingly, the genetically modified, cross-linkable, plant-derived human collagen of the present method provides an improved collagen-containing dermal filler and improved methods of dermal filling by enabling the use of smaller gauge needles and a decreased force of injection, as well as by its ability to fill smaller tissue spaces.

The "expression force" of an injection (newtons, N) includes the force required for injection from the needle or cannula.

"Absolute viscosity" ("dynamic viscosity") is a fluid's resistance to flow when a force is applied. It is proportional to the force to velocity ratio. The Greek letter η (eta) represents absolute viscosity in calculations. It is commonly measured in cP because many common fluids have viscosities between 0.5 cP and 1000 cP.

A "gel" is a semirigid slab or cylinder of an organic polymer used as a medium for the separation of macromolecules. A gel is a substantially dilute cross-linked system, which exhibits no flow when in the steady-state. Gels are principally liquid by weight yet behave as partly as solids due to a three-dimensional cross-linked network within the liquid while retaining some properties of a liquid, such as deformability. It is the crosslinking within the fluid that gives a gel its structure (hardness) and contributes to the adhesive stick (tack). As a result, gels can be viewed as a dispersion of liquid molecules within a solid, i.e., liquid particles dispersed within a solid medium. "Gelation time" is the time it takes for the polymerizable solution to form a gel.

A "hydrogel" is a network of polymer chains that are hydrophilic, sometimes found as a colloidal gel in which water is the dispersion medium. Hydrogels are highly absorbent (e.g., able to contain over 90% water) polymeric networks and have a flexibility very similar to natural tissue, due to their significant water content.

A "polymer" is a macromolecule composed of a series of repeating subunits. The basic repeating subunit is known as a "monomer." As a group, polymers are known for their tensile strength and elasticity.

A "photoinitiator" is a molecule that creates reactive species (free radicals, cations or anions) when exposed to radiation (UV or visible). The photoinitiator of the present invention induces polymerization of the polymerizable solution. Examples of photoinitiators useful in the present method include, but are not limited to lithium phenyl-2,4,6-trimethylbenzoylphosphinate (LAP), 1-[4 2-hydroxy-1-[4-(2-hydroxyethoxy)phenyl]-2-methylpropan-1-one (IRGACURE® 2959), Eosin Y+Triethanolamin, or riboflavin.

Methacrylate is an ester or salt derived from methacrylic acid. Methacrylates are common monomers in polymer plastics, forming the acrylate polymers. Addition of methacrylate groups to collagen results in collagen methacrylate (rhCollagen-MA or MA-rhCollagen) which is photocurable. Addition of methacrylate groups to hyaluronic acid (HA) results in hyaluronic acid-methacrylate (HAMA or MA-HA) which is photocurable.

In some embodiments, rhCollagen used in a dermal filler described herein comprises a combination of non-modified rhCollagen and MA-rhCollagen. In some embodiments, the ratio of non-modified rhCollagen to MA-rhCollagen is about 1:0, 1:1, 1:2, 1:3, 1:4, 0:1, 2:1, 3:1, or 4:1. In some embodiments, the final concentration range of MA-rhCollagen comprises between about 0-12 mg/ml. In some embodiments, the final concentration range of non-modified rhCollagen comprises between about 0-12 mg/ml. In some embodiments, the final concentration range of MA-rhCollagen comprises between about 0-12 mg/ml, and the final concentration range of non-modified rhCollagen comprises between about 0-12 mg/ml. In some embodiments, the final concentration range of MA-rhCollagen comprises between about 0 mg/ml-6 mg/ml. In some embodiments, the final concentration range of non-modified rhCollagen comprises between about 0 mg/ml-6 mg/ml. In some embodiments, the final concentration of MA-rhCollagen comprises about 0, 1, 2, 3, 4, 5, 6, 7, 8, 9, 10, 11, or 12 mg/ml. In some embodiments, the final concentration of non-modified-rhCollagen comprises about 0, 1, 2, 3, 4, 5, 6, 7, 8, 9, 10, 11, or 12 mg/ml.

A thiol is an organosulfur compound that contains a carbon-bonded sulfhydryl (R-SH) group (where R represents an alkyl or other organic substituent). Thiolation of collagen can improve cohesion and mucoadhesion properties and affects swelling ability.

Light is a form of electromagnetic radiation. "Visible light" is light having a wavelength in the range of 380-800 nm or at least 390-700 nm. "Ultraviolet light" has shorter wavelengths, while "infrared" has longer wavelengths.

An illuminating means can be a light source suitable for activating the photoinitiator used, and which can activate the photoinitiator from outside of the body. While thermal initiators can be used and thus, an infrared source used, and ultraviolet-activated initiators can be used, and thus, a suitable ultraviolet source used, a preferred light source is a white light source. Thus, a suitable photoinitiator is used, so that the maximum absorption of the initiator and the light source are tuned. As mentioned hereinabove, one such visible light source is light-emitting diode (LED). Other suitable light sources can be used so long as gelation occurs in the body, at the site, under the skin surface and so on, such as, by applying the electromagnetic radiation to the body, to the site as needed, or from above the skin surface. The electromagnetic radiation is applied at an intensity, for a time and for a duration that enables gelation. The light source can be situated above the skin surface or directly on the skin surface, typically above the location of the molded or sculpted polymerizable solution.

The monomer solution of some embodiments, can contain any of a variety of other materials, such as, inert materials, such as, preservatives, fillers, excipients or diluents, pharmacologically active molecules or agents, such as a small molecule or a biological, cells and so on, as known in the pharmaceutic arts. Thus, a suitable inert or biologically active agent can be added to the monomer solution. In the case of the latter, the active agent may exert a pharmacologic action locally at the site or in the vicinity of the polymerized or networked structure of interest, or can be released from the formed scaffold, matrix or network to move though the adjoining tissue spaces or may enter the circulatory system for a less local effect.

As discussed above, the polymerizable solution methods of interest also can be used in combination with other dermatology, orthopedic, cosmetic, and other medical treatments.

In some embodiments, the polymerizable solution is mixed with a known filler to provide a composition which is moldable, contourable, has a long residence time and so on. Examples of fillers include, but are not limited to, hyaluronic acid (HA), poly(vinyl alcohol) (PVA), polyethylene glycol (PEG), oxidized cellulose (OC), or modified derivatives thereof, or a combination thereof. In some embodiments, the polymerizable solution in a semiliquid phase, is independently injected into the dermis as is a known filler also in a semiliquid phase, that together will provide a composition which is moldable, contourable, has a long residence time and so on. Examples of fillers that may be injected independently include, but are not limited to, hyaluronic acid (HA), poly(vinyl alcohol) (PVA), polyethylene glycol (PEG), oxidized cellulose (OC), or modified derivatives thereof, or a combination thereof. In some embodiments, the polymerizable solution in a semiliquid phase, is injected into the dermis as a mixture that together will provide a composition which is moldable, contourable, has a long residence time and so on. Examples of fillers that may be injected mixed with rhCollagen include, but are not limited to, hyaluronic acid (HA), poly(vinyl alcohol) (PVA), polyethylene glycol (PEG), oxidized cellulose (OC), or modified derivatives thereof, or a combination thereof.

In yet another aspect, disclosed herein is methods of inducing a cellular growth promoting scaffold in a tissue space under an epidermis comprising introducing a solution into the tissue space, the solution comprising: (a) a plant-derived human collagen; and (b) at least one growth factor or source thereof.

In one embodiment, the source of the at least one growth factor comprises a plasma or a platelet-rich plasma.

In one embodiment, the cellular growth promoting scaffold promotes healing or replacement due to degradation or injury of a collagen-comprising tissue. In one embodiment, the collagen-comprising tissue is selected from the group consisting of a tendon, a ligament, skin, a cornea, a cartilage, a blood vessel, an intestine, an intervertebral disc, a muscle, a bone, or a tooth. In a particular embodiment, the cellular growth promoting scaffold promotes healing of tendinitis.

In one embodiment, the plant-derived collagen comprises rhCollagen. In one embodiment, the plant-derived collagen is obtained from a genetically modified plant. In various embodiments, the genetically modified plant is a genetically modified plant selected from the group consisting of tobacco, maize, alfalfa, rice, potato, soybean, tomato, wheat, barley, canola, carrot, and cotton. In one embodiment, the genetically modified plant is a tobacco plant.

In one embodiment, the genetically modified plant comprises an expressible sequence of at least one gene sequence of human deoxyribonucleic acid (DNA) selected from the group consisting of: COL1, COL2, P4H-alpha, P4H-beta, and LH3.

In a particular embodiment, the plant-derived human collagen comprises at least modified one human collagen alpha-1 chain as set forth in SEQ ID NO: 3 and as expressed in the genetically modified plant; and at least one modified human collagen alpha-2 chain as set forth in SEQ ID NO: 6 and as expressed in the genetically modified plant; and the genetically modified plant further expresses an exogenous prolyl-4-hydroxylase (P4H).

In another particular embodiment, the method further comprises expressing an exogenous polypeptide selected from the group consisting of lysyl hydroxylase (LH), protease N, and protease C.

In one particular embodiment, the human collagen alpha-1 chain is encoded by a sequence as set forth in SEQ ID NO: 1. In another particular embodiment, the human collagen alpha-2 chain is encoded by a sequence as set forth in SEQ ID NO: 2.

In one embodiment, the exogenous P4H is a mammalian P4H. In one particular embodiment, the exogenous P4H is a human P4H.

In one embodiment, the method further comprises targeting the human collagen alpha-1 to a vacuole of the plant or the genetically modified plant and digesting it with ficin. In one embodiment, the method further comprises targeting the human collagen alpha-2 to a vacuole of the plant or the genetically modified plant and digesting it with ficin.

In one particular embodiment, the plant-derived human collagen is atelocollagen.

A skilled artisan would appreciate that the term "dermal filler" encompasses in some embodiments a solution comprising a plant-derived human collagen, for example a type 1 recombinant human collagen (rhCollagen) or a derivative thereof. The term "dermal filler" also encompass in some embodiments, a solution comprising a plant-derived human collagen, for example a type 1 recombinant human collagen (rhCollagen) or a derivative thereof, and a filler or a derivative thereof, or a crosslinked filler or a derivative thereof, having all the same meanings and qualities, wherein a dermal filler may be used to augment tissue structure, or may be used for reducing lines, folds, fine lines, wrinkles, or scars, or any combination thereof.

A skilled artisan would appreciate that dermal fillers described herein comprise different formulation, for example but not limited to:

An rhCollagen or a MA or Thiol derivative thereof;

an IPN or semi-IPN or double crosslinked network comprising rhCollagen or rhCollagen-MA or rhCollagen-Thiol, and a filler or derivative thereof;

an IPN or semi-IPN or double crosslinked network comprising rhCollagen or rhCollagen-MA or rhCollagen-Thiol, and HA or MA-HA or Thiol-HA;

an IPN or semi-IPN or double crosslinked network comprising rhCollagen or rhCollagen-MA or rhCollagen-Thiol, and PVA or MA-PVA or Thiol-PVA;

an IPN or semi-IPN or double crosslinked network comprising rhCollagen or rhCollagen-MA or rhCollagen-Thiol, and PEG or MA-PEG or Thiol-PEG;

an IPN or semi-IPN or double crosslinked network comprising rhCollagen or rhCollagen-MA or rhCollagen-Thiol, and OC or MA-OC or thiol-OC;

an IPN or semi-IPN or double crosslinked network or a cellular growth promoting scaffold comprising rhCollagen, and an autologous platelet rich plasma (PRP) fraction of blood containing high concentration of platelets;

an IPN or semi-IPN or double crosslinked network or a cellular growth promoting scaffold, each comprising rhCollagen and an autologous platelet rich plasma (PRP) fraction of blood containing high concentration of platelets, wherein the platelets release various types of growth factors (GFs) comprising vasculo-endothelial growth factor (VEGF), transforming beta growth factor (TGF-beta), platelet derived growth factor (PDGF), platelet derived epidermal growth factor (PDEGF), fibroblast growth factors (bFGF), epidermal growth factors (EGF) or hepatocyte growth factors (HGF), or a combination thereof;

a double crosslinked dermal filler comprising rhCollagen or rhCollagen-MA or rhCollagen-Thiol crosslinked to a crosslinked filler or derivative thereof;

a double crosslinked dermal filler comprising a rhCollagen or rhCollagen-MA or rhCollagen-Thiol crosslinked to a crosslinked HA or crosslinked MA-HA or crosslinked Thiol-HA;

a double crosslinked dermal filler comprising a rhCollagen or rhCollagen-MA or rhCollagen-Thiol crosslinked to a crosslinked PVA or crosslinked MA-PVA or crosslinked Thiol-PVA;

a double crosslinked dermal filler comprising a rhCollagen or rhCollagen-MA or rhCollagen-Thiol crosslinked to a crosslinked PEG or crosslinked MA-PEG or crosslinked Thiol-PEG; or a double crosslinked dermal filler comprising a rhCollagen or rhCollagen-MA or rhCollagen-Thiol crosslinked to a crosslinked OC or crosslinked MA-OC or crosslinked thiol-OC.

A skilled artisan would appreciate that in some embodiments, the term "cellular growth promoting scaffold" encompasses dermal fillers comprising collagen and an autologous platelet rich plasma (PRP) fraction of blood or components thereof. In some embodiments, PRP does not include "cells" but membranous vesicles (of cellular origin) containing growth factors and plasma components like fibrinogen and pro-thrombin. in some embodiments, a "cellular growth promoting scaffold" encompasses dermal fillers comprising collagen and an autologous platelet rich plasma (PRP) fraction of blood or components thereof, and an at least additional filler component.

In some embodiments, a cellular growth promoting scaffold comprises a dermal filler that may be an IPN networks, a semi-IPN networks, or a double crosslinked dermal filler that further comprises an autologous platelet rich plasma (PRP) fraction of blood containing high concentration of platelets, wherein the autologous PRP fraction of blood containing high concentration of platelets, wherein the platelets release various types of growth factors (GFs) comprising vasculo-endothelial growth factor (VEGF), transforming beta growth factor (TGF-beta), platelet derived growth factor (PDGF), platelet derived epidermal growth factor (PDEGF), fibroblast growth factors (bFGF), epidermal growth factors (EGF) or hepatocyte growth factors (HGF), or a combination thereof. In some embodiments, a cellular growth promoting scaffold comprises a dermal filler comprising an IPN networks, a semi-IPN networks, or a double crosslinked dermal filler that further comprises, and at least one growth factor comprising vasculo-endothelial growth factor (VEGF), transforming beta growth factor (TGF-beta), platelet derived growth factor (PDGF), platelet derived epidermal growth factor (PDEGF), fibroblast growth factors (bFGF), epidermal growth factors (EGF) or hepatocyte growth factors (HGF), or a combination thereof. In some embodiments, a cellular growth promoting scaffold comprises a dermal filler comprising an IPN networks, a semi-IPN networks, or a double crosslinked dermal filler that further comprises, and a subset or fraction of PRP components.

In some embodiments, a dermal filler described herein comprises a polymerizable solution. In some embodiments, a dermal filler described herein comprises a non-polymerizable solution. In some embodiments, polymerization of a dermal filler solution occurs in vivo. In some embodiments, components of a polymerizable dermal filler solution are injected together and then polymerized to form the cured dermal filler. In some embodiments, components of a polymerizable dermal filler solution are injected independently and then polymerized to form the cured dermal filler. An example of the unique approach of independently injection dermal filler components may in some embodiments comprising, injecting a filler into the skin dermis, for example but not limited to HA or a deriviatives thereof, and separately injecting a methacrylated or thiol-rhCollagen into the skin dermis within close proximity of the first injection, wherein the components are in a semiliquid phase, and then crosslinking in situ. This approach, in some embodiments allows for easier injection and in situ sculturing prior to curing the dermal filler components together by light polymerization.

In some embodiments, a dermal filler provided herein is used in a method of soft tissue augmentation. In some embodiments, a dermal filler provided herein enhances cell proliferation. In some embodiments, a dermal filler provided and used in a method of soft tissue augmentation, degrades over time. In some embodiments, a dermal filler provided herein is used in a method of soft tissue augmentation wherein the dermal filler fills a tissue space under an epidermis. In some embodiments, a dermal filler provided herein is used in a method of soft tissue augmentation, wherein the use reduces lines, folds, fine lines, wrinkles, or scars.

In one embodiment, the solution comprising the plant-derived human collagen has a reduced viscosity at room temperature in comparison with an analogous solution comprising a tissue-extracted human or animal-derived collagen in the same concentration and formulation. In another embodiment, the solution comprising the plant-derived human collagen has a reduced viscosity at 37° C. in comparison with an analogous solution comprising a tissue-extracted human or animal-derived collagen in the same concentration and formulation. In yet another embodiment, the solution comprising the plant-derived human collagen is introduced into the tissue space with a reduced force at room temperature as compared with an analogous solution comprising a tissue-extracted human or animal-derived collagen in the same concentration and formulation. In still another embodiment, the solution comprising the plant-derived human collagen is introduced into the tissue space with a reduced force at 37° C. as compared with an analogous solution comprising a tissued-extracted human or animal-derived collagen in the same concentration and formulation. In one particular embodiment, the solution comprising the plant-derived human collagen has an increased scaffolding formation or promotes an increase in cellular growth as compared with an analogous solution comprising a tissue-extracted human or animal-derived collagen in the same concentration and formulation.

In yet another aspect, disclosed herein is a use of a solution injected into a tissue space under an epidermis to induce a cellular growth promoting scaffold, the solution comprising a plant-derived human collagen and at least one growth factor or source thereof, to promote healing or replacement due to degradation or injury of a collagen-comprising tissue. In a particular embodiment, the source of the at least one growth factor comprises a plasma or a platelet-rich plasma.

In embodiment, the collagen-comprising tissue is selected from the group consisting of a tendon, a ligament, skin, a cornea, a cartilage, a blood vessel, an intestine, an intervertebral disc, a muscle, a bone, or a tooth. In another embodiment, the cellular growth promoting scaffold promotes healing of tendinitis. In embodiment, the collagen-comprising tissue is skin.

In some embodiments, there is provided a genetically modified plant which is capable of expressing at least one type of a collagen alpha chain and accumulating it in a subcellular compartment which is devoid of endogenous P4H activity.

As used herein, the phrase "genetically modified plant" refers to any lower (e.g. moss) or higher (vascular) plant or a tissue or an isolated cell thereof (e.g., of a cell suspension) which is stably or transiently transformed with an exogenous polynucleotide sequence. Examples of plants include tobacco, maize, alfalfa, rice, potato, soybean, tomato, wheat, barley, canola, cotton, carrot as well as lower plants such as moss.

As used herein, the phrase "collagen chain" refers to a collagen subunit such as the alpha 1 or 2 chains of collagen fibers, preferably type I fibers. As used herein, the phrase "collagen" refers to an assembled collagen trimer, which in the case of type I collagen includes two alpha 1 chains and one alpha 2 chain. A collagen fiber is collagen which is devoid of terminal propeptides C and N.

As is used herein, the phrase "subcellular compartment devoid of endogenous P4H activity" refers to any compartmentalized region of the cell which does not include plant P4H or an enzyme having plant-like P4H activity. Examples of such subcellular compartments include the vacuole, apoplast and cytoplasm as well as organelles such as the chloroplast, mitochondria and the like.

Any type of collagen chain can be expressed by the genetically modified plant of the present invention. Examples include fibril-forming collagens (types I, II, III, V, and XI), networks forming collagens (types IV, VIII, and X), collagens associated with fibril surfaces (types IX, XII, and XIV), collagens which occur as transmembrane proteins (types XIII and XVII), or form 11-nm periodic beaded filaments (type VI).

In one embodiment, the collagen chain expressed is an alpha 1 and/or 2 chain of type I collagen. The expressed collagen alpha chain can be encoded by any polynucleotide sequences derived from any mammal. In a particular embodiment, the sequences encoding collagen alpha chains are human and are set forth by SEQ ID NOs: 1 and 4.

Typically, alpha collagen chains expressed in plants may or may not include their terminal propeptides (i.e. propeptide C and propeptide N).

Processing of procollagen by plant proteolytic activity is different then normal processing in human and that propeptide C is removed by plant proteolytic activity although the cleavage site is unknown. Cleavage of the C propeptide may take place on a procollagen peptide before the assembly of trimmer (association of three C-Propeptides is essential for initiating the assembly of trimmers).

N-propeptide cleavage by plant proteolytic activity takes place in mature plants but not in plantlets. Such cleavage removes 2 amino acids from the N telopeptide (2 out of 17).

The C-propeptides (and to a lesser extent the N-propeptides) maintain the procollagen soluble during its passage through the animal cell (Bulleid et al., 2000) and are expected to have a similar effect in the plant cell. Following or during secretion of procollagen molecules into the extracellular matrix, propeptides are removed by procollagen N- and C-proteinases, thereby triggering spontaneous self-assembly of collagen molecules into fibrils. Removal of the propeptides by procollagen N- and C-proteinases lowers the solubility of procollagen by >10000-fold and is necessary and sufficient to initiate the self-assembly of collagen into fibers. Crucial to this assembly process are short non-triple-helical peptides called telopeptides at the ends of the triple-helical domain, which ensure correct registration of the collagen molecules within the fibril structure and lower the critical concentration for self-assembly. Pepsin can cleave the propeptides during production of collagen. However, pepsin damages the telopeptides and as a result, pepsin-extracted collagen is unable to form ordered fibrillar structures.

Protein disulfide isomerase (PDI) that forms the beta subunit of human P4H was shown to bind to the C-propeptide prior to trimmer assembly thereby also acting as a molecular chaperone during chain assembly.

The use of human Procollagen I N-proteinase and Procollagen C-proteinase expressed in different plants may generate collagen that is more similar to the native human collagen and can form ordered fibrillar structures.

In a case where N or C propeptides or both are included in the expressed collagen chain, the genetically modified plant of the present invention can also express the respective protease (i.e. C or N or both). Polynucleotide sequences encoding such proteases are exemplified by SEQ ID NOs: 18 (Protease C) and 20 (Protease N). Such proteases can be expressed such that they are accumulated in the same subcellular compartment as the collagen chain.

Accumulation of the expressed collagen chain in a subcellular compartment devoid of endogenous P4H activity can be effected via any one of several approaches.

For example, the expressed collagen chain can include a signal sequence for targeting the expressed protein to a subcellular compartment such as the apoplast or an organelle (e.g. chloroplast). Examples of suitable signal sequences include the chloroplast transit peptide (included in Swiss-Prot entry P07689, amino acids 1-57) and the mitochondrion transit peptide (included in Swiss-Prot entry P46643, amino acids 1-28). The Examples section which follows provides additional examples of suitable signal sequences as well as guidelines for employing such signal sequences in expression of collagen chains in plant cells.

Alternatively, the sequence of the collagen chain can be modified in a way which alters the cellular localization of collagen when expressed in plants.

As is mentioned hereinabove, the ER of plants includes a P4H which is incapable of correctly hydroxylating collagen chains. Collagen alpha chains natively include an ER targeting sequence which directs expressed collagen into the ER where it is post-translationally modified (including incorrect hydroxylation). Thus, removal of the ER targeting sequence will lead to cytoplasmic accumulation of collagen chains which are devoid of post translational modification including any hydroxylations.

Example 1 of the Examples section which follows describes generation of collagen sequences which are devoid of ER sequences.

Still alternatively, collagen chains can be expressed and accumulated in a DNA containing organelle such as the chloroplast or mitochondria. Further description of chloroplast expression is provided hereinbelow.

As is mentioned hereinabove, hydroxylation of alpha chains is required for assembly of a stable type I collagen. Since alpha chains expressed by the genetically modified plant of the present invention accumulate in a compartment devoid of endogenous P4H activity, such chains must be isolated from the plant, plant tissue or cell and in-vitro hydroxylated. Such hydroxylation can be achieved by the method described by Turpeenniemi-Hujanen and Myllyla (Concomitant hydroxylation of proline and lysine residues in collagen using purified enzymes in vitro. Biochim Biophys Acta. 1984 Jul. 16; 800(1):59-65).

Although such in-vitro hydroxylation can lead to correctly hydroxylated collagen chains, it can be difficult and costly to achieve.

To overcome the limitations of in-vitro hydroxylation, the genetically modified plant of the present invention preferably also co-expresses P4H which is capable of correctly hydroxylating the collagen alpha chain(s) [i.e., hydroxylating only the proline (Y) position of the Gly-X-Y triplets]. P4H is an enzyme composed of two subunits, alpha and beta. Both are needed to form an active enzyme while the Beta subunit also posses a chaperon function.

The P4H expressed by the genetically modified plant of the present invention is preferably a human P4H which is encoded by, for example, SEQ ID NOs:12 and 14. In addition, P4H mutants which exhibit enhanced substrate specificity, or P4H homologues can also be used.

A suitable P4H homologue is exemplified by an *Arabidopsis* oxidoreductase identified by NCBI accession NP 179363. Pairwise alignment of this protein sequence and a human P4H alpha subunit conducted by the present inventors revealed the highest homology between functional domains of any known P4H homologs of plants.

Since P4H needs to co-accumulate with the expressed collagen chain, the coding sequence thereof is preferably modified accordingly (addition of signal sequences, deletions which may prevent ER targeting etc).

In mammalian cells, collagen is also modified by Lysyl hydroxylase, galactosyltransferase and glucosyltransferase. These enzymes sequentially modify lysyl residues in specific positions to hydroxylysyl, galactosylhydroxylysyl and glucosylgalactosyl hydroxylysyl residues. A single human enzyme, Lysyl hydroxylase 3 (LH3) can catalyze all three consecutive steps in hydroxylysine linked carbohydrate formation.

Thus, the genetically modified plant of the present invention preferably also expresses mammalian LH3. An LH3 encoding sequence such as that set forth by SEQ ID NO: 22 can be used for such purposes.

The collagen chain(s) and modifying enzymes described above can be expressed from a stably integrated or a transiently expressed nucleic acid construct which includes polynucleotide sequences encoding the alpha chains and/or modifying enzymes (e.g. P4H and LH3) positioned under the transcriptional control of plant functional promoters. Such a nucleic acid construct (which is also termed herein as an expression construct) can be conFIG.d for expression throughout the whole plant, defined plant tissues or defined plant cells, or at define developmental stages of the plant. Such a construct may also include selection markers (e.g. antibiotic resistance), enhancer elements and an origin of replication for bacterial replication.

It will be appreciated that constructs including two expressible inserts (e.g. two alpha chain types, or an alpha chain and P4H) preferably include an individual promoter for each insert, or alternatively such constructs can express a single transcript chimera including both insert sequences from a single promoter. In such a case, the chimeric transcript includes an IRES sequence between the two insert sequences such that the downstream insert can be translated therefrom.

Numerous plant functional expression promoters and enhancers which can be either tissue specific, developmentally specific, constitutive or inducible can be utilized by the constructs of the present invention, some examples are provided hereinunder.

As used herein in the specification and in the claims section that follows the phrase "plant promoter" or "promoter" includes a promoter which can direct gene expression in plant cells (including DNA containing organelles). Such a promoter can be derived from a plant, bacterial, viral, fungal or animal origin. Such a promoter can be constitutive, i.e., capable of directing high level of gene expression in a plurality of plant tissues, tissue specific, i.e., capable of directing gene expression in a particular plant tissue or tissues, inducible, i.e., capable of directing gene expression under a stimulus, or chimeric, i.e., formed of portions of at least two different promoters.

Thus, the plant promoter employed can be a constitutive promoter, a tissue specific promoter, an inducible promoter or a chimeric promoter.

Examples of constitutive plant promoters include, without being limited to, CaMV35S and CaMV19S promoters, FMV34S promoter, sugarcane bacilliform badnavirus promoter, CsVMV promoter, *Arabidopsis* ACT2/ACT8 actin promoter, *Arabidopsis* ubiquitin UBQI promoter, barley leaf thionin BTH6 promoter, and rice actin promoter.

Examples of tissue specific promoters include, without being limited to, bean phaseolin storage protein promoter, DLEC promoter, PHS promoter, zein storage protein promoter, conglutin gamma promoter from soybean, AT2S1 gene promoter, ACT11 actin promoter from *Arabidopsis*, napA promoter from *Brassica napus* and potato patatin gene promoter.

The inducible promoter is a promoter induced by a specific stimuli such as stress conditions comprising, for example, light, temperature, chemicals, drought, high salinity, osmotic shock, oxidant conditions or in case of pathogenicity and include, without being limited to, the light-inducible promoter derived from the pea rbcS gene, the promoter from the alfalfa rbcS gene, the promoters DRE, MYC and MYB active in drought; the promoters INT, INPS, prxEa, Ha hsp17.7G4 and RD21 active in high salinity and osmotic stress, and the promoters hsr203J and str246C active in pathogenic stress.

Preferably the promoter utilized by the present invention is a strong constitutive promoter such that over expression of the construct inserts is effected following plant transformation.

It will be appreciated that any of the construct types used in the present invention can be co-transformed into the same plant using same or different selection markers in each construct type. Alternatively, the first construct type can be introduced into a first plant while the second construct type can be introduced into a second isogenic plant, following which the transgenic plants resultant therefrom can be crossed and the progeny selected for double transformants. Further self-crosses of such progeny can be employed to generate lines homozygous for both constructs.

There are various methods of introducing nucleic acid constructs into both monocotyledonous and dicotyledenous plants (Potrykus, I., Annu. Rev. Plant. Physiol., Plant. Mol. Biol. (1991) 42:205-225; Shimamoto et al., Nature (1989) 338:274-276). Such methods rely on either stable integration of the nucleic acid construct or a portion thereof into the genome of the plant, or on transient expression of the nucleic acid construct in which case these sequences are not inherited by a progeny of the plant.

In addition, several methods exist in which a nucleic acid construct can be directly introduced into the DNA of a DNA containing organelle such as a chloroplast.

There are two principle methods of effecting stable genomic integration of exogenous sequences such as those included within the nucleic acid constructs of the present invention into plant genomes:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif.

(1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledenous plants.

There are various methods of direct DNA transfer into plant cells. In electroporation, protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals, tungsten particles or gold particles, and the microprojectiles are physically accelerated into cells or plant tissues.

Following transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different, and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Transient expression methods which can be utilized for transiently expressing the isolated nucleic acid included within the nucleic acid construct of the present invention include, but are not limited to, microinjection and bombardment as described above but under conditions which favor transient expression, and viral mediated expression wherein a packaged or unpackaged recombinant virus vector including the nucleic acid construct is utilized to infect plant tissues or cells such that a propagating recombinant virus established therein expresses the non-viral nucleic acid sequence.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, the constructions can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of the present invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that said sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

The above described transformation approaches can be used to produce collagen chains and/or modifying enzymes as well as assembled collagen (with or without propeptides) in any species of plant, or plant tissue or isolated plants cell derived therefrom.

Preferred plants are those which are capable of accumulating large amounts of collagen chains, collagen and/or the processing enzymes described herein. such plants may also be selected according to their resistance to stress conditions and the ease at which expressed components or assembled collagen can be extracted. examples of preferred plants include tobacco, maize, alfalfa, rice, potato, soybean, tomato, wheat, barley, canola and cotton.

Collagen fibers are extensively used in the food and cosmetics industry. thus, although collagen fiber components (alpha chains) and modifying enzymes expressed by plants find utility in industrial synthesis of collagen, complete collagen production in plants is preferred for its simplicity and cost effectiveness.

Several approaches can be used to generate type I collagen in plants. For example, collagen alpha 1 chain can be isolated from a plant expressing collagen alpha 1 and P4H (and optionally LH3) and mixed with a collagen alpha 2 chain which is isolated from a plant expressing collagen alpha 2 and P4H (and optionally LH3 and protease C and/or N). Since collagen alpha 1 chain self assembles into a triple helix by itself, it may be necessary to denature such a homo-trimer prior to mixing and renaturation with the collagen alpha 2 chain.

Preferably, a first plant expressing collagen alpha 1 and P4H (and optionally LH3 and protease C and/or N) can be crossed with a second (and preferably isogenic) plant which expresses collagen alpha 2 or alternatively, a first plant expressing both alpha chains can be crossed with a second plant expressing P4H and optionally LH3 and protease C and/or N.

It should be noted that although the above described plant breeding approaches utilize two individually transformed plants, approaches which utilize three or more individually transformed plants, each expressing one or two components can also be utilized.

One of ordinary skill in the art would be well aware of various plant breeding techniques and as s such no further description of such techniques is provided herein.

Although plant breeding approaches are preferred, it should be noted that a single plant expressing collagen alpha 1 and 2, P4H and LH3 (and optionally protease C and/or N) can be generated via several transformation events each designed for introducing one more expressible components into the cell. In such cases, stability of each transformation event can be verified using specific selection markers.

In any case, transformation and plant breeding approaches can be used to generate any plant, expressing any number of components. Presently preferred are plants which express collagen alpha 1 and 2 chains, P4H, LH3 and at least one protease (e.g. protease C and/or N). As is further described in the Examples section which follows, such plants accumulate collagen which exhibits stability at temperatures of up to 42° C.

Progeny resulting from breeding or alternatively multiple-transformed plants can be selected, by verifying presence of exogenous mRNA and/or polypeptides by using nucleic acid or protein probes (e.g. antibodies). The latter approach is preferred since it enables localization of the expressed polypeptide components (by for example, probing fractionated plants extracts) and thus also verifies a potential for correct processing and assembly. Examples of suitable probes are provided in the Examples section which follows Once collagen-expressing progeny is identified, such plants are further cultivated under conditions which maximize expression of the collagen chains as well as the modifying enzymes.

Since free proline accumulation may facilitate over production of different proline-rich proteins including the collagen chains expressed by the genetically modified plants of the present invention, preferred cultivating conditions are those which increase free proline accumulation in the cultivated plant.

Free proline accumulates in a variety of plants in response to a wide range of environmental stresses including water deprivation, salinization, low temperature, high temperature, pathogen infection, heavy metal toxicity, anaerobiosis, nutrient deficiency, atmospheric pollution and UV-irradiation (Hare and Cress, 1997).

Free proline may also accumulate in response to treatment of the plant or soil with compounds such as ABA or stress inducing compounds such as copper salt, paraquat, salicylic acid and the like.

Thus, collagen-expressing progeny can be grown under different stress conditions (e.g. different concentrations of NaCl ranging from 50 mM up to 250 mM). In order to further enhance collagen production, the effect of various stress conditions on collagen expression will examined and optimized with respect to plant viability, biomass and collagen accumulation.

Plant tissues/cells are preferably harvested at maturity, and the collagen fibers are isolated using well know prior art extraction approaches, one such approach is detailed below.

Leaves of transgenic plants are ground to a powder under liquid nitrogen and the homogenate is extracted in 0.5 M acetic acid containing 0.2 M NaCl for 60 h at 4° C. Insoluble material is removed by centrifugation. The supernatant containing the recombinant collagen is salt-fractionated at 0.4 M and 0.7 M NaCl. The 0.7 M NaCl precipitate, containing the recombinant heterotrimeric collagen, is dissolved in and dialyzed against 0.1 M acetic acid and stored at −20° C. (following Ruggiero et al., 2000).

In one embodiment, disclosed herein is a method of processing procollagen in order to generate homogeneous, soluble, fibril-forming atelocollagen.

Figure 26:
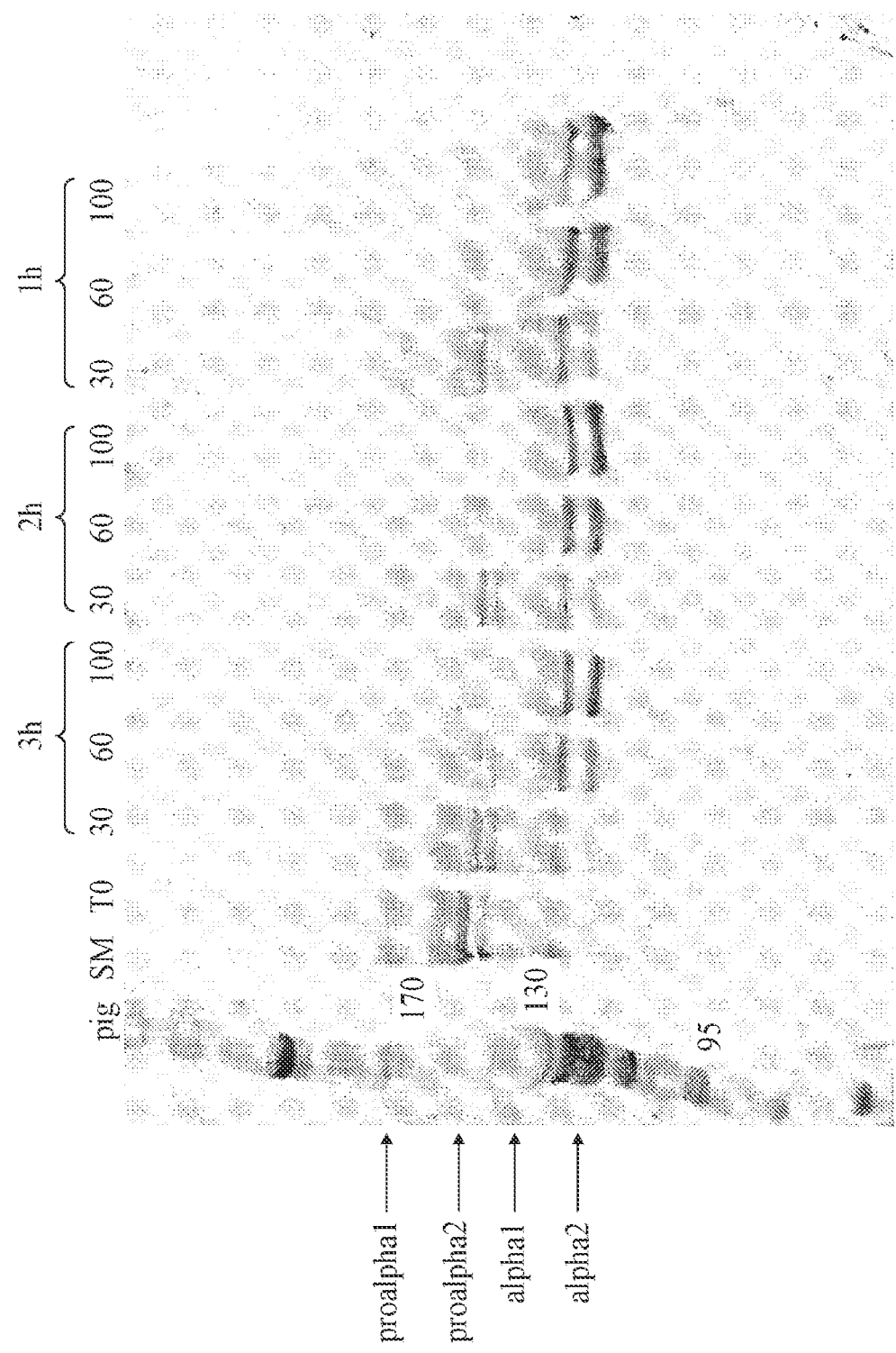
FIG. 26 shows effective procollagen digestion by recombinant trypsin at pH 7.5. AMS-pelleted procollagen-expressing tobacco leaf extracts were resuspended in extraction buffer (pH 7.5) containing L-cystein and EDTA. Samples were then incubated with 30-100 mg/L recombinant trypsin at 15° C. for 1-3 hrs. Cleavage was terminated by centrifugation and protein samples were separated on 8% SDS-PAGE, transferred to nitrocellulose membranes and immunoblotted for alpha-1 and alpha-2 collagen chains with anti-collagen I.

In some embodiments, as shown herein by analysis of proteolysis results by SDS PAGE, certain plant-derived proteases, (e.g. papain), are not capable of cleaving the propeptide portion from soluble procollagen without proteolytic cleavage within the helical region (even though they are capable of removing telopeptides from telocollagen originating from animal sources), while other proteases (e.g. esperase, savinase) do not effectively cleave the propeptide region from soluble procollagen, thereby hindering effective fibrillogenesis. Through meticulous experimentation, the present inventors uncovered that only particular plant-derived proteases such as ficin, and bacterial-derived proteases such as neutrase and subtilisin may be used to correctly cleave the propeptide portion (including the telopeptides) from soluble procollagen to generate a homogeneous preparation of soluble atelocollagen (FIGS. 13, 15, 17, 19, and 20) without digesting the helical region of the non-animal procollagen. In addition, the present inventors showed that a recombinant trypsin is also capable of correct cleavage (FIG. 26). The present inventors further showed that cleavage with ficin allows the resultant atelocollagen to retain its fibrillogenic capacity (Table 5 of the Examples section herein below).

Thus, according to one aspect, there is provided a method of generating atelocollagen. The method comprises contacting a human recombinant telopeptide-comprising collagen with a protease selected from the group consisting of neutrase, subtilisin, recombinant trypsin, recombinant pepsin and ficin, wherein the human recombinant telopeptide-comprising collagen is expressed in a non-animal cell, thereby generating the atelocollagen.

As used herein, the phrase "telopeptide-comprising collagen" refers to a soluble collagen molecule which comprises telopeptides that are longer than the telopeptide remnants comprised in atelocollagen. Thus, the telopeptide-comprising collagen may be procollagen which comprises full length propeptides. Alternatively, the telopeptide-comprising collagen may be a procollagen molecule which comprises partially digested propeptides. Still alternatively, the telopeptide-comprising collagen may be telocollagen.

The term "procollagen" as used herein, refers to a collagen molecule (e.g. human) that comprises either an N-terminal propeptide, a C-terminal propeptide or both. Exemplary human procollagen amino acid sequences are set forth by SEQ ID NOs: 30, 31, 36, and 37.

The term "telocollagen" as used herein, refers to collagen molecules that lack both the N- and C-terminal propeptides typically comprised in procollagen but still contain the telopeptides. As mentioned in the Background section herein above, the telopeptides of fibrillar collagen are the remnants of the N- and C-terminal propeptides following digestion with native N/C proteinases.

Recombinant human telocollagen may be generated in cells which have been transformed to express both exogenous human procollagen and the respective protease (i.e. C or N or both). Polynucleotide sequences encoding such proteases are exemplified by SEQ ID NOs: 39 (Protease C) and 40 (Protease N). Such proteases can be expressed such that they are accumulated in the same subcellular compartment as the collagen chain, as further described herein below.

As used herein, the term "atelocollagen" refers to collagen molecules lacking both the N- and C-terminal propeptides typically comprised in procollagen and at least a portion of its telopeptides but including a sufficient portion of its telopeptides such that under suitable conditions it is capable of forming fibrils.

Any type of atelocollagen may be generated according to the methods disclosed herein. Examples include fibril-forming collagens (types I, II, III, V, and XI), network-forming collagens (types IV, VIII, and X), collagens associated with fibril surfaces (types IX, XII, and XIV), collagens which occur as transmembrane proteins (types XIII and XVII), or form 11-nm periodic beaded filaments (type VI). According to one embodiment, the atelocollagen comprises an alpha-1 and/or alpha-2 chain of type I collagen.

It will be appreciated that in some embodiments, disclosed herein are genetically modified forms of collagen/atelocollagen—for example collagenase-resistant collagens and the like.

The recombinant human procollagen or telocollagen may be expressed in any non-animal cell, including but not limited to plant cells and other eukaryotic cells such as yeast and fungus.

Plants in which the human procollagen or telocollagen may be produced (i.e. expressed) may be of lower (e.g. moss and algae) or higher (vascular) plant species, including tissues or isolated cells and extracts thereof (e.g. cell suspensions). Preferred plants are those which are capable of accumulating large amounts of collagen chains, collagen and/or the processing enzymes described herein below. Such plants may also be selected according to their resistance to stress conditions and the ease at which expressed components or assembled collagen can be extracted. Examples of plants in which human procollagen may be expressed include, but are not limited to tobacco, maize, alfalfa, rice, potato, soybean, tomato, wheat, barley, canola, carrot, lettuce and cotton.

Production of recombinant human procollagen is typically effected by stable or transient transformation with an exogenous polynucleotide sequence encoding human procollagen.

Exemplary polynucleotide sequences encoding human procollagen are set forth by SEQ ID NOs: 32, 33, 41, and 42.

As mentioned, production of human telocollagen is typically effected by stable or transient transformation with an exogenous polynucleotide sequence encoding human procollagen and at least one exogenous polynucleotide sequence encoding the relevant protease.

The stability of the triple-helical structure of collagen requires the hydroxylation of prolines by the enzyme prolyl-4-hydroxylase (P4H) to form residues of hydroxyproline within the collagen chain. Although plants are capable of synthesizing hydroxyproline-containing proteins, the prolyl hydroxylase that is responsible for synthesis of hydroxyproline in plant cells exhibits relatively loose substrate sequence specificity as compared with mammalian P4H. Thus, production of collagen containing hydroxyproline only in the Y position of Gly-X-Y triplets requires co-expression of collagen and human or mammalian P4H genes.

Thus, according to one embodiment, the procollagen or telocollagen is expressed in a subcellular compartment of a plant that is devoid of endogenous P4H activity so as to avoid incorrect hydroxylation thereof. As is used herein, the phrase "subcellular compartment devoid of endogenous P4H activity" refers to any compartmentalized region of the cell which does not include plant P4H or an enzyme having plant-like P4H activity. According to one embodiment, the subcellular compartment is a vacuole.

Accumulation of the expressed procollagen in a subcellular compartment devoid of endogenous P4H activity can be affected via any one of several approaches.

For example, the expressed procollagen/telocollagen can include a signal sequence for targeting the expressed protein to a subcellular compartment such as the apoplast or an organelle (e.g. chloroplast). Examples of suitable signal sequences include the chloroplast transit peptide (included in Swiss-Prot entry P07689, amino acids 1-57) and the Mitochondrion transit peptide (included in Swiss-Prot entry P46643, amino acids 1-28).

Alternatively, the sequence of the procollagen can be modified in a way which alters the cellular localization of the procollagen when expressed in plants.

In some embodiments, disclosed herein are genetically modified cells co-expressing both human procollagen and a P4H, capable of correctly hydroxylating the procollagen alpha chain(s) [i.e. hydroxylating only the proline (Y) position of the Gly-X-Y triplets]. P4H is an enzyme composed of two subunits, alpha and beta as set forth in Genbank Nos. P07237 and P13674. Both subunits are necessary to form an active enzyme, while the beta subunit also possesses a chaperon function.

The P4H expressed by the genetically modified cells of the present invention is preferably a human P4H which is encoded by, for example, SEQ ID NOs: 34 and 35. In addition, P4H mutants which exhibit enhanced substrate specificity, or P4H homologues can also be used. A suitable P4H homologue is exemplified by an *Arabidopsis* oxidoreductase identified by NCBI accession no: NP_179363.

Since it is essential that P4H co-accumulates with the expressed procollagen chain, the coding sequence thereof is preferably modified accordingly (e.g., by addition or deletion of signal sequences).

In mammalian cells, collagen is also modified by Lysyl hydroxylase, galactosyltransferase and glucosyltransferase. These enzymes sequentially modify lysyl residues in specific positions to hydroxylysyl, galactosylhydroxylysyl and glucosylgalactosyl hydroxylysyl residues at specific positions. A single human enzyme, Lysyl hydroxylase 3 (LH3), as set forth in Genbank No. 060568, can catalyze all three consecutive modifying steps as seen in hydroxylysine-linked carbohydrate formation.

Thus, the genetically modified cells disclosed herein, may also express mammalian LH3. An LH3 encoding sequence such as that set forth by SEQ ID NO: 38 can be used for such purposes.

The procollagen (s) and modifying enzymes described above can be expressed from a stably integrated or a transiently expressed nucleic acid construct which includes polynucleotide sequences encoding the procollagen alpha chains and/or modifying enzymes (e.g. P4H and LH3) positioned under the transcriptional control of functional promoters. Such a nucleic acid construct (which is also termed herein as an expression construct) can be configured for expression throughout the whole organism (e.g. plant, defined tissues or defined cells), and/or at defined developmental stages of the organism. Such a construct may also include selection markers (e.g. antibiotic resistance), enhancer elements and an origin of replication for bacterial replication.

It will be appreciated that constructs including two expressible inserts (e.g. two alpha procollagen chain types, or a procollagen alpha chain and P4H) preferably include an individual promoter for each insert, or alternatively such constructs can express a single transcript chimera including both insert sequences under a single promoter. In such a case, the chimeric transcript may include an intraribosomal entry region (IRES) sequence between the two insert sequences such that the downstream insert can be translated therefrom.

Numerous functional expression promoters and enhancers which can be either tissue specific, developmentally specific, constitutive or inducible can be utilized by the constructs of the present invention, some examples are provided herein under.

Regardless of the transformation technique employed, once procollagen-expressing progeny are identified, such plants are further cultivated under conditions which maximize expression thereof. Progeny resulting from transformed plants can be selected, by verifying presence of exogenous mRNA and/or polypeptides by using nucleic acid or protein probes (e.g. antibodies). The latter approach enables localization of the expressed polypeptide components (by for example, probing fractionated plants extracts) and thus also verifies the plant's potential for correct processing and assembly of the foreign protein.

Following cultivation of such plants, the telopeptide-comprising collagen is typically harvested. Plant tissues/cells are preferably harvested at maturity, and the procollagen molecules are isolated using extraction approaches. Preferably, the harvesting is effected such that the procollagen remains in a state that it can be cleaved by protease enzymes. According to one embodiment, a crude extract is generated from the transgenic plants of the present invention and subsequently contacted with the protease enzymes. An exemplary method for generating a plant crude extract is described in the Examples section herein under.

It will be appreciated that the propeptide or telopeptide-comprising collagen may be purified from the genetically engineered cells of the present invention prior to incubation with protease, or alternatively may be purified following incubation with the protease. Still alternatively, the propeptide or telopeptide-comprising collagen may be partially purified prior to protease treatment and then fully purified following protease treatment. Yet alternatively, the propeptide or telopeptide-comprising collagen may be treated with protease concomitant with other extraction/purification procedures.

Exemplary methods of purifying or semi-purifying the telopeptide-comprising collagen of the present invention include, but are not limited to, salting out with ammonium sulfate or the like and/or removal of small molecules by ultrafiltration.

As described in the Background herein above, there is a risk involved in using animal source material for medical purposes. This risk is also relevant when selecting the proteolytic enzymes used in processing the procollagen expressed in plants to atelocollagen. Application of animal-derived source enzymes such as trypsin or pepsin, may in itself contaminate the final preparation with disease carriers. It is therefore desired to devise a production system where all components are free of animal source.

It has been disclosed herein that only particular proteases are capable of correctly cleaving recombinant propeptide or telopeptide-comprising collagen. These include certain plant derived proteases e.g. ficin (EC 3.4.22.3) and certain bacterial derived proteases e.g. subtilisin (EC 3.4.21.62), neutrase. In some embodiments, disclosed herein is a use of recombinant enzymes such as rhTrypsin and rhPepsin Such enzymes are commercially available e.g. Ficin from Fig tree latex (Sigma, catalog #F4125 and Europe Biochem), Subtilisin from *Bacillus licheniformis* (Sigma, catalog #P5459) Neutrase from bacterium *Bacillus amyloliquefaciens* (Novozymes, catalog #PW201041) and TrypZean™, a recombinant human trypsin expressed in corn (Sigma catalog #T3449).

The procollagen or telocollagen is preferably contacted with the proteases under conditions such that the proteases are able to cleave the propeptides or telopeptides therefrom. Typically, the conditions are determined according to the particular protease selected. Thus, for example procollagen may be incubated with a protease for up to 15 hours, at a concentration of 1-25 mg/ml and a temperature of about 10-20° C.

Following protease digestion, the generated atelocollagen may be further purified e.g. by salt precipitation, as described in the Examples section below so that the end product comprises a purified composition of atelocollagen having been processed from plant or plant-cell generated procollagen by a protease selected from the group consisting of neutrase, subtilisin, ficin and recombinant human trypsin and analyzed using methods known in the art (e.g. size analysis via Coomassie staining, Western analysis, etc.).

Following purification, the atelocollagen may be resolubilized by addition of acidic solutions (e.g. 10 mM HCl). Such acidic solutions are useful for storage of the purified atelocollagen.

The present inventors have shown that following digestion with ficin, the atelocollagen maintains its ability to form fibrils upon neutralization of the above described acid solutions. According to one embodiment, at least 70% of the purified and resolubilized atelocollagen generated according to the method of the present invention is capable of forming fibrils. According to one embodiment, at least 88% of the purified and resolubilized atelocollagen generated according to the method of the present invention is capable of forming fibrils.

The ability to form fibrils demonstrates that the generated atelocollagen is useful for medical purposes including, but not limited to cosmetic surgery, healing aid for burn patients, reconstruction of bone and a wide variety of dental, orthopedic and surgical purposes.

As noted in the Background section, Type I collagen is considered a perfect candidate for use as a major component of a building material in 3D-bioprinting. Despite the significant advantages offered by this natural polymer, a number of factors hinder its use for 3D bioprinting. The use of tissue extracted collagen for this purpose is limited due to its sensitivity to temperature and ionic strength which drives spontaneous gel formation at temperatures higher than 20° C., under physiological conditions [see, for example, PureCol, Advanced BioMatrix, Inc.]. The typical temperature-dependent formation of gel of tissue extracted-collagens hampers significantly the precise fluidity during printing. Keeping the printing media at low temperature until application is a possible solution for this phenomenon but implies a serious technical limitation. Another solution is the use of gelatin, the denatured form of collagen which does not become gel-like under these conditions. However, gelatin lacks the genuine tissue and cell interactions of native collagen and thus crucial biological functions are lost.

Recent developments in technology have resulted in the development of a system for the purification of naïve human Type I collagen (rhCollagen) by introducing into tobacco plants, five human genes encoding heterotrimeric type I collagen (COLLPLANT™, Israel; now also available at SIGMA-ALDRICH®, St. Louis, MO, USA). The protein is purified to homogeneity through a cost-effective industrial process taking advantage of collagen's unique properties. See also WO 2006/035442, WO 2009/053985, and patents and patent applications deriving therefrom, all of which are incorporated by reference as if fully set forth herein.

Thus, according to one aspect, disclosed herein is a genetically modified plant which is capable of expressing at least one type of a collagen alpha chain and accumulating it in a subcellular compartment which is devoid of endogenous P4H activity.

Type I collagen and rhCollagen are considered candidates for use as a major component of a building material in 3D-bioprinting. Scaffolding of various types has been used for cosmetic and other reconstructive applications.

In addition, there has been an increase in the use of dermal fillers for soft tissue augmentation, e.g., the reduction of wrinkles. One possible method for the use of dermal fillers includes injection of a polymerizable dermal filler material into the desired area, followed by the contouring or molding of the filler into the desired conformation. Polymerization and cross-linking of the material by one of various methods can transform the monomers in the injected material to form polymers and chains, which can form networks, retaining the desired molded conformation. There are a number of methods to form polymers and to crosslink polymers. One method involves light-reactive reagents and light-induced reactions which create reactive species in a monomer solution.

However, at least some of these approaches continue to focus on tissue-derived collagens or non-collagen polymers (e.g., poly(vinyl alcohol) or hyaluronic acid). Moreover, the use of tissue extracted collagen is limited due to its sensitivity to temperature and ionic strength which drives spontaneous gel formation at temperatures higher than 20° C., under physiological conditions [see, for example, PureCol, Advanced BioMatrix, Inc.]. The typical temperature-dependent formation of gel of tissue extracted-collagens hampers significantly the precise fluidity. Keeping the collagens at low temperature until application is a possible solution for this phenomenon but implies a serious technical limitation. Another solution is the use of gelatin, the denatured form of collagen which does not become gel-like under these conditions. However, gelatin lacks the genuine tissue and cell interactions of native collagen and thus crucial biological functions are lost. Moreover, the viscosity makes it more difficult to be injected under the dermis using fine-gauge needles and also makes it more difficult to spread and mold it into smaller cavities.

Embodiments of dermal fillers and uses thereof disclosed herein, include but are not limited to:

1. A method of filling a tissue space under an epidermis comprising:
   a. introducing a polymerizable solution into the tissue space, the polymerizable solution comprising:
      i. a cross-linkable, plant-derived human collagen; and
      ii. a photoinitiator; and
   b. applying light to the surface of the epidermis superficial to said space to induce polymerization.
2. A method of filling a tissue space under an epidermis, further comprising:
   (a) a step of molding or sculpting the polymerizable solution into a desired configuration in the tissue space, wherein said step is concomitant with, or subsequent to, the step of applying light.
3. A method of filling a tissue space under an epidermis, wherein the molding or sculpting step reduces lines, folds, fine lines, wrinkles, or scars.
4. A method of filling a tissue space under an epidermis, wherein the cross-linkable, plant-derived human collagen is methacrylated or thiolated.
5. A method of filling a tissue space under an epidermis, the polymer solution further comprising a hyaluronic acid (HA) or modified derivative thereof, a poly(vinyl alcohol) (PVA) or modified derivative thereof, a polyethylene glycol (PEG) or modified derivative thereof, oxidized cellulose (OC) or a modified derivate thereof, polymethylmethacrylate (PMMA) microspheres or a modified derivative thereof, tricalcium phosphate (TCP) or a modified derivative thereof, calcium hydroxylapatite (CaHA) or a modified derivative thereof, carboxymethylcellulose or a modified derivative thereof, crystalline nanocellulose (CNC) or a modified derivative thereof, or a combination thereof.
6. A method of filling a tissue space under an epidermis, wherein the modified derivative of hyaluronic acid (HA), a poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, or crystalline nanocellulose (CNC) comprises a photopolymerizable modified derivative.
7. The method of claim 5, wherein the modified derivative of hyaluronic acid (HA), a poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, or crystalline nanocellulose (CNC) comprises a methacrylated or thiolated derivative.
8. A method of filling a tissue space under an epidermis, wherein the plant-derived collagen comprises rhCollagen.
9. A method of filling a tissue space under an epidermis, wherein the plant-derived collagen is obtained from a genetically modified plant.
10. A method of filling a tissue space under an epidermis, wherein the genetically modified plant is a genetically modified plant selected from the group consisting of: tobacco, maize, alfalfa, rice, potato, soybean, tomato, wheat, barley, canola, carrot, and cotton.
11. A method of filling a tissue space under an epidermis, wherein the genetically modified plant is a tobacco plant.
12. A method of filling a tissue space under an epidermis, wherein the genetically modified plant comprises an expressible sequence of at least one gene sequence of human deoxyribonucleic acid (DNA) selected from the group consisting of: COL1, COL2, P4H-alpha, P4H-beta, and LH3.
13. A method of filling a tissue space under an epidermis, wherein the plant-derived human collagen comprises at least modified one human collagen alpha-1 chain as set forth in SEQ ID NO: 3 and as expressed in the genetically modified plant; and at least one modified human collagen alpha-2 chain as set forth in SEQ ID NO: 6 and as expressed in the genetically modified plant; and wherein the genetically modified plant further expresses an exogenous prolyl-4-hydroxylase (P4H).
14. A method of filling a tissue space under an epidermis, further comprising expressing an exogenous polypeptide selected from the group consisting of lysyl hydroxylase (LH), protease N, and protease C.
15. A method of filling a tissue space under an epidermis, wherein the human collagen alpha-1 chain is encoded by a sequence as set forth in SEQ ID NO: 1.
16. A method of filling a tissue space under an epidermis, wherein the human collagen alpha-2 chain is encoded by a sequence as set forth in SEQ ID NO: 2.
17. A method of filling a tissue space under an epidermis, wherein the exogenous P4H is a mammalian P4H.
18. A method of filling a tissue space under an epidermis, wherein the exogenous P4H is a human P4H.
19. A method of filling a tissue space under an epidermis, further comprising targeting the human collagen alpha-1 to a vacuole of the plant or the genetically modified plant and digesting it with ficin.
20. A method of filling a tissue space under an epidermis, further comprising targeting the human collagen alpha-2 to a vacuole of the plant or the genetically modified plant and digesting it with ficin.
21. A method of filling a tissue space under an epidermis, wherein the plant-derived human collagen is atelocollagen.
22. A method of filling a tissue space under an epidermis, wherein the light source comprises a light-emitting diode (LED), laser, or xenon lamp.
23. A method of filling a tissue space under an epidermis, wherein the photoinitiator induces polymerization of the polymerizable solution in response to visible light.
24. A method of filling a tissue space under an epidermis, wherein the visible light has a wavelength of 390-700 nm.
25. A method of filling a tissue space under an epidermis, wherein the photoinitiator is selected from the group consisting of Eosin Y+triethanolamine or riboflavin.
26. A method of filling a tissue space under an epidermis, wherein the photoinitiator induces polymerization of the polymerizable solution in response to ultraviolet (uv) light.
27. A method of filling a tissue space under an epidermis, wherein the photoinitiator is selected from the group consisting of lithium phenyl-2,4,6-trimethylbenzoylphosphinate (LAP) or 1-[4 2-hydroxy-1-[4-(2-hydroxyethoxy)phenyl]-2-methylpropan-1-one (IRGACURE® 2959).

28. A method of filling a tissue space under an epidermis, wherein the photoinitiator induces polymerization of the polymerizable solution in response to infrared light.
29. A method of filling a tissue space under an epidermis, wherein the polymerizable solution is introduced into the tissue space via a hollow needle or cannula in the range of 27-gauge to 33-gauge.
30. A method of filling a tissue space under an epidermis, wherein the polymerizable solution in the tissue space is molded or sculpted into the desired configuration via manual massage.
31. A method of filling a tissue space under an epidermis, wherein the polymerizable solution in the tissue space is molded or sculpted into the desired configuration using a molding or sculpting implement.
32. A method of filling a tissue space under an epidermis, wherein the polymerizable solution in the tissue space is essentially non-gellable at room temperature.
33. A method of filling a tissue space under an epidermis, wherein the polymerizable solution in the tissue space is essentially non-gellable at 37° C.
34. A method of filling a tissue space under an epidermis, wherein the polymerizable solution comprising the plant-derived human collagen has a reduced viscosity at room temperature in comparison with an analogous polymerizable solution comprising a tissue-extracted human or bovine collagen in the same concentration and formulation.
35. A method of filling a tissue space under an epidermis, wherein the polymerizable solution comprising the plant-derived human collagen has a reduced viscosity at 37° C. in comparison with an analogous polymerizable solution comprising a tissue-extracted human or bovine collagen in the same concentration and formulation.
36. A method of filling a tissue space under an epidermis, wherein the polymerizable solution comprising the plant-derived human collagen is introduced into the tissue space with a reduced force at room temperature as compared with an analogous polymerizable solution comprising a tissue-extracted human or bovine collagen in the same concentration and formulation.
37. A method of filling a tissue space under an epidermis, wherein the polymerizable solution comprising the plant-derived human collagen is introduced into the tissue space with a reduced force at 37° C. as compared with an analogous polymerizable solution comprising a tissued-extracted human or bovine collagen in the same concentration and formulation.
38. A method of filling a tissue space under an epidermis, wherein the polymerizable solution comprising the plant-derived human collagen has an increased tissue augmentation as compared with an analogous polymerizable solution comprising a tissue-extracted human or bovine collagen in the same concentration and formulation.
39. Use of a polymerizable solution injected into a tissue space under an epidermis to reduce lines, folds, fine lines, wrinkles, or scars, the polymerizable solution comprising a cross-linkable, plant-derived human collagen and a photoinitiator to induce polymerization prior to, on concomitant with, application of visible light, and molding or sculpting the polymerizable solution into a desired configuration to reduce lines, folds, fine lines, wrinkles, or scars.
40. Use of a polymerizable solution injected into a tissue space under an epidermis to reduce lines, folds, fine lines, wrinkles, or scars, wherein the cross-linkable, plant-derived human collagen is methacrylated or thiolated.
41. Use of a polymerizable solution injected into a tissue space under an epidermis to reduce lines, folds, fine lines, wrinkles, or scars, wherein the polymer solution further comprises a hyaluronic acid (HA) or a modified derivative thereof, a poly(vinyl alcohol) (PVA) or a modified derivative thereof, a polyethylene glycol (PEG) or a modified derivative thereof, polymethylmethacrylate (PMMA) microspheres or a modified derivative thereof, tricalcium phosphate (TCP) or a modified derivative thereof, calcium hydroxylapatite (CaHA) or a modified derivative thereof, carboxymethylcellulose or a modified derivative thereof, crystalline nanocellulose (CNC) or a modified derivative thereof, or a combination thereof.
42. Use of a polymerizable solution injected into a tissue space under an epidermis to reduce lines, folds, fine lines, wrinkles, or scars, wherein the modified derivative of hyaluronic acid (HA), a poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, or crystalline nanocellulose (CNC) comprises a photopolymerizable modified derivative.
43. Use of a polymerizable solution injected into a tissue space under an epidermis to reduce lines, folds, fine lines, wrinkles, or scars, wherein the modified derivative of hyaluronic acid (HA), a poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, or crystalline nanocellulose (CNC) comprises a methacrylated or thiolated derivative.
44. A method of filling a tissue space under an epidermis comprising:
introducing a polymerizable solution into the tissue space, the polymerizable solution comprising a cross-linkable, plant-derived human collagen.
45. A method of filling a tissue space under an epidermis, further comprising:
(a) a step of molding or sculpting the polymerizable solution into a desired configuration in the tissue space.
46. A method of filling a tissue space under an epidermis, wherein the molding or sculpting step reduces lines, folds, fine lines, wrinkles, or scars.
47. A method of filling a tissue space under an epidermis, the polymerizable solution further comprising a hyaluronic acid (HA) or modified derivative thereof, a poly(vinyl alcohol) (PVA) or modified derivative thereof, a polyethylene glycol (PEG) or modified derivative thereof, oxidized cellulose (OC) or a modified derivate thereof, polymethylmethacrylate (PMMA) microspheres or a modified derivative thereof, tricalcium phosphate (TCP) or a modified derivative thereof, calcium hydroxylapatite (CaHA) or a modified derivative thereof, carboxymethylcellulose or a modified derivative thereof, crystalline nanocellulose (CNC) or a modified derivative thereof, or a combination thereof.
48. A method of filling a tissue space under an epidermis, wherein the plant-derived collagen comprises rhCollagen.

49. A method of filling a tissue space under an epidermis, wherein the plant-derived collagen is obtained from a genetically modified plant.
50. A method of filling a tissue space under an epidermis, wherein the genetically modified plant is a genetically modified plant selected from the group consisting of tobacco, maize, alfalfa, rice, potato, soybean, tomato, wheat, barley, canola, carrot, and cotton.
51. A method of filling a tissue space under an epidermis, wherein the genetically modified plant is a tobacco plant.
52. A method of filling a tissue space under an epidermis, wherein the genetically modified plant comprises an expressible sequence of at least one gene sequence of human deoxyribonucleic acid (DNA) selected from the group consisting of: COL1, COL2, P4H-alpha, P4H-beta, and LH3.
53. A method of filling a tissue space under an epidermis, wherein the plant-derived human collagen comprises at least modified one human collagen alpha-1 chain as set forth in SEQ ID NO: 3 and as expressed in the genetically modified plant; and at least one modified human collagen alpha-2 chain as set forth in SEQ ID NO: 6 and as expressed in the genetically modified plant; and wherein the genetically modified plant further expresses an exogenous prolyl-4-hydroxylase (P4H).
54. A method of filling a tissue space under an epidermis, further comprising expressing an exogenous polypeptide selected from the group consisting of lysyl hydroxylase (LH), protease N, and protease C.
55. A method of filling a tissue space under an epidermis, wherein the human collagen alpha-1 chain is encoded by a sequence as set forth in SEQ ID NO: 1.
56. A method of filling a tissue space under an epidermis, wherein the human collagen alpha-2 chain is encoded by a sequence as set forth in SEQ ID NO: 2.
57. A method of filling a tissue space under an epidermis, wherein the exogenous P4H is a mammalian P4H.
58. A method of filling a tissue space under an epidermis, wherein the exogenous P4H is a human P4H.
59. A method of filling a tissue space under an epidermis, further comprising targeting the human collagen alpha-1 to a vacuole of the plant or the genetically modified plant and digesting it with ficin.
60. A method of filling a tissue space under an epidermis, further comprising targeting the human collagen alpha-2 to a vacuole of the plant or the genetically modified plant and digesting it with ficin.
61. A method of filling a tissue space under an epidermis, wherein the plant-derived human collagen is atelocollagen.
62. A method of filling a tissue space under an epidermis, wherein the polymerizable solution is introduced into the tissue space via a hollow needle or cannula in the range of 27-gauge to 33-gauge.
63. A method of filling a tissue space under an epidermis, wherein the polymerizable solution in the tissue space is molded or sculpted into the desired configuration via manual massage.
64. A method of filling a tissue space under an epidermis, wherein the polymerizable solution in the tissue space is molded or sculpted into the desired configuration using a molding or sculpting implement.
65. A method of filling a tissue space under an epidermis, wherein the polymerizable solution in the tissue space is essentially non-gellable at room temperature.
66. A method of filling a tissue space under an epidermis, wherein the polymerizable solution in the tissue space is essentially non-gellable at 37° C.
67. A method of filling a tissue space under an epidermis, wherein the polymerizable solution comprising the plant-derived human collagen has a reduced viscosity at room temperature in comparison with an analogous polymerizable solution comprising a tissue-extracted human or bovine collagen in the same concentration and formulation.
68. A method of filling a tissue space under an epidermis, wherein the polymerizable solution comprising the plant-derived human collagen has a reduced viscosity at 37° C. in comparison with an analogous polymerizable solution comprising a tissue-extracted human or bovine collagen in the same concentration and formulation.
69. A method of filling a tissue space under an epidermis, wherein the polymerizable solution comprising the plant-derived human collagen is introduced into the tissue space with a reduced force at room temperature as compared with an analogous polymerizable solution comprising a tissue-extracted human or bovine collagen in the same concentration and formulation.
70. A method of filling a tissue space under an epidermis, wherein the polymerizable solution comprising the plant-derived human collagen is introduced into the tissue space with a reduced force at 37° C. as compared with an analogous polymerizable solution comprising a tissued-extracted human or bovine collagen in the same concentration and formulation.
71. A method of filling a tissue space under an epidermis, wherein the polymerizable solution comprising the plant-derived human collagen has an increased tissue augmentation as compared with an analogous polymerizable solution comprising a tissue-extracted human or bovine collagen in the same concentration and formulation.
72. Use of a polymerizable solution injected into a tissue space under an epidermis to reduce lines, folds, fine lines, wrinkles, or scars, the polymerizable solution comprising a cross-linkable, plant-derived human collagen and molding or sculpting the polymerizable solution into a desired configuration to reduce lines, folds, fine lines, wrinkles, or scars.
73. A method of inducing a cellular growth scaffold in a tissue space under an epidermis comprising introducing a solution into the tissue space, the solution comprising:
    (a) a plant-derived human collagen; and
    (b) at least one growth factor or source thereof.
74. A method of inducing a cellular growth scaffold in a tissue space under an epidermis, wherein the source of the at least one growth factor comprises a plasma or a platelet-rich plasma.
75. A method of inducing a cellular growth scaffold in a tissue space under an epidermis, wherein the cellular growth scaffold promotes healing or replacement due to degradation or injury of a collagen-comprising tissue.
76. A method of inducing a cellular growth scaffold in a tissue space under an epidermis, wherein the collagen-comprising tissue is selected from the group consisting of a tendon, a ligament, skin, a cornea, a cartilage, a blood vessel, an intestine, an intervertebral disc, a muscle, a bone, or a tooth.

77. A method of inducing a cellular growth scaffold in a tissue space under an epidermis, wherein the cellular growth scaffold promotes healing of tendinitis.

78. A method of inducing a cellular growth scaffold in a tissue space under an epidermis, wherein the plant-derived collagen comprises rhCollagen.

79. A method of inducing a cellular growth scaffold in a tissue space under an epidermis, wherein the plant-derived collagen is obtained from a genetically modified plant.

80. A method of inducing a cellular growth scaffold in a tissue space under an epidermis, wherein the genetically modified plant is a genetically modified plant selected from the group consisting of tobacco, maize, alfalfa, rice, potato, soybean, tomato, wheat, barley, canola, carrot, and cotton.

81. A method of inducing a cellular growth scaffold in a tissue space under an epidermis, wherein the genetically modified plant is a tobacco plant.

82. A method of inducing a cellular growth scaffold in a tissue space under an epidermis, wherein the genetically modified plant comprises an expressible sequence of at least one gene sequence of human deoxyribonucleic acid (DNA) selected from the group consisting of: COL1, COL2, P4H-alpha, P4H-beta, and LH3.

83. A method of inducing a cellular growth scaffold in a tissue space under an epidermis, wherein the plant-derived human collagen comprises at least modified one human collagen alpha-1 chain as set forth in SEQ ID NO: 3 and as expressed in the genetically modified plant; and at least one modified human collagen alpha-2 chain as set forth in SEQ ID NO: 6 and as expressed in the genetically modified plant; and wherein the genetically modified plant further expresses an exogenous prolyl-4-hydroxylase (P4H).

84. A method of inducing a cellular growth scaffold in a tissue space under an epidermis, further comprising expressing an exogenous polypeptide selected from the group consisting of lysyl hydroxylase (LH), protease N, and protease C.

85. A method of inducing a cellular growth scaffold in a tissue space under an epidermis, wherein the human collagen alpha-1 chain is encoded by a sequence as set forth in SEQ ID NO: 1.

86. A method of inducing a cellular growth scaffold in a tissue space under an epidermis, wherein the human collagen alpha-2 chain is encoded by a sequence as set forth in SEQ ID NO: 2.

87. A method of inducing a cellular growth scaffold in a tissue space under an epidermis, wherein the exogenous P4H is a mammalian P4H.

88. A method of inducing a cellular growth scaffold in a tissue space under an epidermis, wherein the exogenous P4H is a human P4H.

89. A method of inducing a cellular growth scaffold in a tissue space under an epidermis, further comprising targeting the human collagen alpha-1 to a vacuole of the plant or the genetically modified plant and digesting it with ficin.

90. A method of inducing a cellular growth scaffold in a tissue space under an epidermis, further comprising targeting the human collagen alpha-2 to a vacuole of the plant or the genetically modified plant and digesting it with ficin.

91. A method of inducing a cellular growth scaffold in a tissue space under an epidermis, wherein the plant-derived human collagen is atelocollagen.

92. A method of inducing a cellular growth scaffold in a tissue space under an epidermis, wherein the solution comprising the plant-derived human collagen has a reduced viscosity at room temperature in comparison with an analogous solution comprising a tissue-extracted human or bovine collagen in the same concentration and formulation.

93. A method of inducing a cellular growth scaffold in a tissue space under an epidermis, wherein the solution comprising the plant-derived human collagen has a reduced viscosity at 37° C. in comparison with an analogous solution comprising a tissue-extracted human or bovine collagen in the same concentration and formulation.

94. A method of inducing a cellular growth scaffold in a tissue space under an epidermis, wherein the solution comprising the plant-derived human collagen is introduced into the tissue space with a reduced force at room temperature as compared with an analogous solution comprising a tissue-extracted human or bovine collagen in the same concentration and formulation.

95. A method of inducing a cellular growth scaffold in a tissue space under an epidermis, wherein the solution comprising the plant-derived human collagen is introduced into the tissue space with a reduced force at 37° C. as compared with an analogous solution comprising a tissued-extracted human or bovine collagen in the same concentration and formulation.

96. A method of inducing a cellular growth scaffold in a tissue space under an epidermis, wherein the solution comprising the plant-derived human collagen has an increased scaffolding formation or promotes an increase in cellular growth as compared with an analogous solution comprising a tissue-extracted human or bovine collagen in the same concentration and formulation.

97. Use of a solution injected into a tissue space under an epidermis to induce a cellular growth scaffold, the solution comprising a plant-derived human collagen and at least one growth factor or source thereof, to promote healing or replacement due to degradation or injury of a collagen-comprising tissue.

98. Use of a solution injected into a tissue space under an epidermis to induce a cellular growth scaffold, wherein the source of the at least one growth factor comprises a plasma or a platelet-rich plasma.

Definitions

As used herein, the singular form "a", "an" and "the" include plural references unless the context clearly dictates otherwise. For example, the term "a molecule" also includes a plurality of molecules.

As used herein the term "about" refers to ±10% or ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the phrase "genetically modified plant" encompasses any lower (e.g. moss) or higher (vascular) plant or a tissue or an isolated cell thereof (e.g., of a cell suspension) which is stably or transiently transformed with an exogenous polynucleotide sequence. Examples of plants include but are not limited to tobacco, maize, alfalfa, rice, potato, soybean, tomato, wheat, barley, canola, cotton, carrot as well as lower plants such as moss.

As used herein, the phrase "collagen chain" encompasses a collagen subunit such as the alpha 1 or 2 chains of collagen fibers, preferably type I fibers. As used herein, the phrase "collagen" refers to an assembled collagen trimer, which in the case of type I collagen includes two alpha 1 chains and one alpha 2 chain. A collagen fiber is collagen which is devoid of terminal propeptides C and N.

As used herein, the phrase "telopeptide-comprising collagen" encompasses a soluble collagen molecule which comprises telopeptides that are longer than the telopeptide remnants comprised in atelocollagen. Thus, the telopeptide-comprising collagen may be procollagen which comprises full length propeptides. Alternatively, the telopeptide-comprising collagen may be a procollagen molecule which comprises partially digested propeptides. Still alternatively, the telopeptide-comprising collagen may be telocollagen.

The term "procollagen" as used herein, encompasses a collagen molecule (e.g. human) that comprises either an N-terminal propeptide, a C-terminal propeptide or both. Exemplary human procollagen amino acid sequences are set forth by SEQ ID NOs: 1, 2, 7 and 8.

The term "telocollagen" as used herein, encompasses collagen molecules that lack both the N- and C-terminal propeptides typically comprised in procollagen but still contain the telopeptides. The telopeptides of fibrillar collagen are the remnants of the N- and C-terminal propeptides following digestion with native N/C proteinases. Recombinant human telocollagen may be generated in cells which have been transformed to express both exogenous human procollagen and the respective protease (i.e. C or N or both). Polynucleotide sequences encoding such proteases are exemplified by SEQ ID Nos: 10 (Protease C) and 11 (Protease N). Such proteases can be expressed such that they are accumulated in the same subcellular compartment as the collagen chain, as further described herein below.

As used herein, the term "atelocollagen" encompasses collagen molecules lacking both the N- and C-terminal propeptides typically comprised in procollagen and at least a portion of its telopeptides, but including a sufficient portion of its telopeptides such that under suitable conditions it is capable of forming fibrils. Any type of atelocollagen may be generated according to the method of the present invention. Examples include fibril-forming collagens (types I, II, III, V, and XI), network-forming collagens (types IV, VIII, and X), collagens associated with fibril surfaces (types IX, XII, and XIV), collagens which occur as transmembrane proteins (types XIII and XVII), or form 11-nm periodic beaded filaments (type VI). According to one embodiment, the atelocollagen comprises an alpha 1 and/or 2 chain of type I collagen.

It will be appreciated dermal fillers disclosed herein may in some embodiments comprise genetically modified forms of collagen/atelocollagen—for example collagenase-resistant collagens and the like.

As used herein, the phrase "plant promoter" or "promoter" includes a promoter which can direct gene expression in cells (including DNA-containing organelles) of plants, fungus and yeast. Such a promoter can be derived from a plant, bacterial, viral, fungal or animal origin. Such a promoter can be constitutive, i.e., capable of directing high levels of gene expression in a plurality of tissues, tissue specific, i.e., capable of directing gene expression in a particular tissue or tissues, inducible, i.e., capable of directing gene expression under a stimulus, or chimeric, i.e., formed of portions of at least two different promoters.

As is used herein, the phrase "subcellular compartment devoid of endogenous P4H activity" refers to any compartmentalized region of the cell which does not include plant P4H or an enzyme having plant-like P4H activity. Examples of such subcellular compartments include the vacuole, apoplast and cytoplasm as well as organelles such as the chloroplast, mitochondria and the like.

Herein throughout, the phrase "building material" encompasses the phrases "uncured building material" or "uncured building material formulation" and collectively describes the materials that are used to sequentially form the layers, as described herein. This phrase encompasses uncured materials which form the final object, namely, one or more uncured modeling material formulation(s), and optionally also uncured materials used to form a support, namely uncured support material formulations. An uncured building material can comprise one or more modeling formulations and can be dispensed such that different parts of the object are made upon curing different modeling formulations, and hence are made of different cured modeling materials or different mixtures of cured modeling materials.

As used herein, "bioprinting" means practicing an additive manufacturing process while utilizing one or more bio-ink formulation(s) that comprises biological components via methodology that is compatible with an automated or semi-automated, computer-aided, additive manufacturing system as described herein (e.g., a bioprinter or a bioprinting system).

Herein throughout, in the context of bioprinting, the term "object" describes a final product of the additive manufacturing which comprises, in at least a portion thereof, biological components. This term refers to the product obtained by a bioprinting method as described herein, after removal of the support material, if such has been used as part of the uncured building material. In some embodiments, the biological components include recombinant human collagen, as described, for example, in WO 2006/035442, WO 2009/053985, and patents and patent applications deriving therefrom, all of which are incorporated by reference as if fully set forth herein.

The term "object" as used herein throughout refers to a whole object or a part thereof.

Herein throughout, a "curable material" is a compound (monomeric or oligomeric or polymeric compound) which, when exposed to a curing condition, as described herein, solidifies or hardens to form a cured modeling material as defined herein. Curable materials are typically polymerizable materials, which undergo polymerization and/or cross-linking when exposed to a suitable energy source. Alternatively, curable materials are thermo-responsive materials, which solidify or harden upon exposure to a temperature change (e.g., heating or cooling). Optionally, curable materials are biological materials which undergo a reaction to form a hardened or solid material upon a biological reaction (e.g., an enzymatically-catalyzed reaction).

A "curing condition" encompasses a curing energy (e.g., temperature, radiation) and/or a material or reagent that promotes curing.

In some of any of the embodiments described herein, a curable material is a photopolymerizable material, which polymerizes or undergoes cross-linking upon exposure to radiation, as described herein, and in some embodiments the curable material is a UV-curable or visible light-curable material, which polymerizes or undergoes cross-linking upon exposure to UV-vis radiation, as described herein.

In some of any of the embodiments described herein, a curable material can be a monomer, an oligomer or a short-chain polymer, each being polymerizable as described herein.

Herein, the term "curable" encompasses the terms "polymerizable" and "cross-linkable".

As used herein, "aeroponics" is the process of growing plants in an air or mist environment without the use of soil or an aggregate medium (known as "geoponics").

As used herein, "hydroponics" is the process of growing plants without soil ("geoponics"), using mineral nutrient solutions in a water solvent.

As used herein, the "endosphere" comprises all endophytes of a plant.

As used herein, an "exudate" is a fluid emitted by an organism through pores or a wound. "Exudation" is the process of emitting an "exudate."

As used herein, "hydroponics" is the process of growing plants without soil ("geoponics"), using mineral nutrient solutions in a water solvent.

As used herein, "integression" or "integression hybridization" is the movement of a gene (i.e., "gene flow") from the gene pool of one species into the gene pool of another species via repeated backcrossing of an interspecific hybrid with one of its parent species, distinct from simple hybridization and resulting in a complex mix of parental genes.

As used herein, the "metabolome" is the complete set of small molecule chemicals found within a "biological sample" (including, but not limited to, a cell, an organelle, an organ, a tissue, a tissue extract, a biofluid, or an organism). The small molecule chemicals of the metabolome may be "endogenous metabolites" or "exogenous chemicals." "Endogenous metabolites" are naturally produced by an organism and include, but are not limited to, amino acids, organic acids, nucleic acids, fatty acids, amines, sugars, vitamins, cofactors, pigments, and antibiotics. "Exogenous chemicals" are not naturally produced by the organism and include, but are not limited to, drugs, environmental contaminants, food additives, toxins, and other xenobiotics. The "endogenous metabolome" is comprised of the endogenous metabolites, while the "exogenous metabolome" is comprised of the "exogenous chemicals." The "endogenous metabolome" is comprised of a "primary metabolome" and a "secondary metabolome," especially with respect to plants, fungi, and prokaryotes. The "primary metabolome" is comprised of "primary metabolites" (i.e., metabolites directly involved in normal growth, development, and reproduction of the organism), while the "secondary metabolome" is comprised of "secondary metabolites (i.e., metabolites not directly involved in the normal growth, development, or reproduction of the organism). Secondary metabolites often have significant ecological functions.

As used herein, a "metabolite" is usually a small molecule having a molecular weight of less than 1500 Da. A "metabolite" can include, but is not limited to, a glycolipid, a polysaccharide, a short peptide, a small oligonucleotide, an organic acid, a taxane, an alkaloid, and strigolactone, while very large macromolecules (e.g., proteins, mRNA, rRNA, and DNA) are not generally not metabolites and are not part of the metabolome.

As used herein, the "SILVA database" is the SILVA ribosomal RNA database.

All samples obtained from an organism, including those subjected to any sort of further processing are considered to be obtained from the organism.

Methods for DNA isolation, sequencing, amplification, and/or cloning are known to a person skilled in the art. Most commonly used method for DNA amplification is PCR (polymerase chain reaction; see, for example, PCR Basics: from background to Bench, Springer Verlag, 2000; Eckert et al., 1991. PCR Methods and Applications 1:17). Additional suitable amplification methods include the ligase chain reaction (LCR), transcription amplification and self-sustained sequence replication, and nucleic acid-based sequence amplification (NASBA). Likewise, methods for RNA and protein isolation, characterization, and the like and for protein expression are known to a person skilled in the art.

The following examples are presented in order to more fully illustrate some embodiments of the dermal fillers and uses thereof, disclosed herein. They should, in no way be construed, however, as limiting the broad scope of dermal fillers disclosed herein nor their uses. One skilled in the art can readily devise many variations and modifications of the principles disclosed herein without departing from the scope of the invention.

EXAMPLES

Example 1. Constructs and Transformation Schemes

Figure 1B:
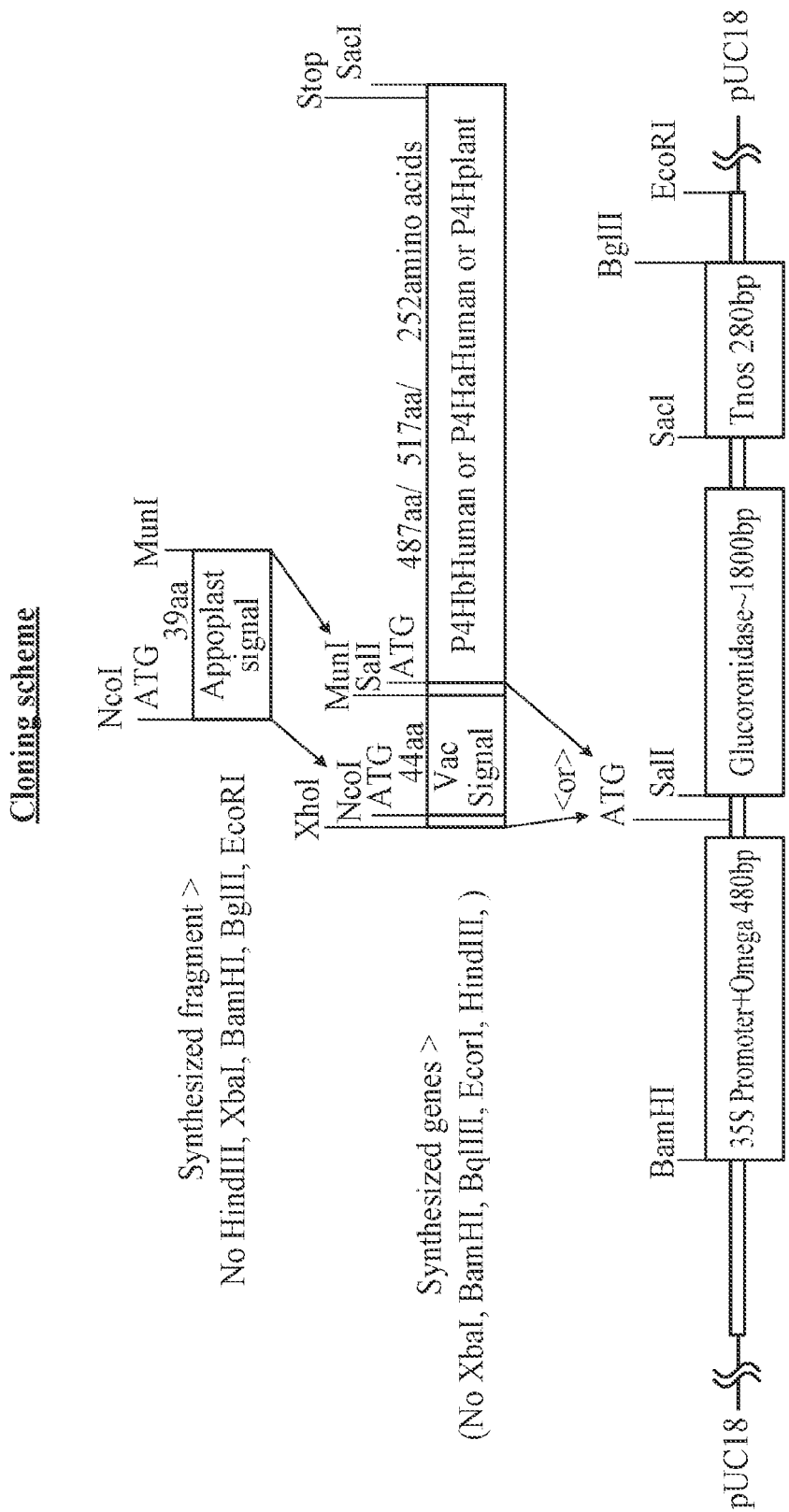
Figure 1C:
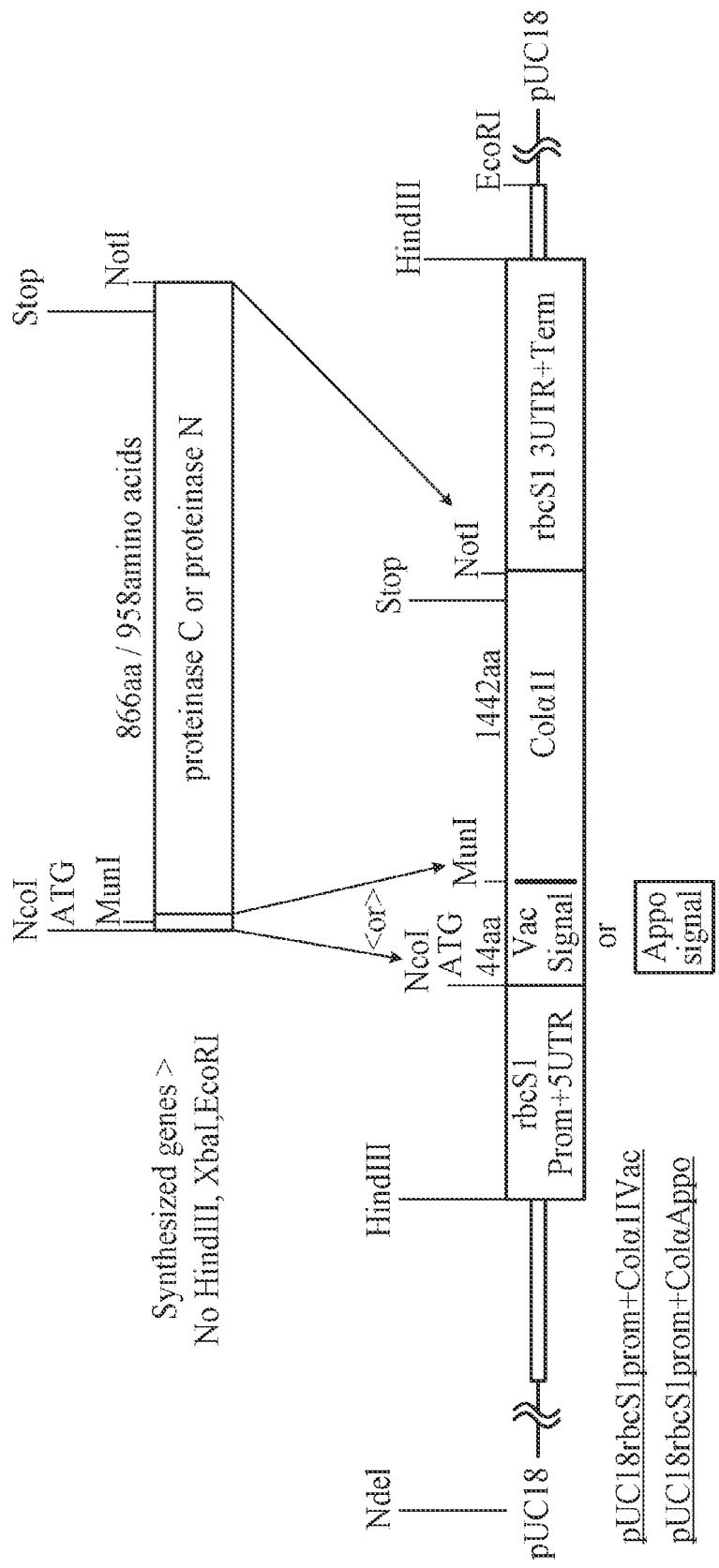
Figure 1D:
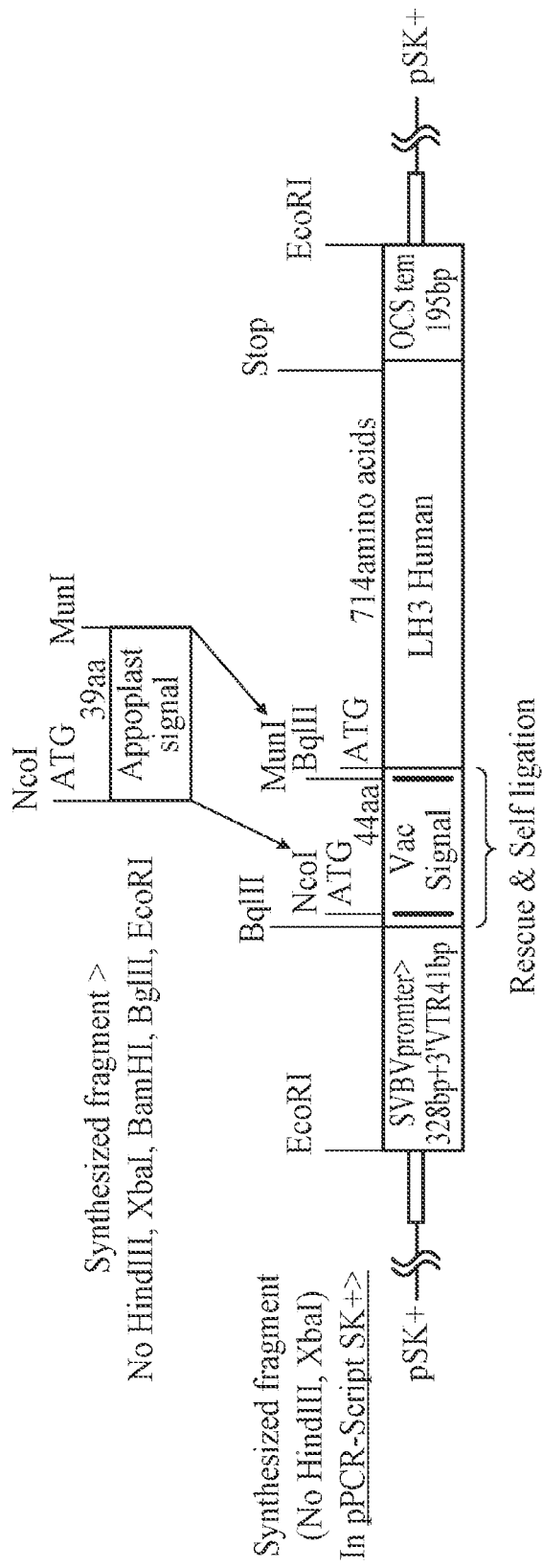

Constructions of expression cassettes and vectors used in this work are illustrated in FIGS. 1a-d (see also U.S. Pat. No. 8,455,717). All of the coding sequences in this work were optimized for expression in tobacco and chemically synthesized with desired flanking regions (SEQ ID NOs: 1, 4, 7, 12, 14, 16, 18, 20, 22). FIG. 1A: The synthetic genes coding for Col1 and Col2 (SEQ ID NOs: 1, 4) fused either to the vacuolar signal or to the apoplast signal (encoded by SEQ ID NO: 7) or without signals were cloned in expression cassettes composed of a *Chrysanthemum* rbcS1 promoter and 5' UTR (SEQ ID NO: 10) and a *Chrysanthemum* rbcS1 3'UTR and terminator (SEQ ID NO: 11). The complete expression cassettes were cloned in the multiple cloning site of the pBINPLUS plant transformation vector (van Engelen et al., 1995, Transgenic Res 4: 288-290). FIG. 1B: The synthetic genes coding for P4H beta-human, P4H alpha-human and P4H-plant (SEQ ID NOs: 12, 14 and 16) fused either to the vacuolar signal or to the apoplast signal (encoded by SEQ ID NO: 7) or without signals were cloned in expression cassettes composed of the CaMV 35S promoter and TMV omega sequence and *Agrobacterium* Nopaline synthetase (NOS) terminator carried by the vector pJD330 (Galili et al., 1987, Nucleic Acids Res 15: 3257-3273). The complete expression cassettes were cloned in the multiple cloning site of the pBINPLUS vectors carrying the expression cassettes of Col1 or Col2. FIG. 1c: The synthetic genes coding for Proteinase C and Proteinase N (SEQ ID NOs: 18, 20) fused either to the vacuolar signal or to the apoplast signal (encoded by SEQ ID NO: 7) were cloned in expression cassettes composed of a *Chrysanthemum* rbcS1 promoter and 5' UTR (SEQ ID NO: 10) and a *Chrysanthemum* rbcS1 3'UTR and terminator (SEQ ID NO: 11). The complete expression cassettes were cloned in the multiple cloning site of the pBINPLUS plant transformation vector. FIG. 1*d*: The synthetic gene coding for LH3 (SEQ ID NO: 22) with flanking Strawberry vein banding virus (SVBV) promoter (NCBI accession AF331666 REGION: 623.950 version AF331666.1 GI:13345788) and terminated by *Agrobacterium* octopin synthase (OCS) terminator (NCBI accession Z37515 REGION: 1344.1538 version Z37515.1 GI:886843) fused either to the vacuolar signal or to the apoplast signal (encoded by SEQ ID NO: 7) or without signals was cloned in the multiple cloning site of the pBINPLUS vector carrying the expression cassettes of Col1 and P4H beta.

Co-transformations schemes utilizing the expression cassettes described in FIGS. 1*a-d* into a host plant are illustrated in FIG. 2. Each expression cassette insert is represented by a short name of the coding sequence. The coding sequences and related SEQ ID NOs. are described in Table 1. Each co-transformation is preformed by two pBINPLUS binary vectors. Each rectangle represents a single pBINPLUS vector carrying one, two or three expression cassettes. Promoters and terminators are specified in FIGS. 1*a-d*.

Example 2. Plant Collagen Expression

Synthetic polynucleotide sequences encoding the proteins listed in Table 1 below were designed and optimized for expression in tobacco plants.

Signal Peptides
1. Vacuole signal sequence of barley gene for Thiol protease aleurain precursor (NCBI accession P05167 GI:113603)

(SEQ ID NO: 24)
MAHARVLLLALAVLATAAVAVASSSSFADSNPIRPVTDRAASTLA.

2. Apoplast signal of *Arabidopsis thaliana* endo-1,4-beta-glucanase (Cell, NCBI accession CAA67156.1 GI:2440033); SEQ ID NO. 9, encoded by SEQ ID NO. 7.

Construction of Plasmids

Plant expression vectors were constructed as taught in Example 1, the composition of each constructed expression vector was confirmed via restriction analysis and sequencing.

Expression vectors including the following expression cassettes were constructed:
1. Collagen alpha 1
2. Collagen alpha 1+human P4H beta subunit
3. Collagen alpha 1+human P4H beta subunit+human LH3
4. Collagen alpha 2
5. Collagen alpha 2+with human P4H alpha subunit
6. Collagen alpha 2+with *Arabidopsis* P4H
7. Human P4H beta subunit+human LH3
8. Human P4H alpha subunit Each of the above described coding sequences was either translationally fused to a vacuole transit peptide or to an apoplasm transit peptide or was devoid of any transit peptide sequences, in which case cytoplasmic accumulation is expected.

TABLE 1

List of expressed proteins

| Name: | Swiss Prot accession | Amino acids | Splicing isoform | Deletions | name | Included in SEQ ID NO. | Encoded by SEQ ID NO. |
|---|---|---|---|---|---|---|---|
| Collagen alpha 1(I) chain [Precursor] | p02452 | 1442 | One version | ER signal | Col1 | 3 | 1 |
| Collagen alpha 2(I) chain [Precursor] | p08123 Two changes done in p08123: D549A and N249I | 1342 | One version | ER signal | Col2 | 6 | 4 |
| Prolyl 4-hydroxylase beta subunit | p07237 | 487 | One version | ER signal, KDEL | P4H betaHuman | 13 | 12 |
| Prolyl 4-hydroxylase alpha-1 subunit | p13674 | 517 | P13674-1 | ER signal | P4H alphaHuman | 15 | 14 |
| Prolyl 4-hydroxylase Plant | No entry in Swissprot. NCBI accession: gi: 15227885 | 252 | One version | Mitochondrial signal predicted as: aa1-39 | P4Hplant | 17 | 16 |
| Procollagen C-proteinase | p13497 | 866 | P13497-1 BMP1-3 | ER signal, propeptide | Proteinase C | 19 | 18 |
| Procollagen I N-proteinase | o95450 | 958 | O95450-1 LpNPI | ER signal, propeptide | Proteinase N | 21 | 20 |
| Lysyl hydroxylase 3 | o60568 | 714 | One version | ER signal | LH3 | 23 | 22 |

Plant Transformation and PCR Screening

Tobacco plants (*Nicotiana tabacum*, Samsun NN) were transformed with the above described expression vectors according to the transformation scheme taught in FIG. 2.

Figure 3:
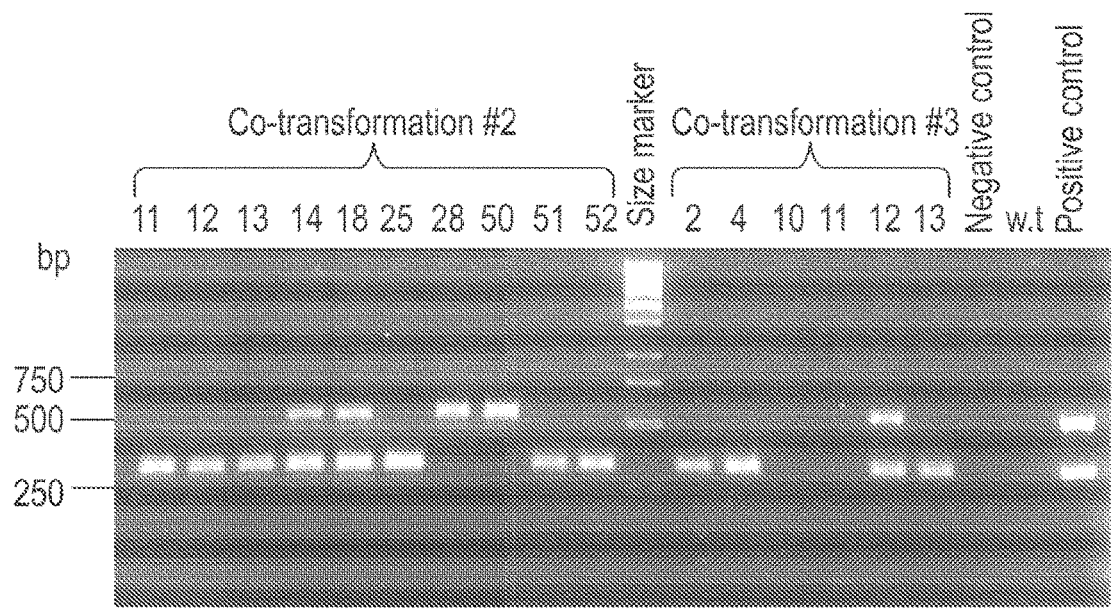
FIG. 3 is a previous multiplex PCR screening of transformants showing plants that were positive for Collagen alpha 1 (324 bp fragment) or Collagen alpha 2 (537 bp fragment) or both.

Resultant transgenic plants were screened via multiplex PCR using four primers which were designed capable of amplifying a 324 bp fragment of Collagen alpha 1 and a 537 bp fragment of Collagen alpha 2 (Table 2). FIG. 3 illustrates the results of one multiplex PCR screen.

TABLE 2

List of primers for multiplex PCR for amplification of a 324 bp fragment of Collagen alpha 1 and a 537 bp fragment of Collagen alpha 2

| | |
|---|---|
| Col1 forward primer (24-mer): | 5' ATCACCAGGAGAACAGGGACCATC 3' SEQ ID 25 |
| Col1 reverse primer (29-mer): | 5' TCCACTTCCAAATCTCTATCCCTAACAAC 3' SEQ ID 26 |
| Col2 forward primer (23-mer): | 5' AGGCATTAGAGGCGATAAGGGAG 3' SEQ ID 27 |
| Col2 reverse primer (27-mer): | 5' TCAATCCAATAATAGCCACTTGACCAC 3' SEQ ID 28 |

Example 3. Detection of Human Collagen in Transgenic Tobacco Plants

Figure 4:
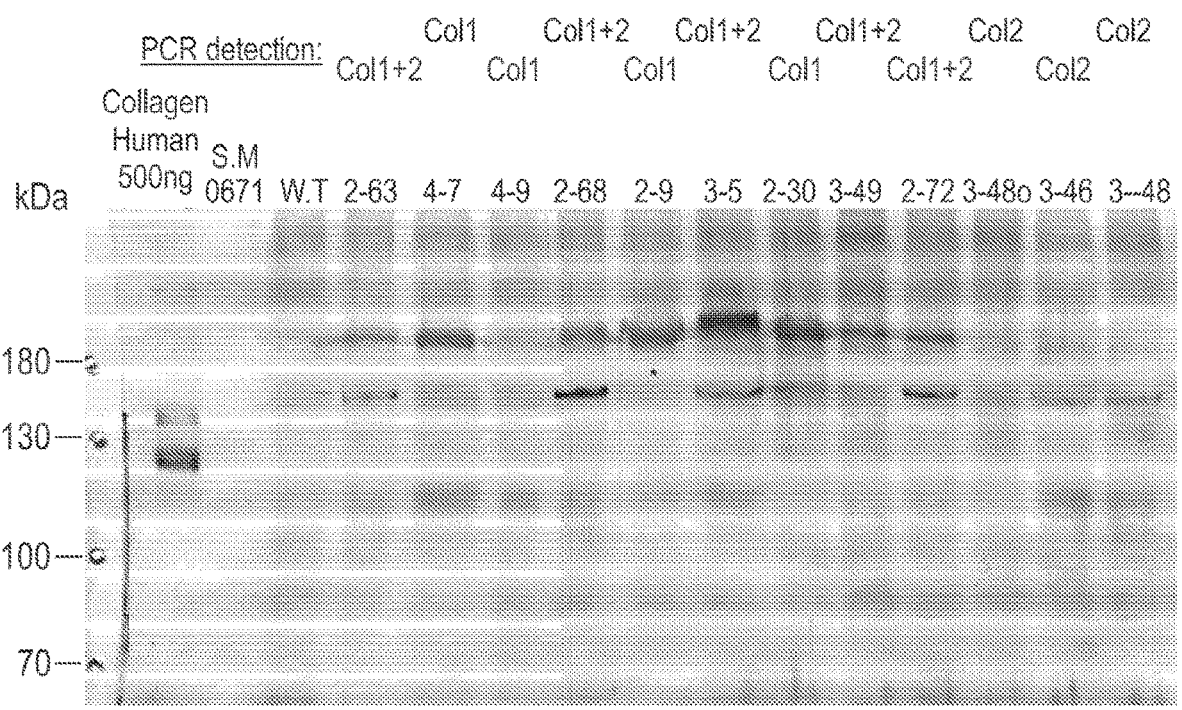
FIG. 4 is a previous Western blot analysis of transgenic plants generated by co-transformations 2, 3 and 4. Total soluble proteins were extracted from tobacco co-transformants #2, #3 and #4 and tested with anti-Collagen I antibody (#AB745 from Chemicon Inc.). Size markers were #SM0671 from Fermentas Inc. W.T. is a wild type tobacco. Positive collagen bands are visible in plants that are PCR positive for collagen typeI alpha 1 or alpha 2 or both. Positive control band of 500 ng collagen type I from human placenta (#CC050 from Chemicon Inc., extracted from human placenta by pepsin digestion) represents about 0.3% of the total soluble proteins (about 150 µg) in the samples from the transgenic plants. The larger band at about 140 kDa in the human collagen sample is a procollagen with its C-propeptide as detected by anti carboxy-terminal propeptide of collagen type I antibody (#MAB1913 from Chemicon Inc.). The smaller band at about 120 kDa in the human collagen sample is a collagen without propeptides. Due to their unusual composition, proline rich proteins (including collagens) consistently migrate on polyacrylamid gels as bands with molecular mass higher than expected. Therefore, the collagen chains without propeptides with a molecular weight of about 95 kDa migrate as a band of about 120 kDa.

Total soluble proteins were extracted from tobacco transformants 2, 3 and 4 by grinding 500 mg of leaves in 0.5 ml 50 mM Tris-HCl pH=7.5 with a "Complete" protease inhibitor cocktail (product #1836145 from Roche Diagnostics GmbH, 1 tablet per 50 ml buffer). The crude extract was mixed with 250 µl 4×. Sample application buffer containing 10% beta-mercapto-ethanol and 8% SDS, the samples were boiled for 7 minutes and centrifuged for 8 minutes in 13000 rpm. 20 µl of the supernatant were loaded in a 10% polyacrylamide gel and tested with anti-Collagen I (denatured) antibody ((#AB745 from Chemicon Inc.) in a standard Western blot procedure (FIG. 4). W.T. is a wild type tobacco. Positive collagen bands are visible in plants that are PCR positive for collagen typeI alpha 1 or alpha 2 or both. Positive control band of 500 ng collagen type I from human placenta (#CC050 from Chemicon Inc.) represents about 0.3% of the total soluble proteins (about 150 µg) in the samples from the transgenic plants.

Figure 5:
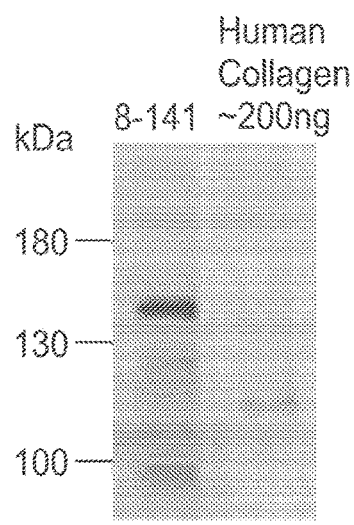
FIG. 5 is a previous Western blot analysis of transgenic plant generated by co-transformation #8 (carrying apoplast signals translationally fused to the collagen chains). Total soluble proteins were extracted from transgenic tobacco leaves and tested with anti-Collagen I antibody (#AB745 from Chemicon Inc.) Positive collagen alpha 2 band is visible in plant 8-141. Collagen type I from human placenta (#CC050 from Chemicon Inc.) served as control.

Plants expressing collagen at the expected molecular weight up to about 1% of the total soluble proteins were detected when collagen was targeted to the vacuole (FIG. 4). Subcellular targeting of full length collagen to the apoplast was successfully achieved (FIG. 5). Plants expressing collagen in the cytoplasm (i.e. no targeting peptide) did not accumulate collagen to detectable levels showing that subcellular targeting of collagen in plants is critical for success.

In addition, in contrast to the studies of Ruggiero et al. 2000 and Merle et al. 2002 which showed that collagen lacking the N-propeptide was subjected to significant proteolysis, using the present approach full length collagen proteins with C-propeptide and N-propeptide accumulated in subcellular compartments at high levels.

The present data also clearly shows that crossing two plants each expressing a different collagen chain type is advantageous in that it enables selection of plants expressing optimal levels of each chain type and subsequent plant crossing to achieve the desired collagen producing plant.

Collagen produced by the plants of the present invention includes the native propeptides and therefore is expected to form a larger protein then the human control that was purified by proteolysis. The calculated molecular weight of Collagen alpha 1 and alpha 2 chains without hydroxylations or glycosylations are the following: Col1 with propeptides—136 kDa, Col1 without propeptides—95 kDa, Col2 with propeptides—127 kDa, Col2 without propeptides—92 kDa.

As can be seen in FIG. 4, the Col1 bands in transformants 3-5 and 3-49 appears larger then Col1 bands in other plants. This indicates prolines hydroxylation in collagen chains by human proline-4-hydroxylase holoenzyme composed of alpha and beta subunits that were coexpressed in these plants and targeted to the same subcellular compartment as the human collagen chains (e.g., vacuole).

Example 4. Collagen Triple Helix Assembly and Thermal Stability in Transgenic Plants Assembly of collagen triple helix and the helix thermal stability in transgenic plants were tested by thermal denaturation followed by trypsin or pepsin digestion of the total crude protein extract of transgenic plants (FIGS. 6a-b).

In a first experiment, total soluble proteins from tobacco 2-9 (expressing only col alfa1 and no P4H) and 3-5 (expressing both col alpha1+2 and P4H) were extracted by grinding 500 mg leaves in 0.5 ml of 50 mM Tris-HCl pH=7.5, centrifuging for 10 minutes in 13000 rpm and collecting the supernatant. 0 µl of the supernatant were subjected to heat treatment (15 minutes in 33° C. or 43° C.) and then immediately placed on ice. Trypsin digestion was initiated by adding to each sample 6 .mu.l of 1 mg/ml Trypsin in 50 mM Tris-HCl pH=7.5. The samples were incubated for 20 minutes at room temperature (about 22° C.). The digestion was terminated by addition of 20 µl 4× sample application buffer containing 10% betamercaptoethanol and 8% SDS, the samples were boiled for 7 minutes and centrifuged for 7 minutes at 13000 rpm. 500 of the supernatant were loaded onto a 10% polyacrylamide gel and tested with anti-Collagen I antibody ((#AB745 from Chemicon Inc.) using a standard Western blot procedure. Positive controls were samples of 500 ng human collagen I (#CC050 from Chemicon Inc., extracted from human placenta by pepsin digestion) which was added to 50 µl total soluble proteins extracted from w.t. tobacco.

Figure 6A:
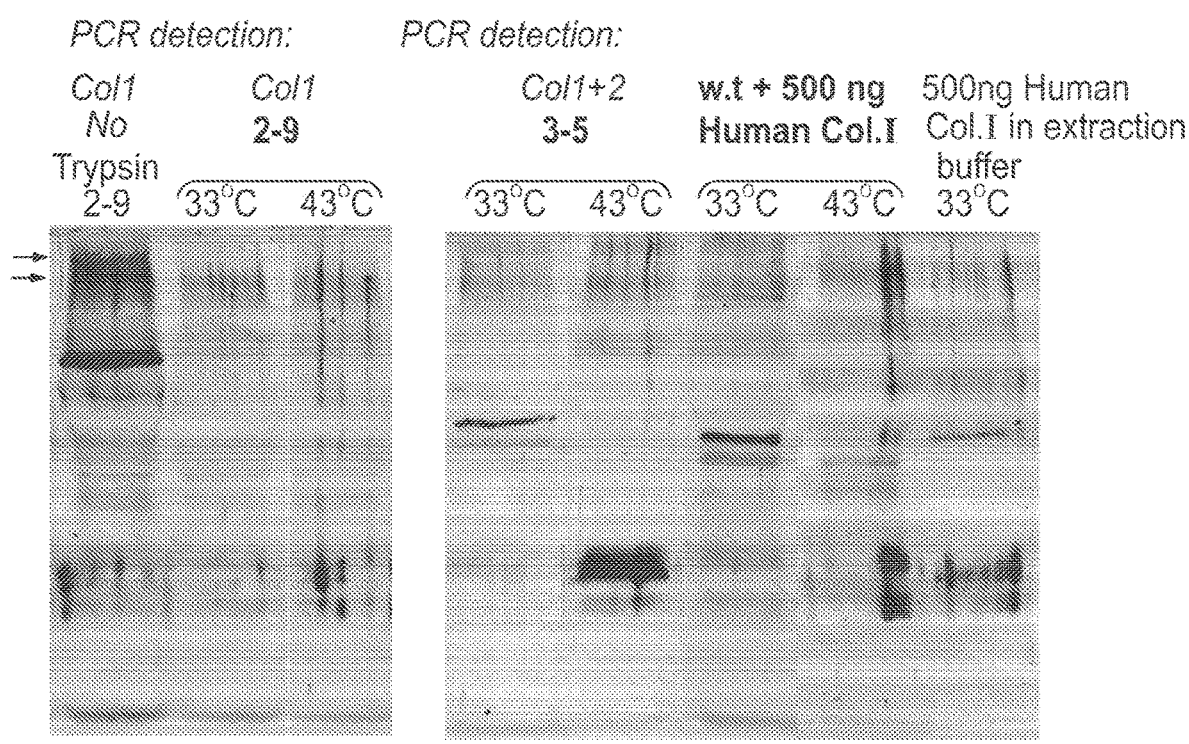

As shown in FIG. 6a, collagen triple helix that formed in plants #3-5 as well as control human collagen was resistant to denaturation at 33° C. In contrast, collagen formed by plants #2-9 denatured at 33° C. This difference in thermal stability indicates a successful triple helix assembly and post translational proline hydroxylation in transformants #3-5 which express both collagen alpha 1 and collagen alpha 2 as well as P4H beta and alpha subunits.

Two bands in transformants #2-9 may represent dimers or trimers, which are stable following 7 minutes of boiling with SDS and mercaptoethanol. Similar bands are visible in human collagen (upper panel) and in transformants #3-5. A possible explanation is a covalent bond between two peptides in different triple helices (cross link), formed following oxidative deamination of two lysines by Lysine oxidase.

In a second experiment, total soluble proteins from transgenic tobacco 13-6 (expressing collagen I alpha 1 and alpha 2 chains—pointed by arrows, human P4H alpha and beta subunits and human LH3) were extracted by grinding 500 mg of leaves in 0.5 ml of 100 mM Tris-HCl pH=7.5 and 300 mM NaCl, centrifuging for 7 minutes at 10000 rpm and collecting the supernatant. 50 µl of the supernatant was subjected to heat treatment (20 minutes in 33° C., 38° C., or 42° C.) and then immediately placed on ice. Pepsin digestion was initiated by adding to each sample 4.5 µl of 0.1M HCl and 4 µl of 2.5 mg/ml Pepsin in 10 mM acetic acid. The samples were incubated for 30 minutes at room temperature (about 22° C.). The digestion was terminated by adding 5 µl of unbuffered 1 M Tris. Each sample was mixed with 22 µl 4× Sample application buffer containing 10% beta-mercapto-ethanol and 8% SDS, boiled for 7 minutes and centrifuged for 7 minutes in 13000 rpm. 40 µl of the supernatant were loaded in a 10% polyacrylamide gel and tested with anti-Collagen I antibody ((#AB745 from Chemicon Inc.) in a standard Western blot procedure. Positive control was sample of about 50 ng human collagen I (#CC050 from Chemicon Inc., extracted from human placenta by pepsin digestion) added to total soluble proteins from w.t. tobacco.

As is illustrated in FIG. 6b, collagen triple helix that formed in plant #13-6 was resistant to denaturation at 42° C. Cleavage of the propeptides is first visible at 33° C. and gradually increases in efficiency when the temperature is raised to 38° C. and again to 42° C. The cleaved collagen triple helix domain shows a similar migration on the gel to the migration of the pepsin treated human collagen. The human collagen that was used in this experiment was extracted from human placenta by pepsin proteolysis and therefore lacks the propeptides and some of the telopeptides.

Example 5. Plant P4H Expression

Induction of Native Plant P4H

Tobacco P4H cDNA was cloned and used as a probe to determine conditions and treatments that would induce endogenous P4H expression. Northern blot analysis (FIG. 7) clearly shows that P4H is expressed at relatively high levels in the shoot apex and at low levels in leaves. P4H level was induced significantly in leaves 4 hours following abrasion treatment ("wounded" in the lower panel). Similar results were achieved using other stress conditions (not shown).

Detection of Human P4H Alpha and Beta Subunits and Collagen Alpha 1 and Alpha 2 Chains in Transgenic Tobacco Plants Detection of human P4H alpha and beta subunits and collagen type I alpha 1 and alpha 2 chains in transgenic tobacco plants was effected using anti-human P4H alpha subunit antibody (#63-163 from ICN Biomedicals Inc.), anti-human P4H beta subunit antibody (#NMAB2701 from Chemicon Inc.) and anti-Collagen I antibody (#AB745 from Chemicon Inc.). The results of a Western blot probed with these antibodies are shown in FIG. 8.

Expression of P4H alpha, P4H beta and collagen 1 alpha 1 and alpha 2 bands was confirmed in plant 13-6 (also transformed also with human LH3). The calculated molecular weights of P4H alpha and beta including the vacuolar signal peptide are 65.5 kDa and 53.4 kDa respectively. The calculated molecular weights of Collagen alpha 1 and alpha 2 chains with propeptides, without hydroxylati-ons or glycosylations are 136 kDa and 127 kDa respectively.

Example 6. Vacuolar Targeted Collagen is Stably Expressed in Dark-Grown Plants

Collagen Expressing Plants:

The 20-279 parental tobacco plant line was generated by co-transformation with an expression vector expressing P4Hbeta+LH3 and another expression vector expressing P4Halpha. Each gene is preceded by a vacuolar targeting determinant of aleurain, a plant vacuolar thiol protease, The 2-300 parental tobacco plant line was generated by co-transformation with an expression vector expressing col1 and another expression vector expressing col2. Each gene is preceded by a vacuolar targeting determinant of aleurain, a plant vacuolar thiol protease.

The 13-652 plant was generated by co-transformation of tobacco plant with an expression vector encoding Col1, P4Hbeta and LH3 and a second expression vector encoding Col2 and P4H alpha. Each gene is preceded by a vacuolar targeting determinant of aleurain, a plant vacuolar thiol protease, Cassette sequences included in the vectors are described in Example 1 above.

Light and Darkness Trial

Analysis of six 13-6/52 homozygote plants. Samples from leaf #4+5/6 were taken daily at the same time (12:30) for 8 days, from 3 plants that were grown at regular conditions (16 hours under light conditions and 8 hours in the dark) and from 3 plants that were grown only in the dark.

Total Protein Extraction and Western Blot Analysis

Ninety mg of tobacco leaves were homogenized by mixer mill Type MM301 (Retsch) in an extraction buffer (100 mM Tris HCl pH=7.5, protease inhibitor cocktail available from Roche Catalog Number, 04-693-116-001) at 4° C. Following 30 min of centrifugation (20,000×g at 4° C.), the supernatant was collected. Protein samples were fractionated on 8% SDS-PAGE (Laemmli 1970) and transferred to a nitrocellulose membrane using BIO-RAD™ Protein TRANS-BLOT™ apparatus. The membrane was blocked for 30 min at room temperature in 3% (g/v) skim milk (Difco), and then reacted with either commercial rabbit anti-human collagen type I polyclonal antibodies (Chemicon), for overnight (o.n.) at room temperature. The membrane was rinsed with water 3-5 times and then washed for 30 min in TBS. Following incubation with a secondary antibody [goat anti rabbit-IgG antibody conjugated to alkaline phosphatase (AP) (Chemicon)] for 2 hours at room temperature, the membrane was rinsed with water for 3-5 times and washed for 30 min in TBS. Immunodetection was effected with nitrotetrazolium blue chloride (NBT, Sigma) and 5-bromo-4-chloro-3-indolyl phosphate p-toluidine salt (BCIP, Sigma), at room temperature for 2 hour-o.n.

Results

As shown in FIG. 9, tobacco plants transgenic for vacuolar targeted collagen express Pro-alpha-1 and Pro-alpha-2 (lane 1). Collagen from dark grown vacuolar targeted plants exhibited similar stability (lane 2), substantiating the exceptional stability of collagen generated according to the teachings of the present invention Examples 7-13

General Materials and Methods

Collagen extraction and enzymatic reaction: In a blender, 300 g of tobacco leaves were blended in a chilled extraction buffer (600 ml of 100 mM Tris-HCl pH 7.5 containing 360 mg potassium-meta-bisulfite, 530 mg L-Cysteine and 1 g EDTA) supplemented with 5 g PVPP and 2 g of activated carbon (see also U.S. Pat. No. 8,759,487). Blending was performed 5 times for 1-minute intervals to keep temperatures below 15° C. Crude extract was filtered through a gauze pad and centrifuged for 30 min, 25000 g, 5° C. The supernatant was collected; $CaCl_2$) was added to a final concentration of 10 mM. The supernatant was divided into 10 ml samples. The desired enzyme was added to each 10 ml sample, according to the conditions set forth in Table 3 herein below.

TABLE 3

Procollagen digestion reaction conditions

| # Sample | Protease: | Concentration of protease (mg/Liter): | Incubation time (Hours): | Incubation temperature (degrees Celcius): |
| --- | --- | --- | --- | --- |
| 1 | Desired enzyme | 1 | 3 | 15 |
| 2 | Desired enzyme | 5 | 3 | 15 |
| 3 | Desired enzyme | 25 | 3 | 15 |
| 4 | Desired enzyme | 1 | 6 | 15 |
| 5 | Desired enzyme | 5 | 6 | 15 |
| 6 | Desired enzyme | 25 | 6 | 15 |
| * | Control-no protease | 0 | 3 | 15 |
| * | Control-no protease | 0 | 6 | 15 |

Enzyme description: Ficin from Fig tree latex (Sigma, catalog #F4125), Subtilisin from *Bacillus licheniformis* (Sigma, catalog #P5459-5 gr), Bromelain from pineapple stem (Sigma, catalog #B4882-10 gr), Papain from *Carica papaya* (Fluka, Catalog #76220-25 gr), Savinase 6.0 t type W from the alkalophilic bacterium *Bacillus lentus* (Novozymes, catalog #PX92500501), Neutrase 1.5 MG from bacterium *Bacillus amyloliquefaciens* (Novozymes, catalog #PW201041), Protamex, a commercial *Bacillus* proteinase complex (Novozymes, catalog #PW2A1021), Alcalase 3.0 T, *Bacillus subtilis* alkaline proteinase (Novozymes, catalog #PJ90000901), Esperase 6.0 T, alkalophilic bacterium *Bacillus lentus* (Novozymes, catalog #PE90110401), Alcalase 2.4 L FG, *Bacillus subtilis* alkaline proteinase (Novozymes, catalog #PLN05330), Esperase 8.0 L, alkalophilic bacterium *Bacillus lentus* (Novozymes, catalog #PE00077) were all donated by Novozymes. Trypsin, pancreatic trypsin 6.0 S type saltfree, from animal pancreas (Novozymes, catalog #P245-D20). TRYPZEAN™, a recombinant trypsin expressed in corn was purchased from Sigma Chemical Co. (catalog #: T3449).

Determination of atelocollagen concentration: The concentration of atelocollagen generated according to Examples 9-10 was assayed by two methods as follows:

SIRCOL™ assay: SIRCOL™ collagen assay kit was purchased from Biocolor Ltd. (Cat. No 85000). This assay is based on the interaction of the Sirius Red dye with the collagen triple helix. The analysis was performed according to the supplier's instruction manual, 4th edition, 2002. Bovine collagen standard was used to prepare a calibration curve (0 to 50 μg collagen). Three samples of 10-50 μl of the collagen solution in 10 mM HCl were placed into a 1.5 ml Eppendorf tube, and the volume was brought to 100 μl with 0.5 M acetic acid. 1 ml SIRCOL™ dye reagent was added to each tube and the tubes were shaken for 30 min at room temperature. Tubes were centrifuged at 12,000 rpm for 10 min at room temperature, the supernatant was aspirated and the tubes were inverted over an absorbing paper to remove the remaining supernatant. Cotton buds were used to remove any access drops from the walls of the tubes. 1 ml of Alkali reagent was added to each tube, mixed well and incubated for 10 min at room temperature. Absorption at 540 nm was measured using a spectrophotometer and the concentration of collagen was calculated against the calibration curve, using 10 mM HCl as a blank sample.

SDS-PAGE Instant Blue assay: Samples were boiled for 5 min in SAB buffer (reducing conditions) and centrifuged at 12,000 rpm for 5 min, prior to loading on a SDS PAGE, 8% acrylamide. The gel was run in a Mini Protean 3 unit (BioRad #165-3301, 165-3302). Instant Blue reagent (Novexin #ISB01L) was applied to the gel until the protein was visualized as blue bands on the gel. The gel was rinsed with water and dried. Concentration of the collagen bands was calculated by densitometry, against a human standard loaded on the same gel.

Coomassie analysis: Samples of collagen (in 10 mM HCl) were titered to pH 7.5 using 1M Tris. Sample Application Buffer containing 10% beta-mercaptoethanol and 8% SDS was added by diluting it fourfold in the 30 μl of pH titered samples. The samples were boiled for 7 minutes. 30 μl of the supernatant were loaded on to a 10% polyacrylamide gel and separated for 2 hours at 100 volts. The gel was transfer to a Coomassie-based solution for 1 hour with shaking. The Coomassie dye was removed using a standard destain solution.

SDS-PAGE and Western blot analysis of alpha-1 and alpha-2 collagen chains: Samples were boiled for 7 minutes in reducing sample application buffer (2.5% beta-mercaptoethanol and 2% SDS) and then centrifuged for 15 minutes at 13,000 rpm. 30 μl of the supernatant were separated on a 10% polyacrylamide gel. Following separation, standard Western blot protocols were employed to blot samples onto nitrocellulose membranes. Following transfer, the membranes were incubated with anti-Collagen I antibody (Chemicon Inc. catalogue #AB745) for immunodetection of alpha-1 and alpha-2 collagen chains. Molecular weight markers were purchased from Fermentas Inc. (catalogue #SM0671).

Controls: A positive control of Human Skin Collagen Type I purchased from Calbiochem (#234138) was employed as a marker for Western blot analyses. The grinding control sample reflects pellets derived from tobacco leaves immediately prior to resuspension in extraction buffer. The "D" control samples reflect the same pellets following resuspension in extraction buffer. "K" control samples include ficin-digested procollagen in 10 mM HCl. To monitor background ficin-independent protease activity, ficin-free cleavage samples were always prepared in parallel to all ficin digestion tests.

Purification of collagen from transgenic plants: Digestion of propeptides in the collagen-containing extract was initiated by the addition of 30 mg/L trypsin or 5 mg/L (50 μl/L) Subtilisin (Sigma #P5459) or 5 mg/L Ficin (Sigma #F4125). Proteolysis was performed at 15° C. for 4 hours. Elimination of non-soluble contaminants was performed by centrifugation for 30 min, 22,000 g, 15° C. The supernatant was recovered, and the collagen was precipitated by slowly adding crystalline NaCl to a final concentration of 3.13 M with constant stirring for 20 min at R.T. The solution was incubated in a cold room O.N. without stirring. Collection of the collagen was effected by centrifugation at 25,000 g, for 2 hours at 5° C.

The supernatant was carefully poured through four layers of gauze pad. The pellets were resuspended in 200 ml of 250 mM acetic acid and 2M NaCl for 5 minutes using a magnetic stirrer. The suspension was centrifuged at 25,000 g, for 40 min at 5° C. Traces of supernatant were eliminated from the glass vials. The pellets were redissolved in 200 ml of 0.5 M acetic acid at room temperature for 1 hour. Elimination of nonsoluble matter was performed by centrifugation at 16,000 g, 30 min, 15° C. The supernatant was poured through 12 layers of gauze pad. Collagen was precipitated by slowly adding NaCl to a final concentration of 3M with constant stirring for 20 min at R.T. The solution was incubated at 4° C. for 8 hours up to O.N. Collection of collagen was performed by centrifugation at 25,000 g, for 2 hours at 5° C. Following aspiration of the supernatant, the pellet was redissolved in 200 ml of 0.5 M acetic acid using a magnetic stirrer at R.T. for 1 hour. Elimination of non-soluble matter was performed by centrifugation at 16,000 g, 30 min, 15° C. The supernatant was poured through 12 layers of gauze pad. Collagen was precipitated by slowly adding NaCl to a final concentration of 3M with constant stirring for 20 min at R.T. The solution was incubated at 4° C. for 8 hours. Collagen was collected by centrifugation at 2,000 g, for 2 hours at 5° C. Supernatent was aspirated. The pellet was redissolved in 40 ml of 10 mM HCl by pipetation and vortexing for 5 min at R.T. The solution was transferred to a dialysis bag (MWCO 14,000 Da) and dialyzed for 4 hours against 4 L of 10 mM HCl at 4° C. This dialysis was repeated O.N.

Sterilization of the collagen was performed by filtering the solution first through a 0.45 μm filter, then through a 0.2 μM filter using a 30 ml syringe. Collagen was further concentrated via ultrafiltration using a Vivaspin PES 20 ml filtration tube (Vivascience, #VS2041, MWCO 100'000). Centrifugation was performed for 45 min at 5000 g at 5° C. until the volume was reduced to 0.75 ml.

Optimization of digestion kinetics and conditions of procollagen cleavage by food-grade ficin: Pellets (collected as described in Example 10), up to saturation in 25% ammonium sulfate (AMS)) were resuspended in a buffer (Buffer A: 4.5 mM potassium metadisulfite, 12.5 mM L-cystein, 7.5 mM EDTA dissolved in 0.1 M sodium phosphate buffer, titrated to pH 7.5 with 10 M NaOH or 6 N HCl) at a ratio of 4.36 g pellet:200 mL ice cold buffer. Samples were then stirred for 20 min at 15° C. Aliquots of 10 mL per 15 mL test tube were then prepared, followed by administration of increasing concentrations (5-15 mg/L) of ficin (Fig tree latex, Biochem Europe food grade ficin). Samples were incubated at 15° C. for 1-3 hours and separated by SDS-PAGE and then analyzed by Western blot for presence of collagen migrating at lower molecular weights than procollagen.

Tobacco leaf-derived pellets resuspended in phosphate Buffer A (27.2 g:800 mL buffer) of varying pH values (5.5, 7.5, or 8.5) were treated with 10 mg/L ficin in the presence of 0-3 M NaCl for 1 h at 15° C. The reaction was terminated by centrifuging 1 mL samples from each reaction mixture (10 min, 15000 g, 4° C.). Pellets were resuspended in 1 mL Buffer A (pH 7.5), separated by SDS-PAGE and analyzed by means of Western blot.

Optimization of digestion kinetics and conditions of procollagen cleavage by pharmaceutical-grade ficin: Tobacco leaf pellets were resuspended in a pharmaceutical-grade (Biochem-Europe Pharm grade) ficin-containing extraction buffer (10 mg/L) of varying pH values (7.5, 8.5, 9.5) along with increasing NaCl concentrations (0-3 M) for 5-45 minutes. Further experiments studied the necessity and optimal conditions and concentrations of EDTA and L-cystein as additives to the extraction buffer. Samples were incubated in the digestion mixture in the presence of 0-100 mM EDTA with 0-80 mM L-cystein for 1-3 h at 15° C., at pH 7.5 and without NaCl.

Fibrillogenesis: Fibrillogenesis is regarded as a collagen functionality test. Hence, the ability of purified collagen digested by ficin to form fibrils is an essential property of the obtained product. Test method: The pH of the collagen-containing solution (duplicate samples) was neutralized to pH 6.7 with sodium phosphate, pH 11.2, and then incubated at 27+/−2 μC for 6 hours. Samples were centrifuged to sediment the hydrogel which was formed. Protein concentration of both pre and post-neutralization (supernatant) samples was determined via the Lowry method. PURE-COL™ (Purchased from NUTACON, Cat No. 5409) was employed as positive control and gelatin as a negative control.

Example 7. Extraction and Purification of Collagen from Transgenic Plants in the Presence of Trypsin and Pepsin The production of human collagen in plants was initiated in order to avoid the use of collagen from mammalian sources since the use of mammalian proteins in human cosmetics or medical applications may be risky to human health as the evolutionary proximity is relativity close. The known disease Creutzfeldt-Jakob disease (CJD) is an example of one which is caused by consumption of infected mammal proteins by humans.

Initially, the purification of collagen from transgenic plants was performed using bovine pancreatic Trypsin and the digestive protease Pepsin, both of which catalyze the hydrolysis of proteins in the animal digestive system. The following examples illustrate the identification of a protease from a non-animal source suitable for use in the collagen purification process.

Results

Figure 10:
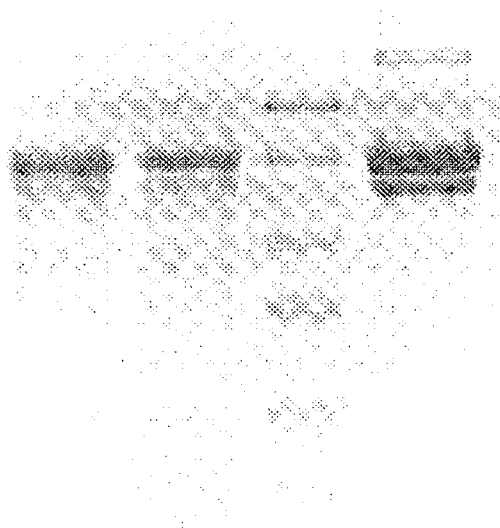
FIG. 10 shows tobacco-leaf derived purified collagen following digestion with trypsin. Collagen was purified from the tobacco plant transgenic leaf line number 13-6 ground in 100 mM Tris buffer, centrifuged, proteolyzed and precipitated in a high salt concentration buffer, as detailed in the Material and Methods section. Following resuspension, collagen-containing pellets were washed, dialyzed and concentrated to the final product. This gel depicts a Coomassie stain analysis of the collected collagen samples where lanes 1 and 2 are the resulting collagen following digestion of procollagen with 300 mg/L Trypsin. Propeptide-free pig-derived collagen (0.5 mg/ml) was loaded and run as a positive control for collagen type 1 alpha 1 and alpha 2 chains.
Figure 11:
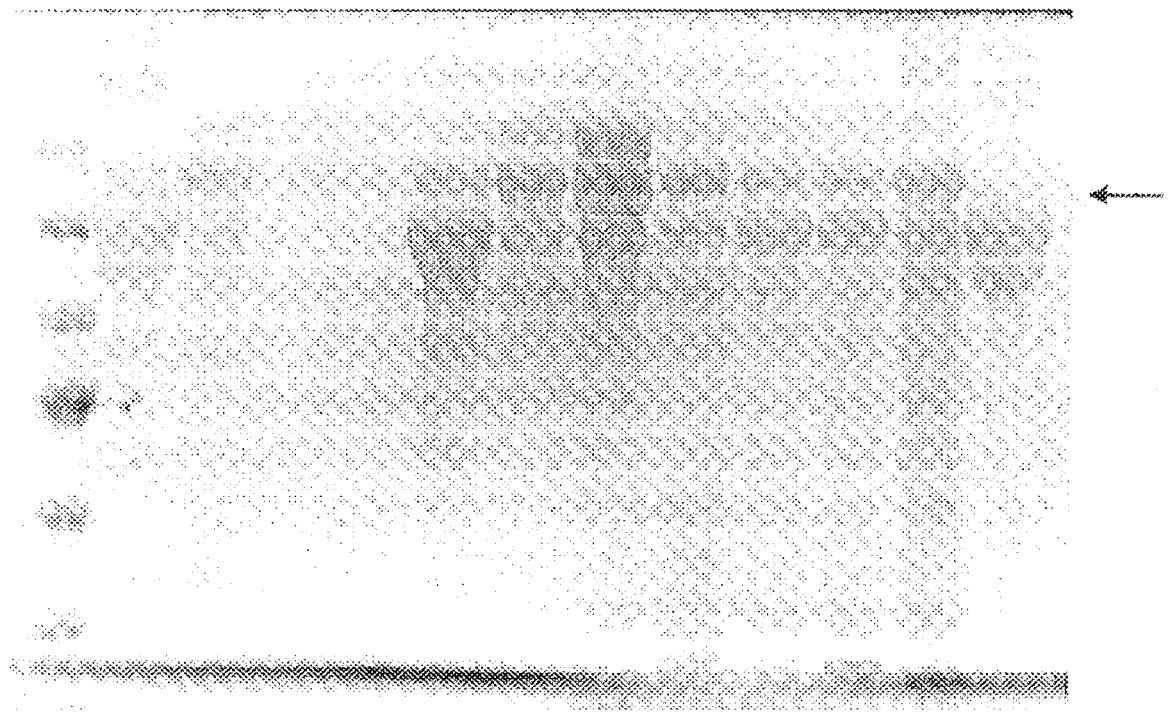
FIG. 11 shows tobacco-leaf derived purified collagen following digestion with varying concentrations of trypsin. Collagen was extracted and purified as in FIG. 10 following digestion with 20 mg/L Trypsin (lanes 1-7) or 30 mg/L (lanes 8-10). Products were separated on a 10% SDS PAGE and analyzed with a Coomassie-based staining solution. Propeptide-free pig-derived collagen (0.5 mg/ml) was loaded and run as a positive control for collagen type 1 alpha 1 and alpha 2 chains.

Propeptide digestion during the purification of collagen was first performed by the pancreatic enzyme Trypsin. Trypsin, at 300 mg/L digested the collagen propeptides, however collagen yield was very low at the end of the purification process (FIG. 10). When the concentration of trypsin was lowered to 20 mg/L or 30 mg/L, the yield was higher, however procollagen digestion was only partial and inconsistent between identical samples (FIG. 11).

Figure 12:
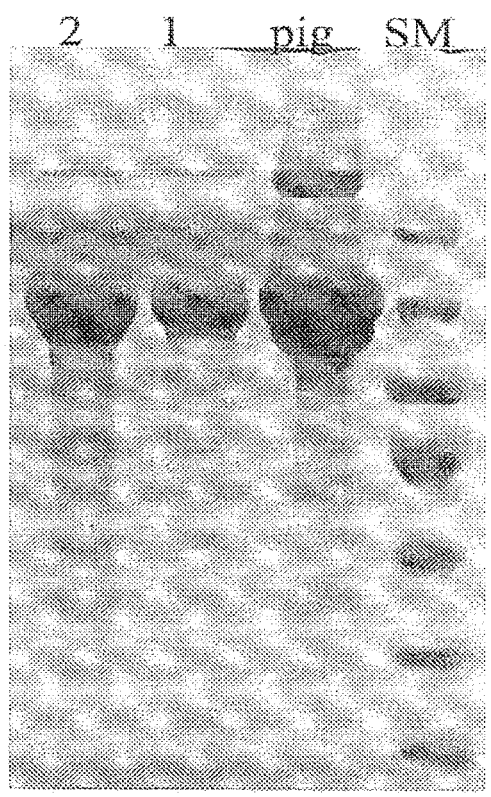
FIG. 12 shows tobacco-leaf derived purified collagen following digestion with trypsin and pepsin. Collagen was extracted and purified as in FIG. 10 following digestion with 30 mg/L Trypsin and 1 µg/200 ml Pepsin (lanes 1-2). Products were separated on a 10% SDS PAGE and analyzed with a Coomassie-based staining solution. Propeptide-free pig-derived collagen (0.5 mg/ml) was loaded and run as a positive control for collagen type 1 alpha 1 and alpha 2 chains.
Figure 13:
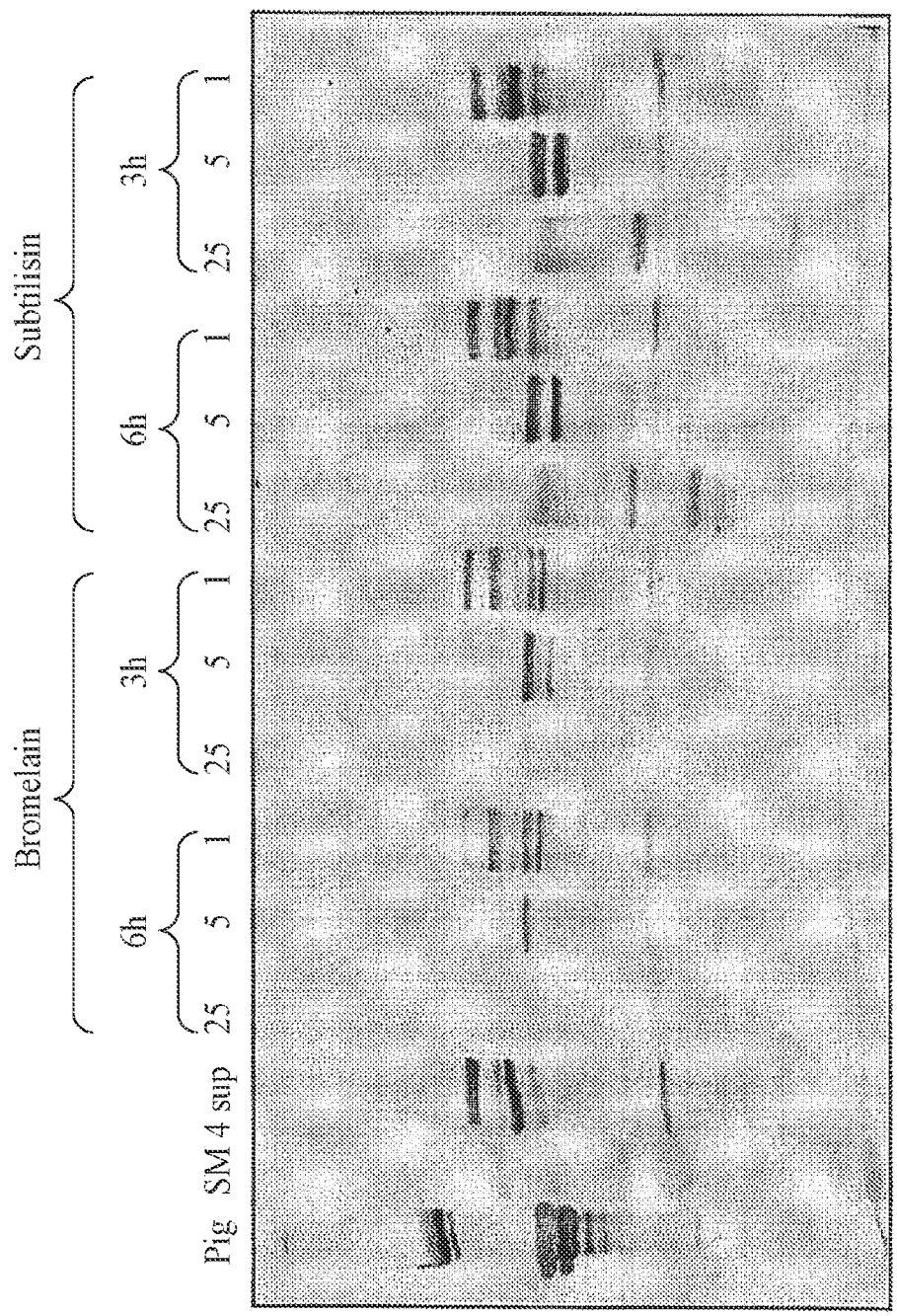
FIG. 13 shows collagen chains obtained upon digestion of procollagen with Subtilisin or Bromelain. Collagen was purified from the tobacco plant transgenic leaf line number 13-361 ground in 100 mM Tris buffer, centrifuged and proteolyzed with either Subtilisin (1-25 mg/L) or Bromelain (1-25 mg/L) incubated for 3 or 6 hrs. Samples were separated on a 10% SDS PAGE and blotted to nitrocellulose membranes. Collagen chains were immunodetected using anti-collagen I. Untreated supernatants collected following homogenization and centrifugation served as collagen-free negative controls (lane 3-4sup). Propeptide-free pig-derived collagen (2.5 µg) served as a positive control for alpha 1 and alpha 2 chains (lane 1).

In an attempt to overcome this problem, varying incubation temperatures and times were tried; however, the results did not lead to a change in yield (data not shown). The addition of Pepsin enzyme later on in the purification process resolved the partial digestion problem (FIG. 12) and yielded alpha-1 and alpha-2 collagen which co-migrated with pig-derived collagen control samples.

Example 8. Collagen Extraction and its Enzymatically-Induced Digestion

Figure 14:
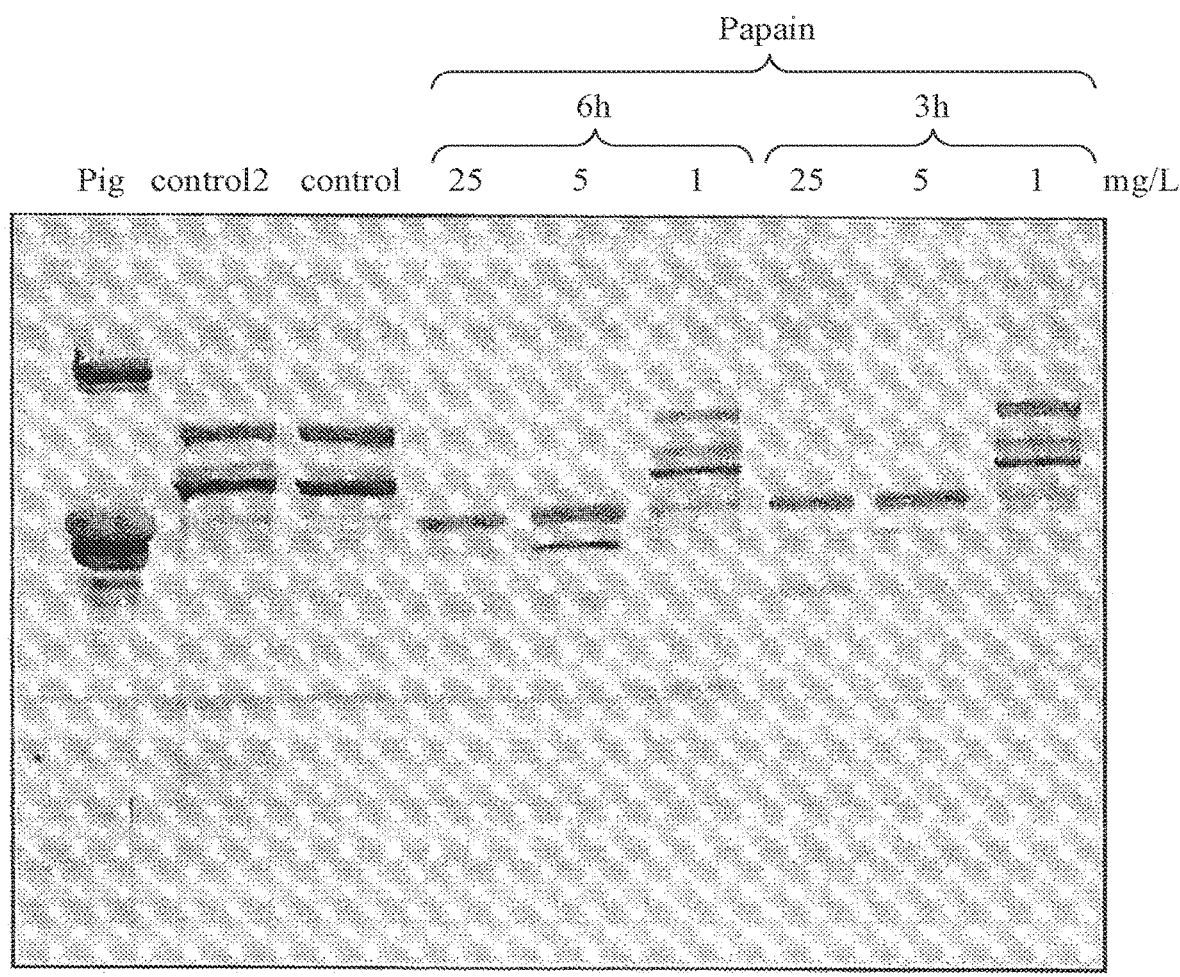
FIG. 14 shows collagen chains obtained upon digestion of procollagen with Papain. Collagen was purified from the tobacco plant transgenic leaf line number 13-361 ground in 100 mM Tris buffer, centrifuged and proteolyzed with Papain (1-25 mg/L) over a 3 or 6 hrs incubation period. Samples were separated on a 10% SDS PAGE and blotted to nitrocellulose membranes. Collagen chains were immunodetected using anti-collagen I. Untreated supernatants collected following homogenization, centrifugation and incubation at 15° C. for 3 hrs (lane 3) or 6 hrs (lane 2) with no enzyme served as collagen-free negative controls. Propeptide-free pig-derived collagen (2.5 µg) served as a positive control for alpha 1 and alpha 2 chains (lane 1).
Figure 15:
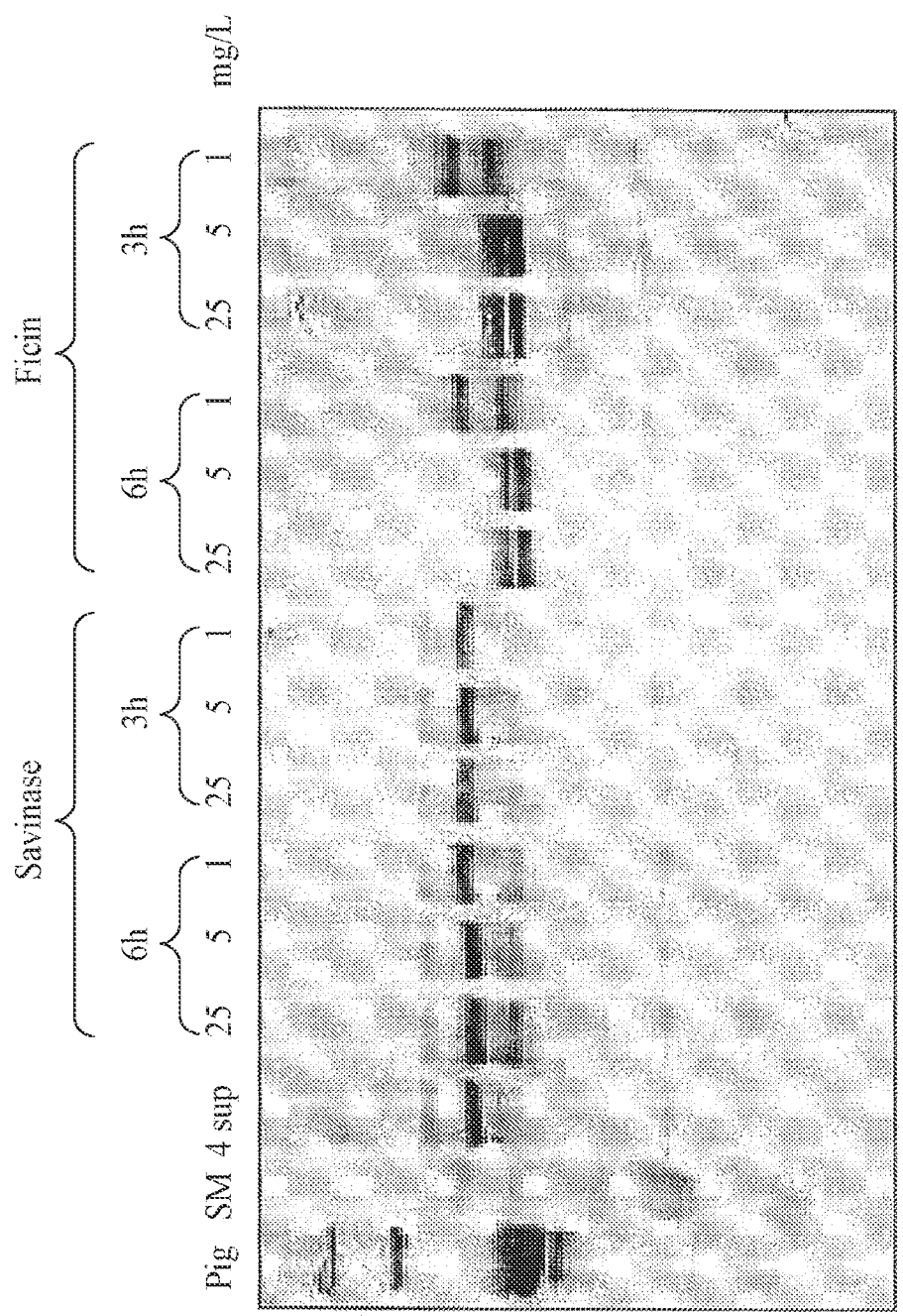
FIG. 15 shows collagen chains obtained upon digestion of procollagen with Ficin or Savinase. Collagen was purified from the tobacco plant transgenic leaf line number 13-361 ground in 100 mM Tris buffer, centrifuged and proteolyzed with Ficin (1-25 mg/L) or Savinase (1-25 mg/L) over a 3 or 6 hrs incubation period. Samples were separated on a 10% SDS PAGE and blotted to nitrocellulose membranes. Collagen chains were immunodetected using anti-collagen I. Untreated supernatants collected prior to proteolysis served as a collagen-free control sample (lane 3). Propeptide-free pig-derived collagen (2.5 µg) served as a positive control for alpha 1 and alpha 2 chains (lane 1).
Figure 16:
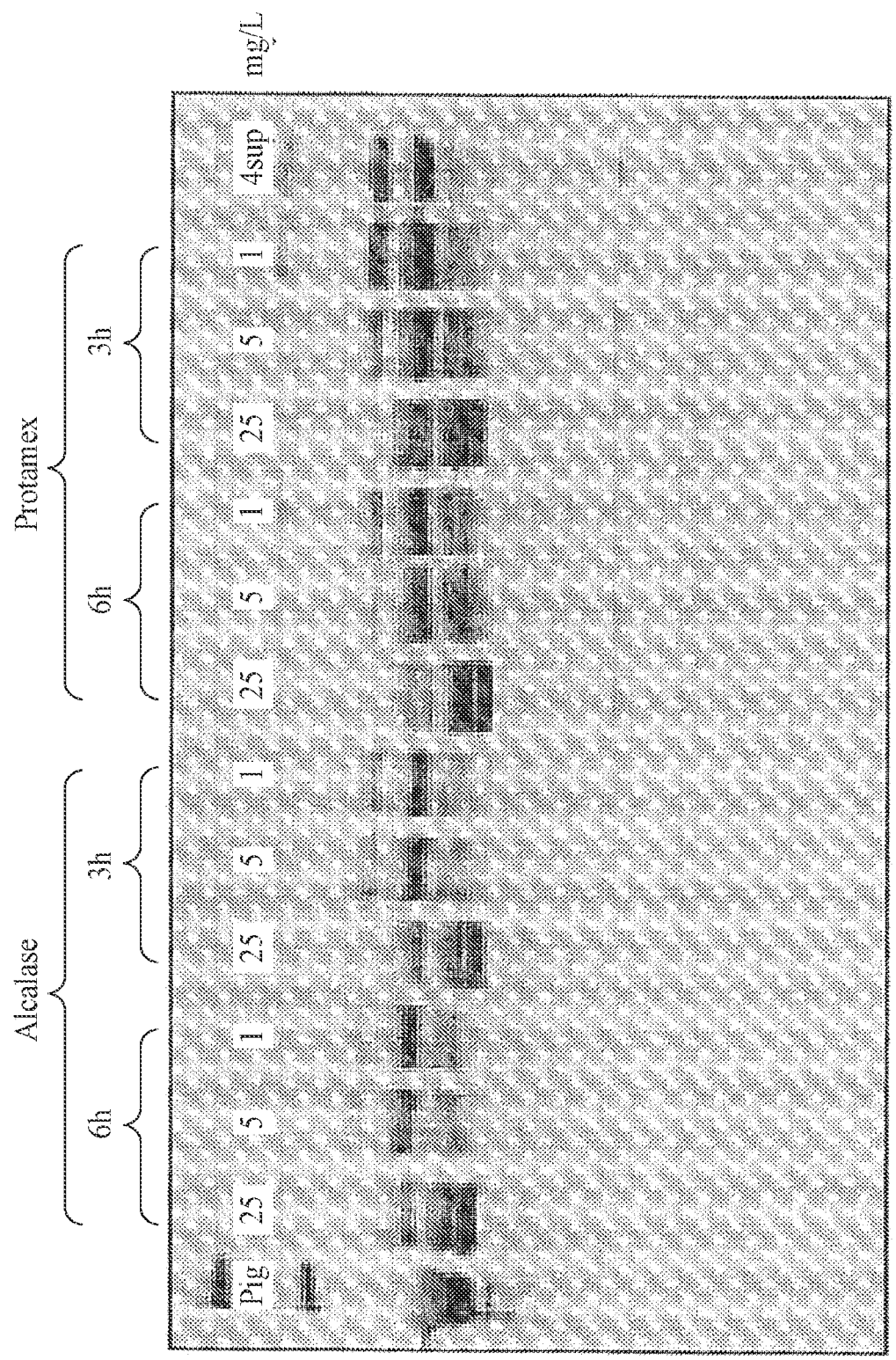
FIG. 16 shows collagen chains obtained upon digestion of procollagen with Protamex or Alcalase. Collagen was purified from the tobacco plant transgenic leaf line number 13-361 ground in 100 mM Tris buffer, centrifuged and proteolyzed with Protamex (1-25 mg/L) or Alcalase (1-25 mg/L) over a 3 or 6 hrs incubation period. Samples were separated on a 10% SDS PAGE and blotted to nitrocellulose membranes. Collagen chains were immunodetected using anti-collagen I. Untreated supernatants collected prior to proteolysis served as a collagen-free control sample (lane 14). Propeptide-free pig-derived collagen (2.5 µg) served as a positive control for alpha 1 and alpha 2 chains (lane 1).
Figure 17:
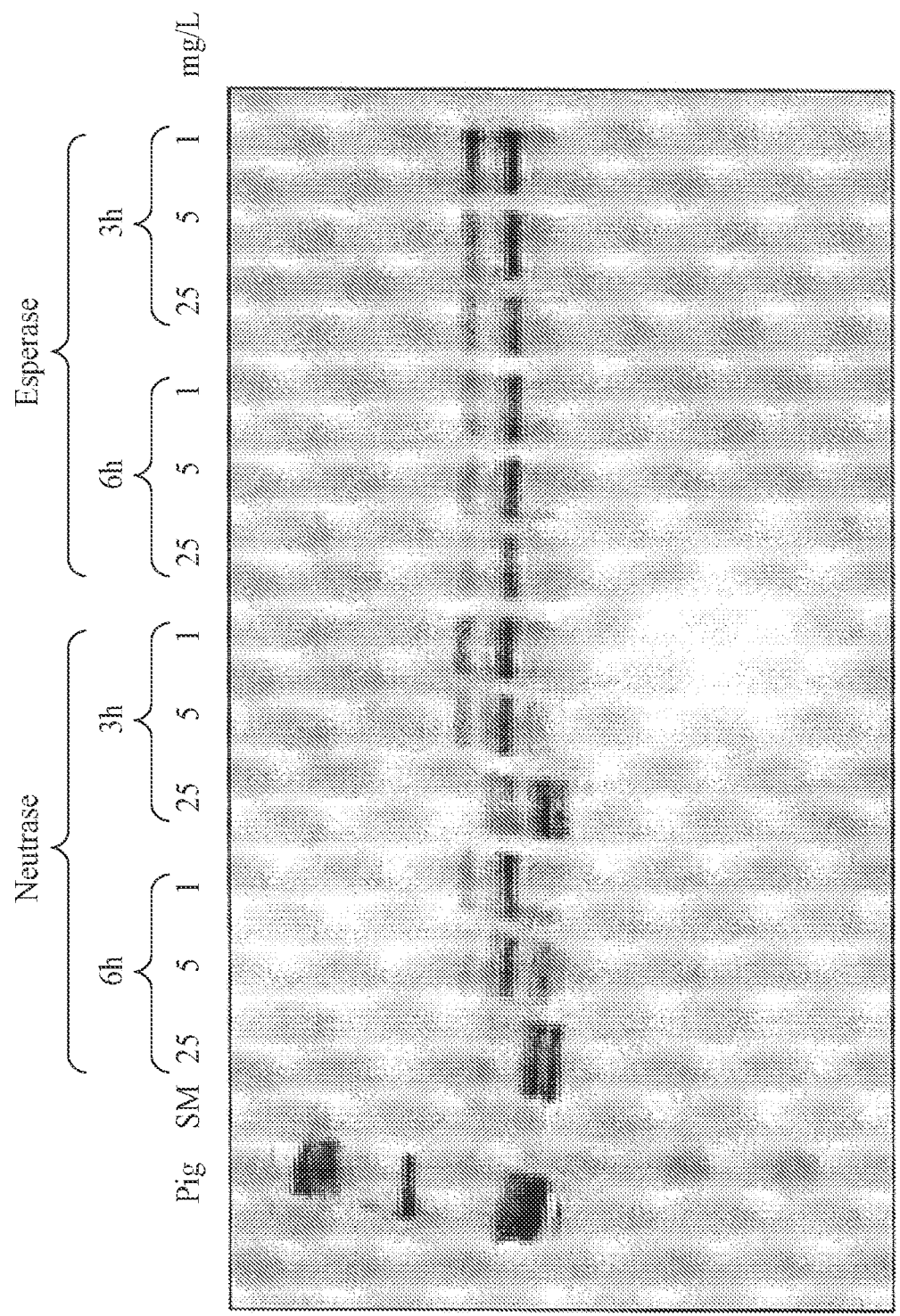
FIG. 17 shows collagen chains obtained upon digestion of procollagen with Esperase or Neutrase. Collagen was purified from the tobacco plant transgenic leaf line number 13-361 ground in 100 mM Tris buffer, centrifuged and proteolyzed with Esperase (1-25 mg/L) or Neutrase (1-25 mg/L) following a 3 or 6 hrs incubation period. Samples were separated on a 10% SDS PAGE and blotted to nitrocellulose membranes. Collagen chains were immunodetected using anti-collagen I. Propeptide-free pig-derived collagen (2.5 µg) served as a positive control for alpha 1 and alpha 2 chains (lane 1).
Figure 18:
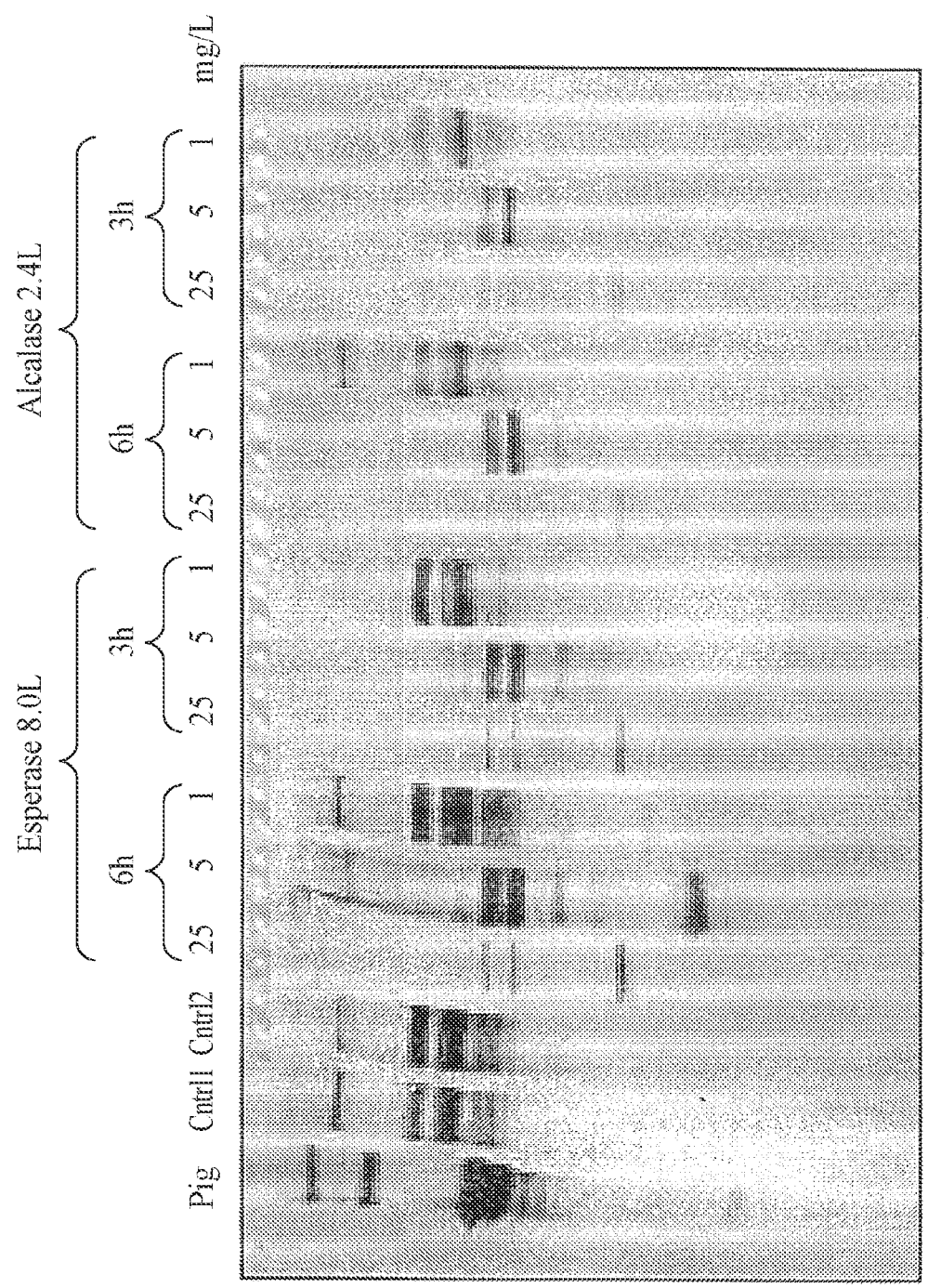
FIG. 18 shows collagen chains obtained upon digestion of procollagen with Esperase 8.0 L or Alcalase. Collagen was purified from the tobacco plant transgenic leaf line number 13-361 ground in 100 mM Tris buffer, centrifuged and proteolyzed with Esperase (1-25 mg/L) or Neutrase (1-25 mg/L) following a 3 or 6 hrs incubation period. Samples were separated on a 10% SDS PAGE and blotted to nitrocellulose membranes. Collagen chains were immunodetected using anti-collagen I. Untreated supernatants collected following homogenization, centrifugation and incubation at 15° C. for 3 h (lane 3) or 6 h (lane 2) with no proteolytic enzyme served as collagen-free negative controls. Propeptide-free pig-derived collagen (2.5 µg) served as a positive control for alpha 1 and alpha 2 chains (lane 1).

However, the trypsin-pepsin solution was not optimal since it required two different enzymes, lengthening the purification process. Furthermore, both enzymes are from animal sources. In order to overcome these issues, a screen of different protease enzymes of non-animal origin, was performed. Varying digestion patterns were obtained by the different enzymes screened. Very little or no observable digestion of the propeptides resulted from the incubation of collagen with the Savinase (FIG. 15) and Esperase (FIG. 17) enzymes. Incubation with Papain (FIG. 14), Bromelain (FIG. 13), Alcalase 2.4 L and Esperase 8.0 L (FIG. 18), led to over- or under-digestion of the propeptides. Alcalase and Protamex enzymes (FIG. 16) led to the desired digestion pattern and level (25 mg/L, 6 hr), with alpha 1 and alpha 2 chains migrating similar to the pig-derived collagen sample. However, not all the molecules were fully digested and may require longer incubation periods. Optimal results were obtained upon procollagen incubation with Ficin (5 mg/L and 25 mg/L) (FIG. 15) where the bands of alpha 1 and alpha 2 chains comigrated with the pig-derived collagen control sample, with no apparent overdigestion. Similar results were demonstrated with Subtilisin 5 mg/L for 3 h (FIG. 13) and Neutrase 25 mg/L for 6 h (FIG. 17).

Figure 19:
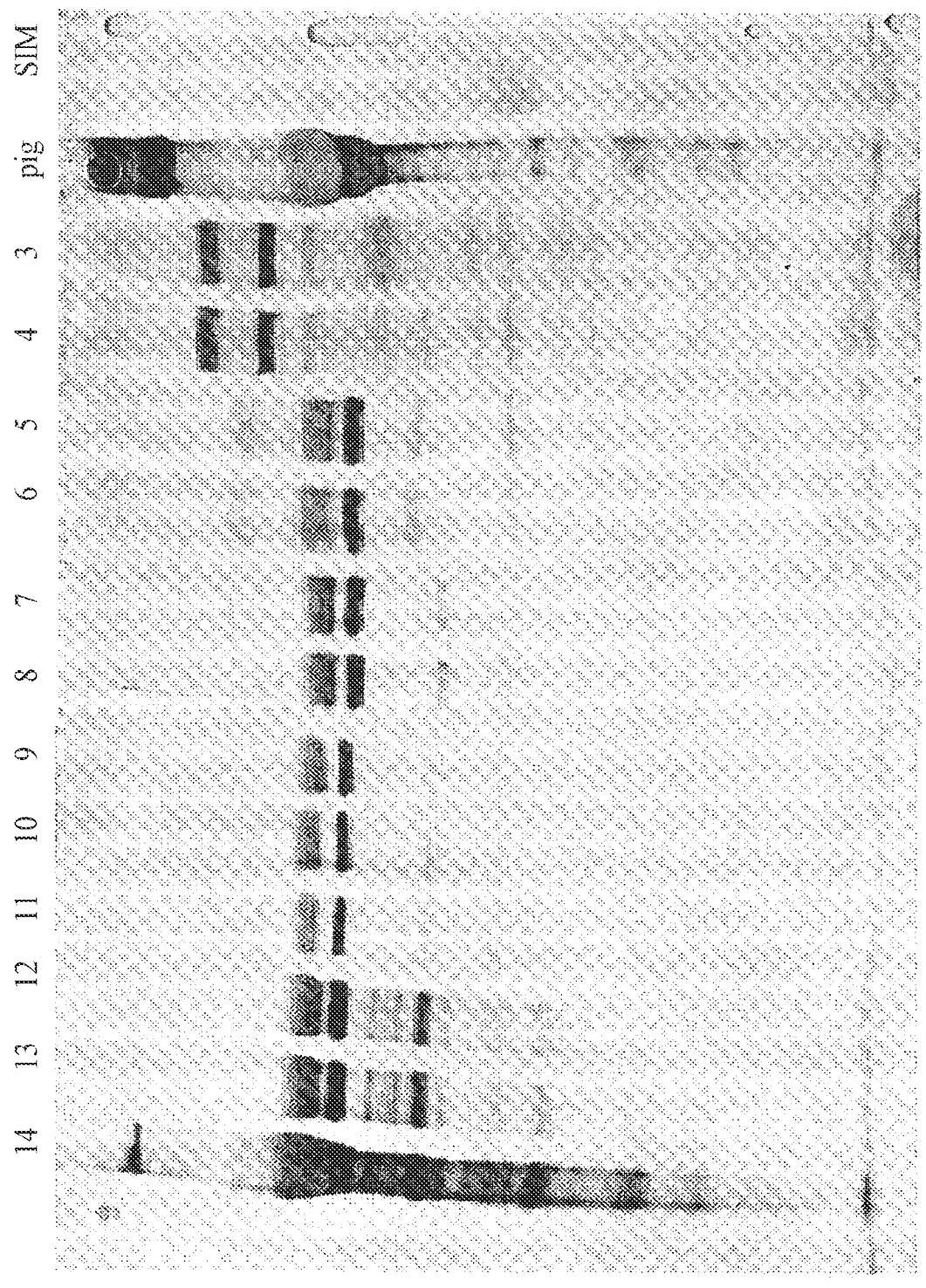
FIG. 19 shows collagen chains obtained at various purification stages following digestion of procollagen with Ficin. Collagen was purified from the tobacco plant transgenic leaf line number 13-361 ground in 100 mM Tris buffer, centrifuged and proteolyzed with Ficin (5 mg/L) following a 3 hrs incubation period at 15° C. Samples were separated on a 10% SDS PAGE and blotted to nitrocellulose membranes. Collagen chains was immunodetected using anti-collagen I. Samples collected after grinding, centrifugation and incubation of supernatant with Ficin were loaded in lane 5. Lanes 6-14 depict samples of ficin-treated collagen at different stages in purification process: lane 6: sample post-ficin incubation and centrifugation; lane 7: following salt precipitation and resuspension in 0.5M acetic acid; lane 8: sample as in lane 7 with an added centrifugation step; lane 9: sample as in lane 8 following resuspension in 0.5 M acetic acid and centrifugation; lane 10: mature collagen following resuspension in 10 mM HCl and dialysis; lane 11: sample as in lane 10 with an additional filtration step; lane 12: sample as in lane 11 with an additional 5× concentration step; lane 13: sample as in lane 11 with an additional 20× concentration step; lane 14: sample as in lane 13 with additional 5× concentration step. Untreated procollagen samples (lanes 3-4) served as negative controls. Propeptide-free pig-derived collagen (2.5 µg) served as a positive control for alpha 1 and alpha 2 chains (lane 1).
Figure 20:
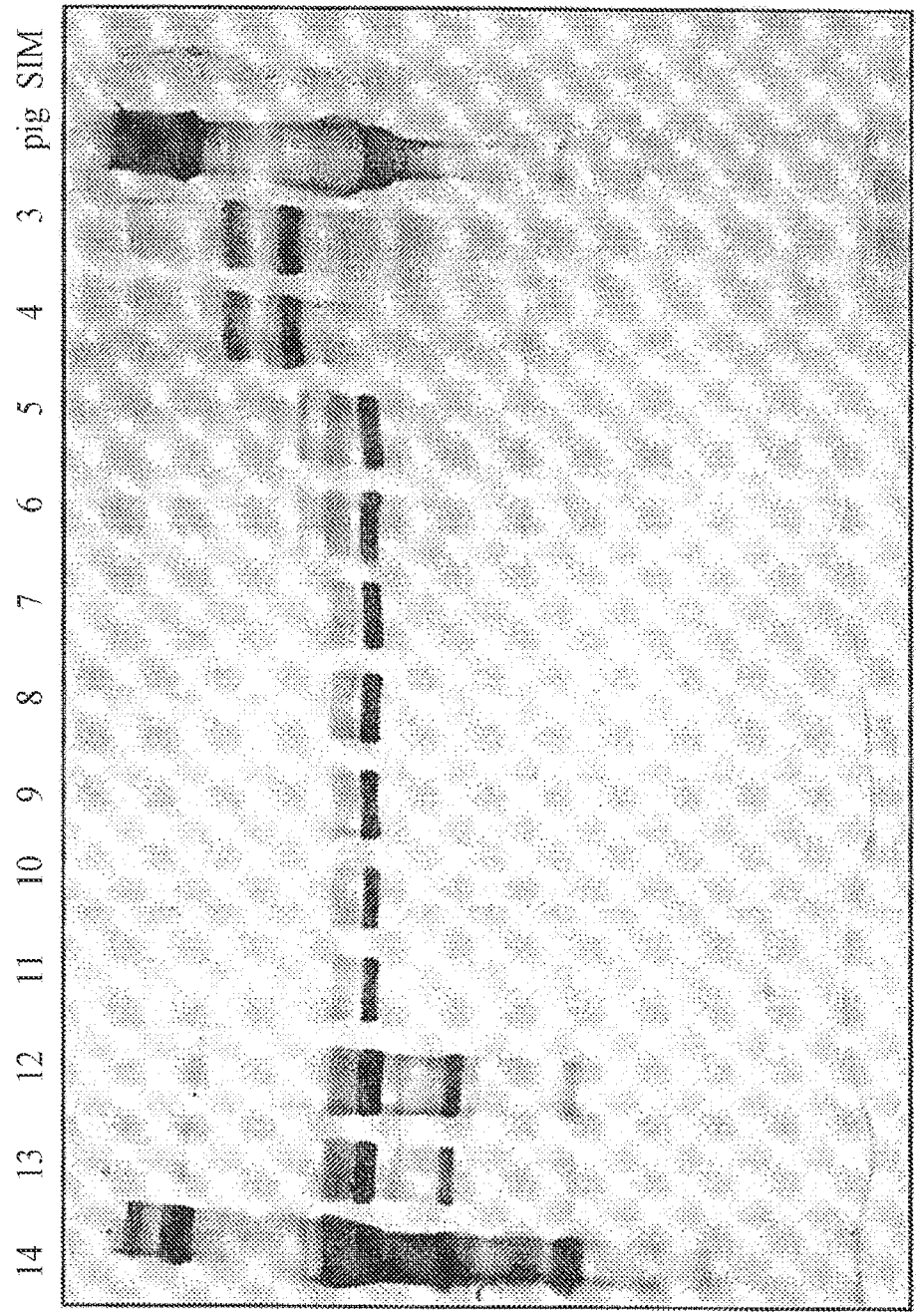
FIG. 20 shows collagen chains obtained at various purification stages following digestion of procollagen with Ficin. Collagen was purified from the tobacco plant transgenic leaf line number 13-361 ground in 100 mM Tris buffer, centrifuged and proteolyzed with Ficin (5 mg/L) following a 3 hrs incubation period at 15° C. Samples were separated on a 10% SDS PAGE and blotted to nitrocellulose membranes. Collagen chains were immunodetected using anti-collagen I. Samples collected after grinding, centrifugation and incubation of supernatant with Ficin were loaded in lane 5. Lanes 6-14 depict samples of ficin-treated collagen at different stages in purification process: lane 6: sample post-ficin incubation and centrifugation; lane 7: following salt precipitation and resuspension in 0.5M acetic acid; lane 8: sample as in lane 7 with an added centrifugation step; lane 9: sample as in lane 8 following resuspension in 0.5 M acetic acid and centrifugation; lane 10: mature collagen following resuspension in 10 mM HCl and dialysis; lane 11: sample as in lane 10 with an additional filtration step; lane 12: sample as in lane 11 with an additional 5× concentration step; lane 13: sample as in lane 11 with an additional 20× concentration step; lane 14: sample as in lane 13 with additional 5× concentration step. Untreated procollagen samples (lanes 3-4) served as negative controls. Propeptide-free pig-derived collagen (2.5 µg) served as a positive control for alpha 1 and alpha 2 chains (lane 1).
Figure 21:
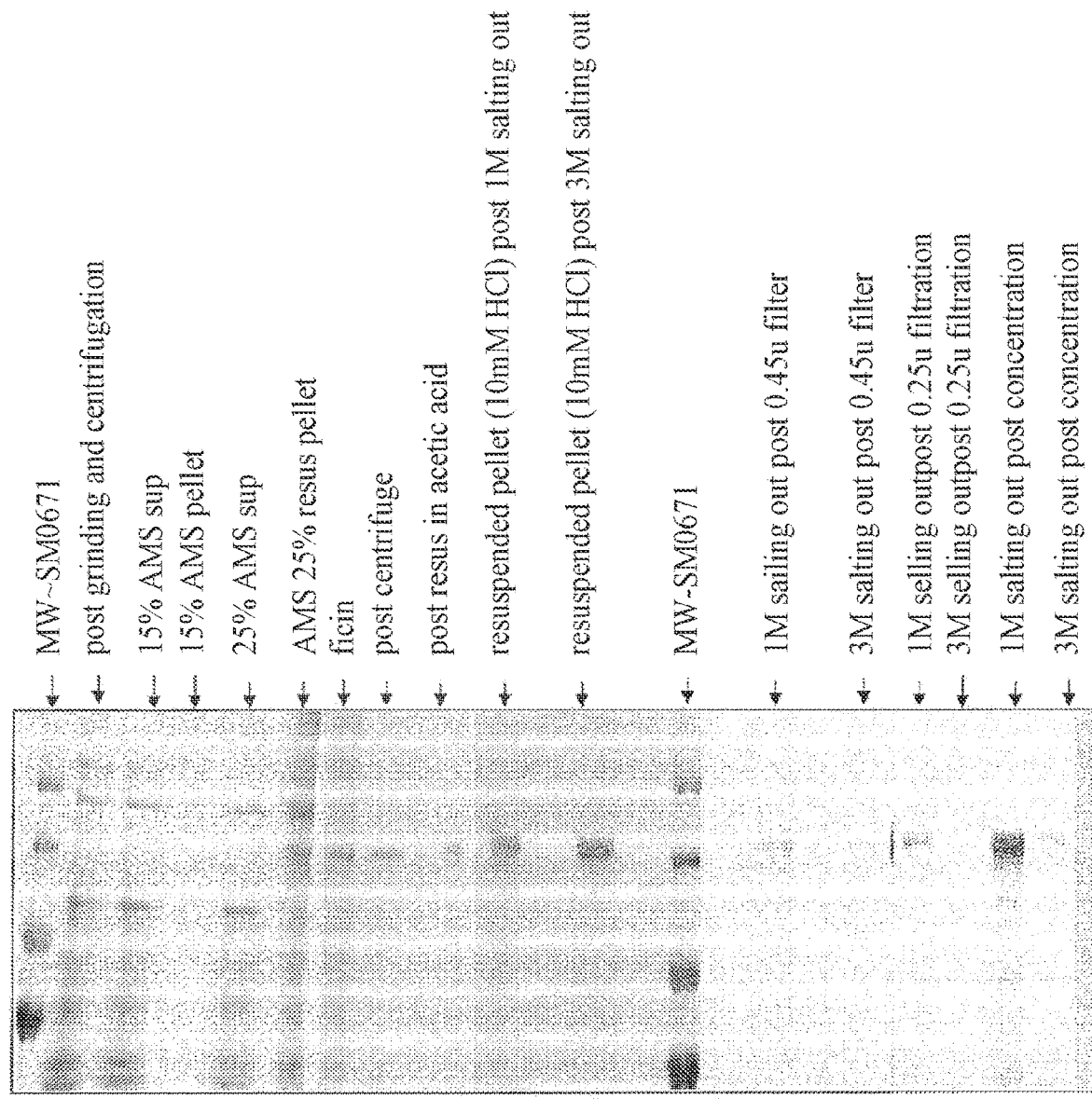
FIG. 21 shows collagen content of post-ficin treated samples at the various stages of purification. Collagen-containing samples were collected at each extraction and purification stage of a reactor size AMS-based purification procedure described in the Material and Methods section. Samples were treated with ficin (5 mg/L, 15° C., 3 h) for propeptide removal, separated on a 10% SDS PAGE and stained with a Coomassie-based staining solution.

Example 9. Extraction and Purification of Collagen from Transgenic Plants Following Digestion with Subtilisin or Ficin Collagen purifications from 450 gr leaves of transgenic plants (13-361 or 13-6-52) were performed followed by procollagen digestion with Ficin (FIG. 19) or Subtilisin (FIG. 20). Samples of the collagen at the various stages of the purification process were analyzed by Western analysis. Propeptide digestion by ficin and subtilisin led to the desirable degree of processing of Collagen 1 and Collagen 2. Bands of lower molecular weight were observed on the Western blots throughout the purification process, however, these bands appeared in the plant extracts prior to the incubation with the enzyme (lanes 3-4) and also in the pig-derived collagen control sample (positive control) (FIG. 19).

Example 10. Scaled Up Extraction and Purification of Collagen from Transgenic Plants Following Digestion with FICIN 1 kg of transgenic tobacco leaves were ground with pre-chilled 2 L extraction buffer (100 mM sodium phosphate buffer pH 7.5, 4.5 mM potassium Meta disulfite, 12.23 mM L-cystein and 7.5 mM EDTA) in a 4 L reactor (ESCO model EL-3) for 20 minutes (5° C., 50% scraper speed and 100% homogenizer blade rpm). 6.68 g charcoal and 16.67 g of PVPP were added to the extract and continuously stirred for 20 minutes (5° C. and 50% scraper speed). Extract was centrifuged (11000 rpm, 5° C., 0.5 H) and supernatant was saturated with 15% ammonium sulfate (1 hour stirring, 5° C.). Following a 6880 rpm, 5° C., 30 min, the supernatant was saturated to 25% ammonium sulfate and stirred for 1 hour (5° C.). Following recentrifugation, the pellet (6880 rpm, 5° C., 30 min) was resuspended (in extraction buffer) in 15% of the volume collected after the first centrifugation step. Removal of propeptides was enabled by a 3 hr digestion, 15° C. with 5 mg/L ficin (Biochem Europe). The sample was centrifuged (11,000 rpm, 15° C., 30 min) and the mature collagen was precipitated using 3 M NaCl (NaCl was added slowly while stirring and left O.N. at 4° C.). Following precipitation (13,000 rpm, 5° C., 2 hours), the supernatant was discarded, and the pellet was resuspended in 0.5M acetic acid. Another round of 3M salting out (O.N) and centrifugation was followed by the resuspension of the pellets in 40 ml of 10 mM HCl. The sample was transferred to a dialysis bag (12-14 kDa) and dialyzed against 4 L 10 mM HCl, at 4° C., for 4 hours. The dialysis was repeated with fresh 4 L 10 mM HCl, O.N. The dialyzed solution was filtered through a 0.45 micron filter (previously washed with 10 mM HCl) and then through a 0.25 micron filter. The samples were finally concentrated in a Vivaspin (Vivascience) filtration tube (100 kDa).

Example 11. Solubility of Atelocollagen Produced as Recombinant Human Procollagen in Transgenic Tobacco Plants The concentration of atelocollagen generated according to Examples 9-10 was assayed by two methods as follows as described in the Methods section. The resulting concentrations obtained for several typical preparations digested with ficin, are listed in Table 4, herein below:

TABLE 4

Collagen concentrations as determined via the Instant blue or Sircol staining methods

| Lot No. | mg/ml collagen by Instant blue | mg/ml collagen by Sircol ™ |
|---|---|---|
| UPEK1 | 15.7 | 9.3 |
| UPEK2 | 5.8 | 4.78 |
| PEK052 | 6.8 | 5.5 |
| UPEK3 | 3.4 | 3.54 |
| UPEK4 | NA | 3.3 |
| UPEK6-1 | 5.9 | 4.7 |
| UPEK6-2 | 4.3 | 3.7 |

Example 12. Ficin-Dependent Proteolysis of Tobacco Leaf-Derived Procollagen

Figure 22:
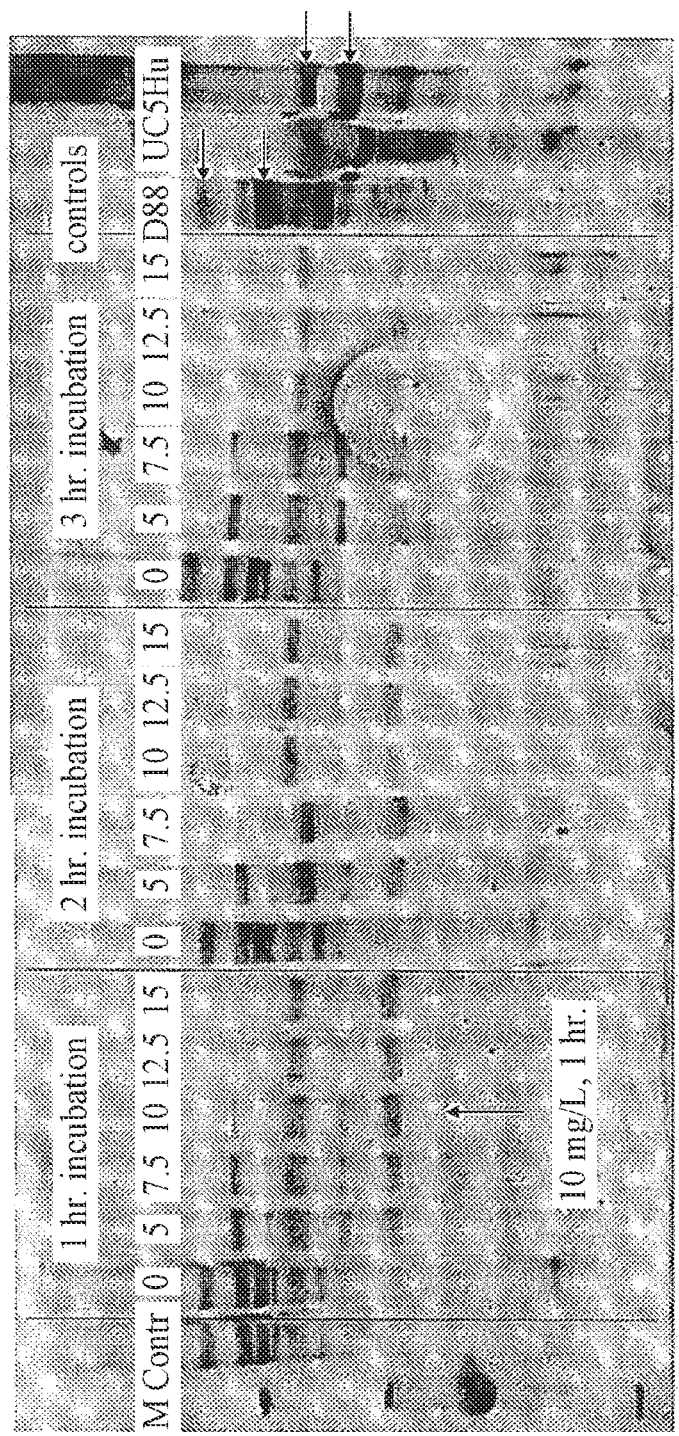
FIG. 22 shows optimization of procollagen cleavage by food-grade ficin: optimization of ficin concentration and reaction time. AMS-pelleted procollagen-expressing tobacco leaf extracts were resuspended in extraction buffer and then incubated with increasing concentrations of food-grade ficin (5-15 mg/L). Reaction mixtures were then incubated at 15° C. for 1-3 hours. Cleavage was terminated by centrifugation and protein samples were separated on 8% SDS-PAGE, transferred to nitrocellulose membranes and immunoblotted for alpha-1 and alpha-2 collagen chains with anti-collagen I. Procollagen bands are indicated by white arrows, while the red arrows indicate cleaved collagen bands.

Digestion kinetics of procollagen by food-grade ficin: To calibrate appropriate ficin concentrations and incubation times allowing for highest collagen yields, procollagen-expressing tobacco leaf pellets were incubated with increasing concentrations of food-grade ficin (5-15 mg/L) at 15° C. for 1-3 hours. Samples were then analyzed by immunodetection of alpha-1 and alpha-2 collagen chains on Western blots. Increased ficin concentrations offered improvement in collagen chain yield following a 1-hour incubation period (FIG. 22, lane 5 vs. 6). However, upon extension of reaction time, increased ficin concentrations led to overdigestion of collagen (FIG. 22, lane 11 vs. 12-14 and lane 17 vs. 18-20). Thus, optimal conditions for digestion of procollagen to collagen were set at addition of 10 mg/L food-grade ficin for 1 hour at 15° C.

Figure 23A:
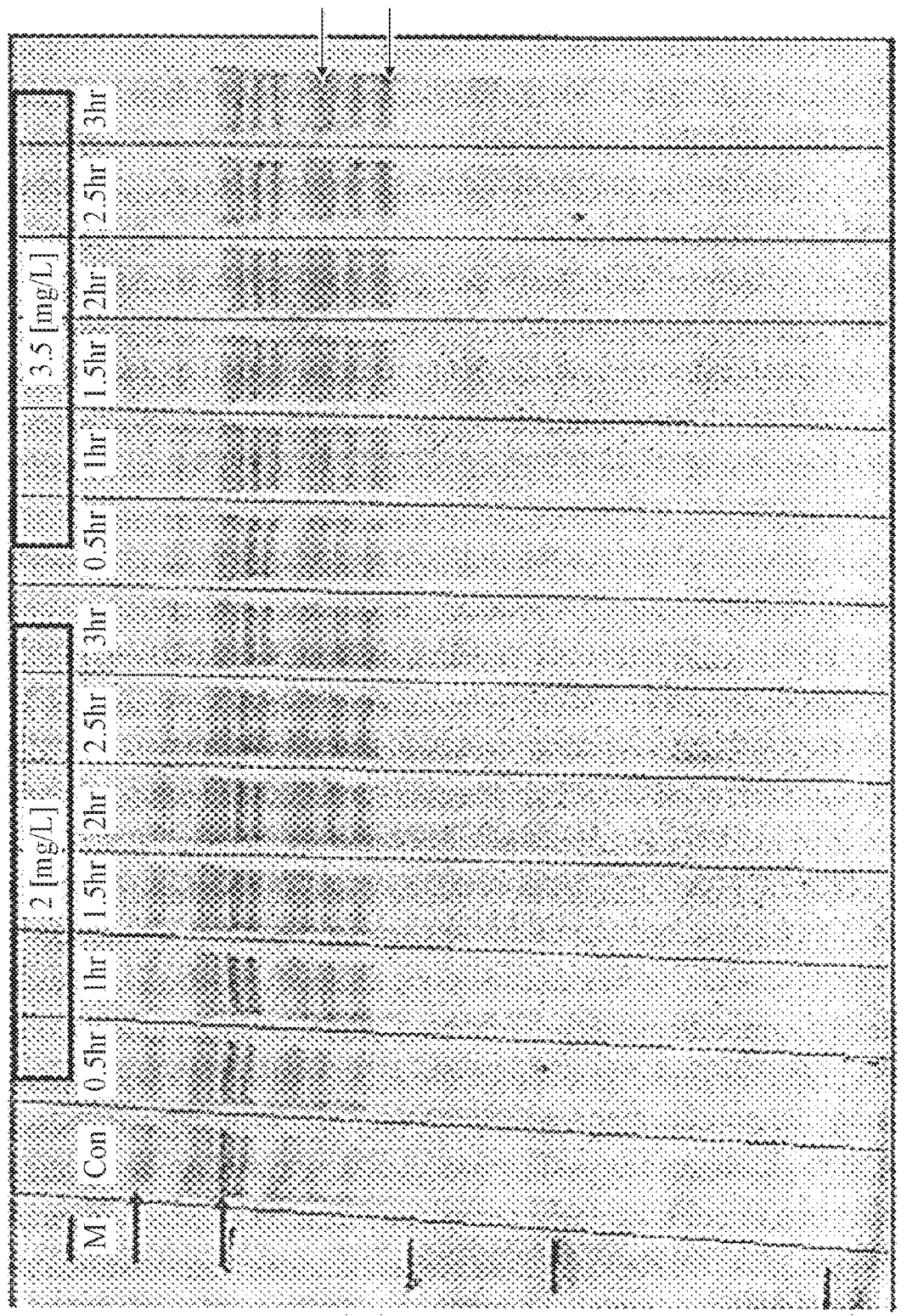
FIGS. 23a-c show optimization of procollagen cleavage by pharmaceutical-grade ficin: optimization of ficin concentration and reaction time. AMS-pelleted procollagen-expressing tobacco leaf extracts were resuspended in extraction buffer and then incubated with increasing concentrations of pharmaceutical-grade ficin (2.5-10 mg/L). Reaction mixtures were then incubated at 15° C. for 0.5-3 hours. Cleavage was terminated by centrifugation and protein samples were separated on 8% SDS-PAGE, transferred to nitrocellulose membranes and immunoblotted for alpha-1 and alpha-2 collagen chains with anti-collagen I. Arrows indicate procollagen band and collagen bands.
Figure 23B:
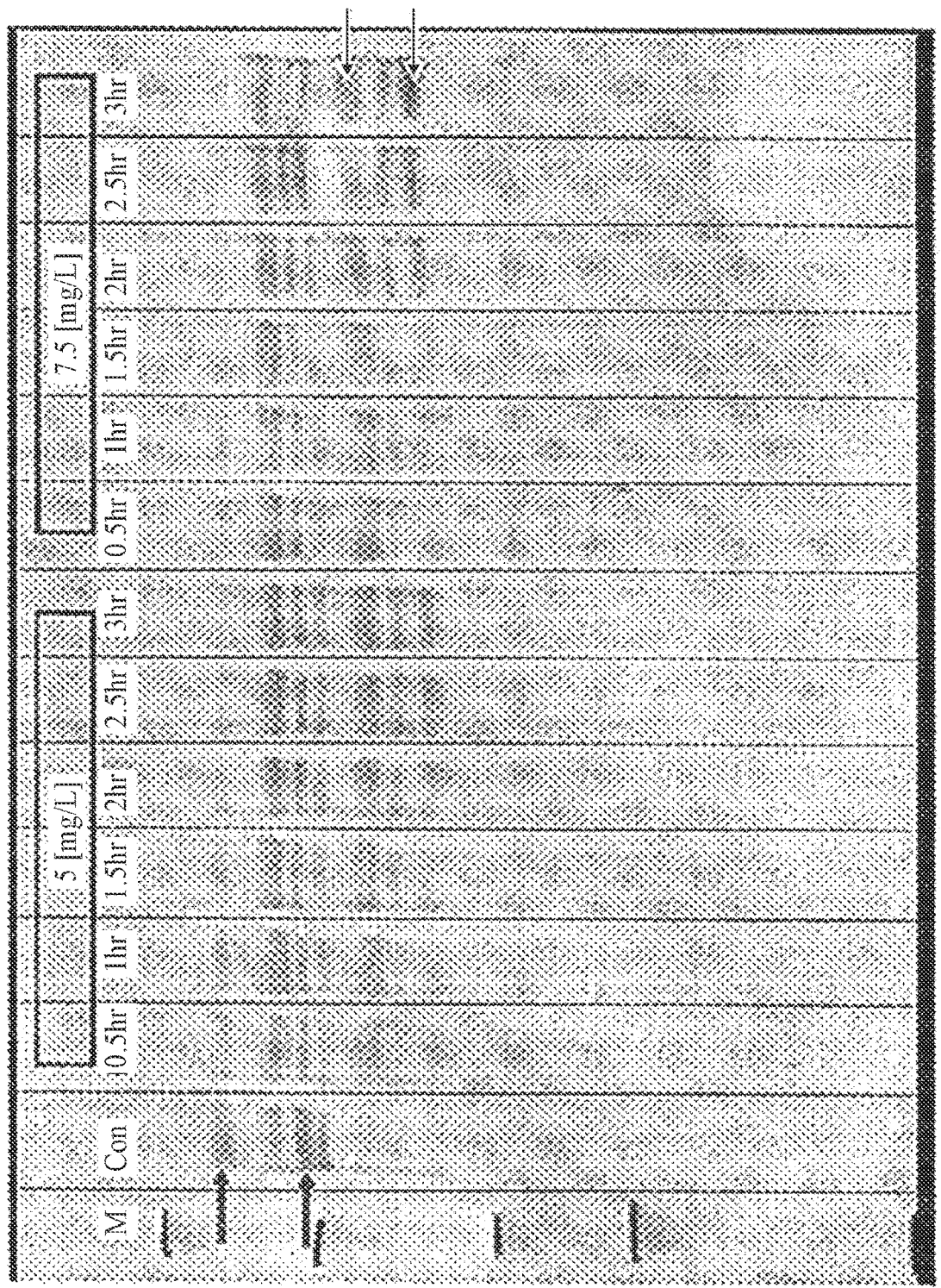
Figure 23C:
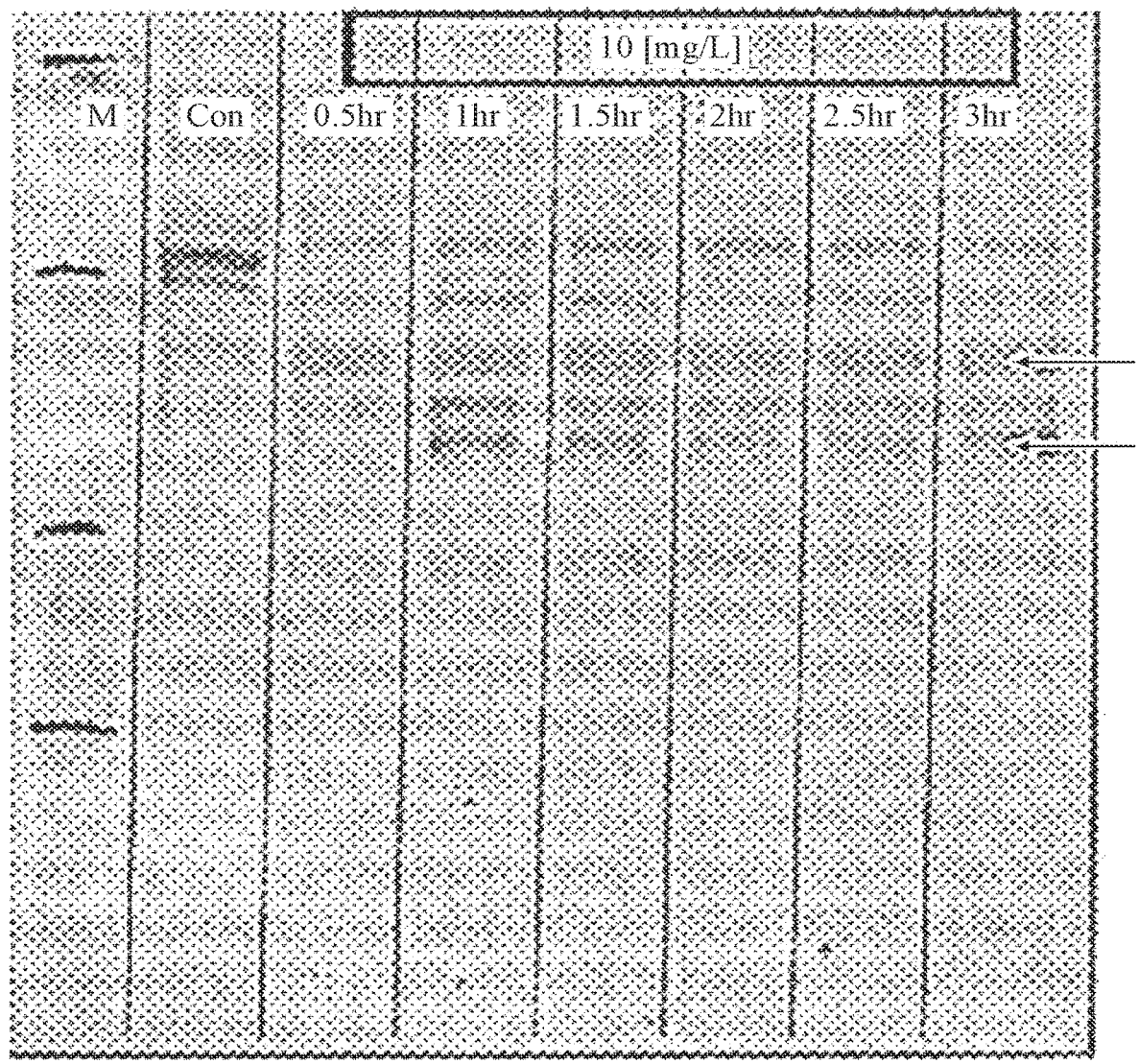

Digestion kinetics of procollagen by pharmaceutical-grade ficin: Similar experiments were carried out on procollagen-expressing tobacco leaf pellets to determine the appropriate conditions for procollagen digestion by pharmaceutical-grade ficin. Pellets were resuspended and incubated with increasing concentrations of pharmaceutical-grade ficin (2.5-10 mg/L), at 15° C. for 0.5-3 hrs. Digestion efficiency was determined by immunodetection of collagen chains on Western blots. As is shown in FIGS. 23A-C, increasing ficin concentrations led to increased collagen yield and decreased procollagen levels. The most effective digestion of procollagen with pharma-grade ficin was seen at 10 mg/L, after a 1-hour reaction time.

Figure 24A:
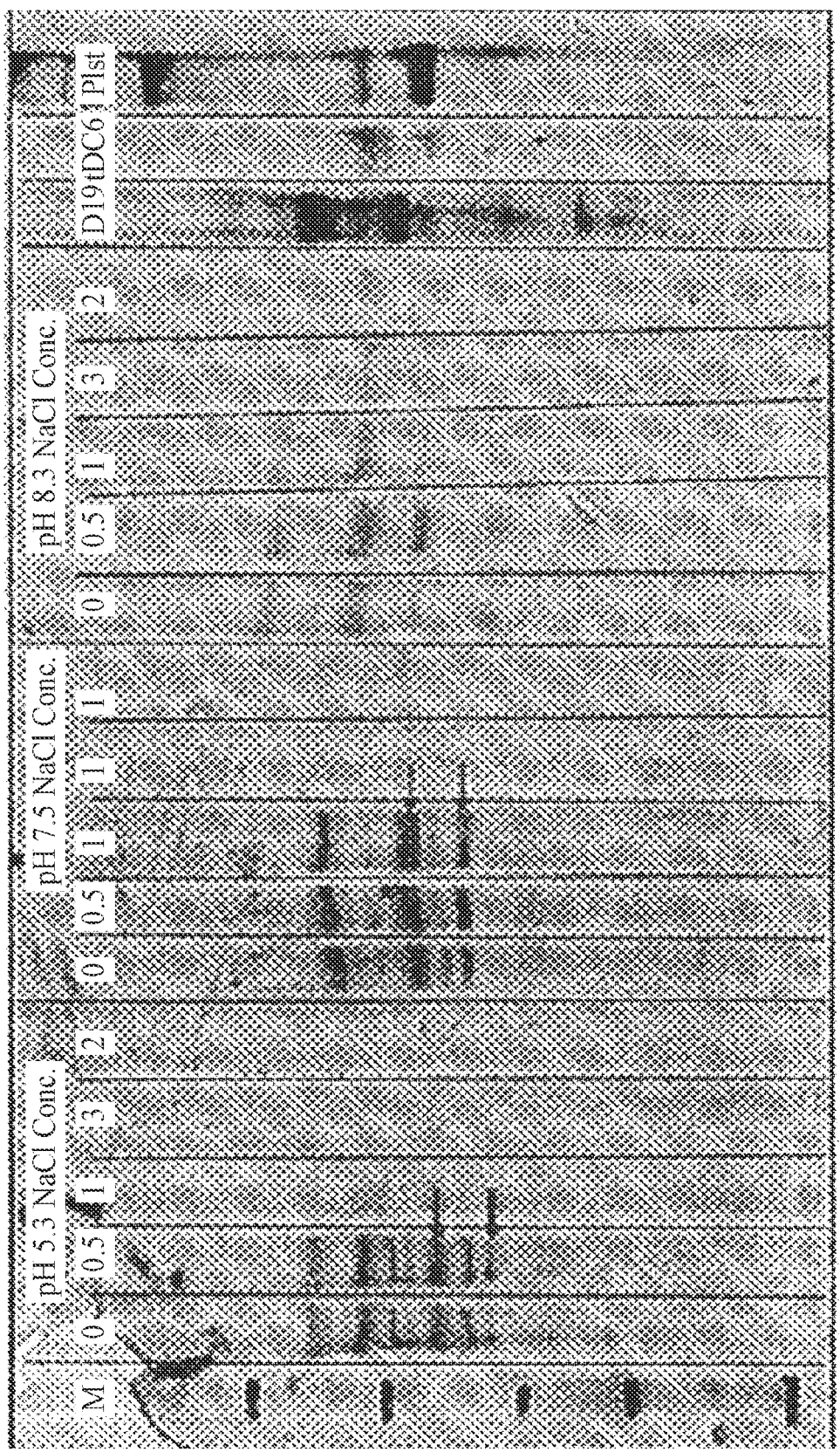
FIGS. 24a-b show optimization of procollagen cleavage by pharmaceutical-grade ficin: optimization of pH and salt concentrations in reaction buffer. AMS-pelleted procollagen-expressing tobacco leaf extracts were resuspended in extraction buffer containing 10 mg/L pharmaceutical-grade ficin at varying pH values (5.5-9.5) and with increasing NaCl concentrations (0.5-3 M). Reaction mixtures were then incubated at 15° C. for 1 hour. Cleavage was terminated by centrifugation and protein samples of both resulting pellets and supernatants were separated on 8% SDS-PAGE, transferred to nitrocellulose membranes and immunoblotted for alpha-1 and alpha-2 collagen chains with anti-collagen I. Arrows indicate collagen bands.
Figure 24B:
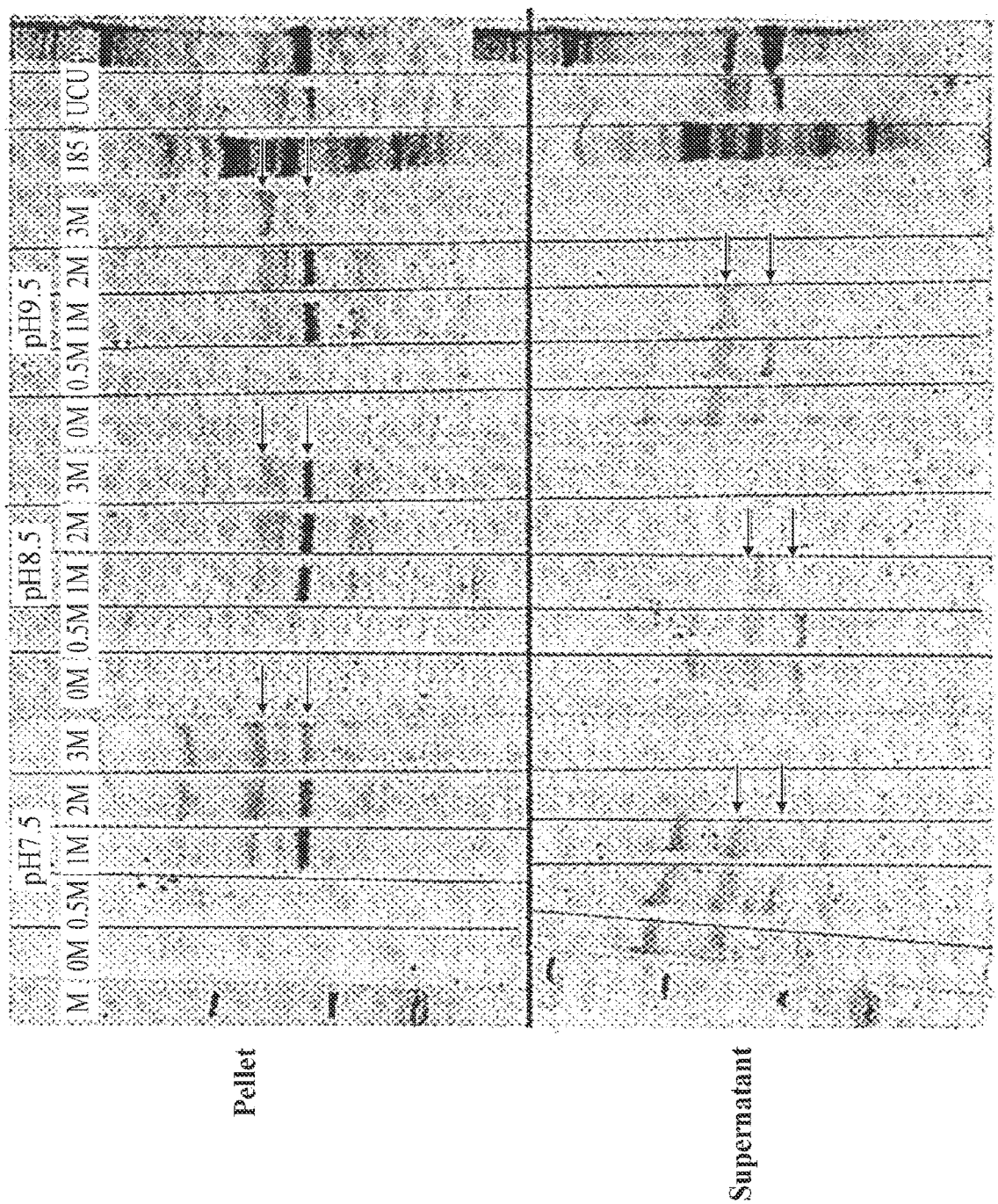

Optimization of pH values and salt concentrations for ficin-dependent procollagen cleavage: The contribution of both digestion buffer pH and salt concentrations were then evaluated. Similar tobacco leaf post-AMS pellets were resuspended in extraction buffer titrated to pH 5.5, 7.5, 8.5, or 9.5 with salt content ranging from 0.5-3 M NaCl. Samples were then incubated with 10 mg/L pharmaceutical-grade ficin at 15° C. for 1 hour prior to immunoanalysis on Western blots. Acidic assay conditions (pH 5.5) led to insufficient collagen yield (FIG. 24A, lanes 2-6), while increases in pH values demonstrated a correlative rise in ficin-dependent collagen content, with peak values observed at pH 8.5 in the presence of 2 M NaCl (FIG. 24B, lane 10). These results were further supported in a scale up extraction and purification experiment performed on two 15 kg pellets pooled for ficin-induced procollagen digestion. Aside from increased collagen chain yield as viewed by immunoblotting, samples digested in buffer of pH 8.5 in the presence of 2 M NaCl fibrillated just as efficiently as those digested in buffer A (pH 7.5, 0 mM NaCl) (see Table 5, herein below—batches YC1 and YC2). Thus, both higher pH and salt concentrations afford improved collagen yield following ficin-induced digestion of procollagen.

Figure 25:
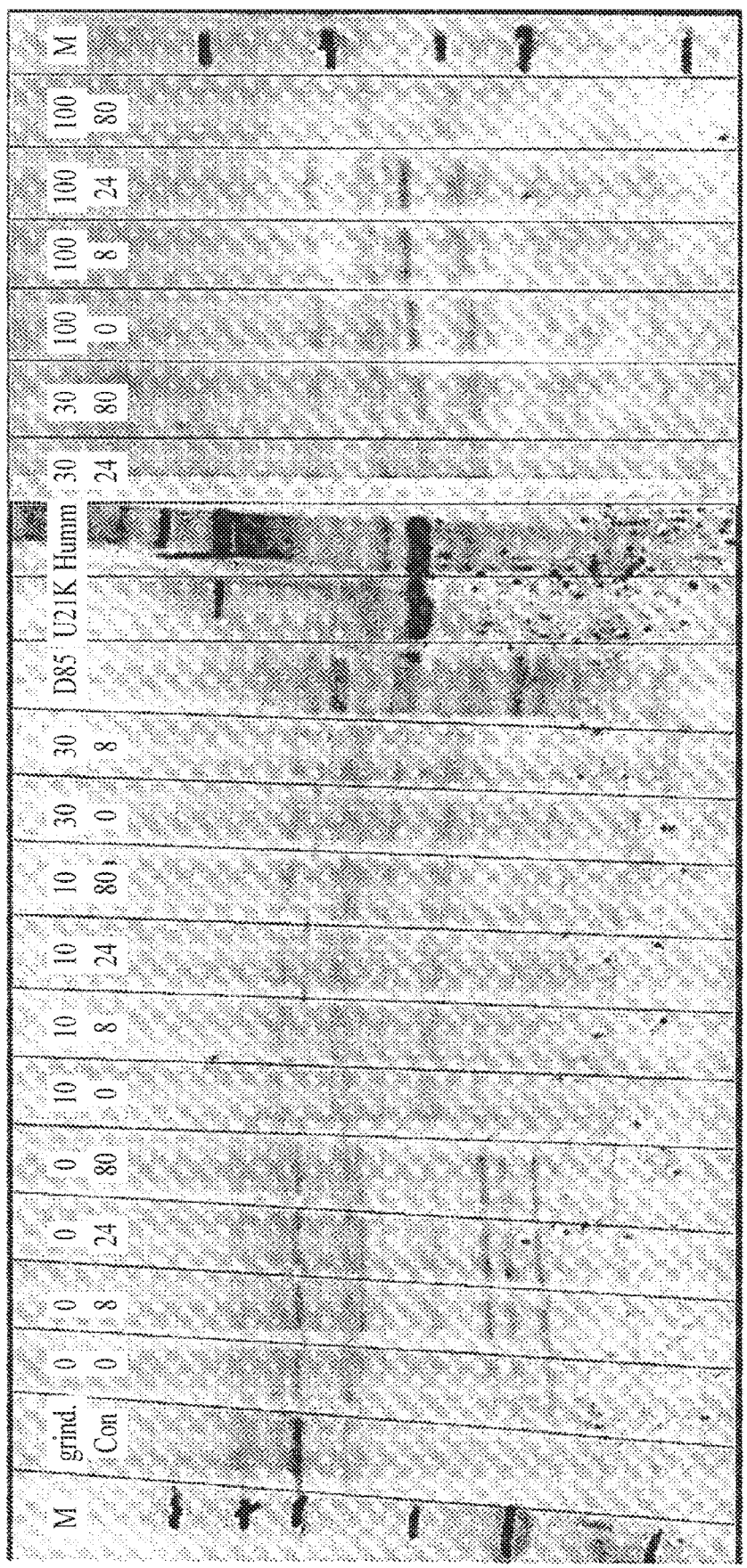
FIG. 25 shows Optimization of procollagen cleavage by pharmaceutical-grade ficin: optimization of EDTA and L-cystein concentrations in reaction buffer. AMS-pelleted procollagen-expressing tobacco leaf extracts were resuspended in extraction buffer (pH 7.5) containing varying concentrations of L-cystein (10-100 mM—upper panel of concentrations) and of EDTA (8-80 mM—lower panel of concentrations). Samples were then incubated with 1 mg/L pharmaceutical-grade ficin at 15° C. for 1 hr. Cleavage was terminated by centrifugation and protein samples were separated on 8% SDS-PAGE, transferred to nitrocellulose membranes and immunoblotted for alpha-1 and alpha-2 collagen chains with anti-collagen I.

Determination of vitalness of EDTA and L-cystein in digestion reaction mixture: Both EDTA and L-cystein are additives present in the extraction buffer at early stages of the collagen purification process. Herein, the essentiality of these two components to effective ficin-dependent collagen cleavage was determined. Procollagen post-AMS pellets were resuspended in extraction buffer containing increasing concentrations of EDTA (8-80 mM) and L-cystein (10-100 mM), and incubated with ficin (10 mg/L) at 15° C. for 1 hour, at pH 7.5. A pronounced enhancing effect was observed on digestion efficiency in the presence of 10 mM L-cystein (FIG. 25, lanes 7-10), with no apparent contribution of EDTA to ficin-dependent collagen output (FIG. 25, lanes 7 vs. 8-10).

Optimization of temperature conditions for ficin-induced procollagen digestion: Procollagen-expressing tobacco leaf pellets were incubated with ficin for 1.5 hours at 15° C. and then transferred to a 30° C. bath for an additional 1.5 hours. Western blot and fibrillogenesis assays did not identify any improvement in collagen yield or sample purity related to increased reaction temperatures.

Fibrillogenesis of collagen extracted from ficin-induced cleavage of procollagen: Following ficin-induced digestion, fibrillogenesis assays were performed to determine the resultant collagen's ability to form fibrils, the ultimate method of determining the collagen's functionality. Table 5, herein below summarizes fibrillogenesis results as determined following ficin cleavage of procollagen using two variant protocols. Both protocols A and B, differing in reaction buffer pH and salt content yielded significant percentage of collagen fibrils. Thus, the proteolysis reaction parameters developed and optimized herein, lead to functional collagen at high yields.

TABLE 5

Percent fibrillogenesis observed by collagen obtained via digestion under varying conditions

| Batch # | Digestion conditions: | % Fibrillogenesis |
|---|---|---|
| C39 | Protocol A: 10 mg/L ficin, 1 hr, pH 7.5 | 94.1 |
| P100 | Protocol B: 10 mg/L ficin, pH 8.5, 2M NaCl, 1 hr | 87.2 |
| P101 | Protocol A | 73.1 |
| YC1 | Protocol A | 95.4 |
| YC2 | Protocol B | 98.4 |
| YC3 | Protocol A | 96 |
| YC4 | Protocol A | 93.1 |
| YC5 | Protocol A | 93.2 |
| YC7-8 | Protocol B | 94.2 |

Example 13. Determination of TRYPZEAN™ Protease Efficacy in Procollagen Cleavage Procollagen-expressing tobacco leaf pellets resuspended in extraction buffer (pH 7.5) enriched with EDTA (7.5 mM) and L-cystein (12.5 mM), were incubated with TRYPZEAN™ (30-100 mg/L) for 1-3 hours at 15° C. Within 1 hour, doses of 60 and 100 mg/L TRYPZEAN™ efficiently cleaved procollagen to yield two distinct alpha collagen chains, with no detectable over-digestion (FIG. 26). Thus, procollagen treatment with TRYPZEAN™ at pH 7.5 lead to its effective digestion to collagen chains alpha-1 and alpha-2.

Discussion

The above Examples 7-13 describe the identification of a non-mammalian protease suitable for use in the process of purification of collagen derived from plants. Proteases from bacterial and plant sources were examined and three enzymes were found suitable for the collagen propeptides digestion, namely, neutrase, subtilisin, TRYPZEAN™ and ficin.

Neutrase and Subtilisin are both secreted by the bacteria *Bacillus* sp. Subtilisin is primarily (>90%) used in detergents and household cleaning products. Approximately 10% of subtilisin use is towards technical applications such as protein hydrolysis, leather treatment, and in the textile and cosmetics industries. Standard use of subtilisin in the collagen purification process at higher concentration is problematic due to overdigestion of collagen. Neutrase is mainly used in the beverage alcohol industry and in cheese ripening. In Examples 7-13, described herein above, neutrase was only effective in digesting the propeptides at high concentrations and at least 6 hours were required for desirable digestion results.

Under the presently described experimental conditions, recombinant trypsin and ficin were found to be the most suitable among the four, since there was no overdigestion of collagen at either high enzyme concentrations or after extended incubation periods. Furthermore, these enzymes apparently did not digest the helical region of the collagen, as determined by SDS PAGE analysis. Ficin, being a natural enzyme extracted for Fig latec plant (*Ficus carica*), is available commercially at several grades including a pharmaceutical grade from several sources at low cost. It is used in the food industries: alcohol and beer industries, hydrolisation of proteins, meat processing, baking industry, and in the preparation of pet food and health food. It is also applied in the pharmaceutical industry in contact lens cleansers, cancer treatment, anti-arthritis treatments, and digestive aids as well as in the cosmetic and textile industries.

Example 14. Further Analysis of rhCollagen Properties

Materials and Methods

Materials

Human recombinant collagen (rhCollagen) type I expressed and isolated from transgenic tobacco plants was produced and supplied by CollPlant Ltd (Israel). Type I Bovine Collagen (PureCol) was purchased from Advanced Biomatrix, USA. Methacrylic anhydride, glycidyl methacrylate, triethylamine, tetrabutylammonium bromide, 2,4,6-Trinitrobenzenesulfonic acid (TNBS), 2-Hydroxy-4'-(2-hydroxyethoxy)-2-methylpropiophenone (Irgacure 2959), sodium phosphate monobasic anhydrous, HCl 1N, HCl ≥37%, sodium bicarbonate and NaOH were purchased from Sigma Aldrich Ltd, Israel. Phosphate buffered saline (PBS), ×10 PBS, Foetal Bovine Serum (FBS), DMEM high glucose and penicilin/streptomicin were purchased from Biological Industries Ltd, Israel. Sodium phosphate dibasic anhydrous was purchased from Canton, India. Ethanol absolute and acetone were purchased from Bio-Lab Ltd, Israel. Hyaluronic acid was purchased by Lifecore, USA.

Buffers and Photoinitiator Stock Solution Preparation

Fibrillogenesis buffer (FB): sodium phosphate dibasic was dissolved in double distilled water (DDW) to final concentration of 162 mM. The solution was titrated to pH 11.2 with 10N NaOH.

Medium preparation: 50 ml of foetal bovine serum and 5 ml of penicillin/streptomycin (10,000 units/mL and 10 mg/mL respectively) were added under aseptic conditions to 500 ml of DMEM high glucose medium. The medium was gently mixed and kept in fridge.

Phosphate Buffer Saline preparation: 39 ml of 0.1M Sodium phosphate monobasic solution were mixed with 61 ml of 0.1M sodium phosphate dibasic solution and final volume adjusted to 200 ml with DDW. Final pH was adjusted to 7 with concentrated NaOH or HCl as needed. NaCl was added to final concentration of 150 mM.

Washing buffer: HCl was added to the fibrillogenesis buffer to reach a final concentration of 16.2 mM sodium phosphate dibasic and 10 mM HCl. pH was adjusted to 7.2-7.4 with 10N NaOH.

Photoinitiator 10% (v/v) stock solution: Irgacure 2959 was dissolved in ethanol absolute/PBS 1:1 solution to a final concentration of 100 mg/mL.

Methacrylation of rhCollagen

Fibrillar rhCollagen-methacrylamide and monomeric rhCollagen-methacrylamide were prepared by reaction of lysine and hydroxylysine collagen residues with methacrylic anhydride in aqueous medium as described below and stored at 4° C. light protected until further use.

Fibrillar rhCollagen-methacrylamide 3 to 10 mg/mL fibrillar rhCollagen-methacrylamide was synthesized either in washing buffer, fibrillogenesis buffer or DDW, at room temperature (R.T.) or at 12° C. For example, in brief, fibrillar collagen-MA was synthesized in DDW as follow: monomeric rhCollagen 3-4 mg/mL solution in 10 Mm HCl, (COLLAGE™) was mixed with fibrillogenesis buffer at 9:1 v/v ratio and stirred for 1 hr at R.T, receiving fibrils. The solution was centrifuge at 7500 rpm at 4° C. for 30 minutes, discarding the supernatant. The pellet was re-suspended in equal volume of washing buffer and centrifuged at the same conditions. After that, the sediment fibrils were re-suspended in DDW to 10 mg/mL. Concentration was confirmed by percent solid measurements. Methacrylic anhydride (MA) was added drop-wise under nitrogen flow at room temperature at 10 to 20 molar ratio with respect to collagen lysines, and the reaction solution pH was monitored over time and adjusted to pH 7 with 10N NaOH. After 24 hours reaction, the mixture was dialyzed against washing buffer (pH 7) using 10 kDa cutoff dialysis tubing (Spectrum Laboratories Inc, CA, US) for 3 days at 4° C. with at least 6 changes of the dialysate (washing buffer in this case), to remove reaction by-products and eventually lyophilized for 3-4 days.

Monomeric rhCollagen-methacrylamide 200 mM MOPS, phosphate, or Tris buffers with the addition of 150 mM NaCl were used. For example, 200 mM MOPS and 150 mM NaCl were added to 3-4 mg/mL COLLAGE™ and stirred at RT until clear solution was obtained. Thereafter, 10 to 20-fold excess of methacrylic anhydride was added drop-wisely under nitrogen flow at 12° C., and the pH was adjusted over time to pH 7 with 10N NaOH. After 24 hours reaction, the mixture was dialyzed against 10 mM HCl and 20 mM NaCl (pH 2) with 10 kDa cutoff dialysis tubing for 3 days at 4° C. with at least 6 changes of the dialysate, followed by 3-4 days lyophilization.

Methacrylation of Hyaluronic Acid (HA)

500 mg of HA were functionalized as described by Leach et al. [Leach et. al. 2002, Biotechnology and Bioengineering, vol. 82, no. 5]. Briefly, 1.8 ml of triethylamine, 1.8 ml of glycidyl methacrylate, and 1.8 g of tetrabutyl ammonium bromide were added separately to 50 ml of 10 mg/mL HA solution in DDW and thoroughly mixed before the next component was added. The reaction was mixed overnight at room temperature and the HAMA precipitated in 20-fold volume of acetone and re-dissolved in DDW. The precipitation process was repeated twice to eliminate all the reaction residues. The material was eventually lyophilized.

Solutions Preparation for Viscosity Measurements

PureCol and Collage™ in PBS: 8 ml of monomeric collagen solutions (3 mg/mL in 10 mM HCl), either rhCollagen (COLLAGE™) or bovine collagen (PureColl) were neutralized by adding 1 ml of PBS×10. The solution was then brought to pH 7-7.5 by titration with 0.1N NaOH. Eventually double distilled water was added to reach a final volume of 10 ml. Samples were incubated at 37° C. for at least 90 min before measurements were performed (either at 37° C. or 4° C.).

COLLAGE™ in fibrillogenesis buffer: 9 ml of monomeric rhCollagen (COLLAGE™) solution (3.79 mg/mL in 10 mM HCl) was neutralized by adding 1 ml of fibrillogenesis buffer. Samples were incubated at 37° C. for at least 90 min before measurements were performed (either at 37° C. or 4° C.).

Fibrillar rhCollagen-methacrylamide in PBS: Lyophilized fibrillar rhCollagen-MA prepared in DDW and dialyzed vs. washing buffer (according to what described above with 10-fold excess of MA) were dissolved in PBS to a concentration of 10 mg/mL. Samples were incubated at 37° C. for at least 90 min before measurements were performed (either at 37° C. or 4° C.).

rhCollagen-methacrylamide in DMEM: Lyophilized fibrillar rhCollagen-methacrylamide (15-fold excess of MA, prepared and dialyzed in washing buffer, according to the description above) was dissolved in DMEM medium to final concentrations of 20 and 26 mg/mL.

rhCollagen-methacrylamide/Hyaluronic Acid in DMEM: Hyaluronic Acid was added to a solution of fibrillar rhCollagen-MA to obtain final concentrations of 10 mg/mL HA and 20 mg/mL rhCollagen-MA in DMEM medium.

rhCollagen-methacrylamide/Hyaluronic Acid methacrylate (HA-MA) in DMEM: Hyaluronic Acid methacrylate (see above) was added to a solution of fibrillar rhCollagen-MA to obtain final concentrations of 10 mg/mL HA-MA and 20 mg/mL rhCollagen-MA in DMEM medium.

rhCollagen-MA Photocrosslinking for Loss and Storage Moduli Measurements rhCollagen-MA crosslinked scaffolds were formed in two different preparations, aimed to be examined in two individual experiments. In the first preparation, 1-2 wt % fibrillar rhCollagen-MA synthesized with 10-fold excess of the methacrylic reagent were dissolved in PBS 0.1 M at R.T, then Irgacure 2959 0.1% was added and 1 mL final volume of solutions was injected into a discoid mold. Following that, curing process was performed from a distance of 1.5 cm for 7 and 10 seconds at an averaged intensity of 670 mW/cm2 using mercury light source, ending up in crosslinked scaffolds. The second preparation included 2 different batches of fibrillar rhCollagen-MA, synthesized with 15- and 20-fold excess of the methacrylic reagent. 1-2 wt % were dissolved in PBS 0.1 M, and Irgacure 2959 0.1% was added to achieve a final volume of 1.5 mL. In order to obtain highly crosslinked scaffolds, curing process was performed from a distance of 2 cm for 60 seconds at an averaged intensity of 420 mW/cm$^2$.

TNBS Assay

The assay protocol was similar to the one reported by Sashidhar et al. [Sashidhar R. B., Capoor, A. K., Ramana, D, Journal of Immunological Methods. 1994, 167, 121-127], and based on Habeeb [Habeeb A. F. S. A, Analytical Biochemistry. 1966, 14, 328-336]. Briefly, freshly prepared 0.4 mL of 0.01% (v/v) TNBS was added to 0.4 mL of 0.1-2 mg/mL fibrillar rhCollagen-MA in sodium bicarbonate 4%. After 2 hours reaction at 40° C., 0.2 mL of 1N HCl and 0.4 mL of 10% (v/v) SDS were added. The absorbance was measured at 335 nm in a spectrophotometer in a 1 mL polystyrene cuvette. A control (blank) was prepared with the same procedure except that sodium bicarbonate buffer was added instead of rhCollagen-MA solution. The absorption of 1-2 mg/mL native fibrillar rhCollagen prepared with the same conditions was recorded for calibration.

Rheological Characterization

Viscosity: Viscosity measurements were performed on a HAAKE RHEOSTRESS600™ rheometer (Thermo Electron Corporation) with a temperature-controlled cell chamber, using a C60/1° Ti cone-plate set up. Viscosity was measured on 1 mL sample in a rotational ramp mode, shear rate ranging from 0.0001 to 1000 sec-1 at 4° C., 25° C. and 37° C.

Scaffolds' storage and loss moduli: The rheological behavior of rhCollagen crosslinked discs was investigated using parallel plate system employing PP20 serrated spindle and 20 mm serrate plate set up. In order to characterize the non-crosslinked rhCollagen-MA, C60/1° Ti cone-plate elements were used. In order to evaluate the rheological behavior of rhCollagen-MA, two sets of experiments were performed individually. In the first, 1 mL samples were subjected to oscillation forces at controlled stress mode, recording storage modulus G' and loss modulus G" values while applying 5 Pa shear stress at 1 Hz frequency and 37° C. for 300 seconds. The gap was adjusted to 90% of the original sample height and G' and G" values were averaged at the range of 150-300 seconds. In the second experiment, 1.5 mL crosslinked discs were tested in frequency sweep oscillations at 37° C., where G' was recorded under 1 Pa shear stress at frequency range of 0.01-100 Hz. To initiate measurement, the spindle was lowered to contact the hydrogel surface, and then further lowered until the axial force of the instrument was equaled to 0.4 N. Prior to all measurements, samples were kept on the plate covered with humidity lid for 1 minute, in order to reach temperature equilibrium.

Results

TNBS Assay

The extent of modification of rhCollagen was quantified using TNBS colorimetric assay. The assay quantifies the molar content of free, non-reacted ε-amino groups derived from lysine and hydroxyl lysine, and subsequently the degree of functionalization. The degree of functionalization of fibrillar rhCollagen 10, 15 and 20-fold different batches was determined by TNBS assay, as shown in Table 6.

TABLE 6

The degree of functionalization of fibrillar rhCollagen from different preparations, as determined by TNBS assay.

| Fibrillar rhCollagen-MA batch | Degree of methacrylation [%] |
|---|---|
| 10-fold | 98.1 |
| 15-fold | 95.5 |
| 20-fold | 92.9 |

The results indicate on high modification capability of the fibrillary rhCollagen and
imply that adding the methacrylic reagent in molar ratio of 10 may be preferable for receiving maximal functionalization of the fibrillar collagen.

Rheology

1. Viscosity

Temperature Dependence of rhCollagen/Bovine Collagen Viscosity

Figure 27:
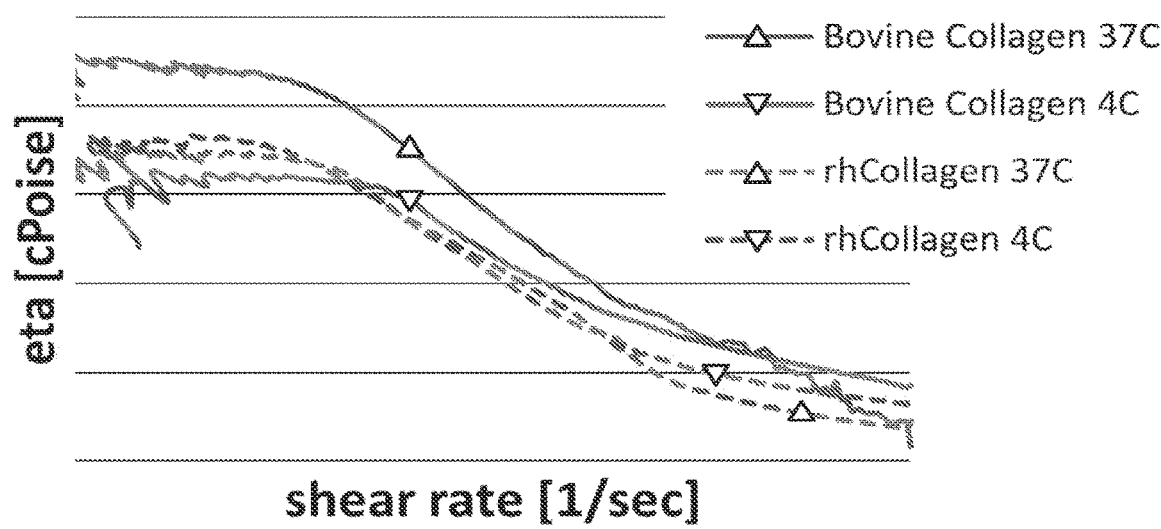
FIG. 27 shows viscosity (eta [η], cP) as a function of shear rate, solid line—2.7 mg/mL bovine collagen in phosphate buffered saline (PBS), dashed line 2.79 mg/mL rhCollagen in PBS. ▼: measurements at 4° C., ▲: measurements at 37° C.
Figure 28:
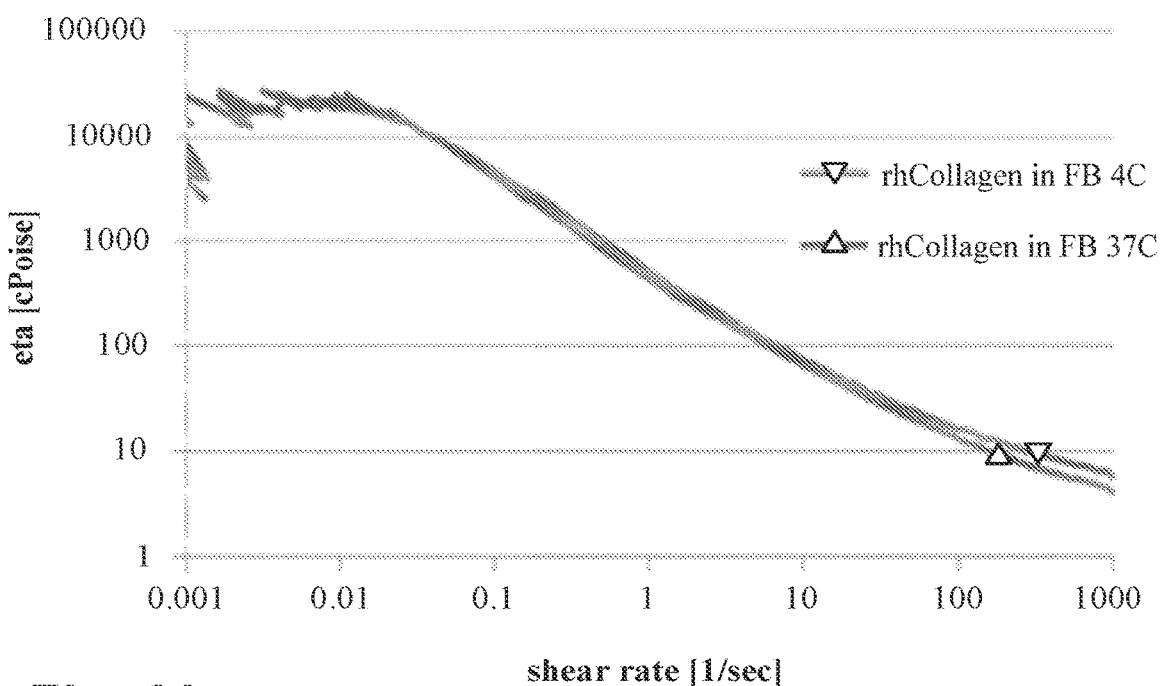
FIG. 28 shows viscosity as a function of shear rate, 3.4 mg/mL bovine collagen in FB. ▼: measurements at 4° C., ▲: measurements at 37° C.
Figure 29:
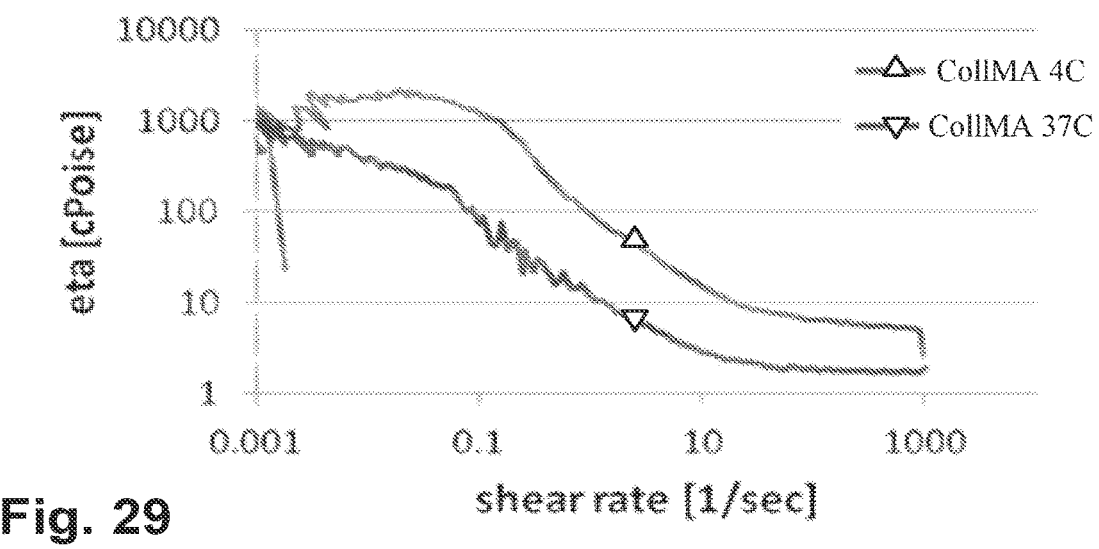
FIG. 29 shows viscosity as a function of shear rate, 10 mg/mL rhCollagen-MA in PBS. ▲: measurements at 4° C., ▼: measurements at 37° C.

FIG. 27 shows the viscosity of rhCollagen (COL-LAGE™) and Bovine Collagen (PureCol) in PBS expressed as a function of shear rate at T=4° C. (blue, dashed and solid line respectively) and T=37° C. (red, dashed and solid line respectively). Bovine collagen (solid lines) shows clear temperature dependence of the zero-shear rate viscosity (η0) i.e. the viscosity plateau at low shear rate values, having at 37° C. (red) η0 values that are more than one order of magnitude higher than the values at 4° C. (blue). On the contrary rhCollagen (dashed lines) shows no significant difference between η0 values at 4° C. and 37° C. rhCollagen neutralized in FB (see methods) shows a very similar behavior (FIG. 28), i.e. the viscosity at 4° C. and 37° C. is almost identical. FIG. 29 shows the viscosity of fibrillar rhCollagen-MA at 4° C. (blue line) and 37° C. (red line). Although the profiles are not identical the zero shear rate values are around 1000 cP at both temperatures.

Viscosity of rhCollagen-methacrylamide

Figure 30:
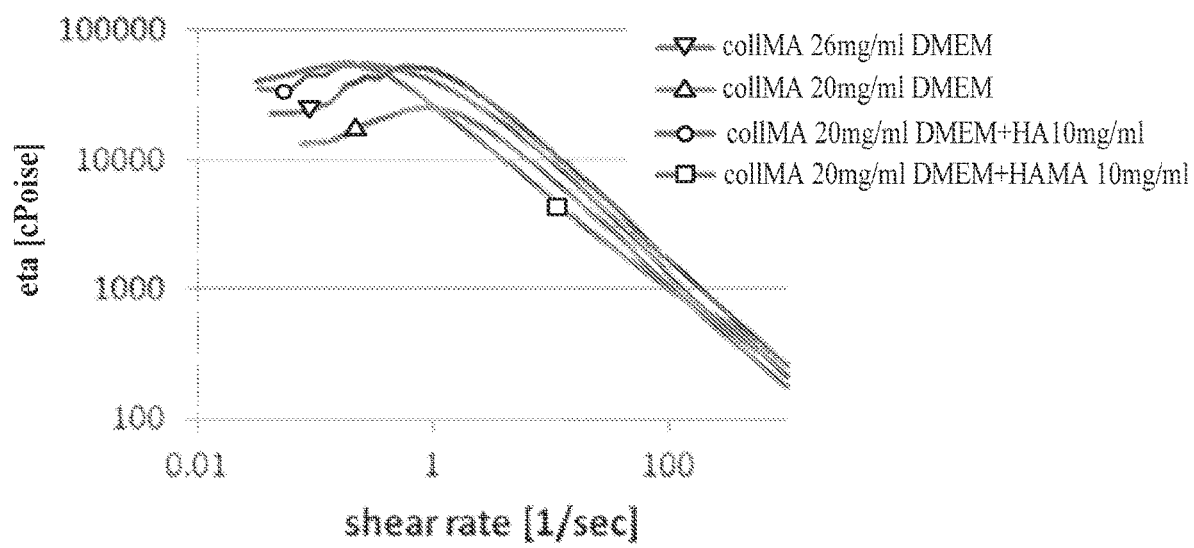
FIG. 30 shows viscosity measurements of rhCollagen-MA in DMEM with and without addition of HA/HAMA.

FIG. 30 shows the viscosity of rhCollagen-MA dissolved in DMEM at 25° C. The typical shear thinning behavior of the rhCollagen seen in FIGS. 27 and 28 is maintained also for the rhCollagen-MA with and without the addition of HA/HA-MA. Increasing the concentration of rhCollagen from 20 to 26 mg/mL (green and red line respectively) the zero-shear viscosity increases as well as by the ulterior addition of 10 mg/mL HA or HAMA which leads to final polymer concentration of 30 mg/mL.

The skilled artisan would recognize that rhCollagen-MA is not crosslinked and that in order to achieve crosslinking, one needs to add a photoinitiator and light.

2. Scaffolds' Loss and Storage Moduli

Figure 31:
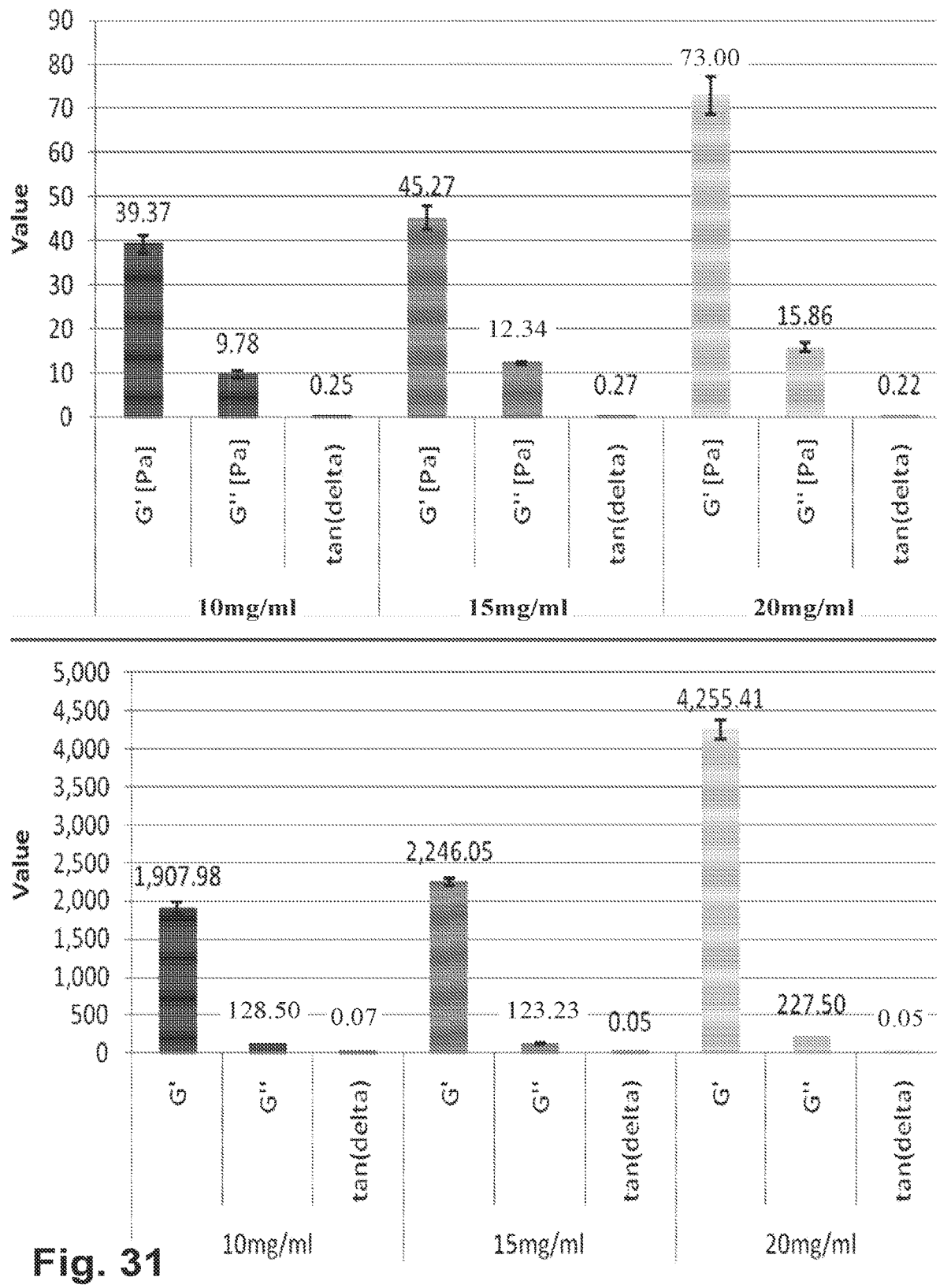
FIG. 31 shows storage and loss moduli and tan phase shift angle of rhCollagen-MA formulation at different concentrations before (upper graph) and after (lower graph) photo-crosslinking.

Rheological analysis of 1 mL discs over time at 37° C. performed in the first experiment are presented in FIG. 31. The upper graph reports loss and storage moduli and the tan (delta) before UV curing while the lower graph reports the values after UV curing (upon addition of photoinitiator). The data demonstrates that the storage modulus of the rhCollagen-MA increases by 2-fold upon illumination in the presence of photoinitiator. Moreover, the results point on the capability of controlling the scaffold properties by changing the rhCollagen-MA concentration. High differences between G' and G" values, and close-to-zero tan (delta) values of the crosslinked discs indicate on their elastic-like behavior. (G'—storage moduli; G"—loss moduli; G', the "storage/elastic modulus," represents the energy fraction of G* stored by the gel during deformation and used to recover the original shape afterwards. G' measures the elastic behavior of a gel or how much it can recover its shape after shear deformation. For example, vulcanized rubber is a purely elastic material as it deforms instantly under stress and completely recovers its shape after the stress is removed (i.e., $G^* \approx G'$). G", the "loss/viscous modulus," represents the energy fraction of $G^*$ lost on shear deformation through internal friction. G" is not directly related to viscosity because HA filler is not purely viscous. Instead, this term reflects the inability of the gel to recover its shape completely after the shear stress is removed.)

Figure 32:
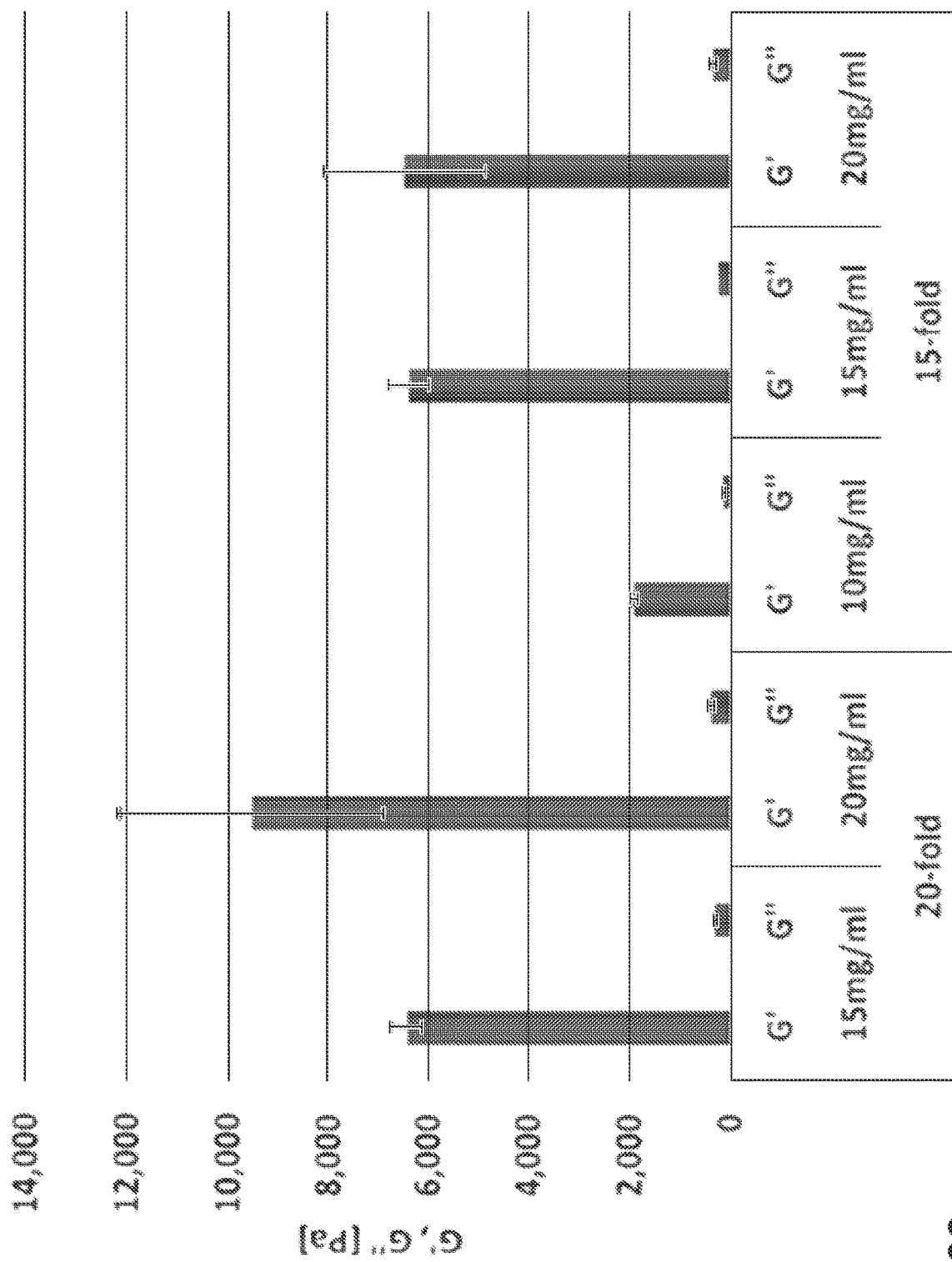
FIG. 32 shows G' and G" values at 37° C. recorded in frequency sweep test and plotted at 1 Hz.

In the second experiment, 1.5 mL discs illuminated for 60 seconds present higher G' values, as shown in FIG. 32. The data shows that G' increases with the rhCollagen-MA concentration and the degree of methacrylation, indicating on capability of controlling the scaffolds properties.

Figure 33A:
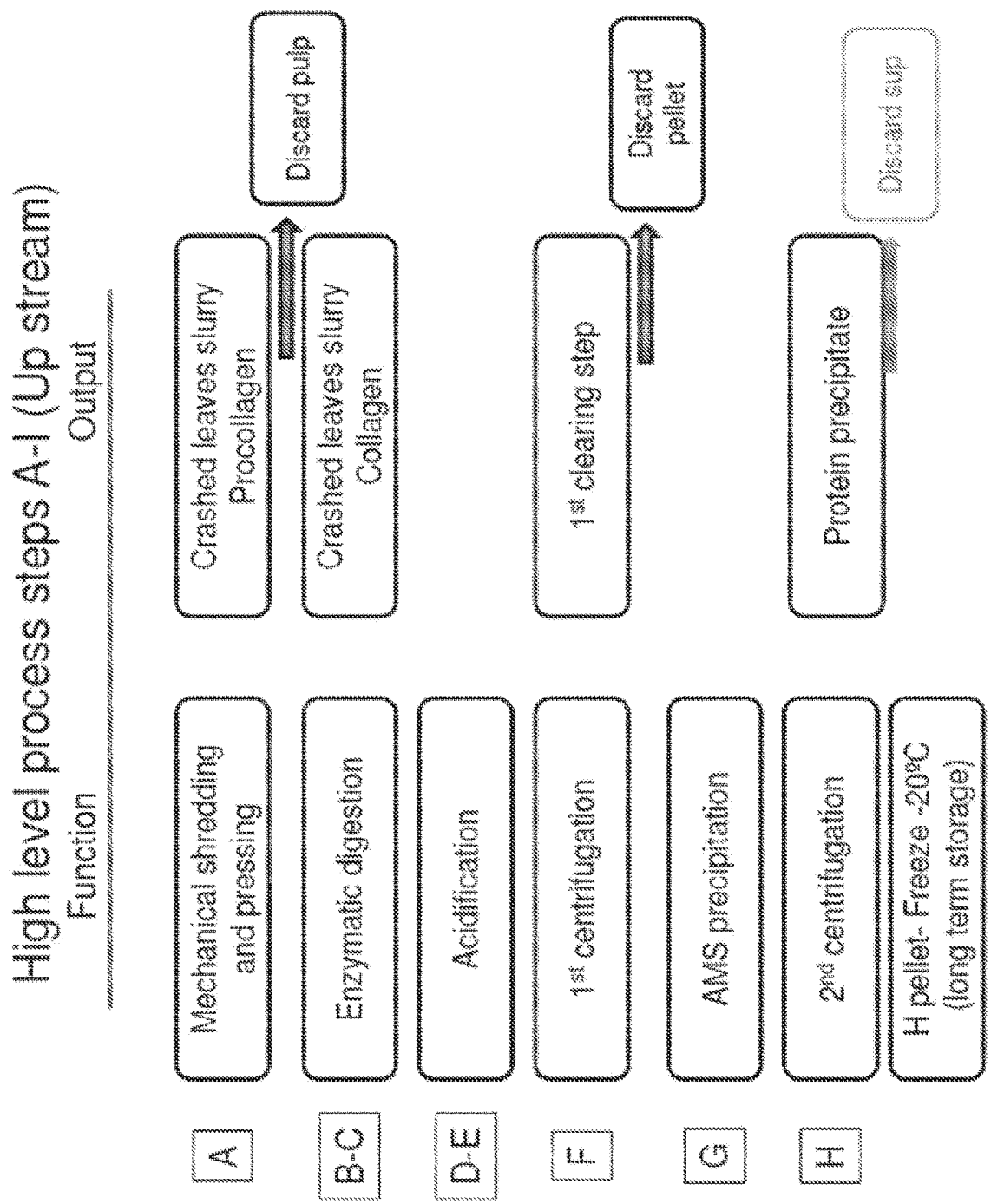
FIGS. 33A-33C provide a flow chart for the processing of rhCollagen and rhCollagen Methacrylate.
Figure 33B:
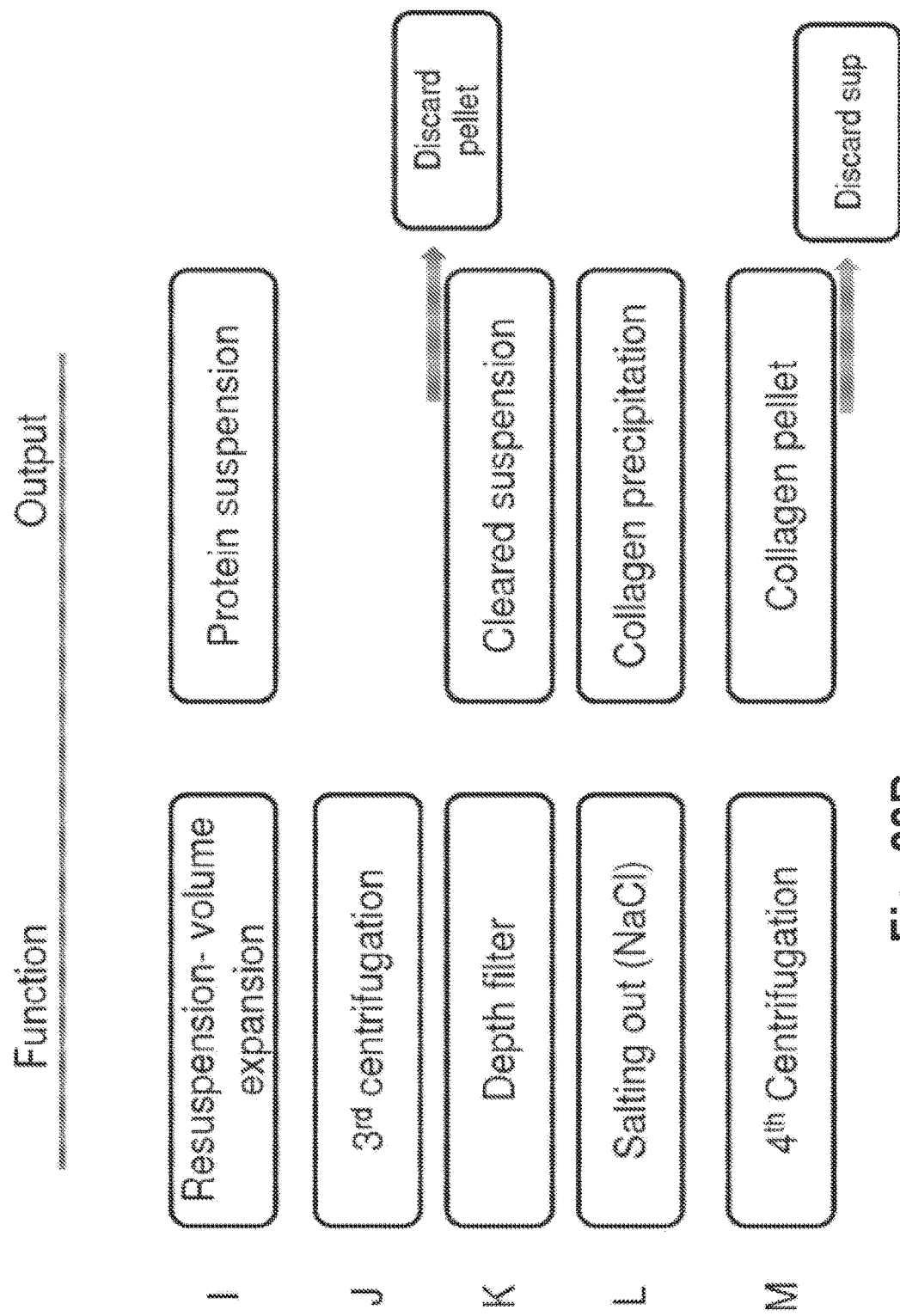
Figure 33C:
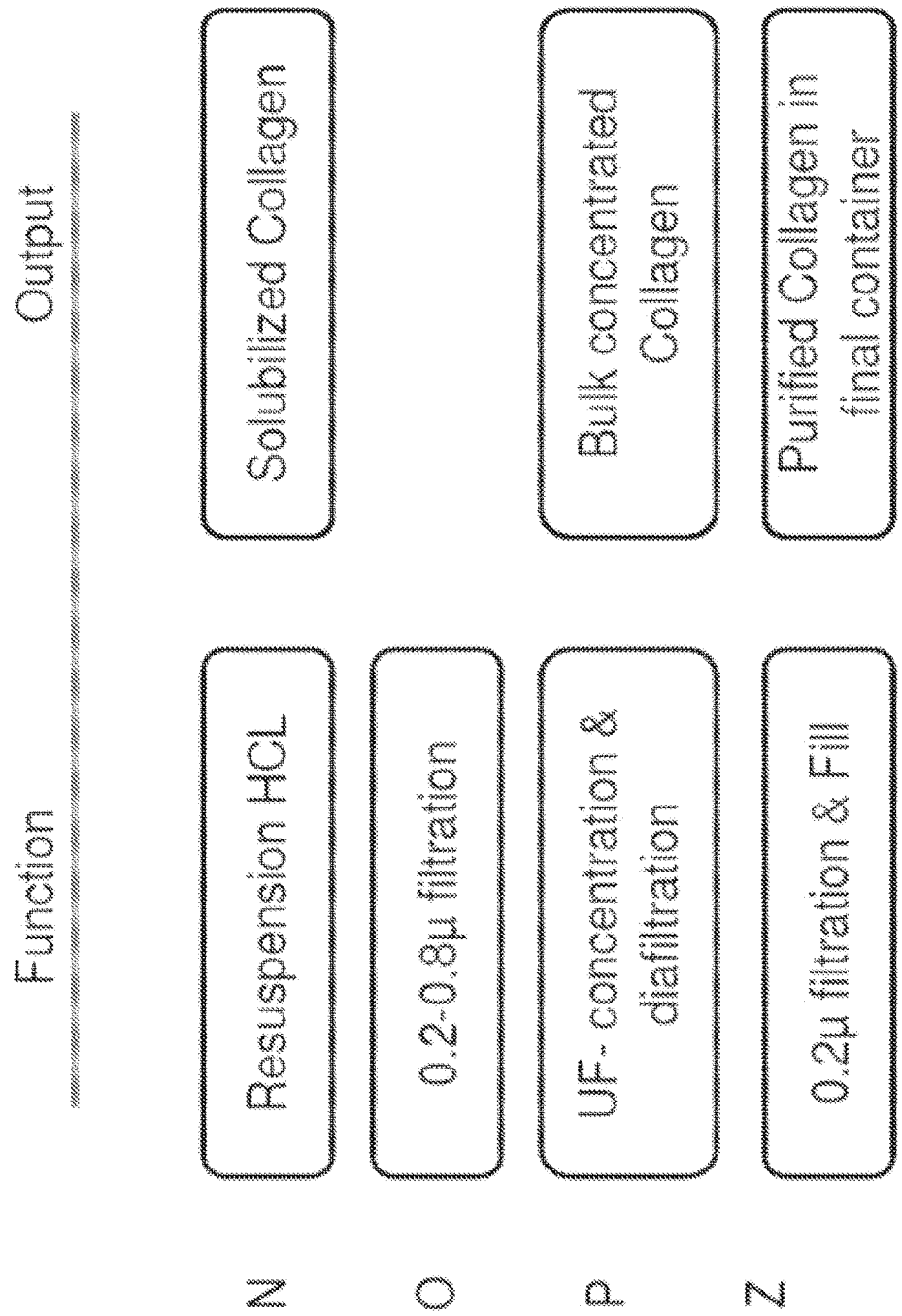
Figure 34:
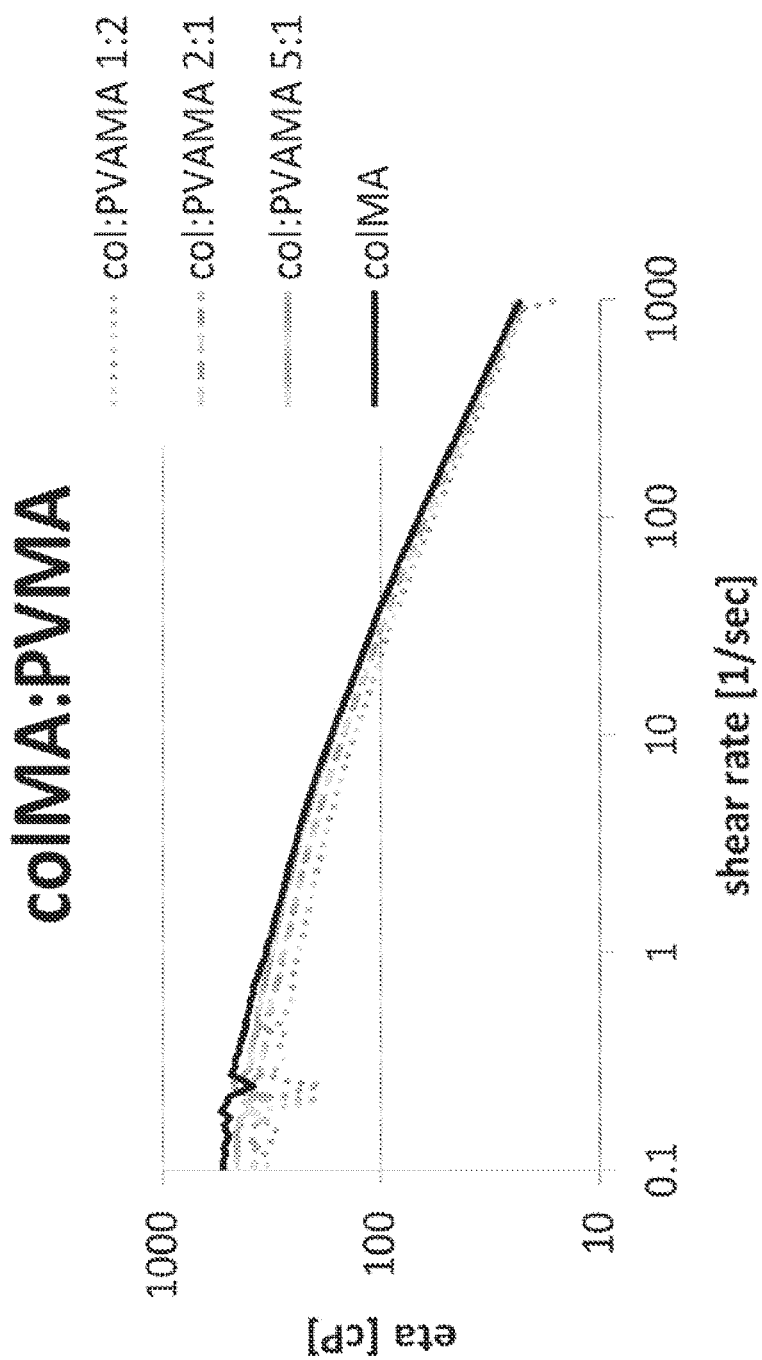
FIG. 34 shows the viscosity (eta [η], cP) of 5 mg/ml rhCollagen Methacrylate (CollMA) (solid black curve) and 5 mg/ml Collagen MA+polyvinyl alcohol methacrylate (PVMA) (light grey curves) at collMA:PVAMA ratio of 5:1 (solid curve), 2:1 (dashed curve), 1:2 (dotted curve). The viscosity of 5 mg/ml rhCollagen methacrylate is reported for comparison (black curve).
Figure 35:
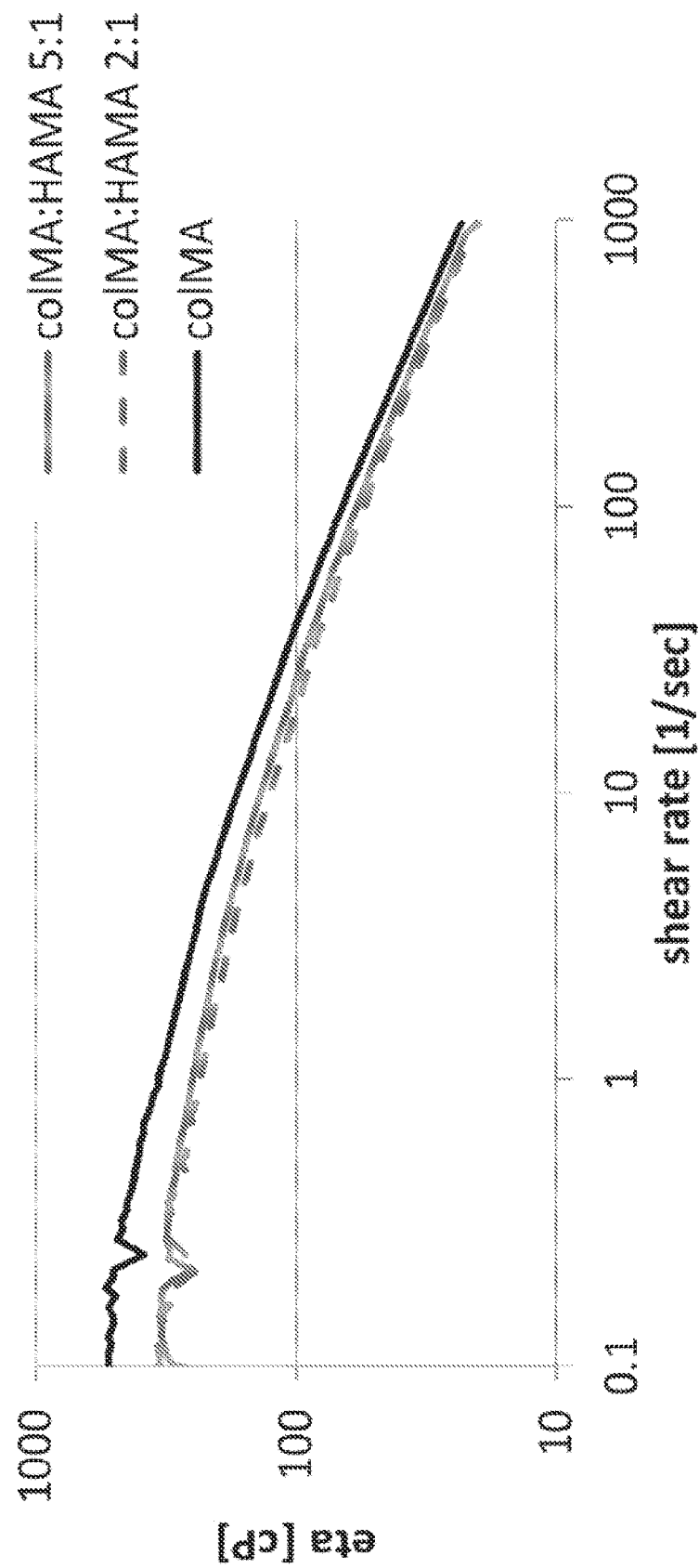
FIG. 35 shows the viscosity of 5 mg/ml CollMA (solid black curve) and 5 mg/ml Collagen MA+hyaluronic acid methacrylate (HAMA) (grey curves) at collMA:HAMA ratio of 5:1 (solid curve), 2:1 (dashed curve). The viscosity of 5 mg/ml rhCollagen methacrylate is reported for comparison (solid black curve). These materials are not yet crosslinked but would be crosslinked after injection. The viscosity is representative of the injectability of the materials. (HAMA-HA methacrylate; Collagen MA (ColMA)-rhCollagen methyacrylate.)
Figure 36:
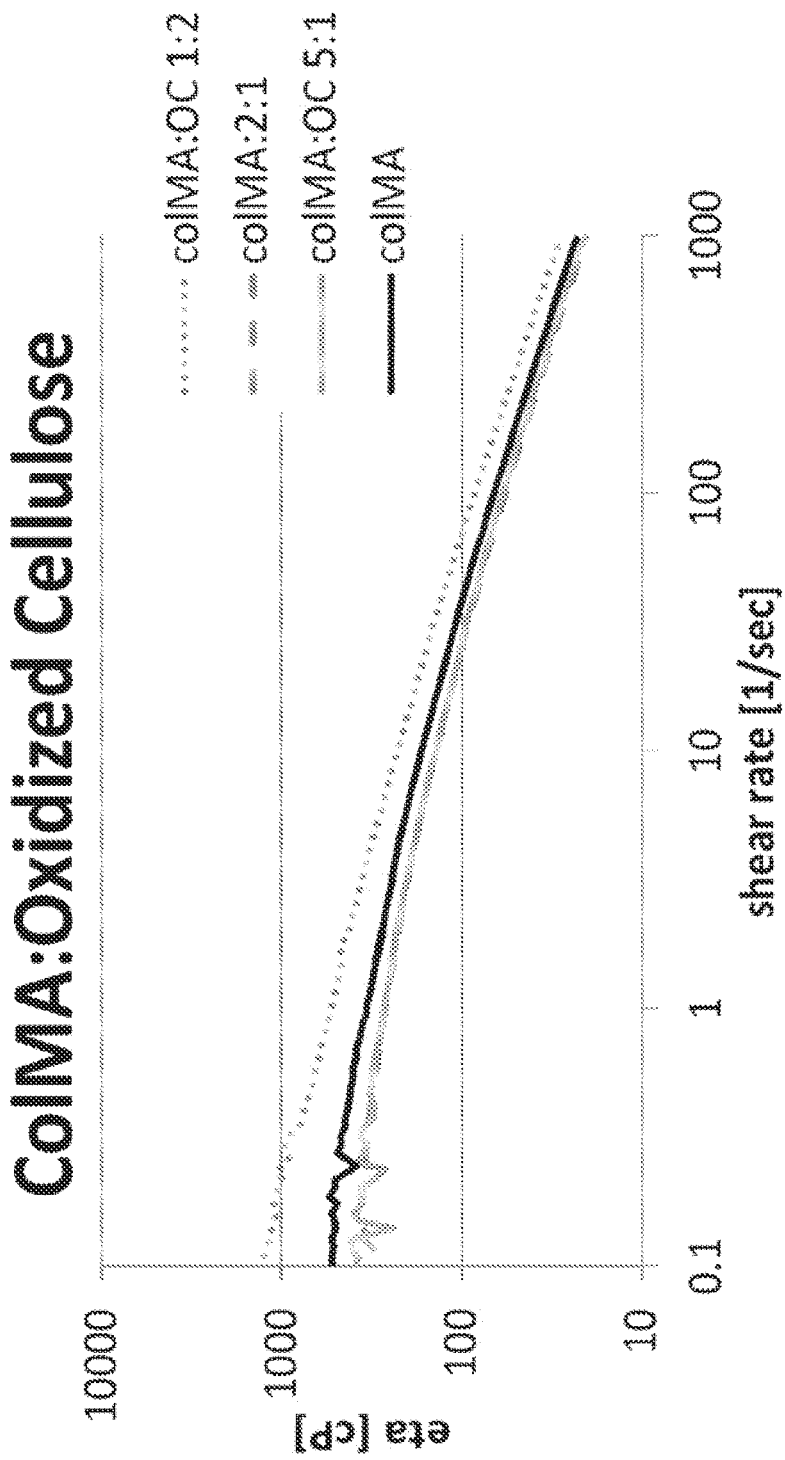
FIG. 36 shows the viscosity of 5 mg/ml CollMA (solid black curve) and 5 mg/ml Collagen MA+oxidized cellulose (OC) (grey curves) at collMA:OC ratio of 5:1 (solid curve), 2:1 (dashed curve), 1:2 (dotted curve). The viscosity of 5 mg/ml rhCollagen methacrylate is reported for comparison (solid black curve).
Figure 37:
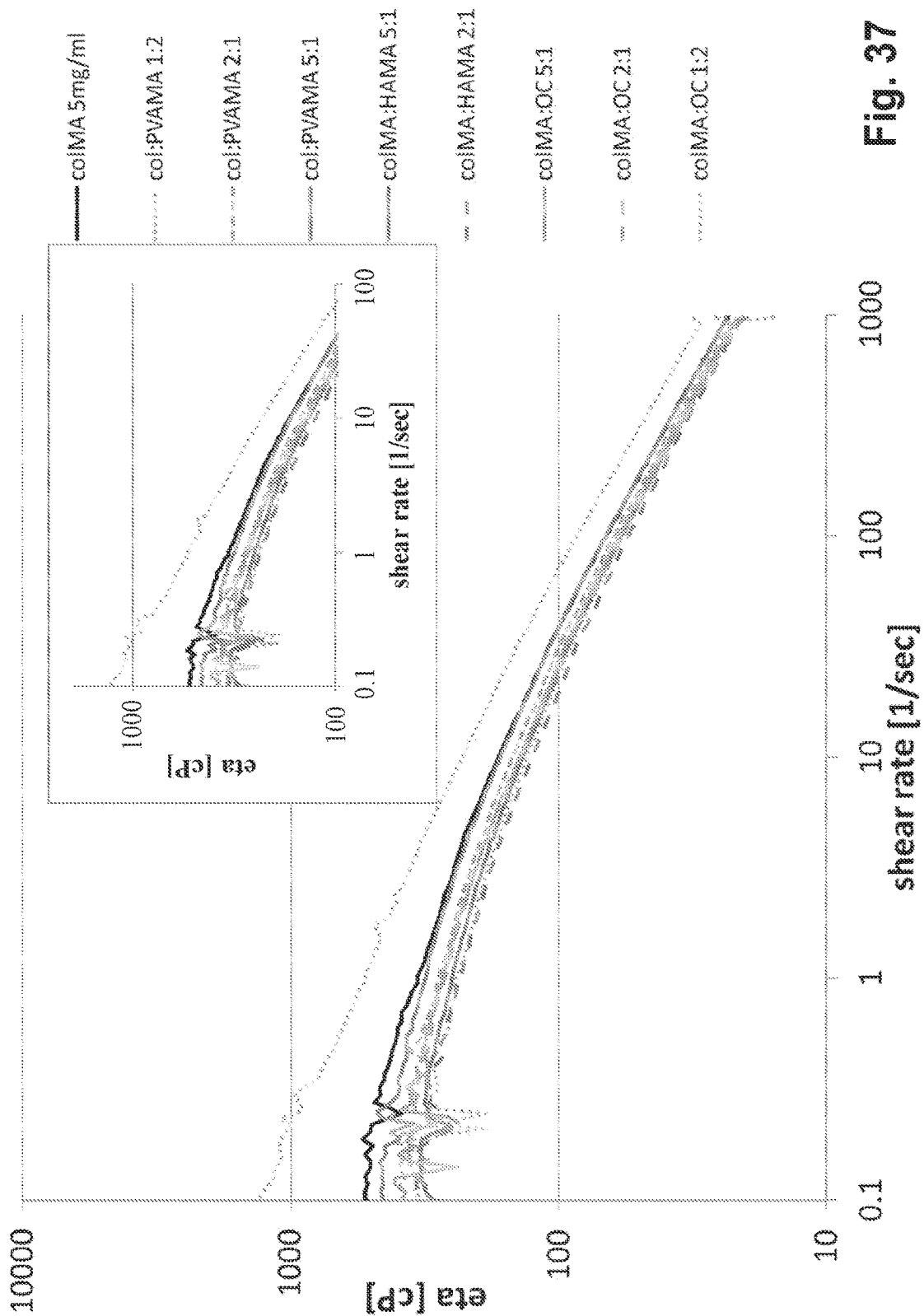
FIG. 37 provides a comparison of the data from FIGS. 33-35. It shows the viscosity of 5 mg/ml CollMA (solid black curve) and 5 mg/ml Collagen MA+different additives (light through dark grey curves as indicated in Figure) at ratio of 5:1 (solid curves), 2:1 (dashed curves), 1:2 (dotted curves). The viscosity of 5 mg/ml rhCollagen methacrylate is reported for comparison (solid black curve).

Example 15. Procedure for Obtaining and Processing rhCollagen from Tobacco Plants Tobacco plants genetically modified as described above are grown, and the leaves are harvested and prepared for initial upstream extraction and purification (FIGS. 33A-C). As shown in FIG. 33A, the leaves are subject to mechanical shredding (step A), and the pulp is removed from the slurry, while the procollagen containing moiety is retained and subjected to enzymatic digestion to convert procollagen to collagen (steps B-C). The pulp is again discarded, and the collagen containing moiety is retained from the slurry (step C). Following an acidification step, the sample undergoes a first centrifugation for a first clearing step, after which the pellet is discarded (steps D-F). After AMS precipitation and a second centrifugation, the protein is precipitated (H pellet), and the supernatant is discarded (steps G-H). The H pellet can be frozen at −20° C. for storage.

As shown in FIG. 33B, the H pellet is resuspended to yield a protein suspension, followed by a third centrifugation, after which the pellet is discarded (steps I-J). A depth filter is used to clear the suspension, which is subjected to salting out with NaCl to precipitate the collagen (steps K-L). A fourth centrifugation yields a collagen pellet, and the supernatant is discarded (step M).

As shown in FIG. 33C, the collagen pellet is resuspended in HCl to yield solubilized collagen (step N). After 0.2-0.8 micron filtration, ultrafiltration (UF) (concentration and diafiltration) results in bulk concentrated collagen (steps O-P). After 0.2 micron filtration and fill, the purified collagen is stored in its final container (step Z).

Example 16. Viscosity and Polymerization of rhCollagen Methacrylate with Additives The viscosity of 5 mg/ml rhCollagen methacrylate enriched with different additives (polyvinyl alcohol methacrylate (PVAMA) (FIGS. 34 and 37), hyaluronic acid methacrylate (HAMA) (FIGS. 35 and 37), and oxidized cellulose (OC) (FIGS. 36 and 37) at collagenMA:additive ratios of 5:1, 2:1 and 1:2 is shown in FIGS. 31-37. The viscosity of 5 mg/ml rhCollagen methacrylate is reported in each FIG. for comparison (black curve). All the samples were prepared in 0.1M Phosphate buffer pH 7.4+11.3 mM NaCl (physiological osmolarity) and measurement done at T=22° C. The data is compared and summarized in FIG. 37.

Figure 38:
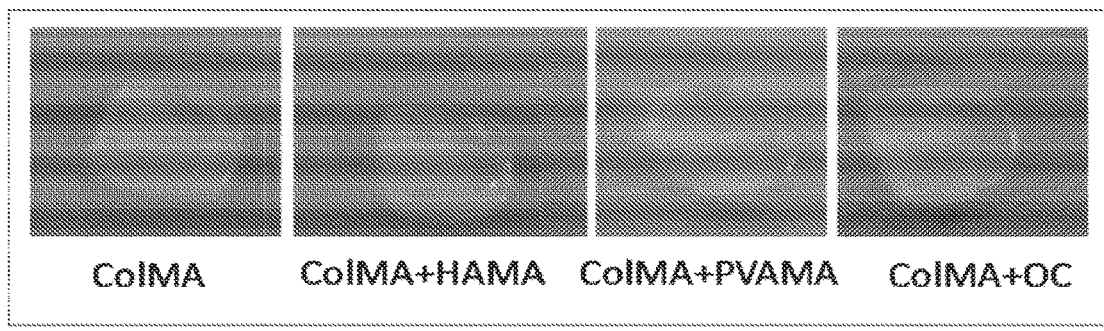
FIG. 38 shows polymerized scaffolds of rhCollagen Methacrylate (ColMA)+additives at collMA:additive ratio of 2:1. ColMA alone was compared with ColMA combined with Polyvinyl alcohol methacrylate (PVMA), hyaluronic acid methacrylate (HAMA), or oxidized cellulose (OC). Solutions were mixed with the photoinitiator 2-hydroxy-4'-(2-hydroxyethoxy)-2-methylpropiophenone (0.1%) and illuminated for 20 sec with ultraviolet (uv) light (365 nm).

The polymerization of rhCollagen methacrylate enriched with different additives is also shown with respect to typical scaffolds of 5 mg/ml collagenMA+ different additives at a ratio of collMA:additive 2:1 (FIG. 38). ColMA alone was compared with ColMA combined with Polyvinyl alcohol methacrylate (PVMA), hyaluronic acid methacrylate (HAMA), or oxidized cellulose (OC). The solutions were mixed with the photoinitiator 2-hydroxy-4'-(2-hydroxyethoxy)-2-methylpropiophenone (0.1%) and illuminated for 20 sec with ultraviolet (uv) light (365 nm).

Example 17. Injectable rhCollagen/Platelet Rich Plasma Scaffold

Injectable rhCollagen/Platelet Rich Plasma (PRP) scaffold was investigated as a scaffold and healing implement for tendonophathy. A slow-degrading rhCollagen matrix combined with a source of growth factors (GFs), such as platelet rich plasma (PRP), was injected at the vicinity of the injured tendon in an effort to provide the required support to enhance the healing of injured tendon. The treatment used a matrix made of plant derived recombinant human Type I collagen (rhCollagen) mixed with PRP, which supports extended release of growth factors at the injured site and promotes healing. The effect of the rhCollagen-PRP matrix was compared to PRP, in vitro and in vivo, in supporting proliferation of fibroblasts, clot degradation, release of GFs and tendon healing in a collagenase-induced Achilles tendon tendinopathy rat model. rhCollagen-PRP demonstrated a superior performance compared to PRP alone in vitro and in vivo. These results are encouraging with respect to the use of the rhCollagen matrix combined with PRP in a clinical trial for a tendinopathy indication.

Materials and Methods rhCollagen Matrix

Monomeric solution of rhCollagen in 10 mM HCl (CollPlant, Ness Ziona, Israel) was fibrillated by pH neutralization in phosphate solution and cross-linked in 18 mM 1-Ethyl-3-(3-dimethylaminopropyl) carbodiimide (Sigma Aldrich, Israel). The cross-linked collagen was then washed by repeated centrifugations in double distilled water and Calcium Chloride (CaCl2) (Merck, Israel) was added, calculated to a final concentration of 20 mM. Syringes filled with rhCollagen slurry were lyophilized and terminally sterilized with Ethylene Oxide.

Platelet Rich Plasma (PRP) Preparation

Granulocyte free PRP was prepared using Tropocell PRP kit (ESTAR, Israel) according to the manufacturer instructions. For the in vitro cell proliferation assay, human blood was collected from healthy human volunteers (Helsinky permission number 2012068). For the in vivo animal studies blood was withdrawn from Hsd:Sprague DawleySD rats (Harlan).

RhCollagen Matrix/PRP and Control Preparation

RhCollagen matrix/PRP: syringes containing lyophilized cross-linked rhCollagen were hydrated with PRP or saline to obtain a final concentration of 20 mg/ml rhCollagen.

Thrombin activated PRP (control): human PRP was mixed with purified Thrombin (Sigma Aldrich, Israel) to obtain final concentration of 100 IU/ml.

CaCl2 activated PRP (control): rat PRP was mixed with CaCl2 (Merck, Israel) to obtain a final concentration of 20 Mm In Vitro Cell Proliferation Assay In this study the effect of GFs on normal human dermal fibroblasts (nHDF) viability and proliferation was assessed. Cell viability and proliferation were compared upon GFs diffusion from either a matrix composed of the crosslinked rhCollagen matrix combined with PRP or from a clot composed of thrombin activated PRP. The rhCollagen matrix combined with PRP or thrombin activated PRP (200 μl each), were injected into transwells (Thincerts™ 24 well 8.0 μm, Greiner bio-one, Israel) placed on top of a 24 well plate (Thermo scientific, Israel) and incubated at 37° C. for 20 minutes to enable clot formation. Normal human dermal fibroblasts (nHDF) (5,000 cells per 0.5 ml), were seeded on the bottom of each well in serum deprived medium (Dulbecco's Modified Eagle's Medium, DMEM, with 1% Fetal Bovine Serum, FBS, Biological Industries, Israel). The transwells containing the matrices (either the rhCollagen matrix combined with PRP or thrombin activated PRP) were placed on top of the seeded well and additional 0.2 ml of medium were added on top of the samples. nHDF in 0.5 ml DMEM, 1% FBS were seeded as control. Samples were tested in triplicates 7 and 10 days after seeding using cell proliferation kit WST-1 (Roche, Israel) according to the manufacturer instructions.

In Vivo Studies

Animals

Hsd:Sprague Dawley SD rats weighing 230 g±20% were chosen for the animal experiments. Animals were given a unique animal identification ear number and randomly assigned to a specific group. Animals were housed in individually ventilated (IVC) cages in dedicated heat, ventilation, air conditioning (HVAC) animal facility. Temperature and humidity were monitored continuously. Animals were provided ad libitum a commercial rodent diet (Harlan Teklad TRM Ra/Mouse Diet) and allowed free access to autoclaved water. The facility had no exposure to outside light and is maintained on automatic alternating cycles of 12 hours light and 12 hours dark. All animals were treated according to the guidelines for laboratory animal treatment and care, and all protocols were approved by the local Institutional Animal Care and Use Committee. No abnormalities were detected in any of the animals throughout the entire study period. No statistically significant differences were found in mean group body weight values and gain. All gains were within the range of normally expected values at termination.

In Vivo Clot Degradation and Growth Factors Release

Degradation time and GFs content over time of rhCollagen matrix combined with PRP, rhCollagen matrix alone or $CaCl_2$ activated PRP were compared in a subcutaneous (SC) rat model (Science in Action Ltd., Ness Ziona, Israel)

Injection sites on the backs of 34 female Sprague Dawley rats (Harlan Laboratories, Ness Ziona Israel) were shaved and marked. Each rat was injected at four distanced locations with 0.5 ml of the same formulation on the dorsal plane, two sites in the anterior portion and two sites in the posterior portion of the rat's back. Animals were sacrificed at time-points 1, 7, 14, 21, 30, and 45 days post-treatment (10 or 12 animals per group, 2 animals per time point). At each time point, the injection sites were exposed and assessed macroscopically. The skin at the injection sites was gently separated from the muscle using scissors, the sites washed with 0.25 ml DMEM, 1% FBS (Biological Industries, Israel) and the clot extracted and weighed. The washing medium was transferred to an Eppendorf tube (1.5-2 ml) while the extracted clot was transferred to a 6 or 12 wells plate. Once weighed, the clot was combined with the respective washing medium, cut with scissors and minced with a pestle to promote the release of GFs from the clot to the surrounding medium. The Eppendorf tubes were then centrifuged for at least 5 minutes to separate between the clot's pellet and the medium. Supernatants were collected and stored at −80° C. until assayed. A control (TO) containing ~0.5 ml of the respective formulation was formed in vitro following the same procedure as described above without injecting into the animal. At the end of the study, PDGF and VEGF contents in the preserved supernatants were assessed by ELISA (Quantikine ELISA Mouse/rat PDGF and Quantikine ELISA Rat VEGF, R&D Systems, Israel).

In Vivo Tendinopathy Induced in Rats

The healing properties of the rhCollagen matrix combined with PRP and of PRP alone were compared in a collagenase induced tendonopathy model in 36 male Sprague Dawley rats (18 rats per group, 6 animals per time point). The experiment was performed at Harlan Laboratories Israel Ltd. (Ness Ziona, Israel).

A skin incision was made over the proximal portion of the right posterior leg of the rat over the Common Calcaneal tendon. Under appropriate magnification, the middle branch of the tendon was identified and isolated and tendinopathy was induced by injecting 0.3 mg collagenase (10 mg/ml, Sigma) under the Common Calcaneal tendon sheath using a 0.5 ml insulin syringe. Eventually the skin was closed with interrupted subcutaneous sutures using 4/0 Vicryl. One week following tendinopathy induction, a stab incision was created in the tendon sheath using an ophthalmic corneal/scleral knife. A tunnel was then created under the tendon sheath using a cannula and 50 μl of rhCollagen combined with PRP or PRP alone were injected into the pre-created canal. Animals were sacrificed at 3, 7, and 14 days post-treatment. The treated tendons were excised and preserved for histopathological evaluation.

Histology

Tissues were embedded in paraffin and serially cut into 4-5 microns thick samples. The slides were stained with Hematoxilyn & Eosin (H&E) for histopathological examination and blinded evaluated by a pathologist.

Results

In Vitro Cell Proliferation Assay

Figure 39:
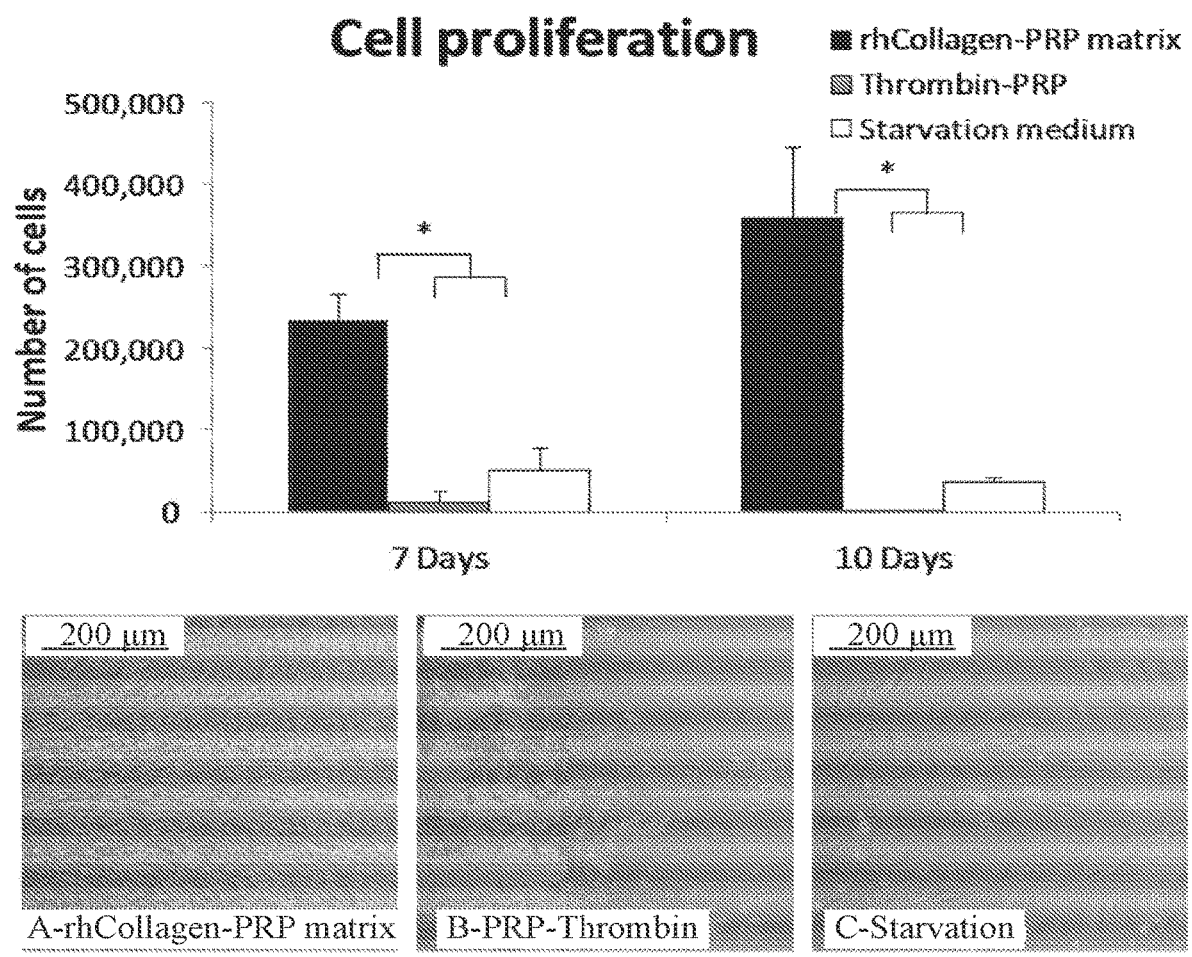
FIG. 39 shows viability studies. Upper graph: Comparison of normal human fibroblasts (nHDF) viability (and proliferation) when cultured in the presence of GFs released from the rhCollagen-PRP matrix (black), in the presence of GFs released from activated PRP (gray) and cultured under starvation conditions (white). The data is an average of two different fibroblasts proliferation assays performed with PRP extracted from 2 different donors. *Significant difference ($p<0.0002$). Lower inset: microscope images of nHDF cells proliferated in the presence of GFs released from the rhCollagen matrix combined with PRP (A), in the presence of GFs released from activated PRP (B) and cultured under starvation conditions (C). Images were taken 7 days after cells were seeded.

In this study viability and proliferation of cells seeded in the vicinity of a matrix composed of rhCollagen combined with PRP and a clot composed of thrombin activated PRP were compared. Cells seeded in untreated wells were used as control. The matrices (either composed of rhCollagen combined with PRP or thrombin activated PRP) were placed in transwells on top of the seeded wells in order to allow the diffusion of GFs from the matrices to the well without being in direct contact with the cell layers. The number of live cells on days 7 and 10 are reported (FIG. 39 Upper) as an average of two different experiments (3 repetitions for experiment) where PRP was extracted from two different blood donors. As shown in FIG. 39, cell viability (on days 7 and 10) in the presence of GFs released from the rhCollagen matrix combined with PRP is significantly higher than in the thrombin activated PRP clot or in the control. Moreover, while in the presence of the rhCollagen matrix combined with PRP the cell number increased from day 7 to day 10, in the presence of thrombin activated PRP and in the control group the number of cells decreased, showing that both cell viability and proliferation are considerably superior in the presence of the rhCollagen matrix. The data was confirmed by microscopy analysis (FIG. 39 Lower). Cells cultured in the presence of the rhCollagen matrix combined with PRP (FIG. 39 Lower, panel A) show an elongated shape and already arrived to full confluence 7 days after seeding while cells cultured in the presence of thrombin activated PRP were hardly alive, which may point to toxic effect of the thrombin in this experimental setup. (FIG. 39 Lower, panel B). Cells cultured in the presence of only medium showed very limited viability (FIG. 39 Lower, panel C).

In Vivo Matrices Degradation Profile and Growth Factors Release

Matrices Degradation Profile

The degradation profile of the injected formulations was determined by weighing the matrices at different time points following subcutaneous injections into rats.

Upon injection of activated PRP, the material disappeared already at day 1 (FIG. 40), suggesting complete degradation of the fibrin clot during the first 24 hours. On the other hand, the rhCollagen matrix alone or combined with PRP had a two-phases degradation profile (FIG. 40) starting with a steep weight decrease during the first day followed by relatively slower degradation rate leading to complete elimination after 30-45 days (final weight <0.5% of initial weight).

Growths Factors Content

Figure 40:
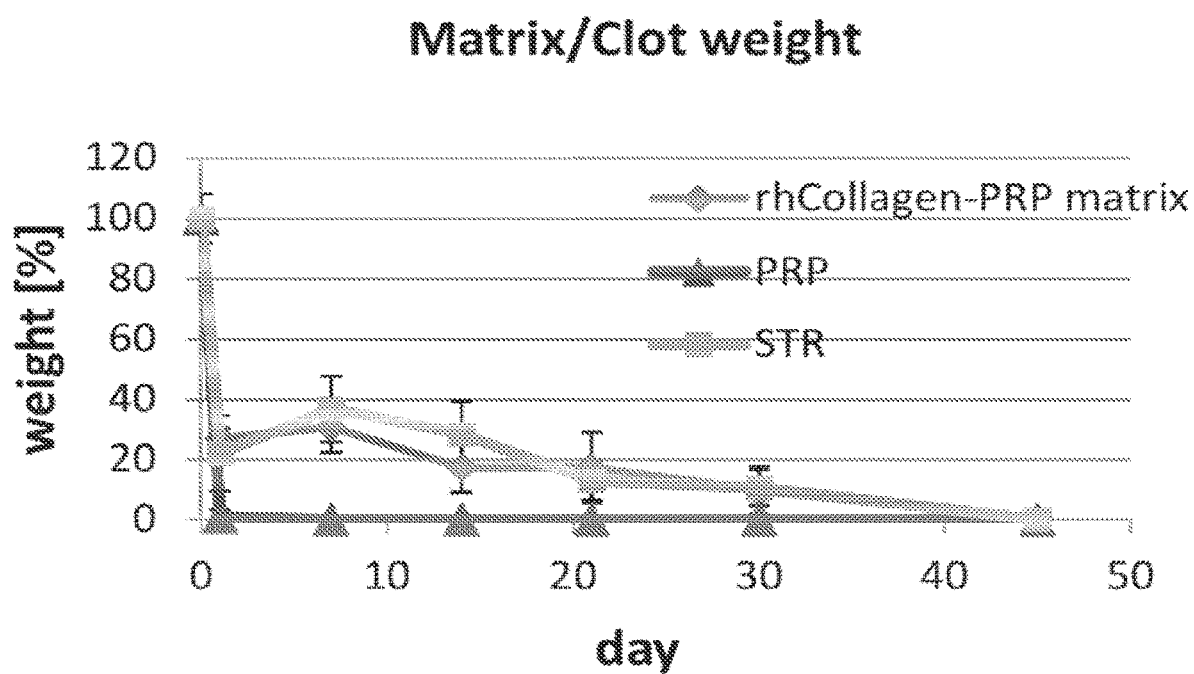
FIG. 40 shows scaffold weight as a function of time (each point is an average of 6 scaffolds, 2 rats per time point, 3 injections per rat).
Figure 41A:
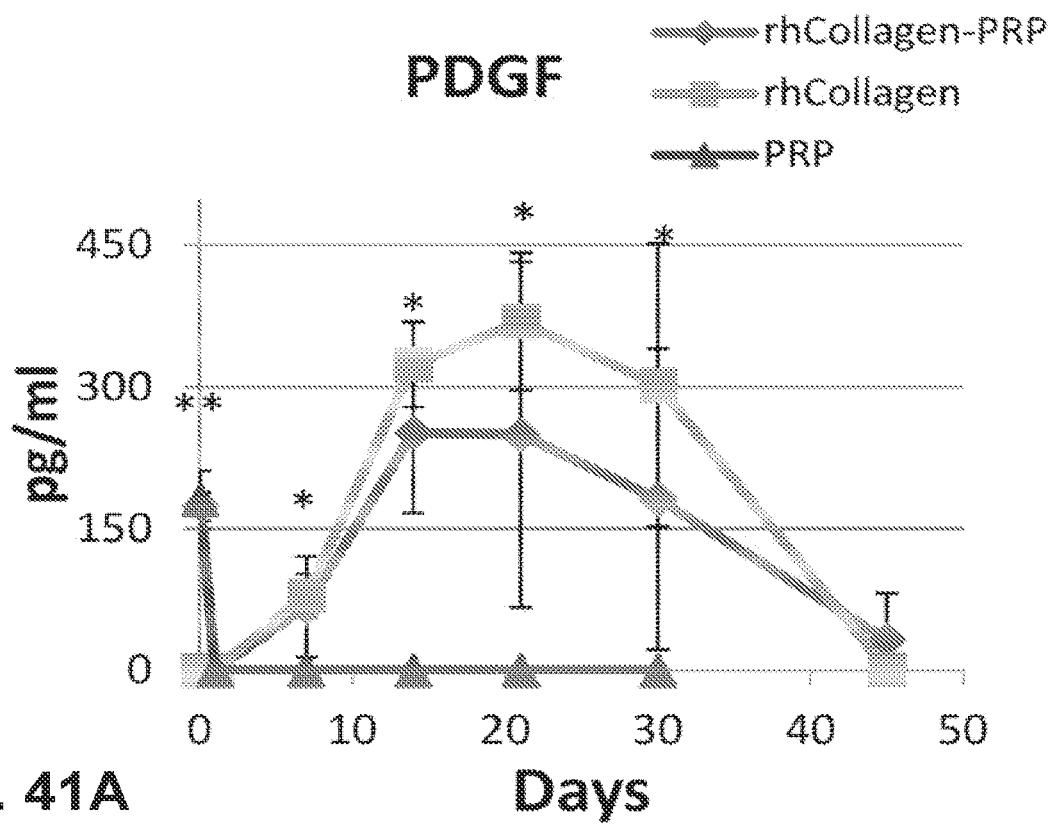
FIGS. 41A-41B show two studies using a subcutaneous rat model. (A) PDGF content as a function of time (B) VEGF content as a function of time in a subcutaneous rat model. *Significant difference between rhCollagen matrix combined with PRP and PRP alone (p<0.038) and between the rhCollagen matrix alone and PRP alone (p<0.004). ** Significant difference (p<0.021) between rhCollagen matrix alone and PRP alone and between rhCollagen matrix alone and rhCollagen matrix combined with PRP (A), and between rhCollagen matrix combined with PRP and PRP alone and rhCollagen matrix combined with PRP and rhCollagen matrix alone (p<0.007) (B).
Figure 41B:
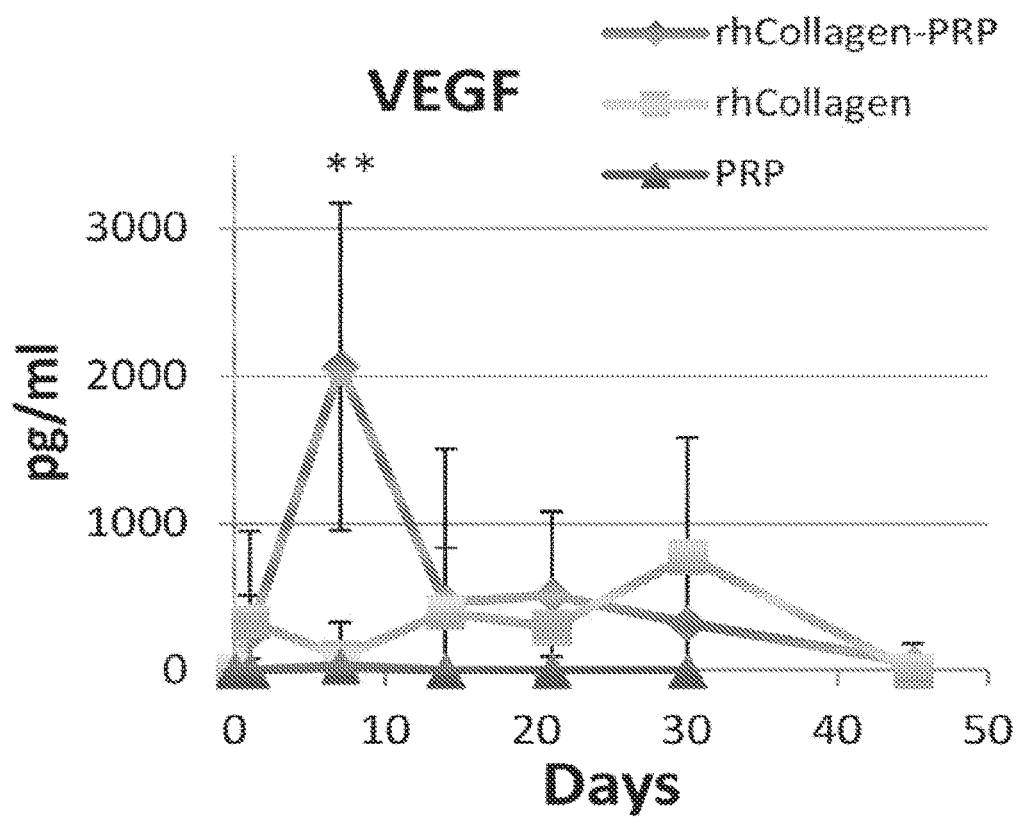
Figure 42:
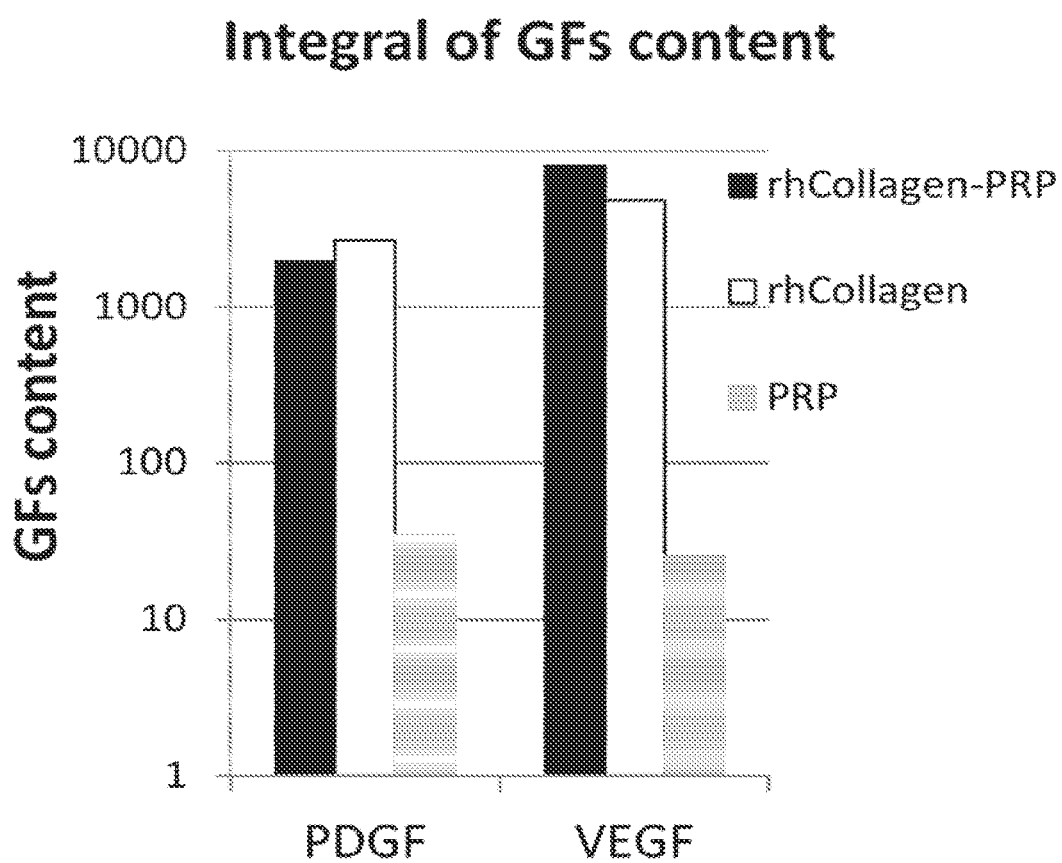
FIG. 42 shows integration of the nominal PDGF and VEGF content in the injected matrices over 45 (or 30) days in a rat model.

GFs content in the injection site as a function of time was assessed by ELISA for PDGF and VEGF (FIGS. 41A-B). PDGF content at time 0 was similar in the rhCollagen matrix in combination with PRP and in the activated PRP treatments (FIG. 41A), suggesting that the PDGFs content at day 0 is a sole contribution of the GFs rich platelets brought by PRP. However, upon injection of PRP alone the PDGF content at the injection site was lower than the detection limit already 1 day after injection and remained undetectable along the whole study, in agreement with the rapid clot degradation (FIG. 40). A different picture is shown when PRP was incorporated in the rhCollagen matrix (FIG. 41A). PDGF content gradually increased from day 1 to day 14 and decreased again until completely eliminated towards day 45, in concomitance with the scaffolds degradation (FIG. 40). Interestingly, the PDGF content in the rhCollagen matrix alone group increased starting from day 7 and followed the pattern shown by the matrix combined with PRP group. The VEGF content at day 0 was lower than the detection limit for all formulations and remained at baseline level in the activated PRP group (FIGS. 41A-B and 42). The VEGF profile of the rhCollagen matrix combined with PRP shows a brisk increase in VEGF content around day 7 followed by a steep decrease to day 14 and a plateau until day 30, VEGF eventually decreases at day 45 in concomitance with scaffold degradation (FIG. 41B).

The GFs increase seen from day 1 to 14 in the PDGF analysis and from day 0 to day 7 in the VEGF analysis testifies the capability of the rhCollagen scaffold to enable GFs accumulation, likely reflecting cells that migrate and proliferate in the scaffold. The integration of the nominal content of PDGF and VEGF over the whole study for each formulation is summarized in FIG. 42. It is clear that the GFs content at the injection site is much higher upon injection of the rhCollagen matrix alone or combined with PRP compared to activated PRP alone.

In Vivo Tendinopathy Induced in Rats

The healing properties of the rhcollagen matrix combined with PRP in comparison to PRP alone were assessed in a rat model for tendinopathy and evaluated by histopathological analysis at different time points. Tendon healing and inflammation were quantified by scoring the level of mature fibrosis, the presence of mononuclear inflammatory cells and the presence of immature granulation tissue (score 0-5 as described in Table 7).

TABLE 7

| Histopathological scoring | |
|---|---|
| Score | Description |
| 0 | No change |
| 1 | Up to 10% of the area of sectioned tissue is involved by the lesion |
| 2 | Up to 25% of the area of sectioned tissue is involved by the lesion |
| 3 | Up to 50% of the area of sectioned tissue is involved by the lesion |
| 4 | Up to 75% of the area of sectioned tissue is involved by the lesion |
| 5 | More than 75% of the area of sectioned tissue is involved by the lesion |

Figure 43A:
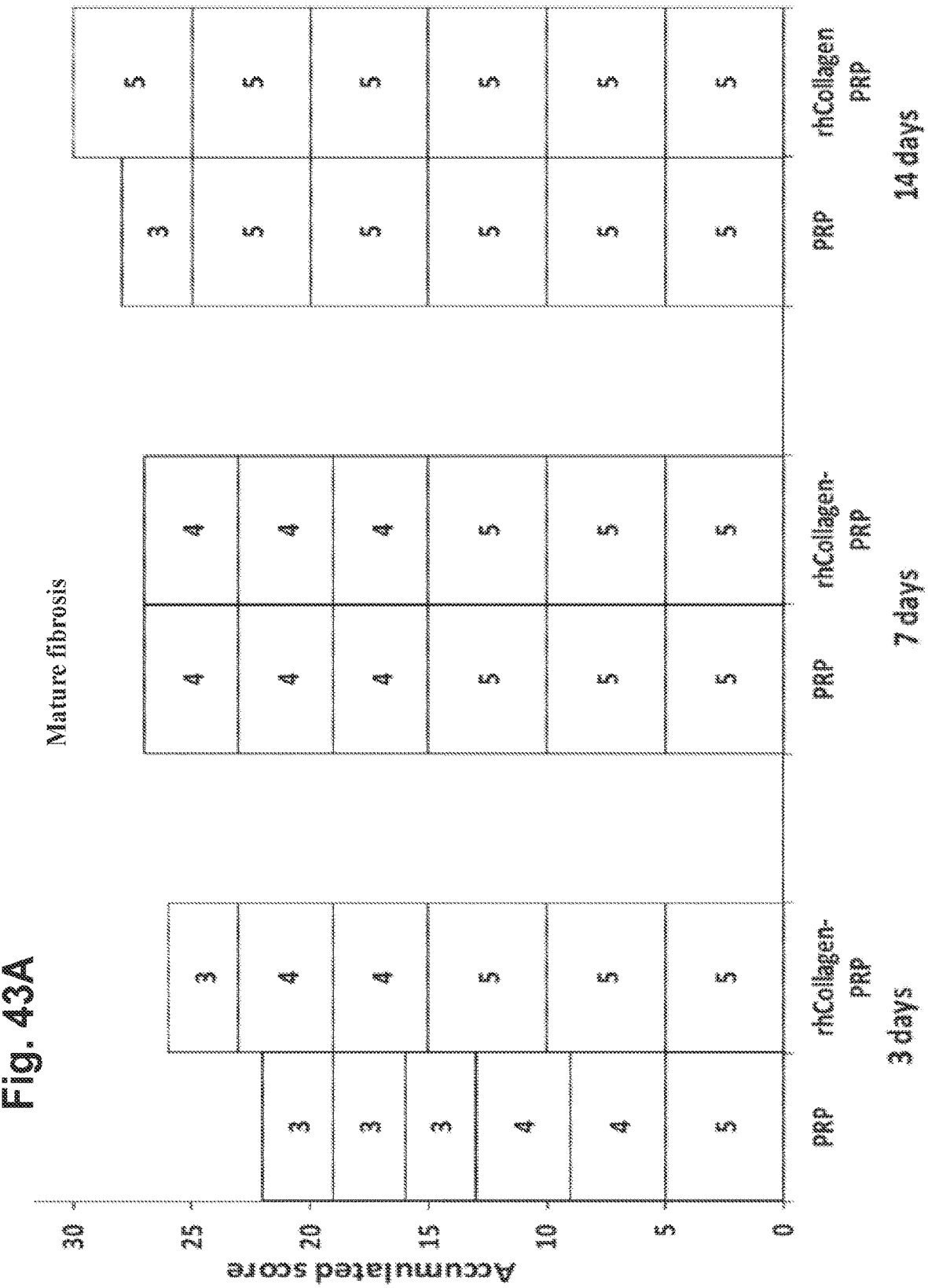

The cumulative values of the histopathological scores associated with each treatment are depicted in FIGS. 43A-C. The group treated with the rhCollagen matrix combined with PRP displayed a slightly more mature fibrosis when compared to the PRP treated group, specifically at day 3 and 14. This is consistent and correlated to the lower level of immature granulation displayed by the group treated with the rhCollagen matrix combined with PRP at day 14 (FIG. 43C). Moreover in FIG. 43B the group treated with the rhCollagen matrix combined with PRP displays a decrease in inflammation as indicated by the low presence of mononuclear inflammatory cells at all time points, especially at day 3 and 14. Overall, the data demonstrates that treating the injured tendon with the rhCollagen matrix combined with PRP promotes faster healing as shown by the higher level of mature fibrosis and lower level of immature granulation tissue accompanied by a major decrease in inflammatory mononuclear cells when compared to the standard PRP injection treatment.

Discussion

Damages to soft tissues, including injuries in tendons and ligaments are very common and cause a significant clinical burden. Although several treatments are available, their clinical benefit is still limited. This encouraged the search for new alternatives with the intent of improving healing and reducing recovery time. An injectable matrix composed of human recombinant type I collagen was developed that, once mixed with PRP, forms a collagen-fibrin-PRP composite that degrades slowly, attracts cell migration and proliferation into the collagen scaffold and allows extended release of GFs at the injured site, thus better supporting the healing process. In vitro experiments (FIG. 39) showed considerably superior nHDF viability and proliferation in the surrounding of the rhCollagen matrix combined with PRP as compared with thrombin activated PRP. The results demonstrated that the sustained growth factors released from the collagen matrix promote and enhance cell proliferation. Type I rhCollagen, when combined to PRP, still provides supportive environment that promotes and enhances cell proliferation even when not in direct contact with the cell layer. SC injections in rats showed for the first time that the GFs containing fibrin-clot formed in situ upon PRP injection, degrades already within twenty-four hours and consequently, the GFs content in the injection site is lower than the ELISA detection limit (FIGS. 41A-B). Once platelets are complexed with the rhCollagen matrix, GFs are released over 45 days, time that coincides with the scaffold degradation (FIGS. 40 and 41A-B). It is interesting to notice that the GFs content profile is not monotonic as it would have been expected by a standard release profile. The PDGF profile in the rhCollagen matrix with PRP treatment (FIGS.

41A-B) demonstrated a first steep decrease in the first day, very similar to the case of PRP alone, followed however, by a gradual increase up to day 21 and a final decrease to reach undetectable levels in concomitance with the scaffold degradation. Interestingly, rhCollagen alone showed a similar pattern of gradual increase in PDGF content during the first couple of weeks and decrease towards the complete degradation of the scaffold. The rhCollagen with PRP scaffold therefore combines the benefits provided by the trapped PRP (early GFs release) to those provided by the rhCollagen scaffold itself which highly promotes and enhances cells recruitment and proliferation. As for the VEGF content profile, while upon PRP injection the VEGF level remained extremely low along the whole study, injection of the rhCollagen matrix combined with PRP resulted in an increase in the VEGF level within the first week to eventually decrease in concomitance with the scaffold degradation. Interestingly, in contrast to PDGF, the VEGF level in the group treated with the rhCollagen matrix alone was still higher than in the PRP alone group but showed a different profile than in that of the rhCollagen matrix with PRP, especially at day 7. This observation stresses the contribution of PRP to the GFs level once combined with the collagen scaffold. The healing properties of rhCollagen and PRP were eventually compared to PRP in a rat model for Common Calcaneal tendon (Achilles tendon) tendinopathy. The histological evaluation confirmed the faster ability of the rhCollagen matrix combined with PRP to build mature fibrotic tissue which is consistent to the scaffold ability to promote cells recruitment and proliferation as anticipated in the previous experiments. Moreover, the histological analysis also demonstrates that once the injured site is treated with rhCollagen matrix combined with PRP, the inflammation substantially decreases in comparison to the standard treatment with PRP alone.

This study demonstrates the biological effects in vitro and in vivo, of an injectable scaffold composed of crosslinked human recombinant type I collagen. Once combined with an autologous source of GFs such as PRP, the formed scaffold accelerates the healing of soft tissue injuries, by controlling the inflammatory response and promoting faster formation of new healthy tissue. The results suggest that the enhanced healing properties reside in the unique combination of rhCollagen and autologous PRP which extends the release of GFs. The data supports the use of the rhCollagen matrix combined with PRP in a clinical trial for tendinopathy.

Example 18. Use of a Plant-Derived Human Recombinant Collagen as a Dermal Filler In order to reduce immunogenicity, to promote tissue regeneration, and to provide a more uniform and potentially longer lasting dermal filler with improved rheological properties, in comparison with tissue-derived human and bovine collagens, a human transgenic collagen (rhCollagen) is produced and isolated from a plant (e.g., a genetically engineered tobacco plant) and then used as a dermal filler. Typically, the genetically modified plant comprises an expressible sequence of at least one gene sequence of human deoxyribonucleic acid (DNA) selected from the group consisting of: COL1, COL2, P4H-alpha, P4H-beta, and LH3. Typically, the plant-derived human collagen comprises at least modified one human collagen alpha-1 chain as set forth in SEQ ID NO: 3 and as expressed in the genetically modified plant; and at least one modified human collagen alpha-2 chain as set forth in SEQ ID NO: 6 and as expressed in the genetically modified plant; and the genetically modified plant further expresses an exogenous prolyl-4-hydroxylase (P4H) (e.g., a human or other mammalian P4H). Optionally, the genetically modified plant further expresses an exogenous polypeptide selected from the group consisting of lysyl hydroxylase (LH), protease N, and protease C. For example, the human collagen alpha-1 chain is encoded by a sequence as set forth in SEQ ID NO: 1, and/or the human collagen alpha-2 chain is encoded by a sequence as set forth in SEQ ID NO: 2. Optionally, the human collagen alpha-1 chain and/or alpha-2 chain is targeted to a vacuole of the plant or the genetically modified plant and digesting it with ficin, resulting in human atelocollagen.

Optionally, the rhCollagen is modified or is formulated with other substances, including those known in the art for dermal fillers. Examples of modification include, but are not limited to, methacrylation and/or thiolation. Examples of other substances include, but are not limited to, hyaluronic acid (HA) or a modified derivative thereof, poly(vinyl alcohol) (PVA) or a modified derivative thereof, polyethylene glycol (PEG) or a modified derivative thereof, oxidized cellulose (OC) or a modified derivative thereof, or a combination of any of these. Examples of other substance include, but are not limited to, hyaluronic acid (HA), poly (vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, crystalline nanocellulose (CNC) or a combination thereof. Modified derivatives of HA, PVA, PEG, or OC include, but are not limited to, photopolymerizable derivatives. Modifications of HA, PVA, PEG, or OC include, but are not limited to, methacrylation and/or thiolation. Examples of other substances include, but are not limited to, polymerizing agents or initiators, such as a photoinitiator (e.g., sensitive to visible, ultraviolet (uv), or infrared light). Examples of visible light photoinitiators include, but are not limited to, Eosin Y+triethanolamine or riboflavin. Examples of ultraviolet photoinitiators include, but are not limited to, lithium phenyl-2,4,6-trimethylbenzoylphosphinate (LAP) or 1-[4 2-hydroxy-1-[4-(2-hydroxyethoxy)phenyl]-2-methylpropan-1-one (IRGACURE® 2959).

An inherent property of tissue-extracted collagen is gelation at room temperature. At relative low concentrations (e.g., 5-15 mg/ml) in physiological buffer, tissue-extracted collagen forms a gel when transformed from cold (approximately 4° C.) to room temperature.

In contrast, rhCollagen has a relatively low viscosity (in the same concentration and formulation) that allows injection through narrow gauge needles or cannulae (27-gauge to 33-gauge) using a relatively decreased expression force, as well as better penetration into tinier spaces, and greater flexibility in post-injection modulation (sculpting).

The rhCollagen is placed in a syringe having a fine-gauge needle or cannula (27-gauge to 33-gauge) and is injected into a cavity or space below the dermis. The injected rhCollagen is then molded, sculpted, or otherwise manipulated into the desired position (e.g., via manual massage or with a molding or sculpting implement, such as a surgical depressor). Polymerization may be initiated before, during, or after this process by exposure to a light source (e.g., a light-emitting diode (LED), laser, or xenon lamp) located on or above the dermis overlying the injected formulation.

Example 19. Use of a Modified Plant-Derived Human Recombinant Collagen Formulated with a Photoinitiator and Additive The rhCollagen is modified by methacrylation, as described in Example 18. The modified rhCollagen is prepared as a polymerizable solution formulation with a photoinitiator (e.g., Eosin Y+triethanolamine or riboflavin). Hyaluronic acid (HA), poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, crystalline nanocellulose (CNC) or some combination thereof are included.

The formulation is placed in a syringe having a fine-gauge needle or a cannula (27-gauge to 33-gauge and is injected into a cavity or space below the dermis. The injected formulation is then molded, sculpted, or otherwise manipulated, either manually or with an appropriate surgical instrument, into the desired position during or after exposure to a light source (e.g., a visible light source), as described in Example 18.

Example 20. Use of a Modified Plant-Derived Human Recombinant Collagen Formulated with a Photoinitiator and Modified Additive The rhCollagen is modified by methacrylation or thiolation as in Example 19. The modified rhCollagen is prepared as a polymerizable solution formulation with a photoinitiator (e.g., Eosin Y+triethanolamine or riboflavin), as described in Example 18. A modified derivative of hyaluronic acid (HA), poly(vinyl alcohol) (PVA), polyethylene glycol (PEG), oxidized cellulose (OC), or some combination thereof is included and is modified by methacrylation or thiolation.

The formulation is placed in a syringe having a fine-gauge needle or a cannula (27-gauge to 33-gauge and is injected into a cavity or space below the dermis. The injected formulation is then molded, sculpted, or otherwise manipulated, either manually or with an appropriate surgical instrument, into the desired position during or after exposure to a light source (e.g., a visible light source), as described in Example 18.

Figure 44:
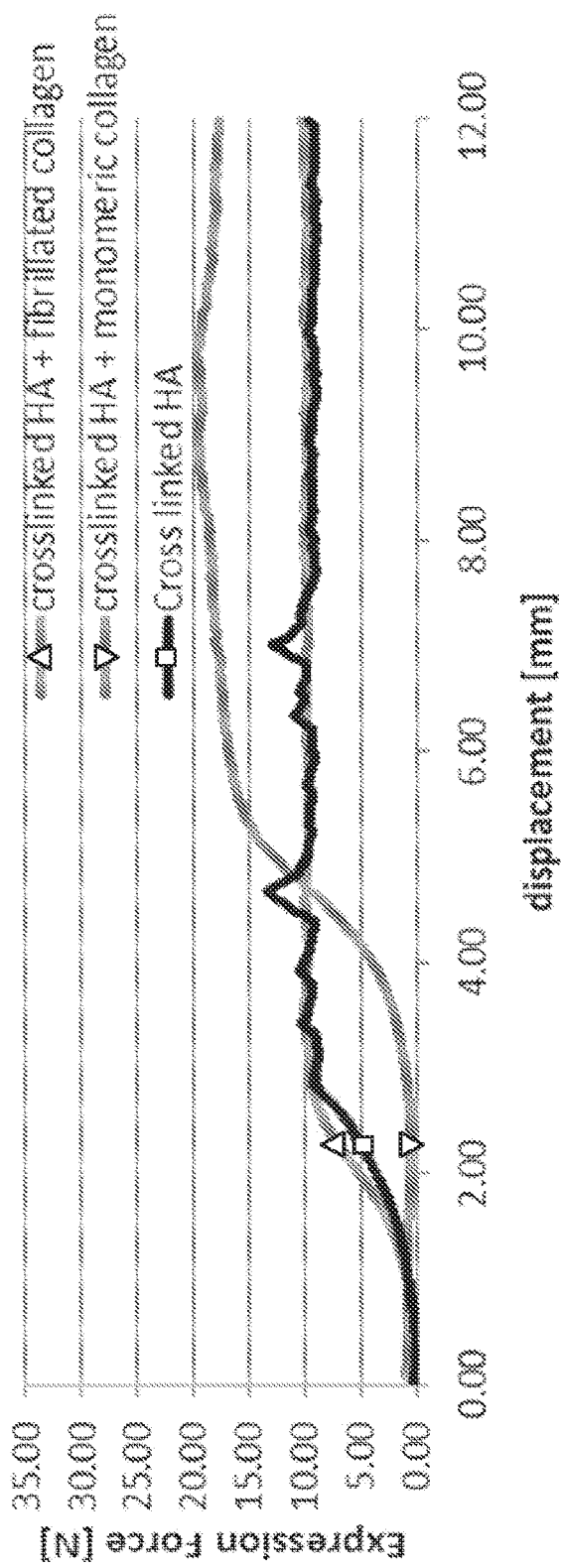
FIG. 44 shows a comparison of the expression force (newtons, N) needed for injections of crosslinked hyaluronic acid (HA) (black curve—□), crosslinked hyaluronic acid (HA)+monomeric collagen (▼), or crosslinked hyaluronic acid (HA)+fibrillated collagen (▲) from a 32-gauge needle and 1 ml syringe (Becton Dickinson [BD], ref. 309628). Crosslinked HA+monomeric collagen and crosslinked HA+fibrillated collagen are semi-Interpenetrated networks, wherein the collagen is not crosslinked to anything.

Example 21. Comparative Injectability and Viscosity of Crosslinked Hyaluronic Acid with Collagens As shown in FIG. 44, the expression force (newtons, N) needed for injecting crosslinked hyaluronic acid (HA) (black □ curve) was compared to the expression force needed for injecting crosslinked hyaluronic acid (HA) with monomeric collagen (▼ curve) or fibrillated collagen (▲ curve). (Crosslinked HA 20 ml/ml; Crosslinked HA 20 mg/ml, monomeric rhCol 7.5 mg/ml; Crosslinked HA 20 mg/ml, fibrillated collagen 10 mg/ml)

Figure 45:
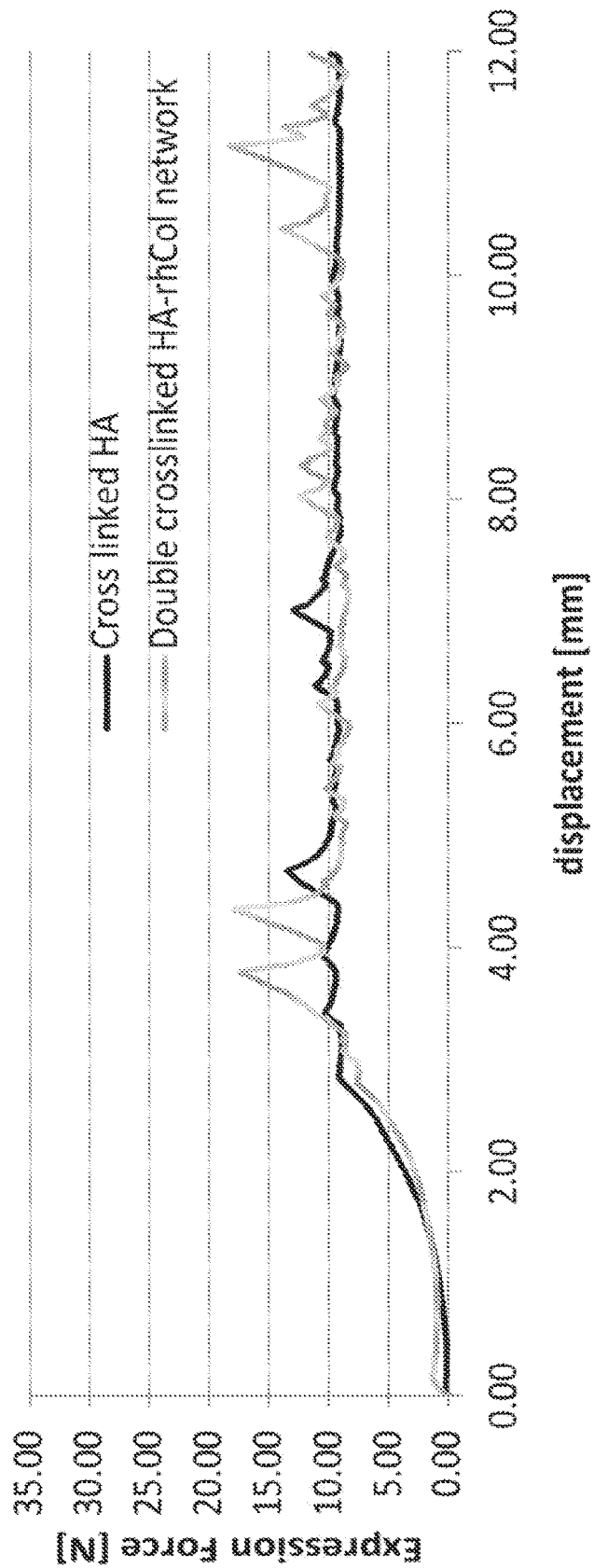
FIG. 45 shows a comparison of the expression force (newtons, N) needed for injections of crosslinked hyaluronic acid (HA) (black) or a double crosslinked network of crosslinked hyaluronic acid (HA) and collagen (grey) from a 32-gauge needle and 1 ml syringe (Becton Dickinson [BD], ref. 309628).

As shown in FIG. 45, the expression force (newtons, N) needed for injecting crosslinked HA was compared to the force needed for injecting a formulation of double crosslinked HA-collagen (grey curve). The two curves were largely similar.

Figure 46:
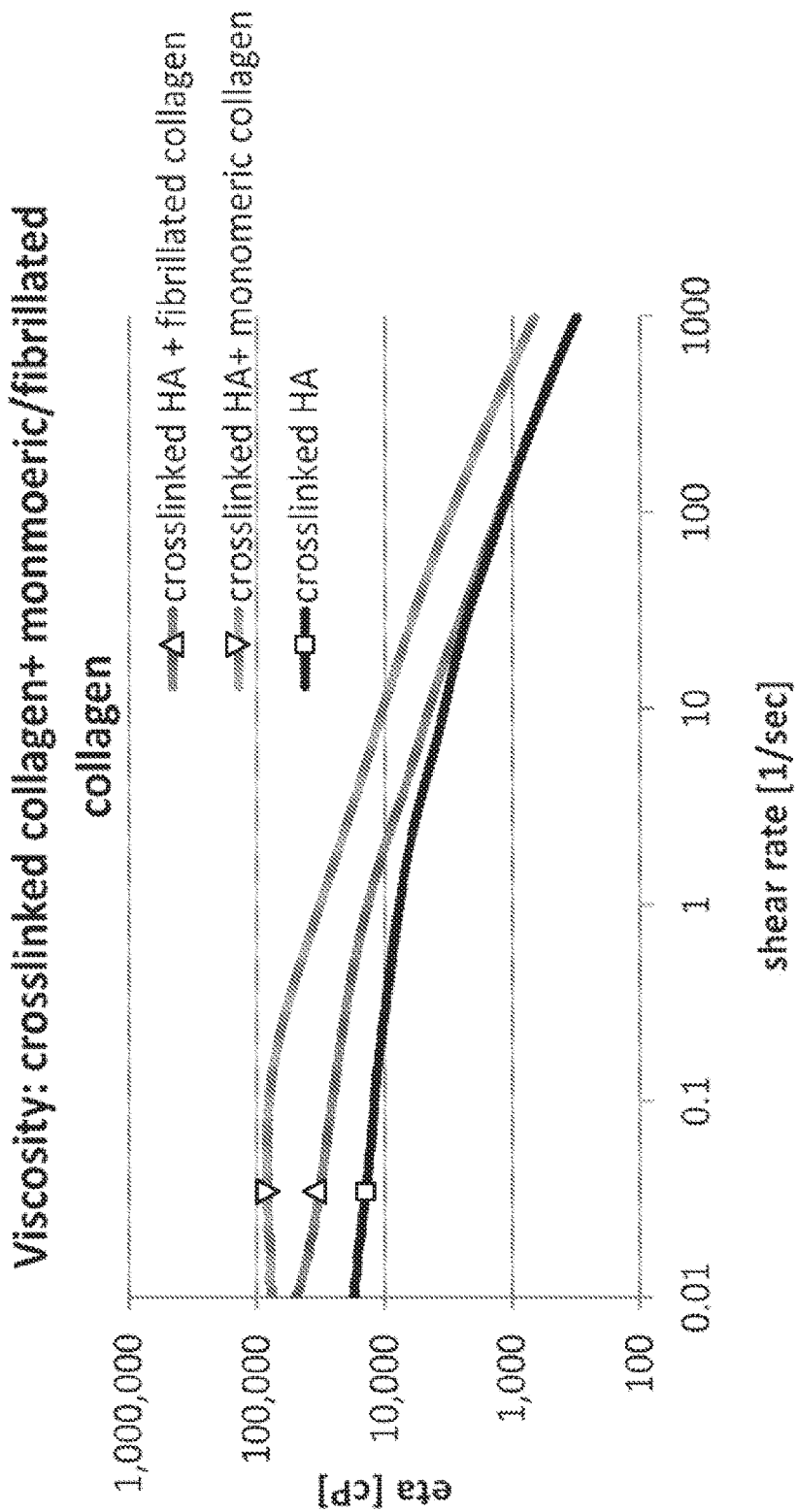
FIG. 46 shows a comparison of the viscosity (eta [η], cP) of crosslinked hyaluronic acid (HA) (black), crosslinked hyaluronic acid (HA)+monomeric collagen (▼), or crosslinked hyaluronic acid (HA)+fibrillated collagen (▲).

As shown in FIG. 46, the viscosity of crosslinked hyaluronic acid (HA) (black □curve) was compared to the viscosity of crosslinked hyaluronic acid (HA) with monomeric collagen (▼ curve) or fibrillated collagen (▲ curve). The viscosity for crosslinked HA with fibrillated collagen was lower than that of crosslinked HA with monomeric collagen, but still greater than that of crosslinked HA alone. Concentrations were as for FIG. 44.

Figure 47:
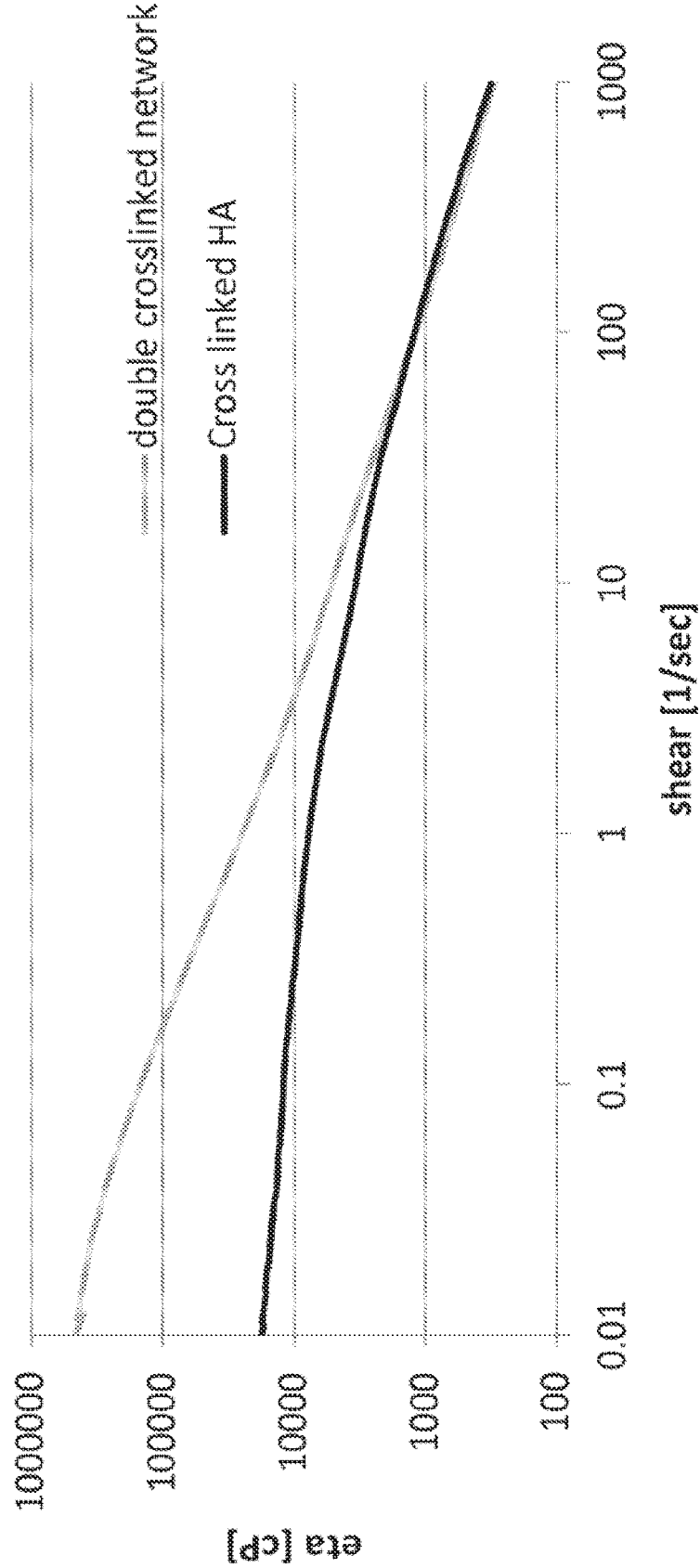
FIG. 47 shows a comparison of the viscosity (eta [η], cP) of crosslinked hyaluronic acid (HA) (black) or a double crosslinked network of crosslinked hyaluronic acid (HA) and collagen (grey).

As shown in FIG. 47, the viscosity of crosslinked hyaluronic acid (HA) was compared to the viscosity of a formulation of double crosslinked hyaluronic acid (HA)-collagen (grey curve). The viscosity for double crosslinked HA-collagen was greater than that of crosslinked HA alone.

The addition of rhCollagen, either monomeric or fibrillated, crosslinked or not crosslinked, to a crosslinked HA dermal filler did not significantly increase the expression force, allowing similar performance to the physician, but on the other hand it significantly increased the material viscosity, allowing better skin lifting upon injection.

Example 22. Transdermal Polymerization of Recombinant Human Collagen Methacrylate (rhCollagenMA)

Figure 48A:
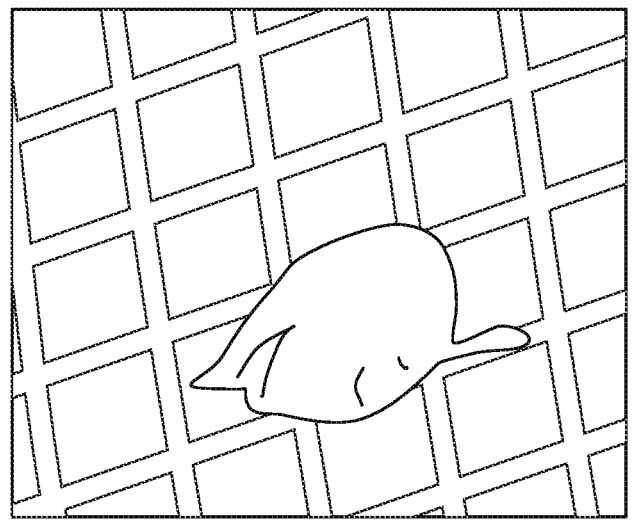
FIGS. 48A-B show photographs of (A) a mouse patch laid on top of a methacrylated collagen (collMA/rhCollagenMA) solution and (B) methacrylated collagen (collMA/rhCollagenMA) polymerized and integrated into the skin tissue upon illumination with a white light-emitting diode (LED) torch through the skin.
Figure 48B:
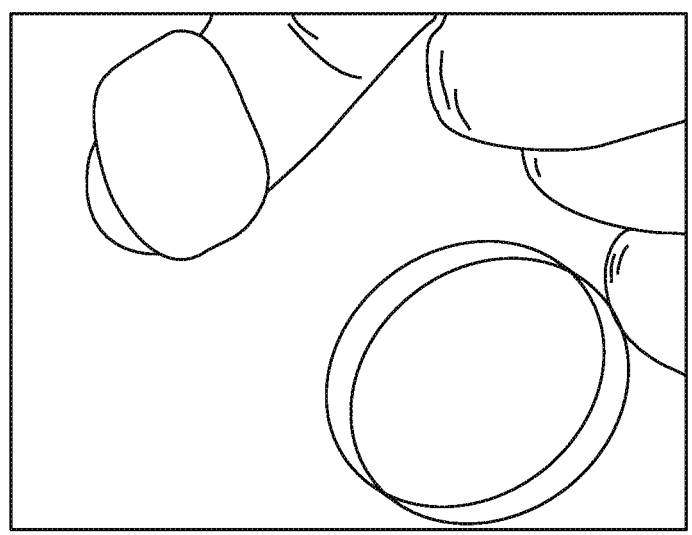

As shown in FIGS. 48A-B, a liquid solution of recombinant human collagen methacrylate (rhCollagenMA) with Eosin Y/TEA as photoinitiator, injected underneath a mouse skin patch (FIG. 48A), was transdermally polymerized by illuminating the skin with LED white light from a white LED torch for 6 minutes. The rhcollagenMA polymerized and was integrated into the skin tissue (FIG. 48B).

The rhCollagenMA polymerizes under the skin when illuminated for 6 minutes with a small LED torch in the presence of eosinY/TEA as photoinitiator.

Example 23. Formulation of Double Crosslinked Dermal Fillers: Two-Step Synthesis Objective: To develop injectable dermal fillers for use improving the appearance of the skin surface for either aesthetic or clinical purposes. The dermal fillers are composed of type I recombinant human Collagen (rhCollagen) or its modified form, methacrylated rhCollagen (MA-rhCol) and crosslinked hyaluronic acid (HA).

The double crosslinked product, wherein crosslinked-HA is further crosslinked to rhCollagen (FIG. 49), is designed to be a scaffold wherein hyaluronic acid provides the structural support and void filling, while the rhCollagen enhances cell proliferation promoting tissue regeneration. The scaffold will eventually degrade leaving the newly formed tissue. Another objective is to analyze the double crosslinked dermal filler, examining the lifting effect (tissue augmentation) provided by crosslinked-HA, with tissue regeneration promoted by type I rhCollagen.
Methods:
Double Crosslinking
—HA Crosslinking—

High Molecular Weight Hyaluronic Acid (range 700 KDa-3 MDa, preferably 1.5M Da) was dissolved under alkaline conditions (pH 12-13, e.g. in 0.3N Na(OH)) at a concentration ranging between 50 to 200 mg/ml (preferably 100 mg/ml). Crosslinker 1, 4-butanediol diglycidyl ether (BDDE) was added to the solvent in a ratio ranging between 1 to 50% of the HA disaccharides amounts (preferably 6, 8, 10%) prior to dissolving the HA. In some embodiments of this formulation, the HA comprises methacrylated-HA (MA-HA).

HA crosslinking was done at room Temp for 24 h.
Addition of Lower MW HA and Neutralization Lower molecular weight HA (50 KDa to 1000 KDa, preferably 300 to 700 KDa) ranging between 1 to 30% of the total HA amount (preferably 5-10%) was dissolved in water at a concentration ranging between 10 to 100 mg/ml (preferably 30 mg/ml). In some embodiments of this formulation, the HA comprises methacrylated-HA (MA-HA).

Prior to mixing the non-crosslinked HA with the crosslinked HA, HCl is added to the non-crosslinked HA in an amount necessary to neutralize the pH of the crosslinked HA. Phosphate buffer (PB) and NaCl are added to a final concentration of 0.1M PB and 0.2M NaCl.

Neutralization of rhCollagen

Prior to mixing the rhCollagen with HA, rhCollagen is brought to 0.1M in PB+0.2M NaCl.

Mixing HA+rhCollagen

HA (crosslinked+non-crosslinked HA) is mixed with rhCollagen in a ratio HA:rhColalgen ranging between (6:1, 5:1, 4:1, 3:1, 2:1, 1:1, 1:2, 1:3, 1:4, 1:5, 1:6) and kept at 2-8° C. The final concentration of HA is between about 5-50 mg/ml. The final concentration of rhCollagen or MA-rhCollagen is between about 1-50 mg/ml.

Second Crosslinking

When HA and rhCollagen were well mixed, a second crosslinking was performed with 1-[3-(Dimethylamino)propyl]-3-ethylcarbodiimide methiodide (EDC): an amount of EDC equal to 10 to 100 fold (preferably 50 fold) the amount of free amines in the rhCollagen was dissolved in (0.1 MPB+0.2M NaCl), added to the crosslinked HA-rhCollagen mixture and mixed. The second crosslinking is performed in the dark for 2-3 h at 2-8° C.

Dialysis

The double crosslinked material was then dialyzed vs. either PBS, 1 mM HCl or vs. low phosphate buffer (Low phosphate buffer preparation: (a) Stock solution: 162 mM Sodium phosphate dibasic brought to pH 11.2 with 10 N Na(OH); (b) dilute the stock solution 1:1000 in 0.1 mM HCL.

Rheological and Mechanical Evaluation

Storage and loss moduli were measured, e.g., using a HAAKE-RHEO STRESS 600 ™ instrument (THERMO SCIENTIFIC™) using a cone (1-degree) vs. plate configuration (C35/1). Frequency sweep measurements were performed at a constant deformation (e.g., 0.8%) with a range of frequencies (e.g., 0.02-100 Hz). Optionally various ratios or crosslinking ratios of one or both components were tested. First and second crosslinking can be tuned to control the final product storage and loss moduli.

Injectability measurements were taken, e.g., using a MULTITEST 1-/i MECMESIN™ machine as a function of plunger displacement (mm) to observe expression force.

Injectability

Injectability measurements were taken using a MULTITEST 1-/i MECMES1N™ machine, as described above. 1 ml LUER-LOK™ syringes (BECTON-DICKINSON™) and 30 G needles were used for Formulations 2, 2A, and 3 (Table 8). Expression force as a function of plunger displacement of representative double crosslinked Formulations 2, 2A, and 3 (Table 8) was compared to a commercially available dermal filler, also using a 30 G needle.

Animal Studies 200 microlitres of Formulation 2, or 2A, or control were injected subcutaneously into the back of Sprague dawley rats. Histology was performed after 1 week.

Results:

A skilled artisan would appreciate that the two-step double cross linking here uses two-types of crosslinker. The 1st step includes HA and BDDE as crosslinker. In the second step collagen and non-crosslinked HA are added and cross linking is achieved using EDC. It is expected that the difference in cross linking chemistry and sequence of actions, as compared to all other methods of dermal filler preparation, should result in dermal filler compositions having different properties including mechanical properties, tissue interaction, and degradation rate.

Formulations of HA:rhCollagen were made using the above methods, with representative formulations shown in Table 8.

TABLE 8

Formulations of compositions.

| Formulation | HA crosslinking ratio | HA:rhCollagen ratio | Comments |
|---|---|---|---|
| 1 | 10% | 2:1 | Dialyzed vs. phosphate buffer saline |
| 1A | 10% | 2:1 | Dialyzed vs. 1 mM HCl and neutralized |
| 2 | 6% | 2:1 | Dialyzed vs. phosphate buffer saline |
| 2A | 6% | 2:1 | Dialyzed vs. 1 mM HCl and neutralized |
| 3 | 8% | 2:1 | Dialyzed vs. phosphate buffer saline |

Rheological and Mechanical Evaluation

Figure 50:
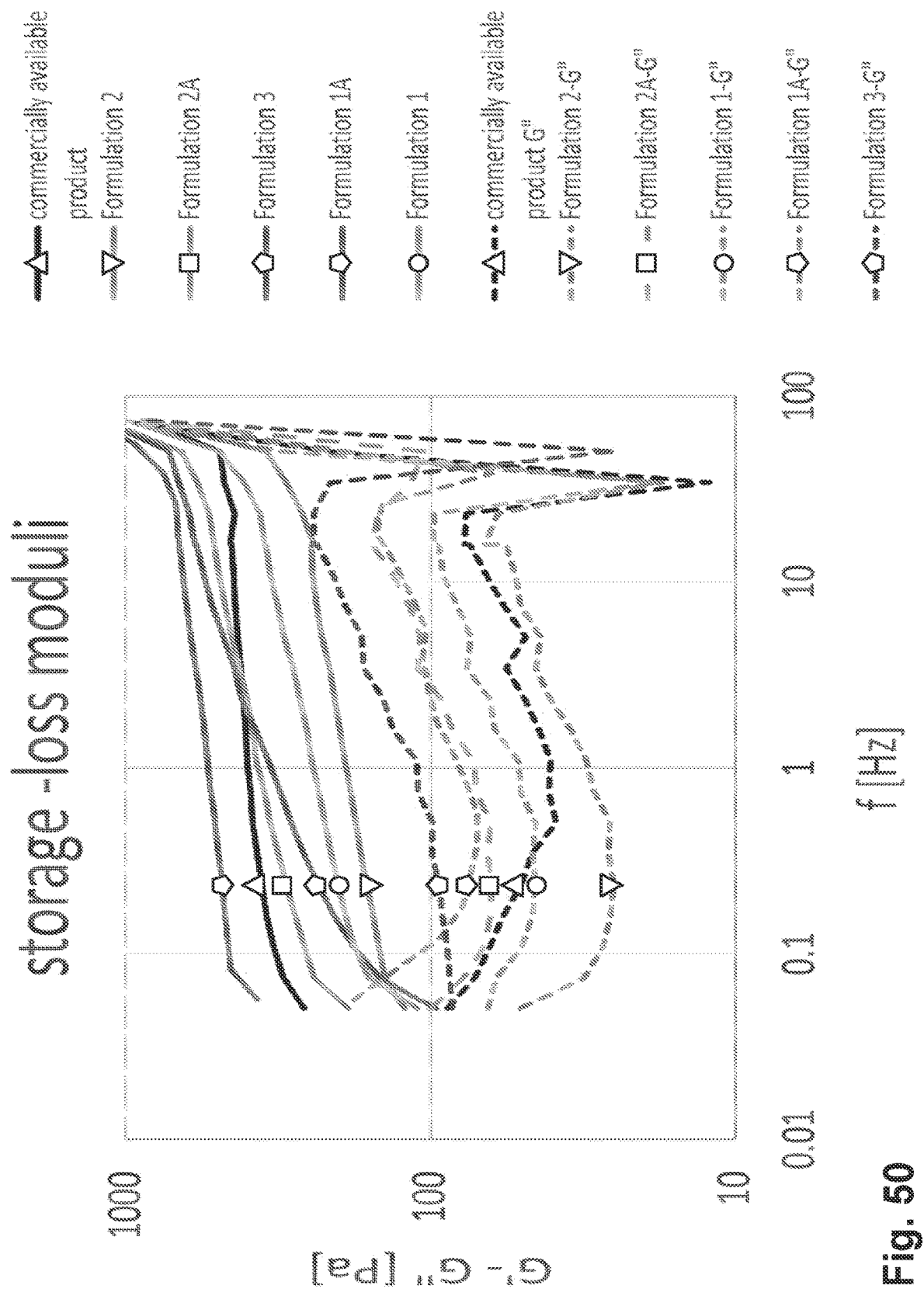
FIG. 50 shows a graph depicting rheological measurements of storage and loss moduli for various double crosslinked formulations measured using a HAAKE-RHEO STRESS 600™ instrument (THERMO SCIENTIFIC™) using a cone (1-degree) vs. plate configuration (C35/1). Frequency sweep measurements were performed at a constant deformation of 0.8% and a frequency ranging from 0.02-100 Hz. Storage (solid lines) and loss (dashed lines) moduli of representative double crosslinked formulations (see Table 7) compared to a commercially available dermal filler (solid and dashed lines: solid black—commercially available product; solid ▼—formulation 2; solid □—formulation 2A; solid upward pentagon—Formulation 3; solid downward pentagon—Formulation 1A; solid ○—Formulation 1; dashed ♦—commercially available product G"; dashed ▼—Formulation 2G"; dashed □—Formulation 2A-G"; dashed ○—Formulation 1G"; dashed downward pentagon—Formulation 1A G"; dashed upward pentagon—Formulation 3").
Figure 51:
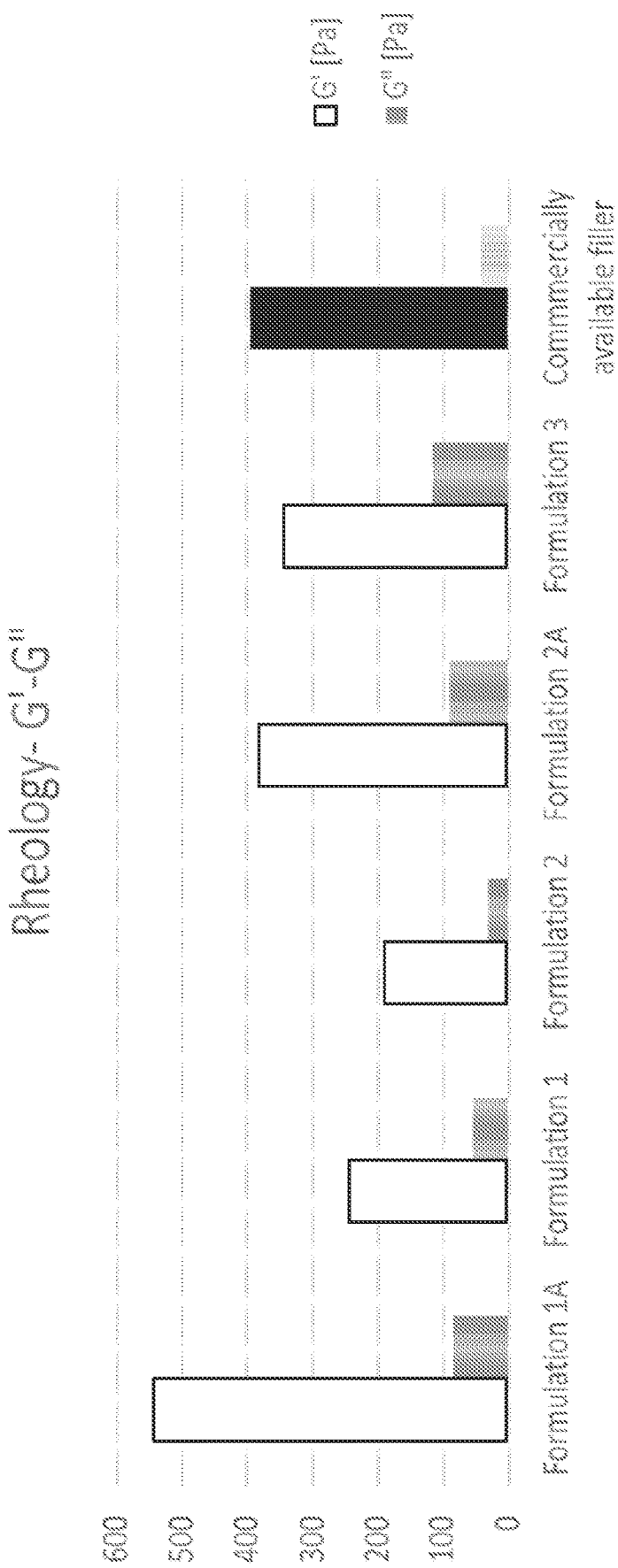
FIG. 51 shows a graph depicting a comparison at f=1 Hz of the storage and loss moduli of formulations reported in FIG. 50. (open barsG' [Pa]; grey bars G" [Pa])

As shown in FIG. 50, storage (solid lines) and loss (dashed lines) moduli of the representative double crosslinked formulations (Table 8) were comparable to the commercially available dermal filler. A comparison of the storage and loss moduli of these formulations and this commercial filler at f=1 Hz is shown in FIG. 51.

Figure 52:
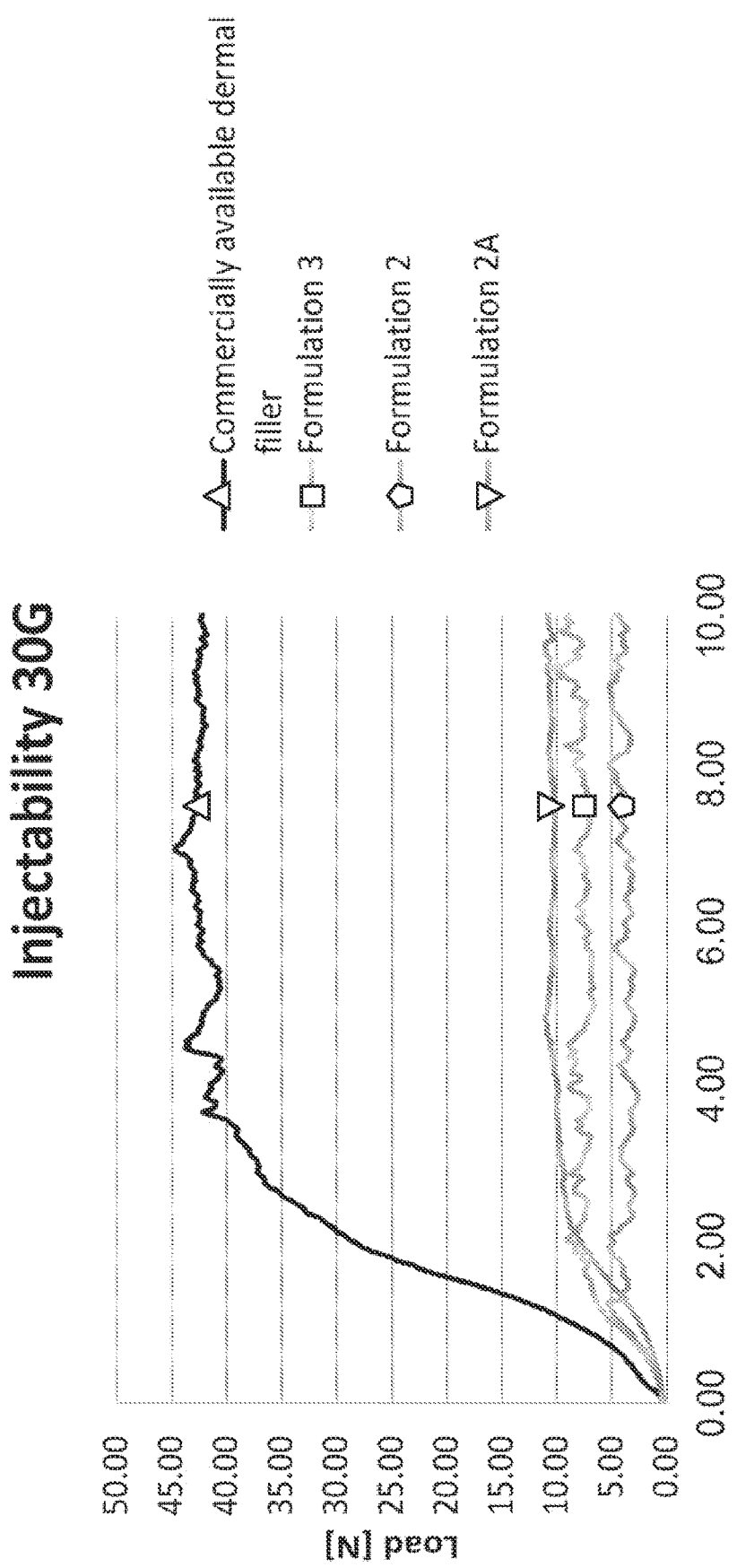
FIG. 52 shows a graph depicting injectability of selected double crosslinked formulations measured using a MULTI-TEST 1-i MECMESIN™ compression tester machine with 1 ml LUER-LOK™ syringes (BECTON-DICKINSON™) and 30 G needles used for Formulations 2, 2A, and 3 (Table 8). The commercially available dermal filler is included for comparison with the double crosslinked formulations. Express force as a function of plunger displacement (12 mm/min) of representative double crosslinked formulations was compared to a commercially available dermal filler. (Black ▲ Commercially available dermal filler; Grey ⌈—Formulation 3; Grey upward pentagon—Formulation 2; Grey ▼—Formulation 2A)

The first and second crosslinking can be adjusted to control the final product storage and loss moduli. As shown in FIG. 52, the expression force required to inject the double crosslinked formulations through a 30 G needle was significantly lower than the expression force required to inject the commercially available dermal filler.

Histology and Animal Studies

Animal studies were conducted as described above. Formulations 2 and 2A (see Tables 8 and 9) were compared with a commercially available dermal filler product following subcutaneous injections. Inflammation is the first step in the regeneration process, as long as it is not too severe.

The average histology scores at day 7 post subcutaneous injections are compared to the commercially available dermal filler in Table 9.

TABLE 9

Day 7 Histology Scores.

| | Inflammation score | % Lymphocytes | % Macrophages | % Neutrophils | Necrosis score | Fibrosis Score |
|---|---|---|---|---|---|---|
| Formulation 2 | 2 | 50 | 40 | 10 | 0 | 2 |
| Formulation 2A | 2.25 | 42.5 | 42.5 | 15 | 0 | 2 |

TABLE 9-continued

Day 7 Histology Scores.

|  | Inflammation score | % Lymphocytes | % Macrophages | % Neutrophils | Necrosis score | Fibrosis Score |
|---|---|---|---|---|---|---|
| Commercially available material/ control | 1.333333 | 36.66667 | 53.33333 | 10 | 0 | 1.333 |

As shown in Table 9, double crosslinked formulations have a higher fibrosis score and a higher inflammation level than the commercially available dermal filler, indicating a more advanced process of tissue regeneration.

FIG. 56. shows representative histology images at day 7 post subcutaneous injection of formulations 2, 2A, or control. Arrows point to the enhanced inflammation reaction in formulation 2 and 2A (but still not severe) indicating initiation of tissue regeneration. "Blebs" refer to bullae formed by the injected material.

Figure 57:
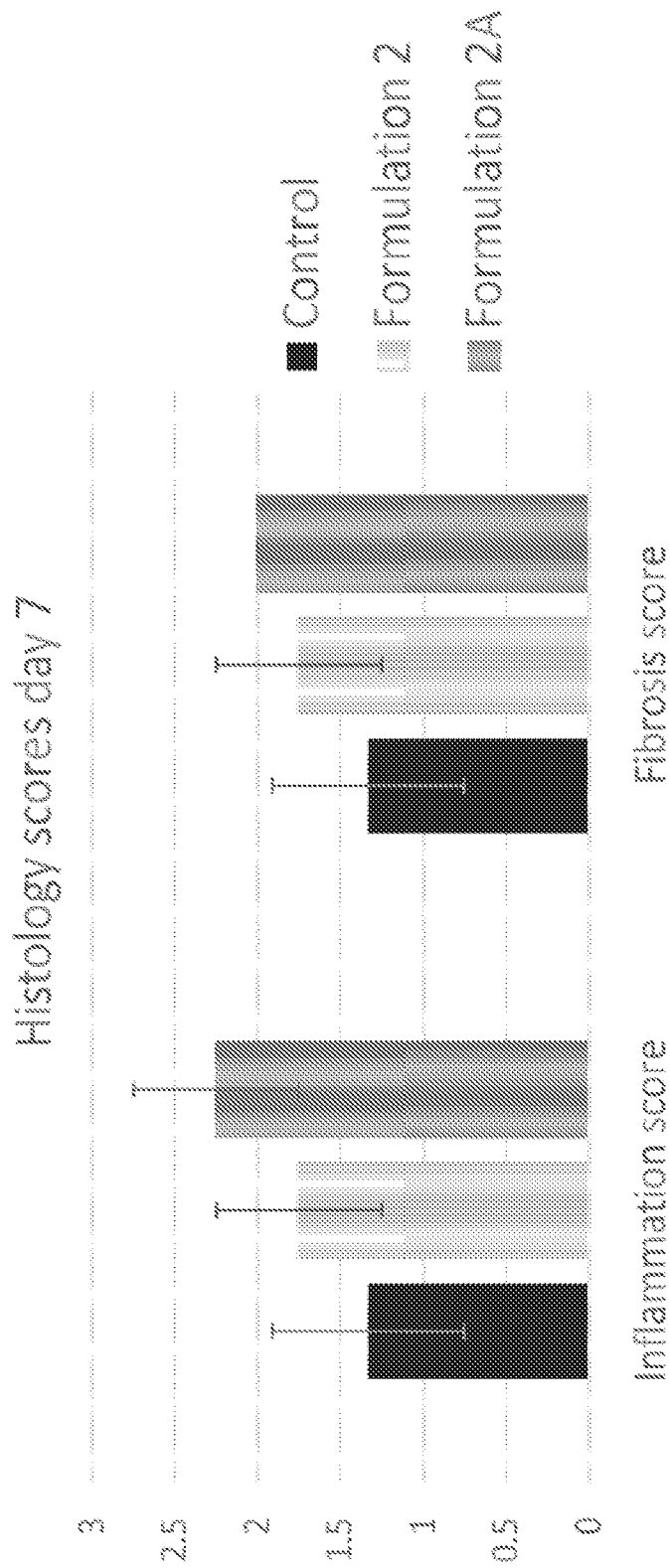
FIG. 57 presents the histology score at day 7 of formulation 2, 2A and control from the tissue analyzed in FIG. 56. (Black—control; Light Grey Formulation 2; Dark Grey Formulation 2A)

Histology scores for the samples shown in FIG. 56 are presented as a bar graph in FIG. 57, wherein the higher inflammation scores and fibrosis scores for double crosslinked Formulations 2 and 2A indicate they shown improved tissue regeneration compared with control.

Summary/Conclusion

Double Crosslinked formulations have been developed to have easy injection through 27 to 32 G needles and a wide range of stiffness G'-G". Histology results following one-week injection show enhanced initiation of the tissue regeneration process.

Example 24. Photocurable Dermal Filler

Objective: To analyze the properties of a photocurable dermal filler. The photocurable formulation is a semi IPN before curing and ends up being an IPN (interpenetrated network) after curing. Meaning two entangled networks, each one crosslinked to itself and not crosslinked to the other.

Methods:

A mixture of rhCollagen and Methacrylated rhCollagen was added to already crosslinked HA, crosslinked as in Example 23, to a final concentration of 1-10 mg/ml wherein the ratio between the methacrylated to non-methacrylated rhCollagen is 1:0, 1:1, 1:2, 1:3, 1:4, 0:1, 2:1, 3:1, or 4:1. The final concentration range of MA-rhCollagen is 0-12/mg/ml and the final concentration range of non-modified rhCollagen is 0-12 mg/ml. The ratio of the crosslinked HA To MA-rhCollagen is 1:1, 2:1, 3:1, 4:1, 5:1, 6:1, 1:2, 1:3, 1:4, 1:5, 1:6, or 0:1. The final concentration of HA is 12-25 mg/ml, the final concentratil of rhCollagen (MA+non-modified) is 1-24 mg/ml.

Visible light photoinitiator was added to the mixture (e.g. compositions of Eosin Y, triethanolamine and N-vinylpyrrolidone).

Rheological Studies 1.6 ml samples of each of representative Formulations 4, 5, and 6 and the Control (see Table 10 below) were poured into cylindrical molds and cylinders of 2 cm diameter and 0.5 mm height and were cured by a constant amount of visible light illumination using a white LED flashlight for 6 minutes.

Formulations of highly crosslinked hyaluronic acid (HA) were mixed with combinations of rhCollagen and/or rH Collagen methacrylate at 3 different representative ratios with a constant amount of visible light photoinitiator, using the above methods, as shown in Table 10. Highly BDDE crosslinked HA (but could be any other crosslinker as well, or even a standard commercial filler made of only crosslinked HA) was mixed with rhCol and rhColMA in different ratios. The result is a crosslinking of the HA and a crosslinking of the entangled rhColMA after curing. This forms an interpenetrated network where the HA is crosslinked to itself and the collagen is crosslinked to itself within the HA network.

TABLE 10

Formulations tested before and after photocuring.

|  | Crosslinked HA | rhCollagen MA | rhCollagen |
|---|---|---|---|
| Control (crosslinked HA) | 23 mg/ml | — | — |
| Formulation 4 | 19 mg/ml | 2.5 | — |
| Formulation 5 | 19 mg/ml | 1.25 | 1.25 |
| Formulation 6 | 19 mg/ml | 0.64 | 1.83 |

Storage and loss moduli were measured before and after illumination as described below.

a. Before Curing

Storage and loss moduli were measured using a HAAKE-RHEO STRESS 600 TH instrument (THERMO SCIENTIFIC™) using a cone(1°) vs. plate configuration (C35/1). Frequency sweep measurements were performed at a constant deformation of 0.8% with a frequency ranging from 0.02 Hz to 100 Hz.

b. After Curing

Storage and loss moduli of photocured cylinders were measured using a HAAKE-RHEO STRESS 600™ instrument (THERMO SCIENTIFIC™) using a serrated plate vs. plate configuration (PP20). Frequency sweep measurements were performed at a constant shear stress of 3 Pa with a frequency ranging from 0.02 Hz to 100 Hz, under a constant normal load of 0.3 N.

Injectability

Injectability measurements were taken using a MULTITEST 1-i MECMESIN™ machine, as described above for Formulations 4, 5, and 6 and for highly crosslinked HA as a control. 1 ml LUER-LOK™ syringes (BECTON-DICKINSON™) and 30 G needles were used for all samples (Table 10). Expression force as a function of plunger displacement (12 mm/min) of representative Formulations 4, 5, and 6 (Table 10) was compared to highly crosslinked HA.

Animal Studies

Animal studies were conducted as described above. Formulation 4 (see Tables 10 and 11) was compared with highly crosslinked HA following subcutaneous injections into the back of rats.

Results:
Rheological and Mechanical Evolution

Figure 53:
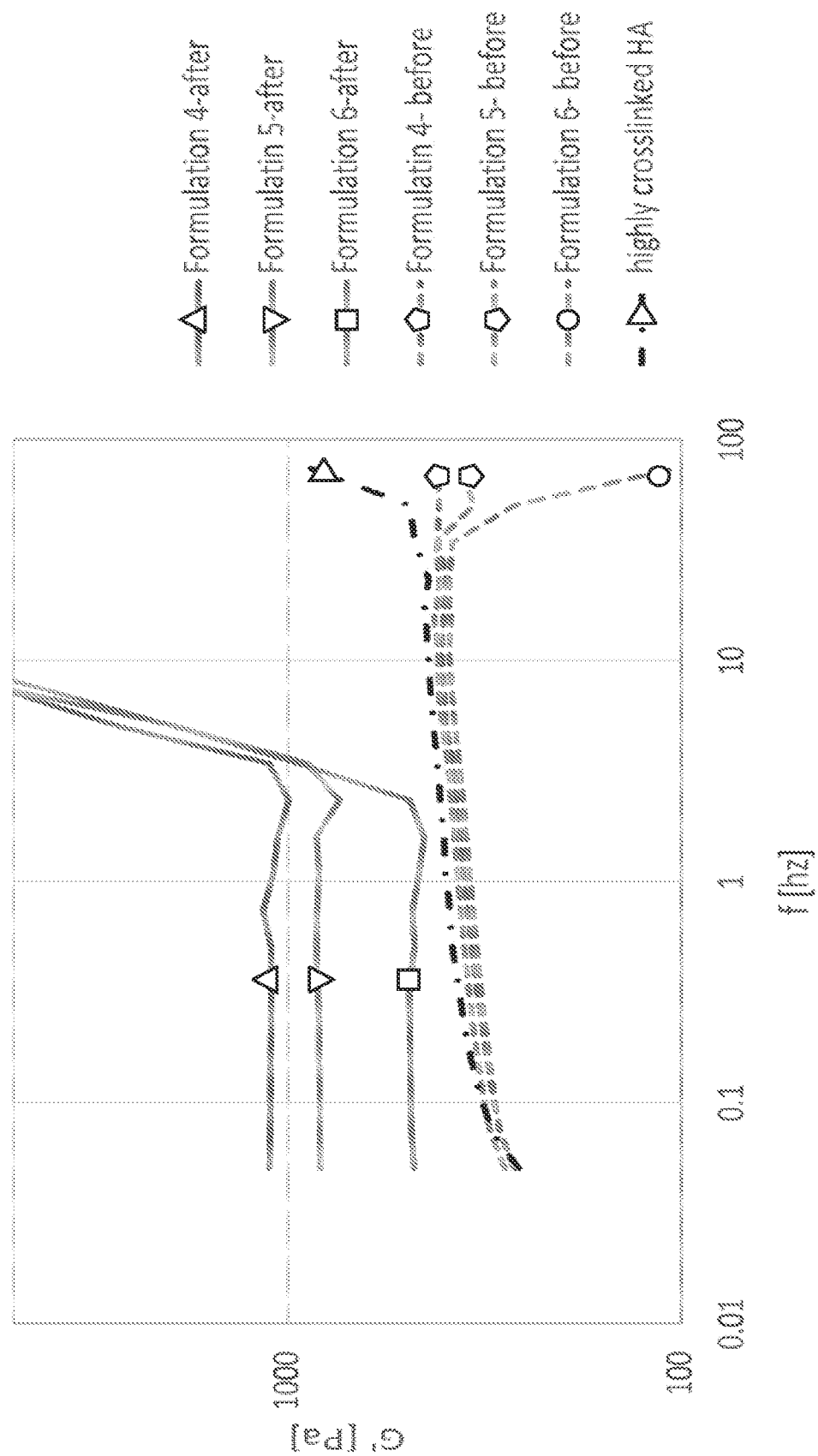
FIG. 53 shows a graph depicting rheological measurements of storage and loss moduli for various combinations (see Table 10) of highly crosslinked hyaluronic acid (HA), rhCollagen methacrylate (MA), and/or rhCollagen before (dashed lines) and after (solid lines) photocuring with visible light, as a comparison with highly crosslinked HA (black intermittent line sideways triangle). Before photocuring, storage and loss moduli were measured using a HAAKE-RHEO STRESS 600™ instrument (THERMO SCIENTIFIC™) using a cone (1-degree) vs. plate configuration (C35/1). Frequency sweep measurements were performed at a constant deformation of 0.8%, frequency ranging 0.02-100 Hz. After photocuring (visible light illumination with a white LED flashlight for 6 minutes), storage and loss moduli were measured using a HAAKE-RHEO STRESS 600™ instrument (THERMO SCIENTIFIC™) using a serrated plate vs. plate configuration (PP20). Frequency sweep measurements were performed at a constant shear stress of 3 Pa, frequency ranging 0.02-100 Hz, under a constant normal load of 0.3 N. (Solid ▲—Formulation 4-after; Solid ▼—Formulation 5-after; Solid □—Formulation 6-after; Dashed upward pentagon—Formulation 4-before; Dashed downward pentagon—Formulation 5-before; Dashed ○—Formulation 6-before; Dashed-dot Black sideways triangle—highly crosslinked HA)
Figure 54:
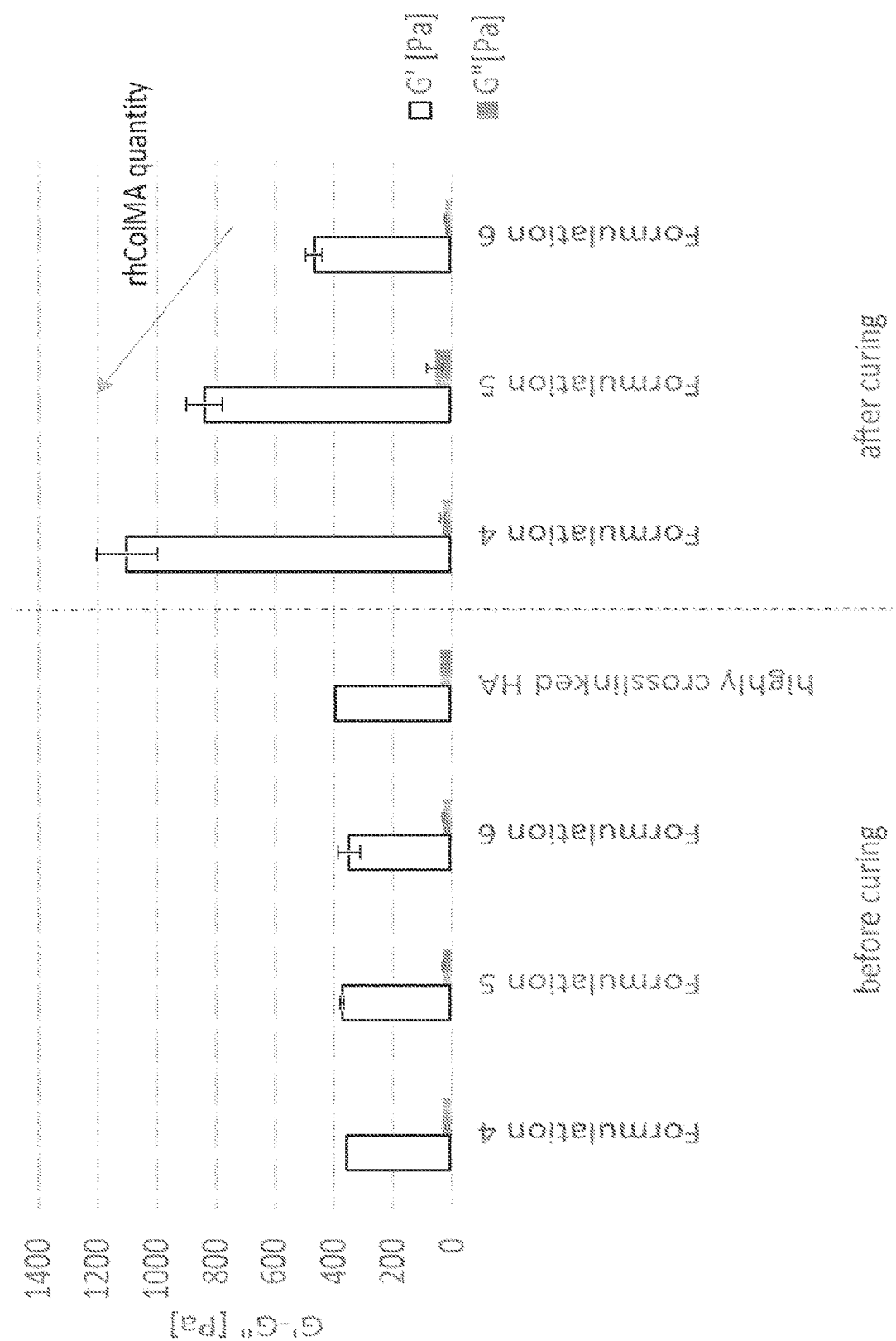
FIG. 54 shows a graph depicting a comparison of the storage and loss moduli before and after photocuring of the formulations 4, 5, and 6 in Table 10, as well as non-curable highly crosslinked HA, at a frequency of F=1 Hz. (Open bar G' [Pa]; Grey bar G" [Pa])

FIG. 53 shows a comparison of storage moduli before and after photocuring of Formulations 4, 5, and 6 with highly crosslinked HA (see Table 10). A comparison of the storage and loss moduli of these formulations, both before and after photocuring, and highly crosslinked HA (not curable) at a frequency of f=1 Hz is shown in FIG. 54. The arrow represents "Trend": the stiffness increase as the quantity of rhColMA increases.

Injectability

Figure 55:
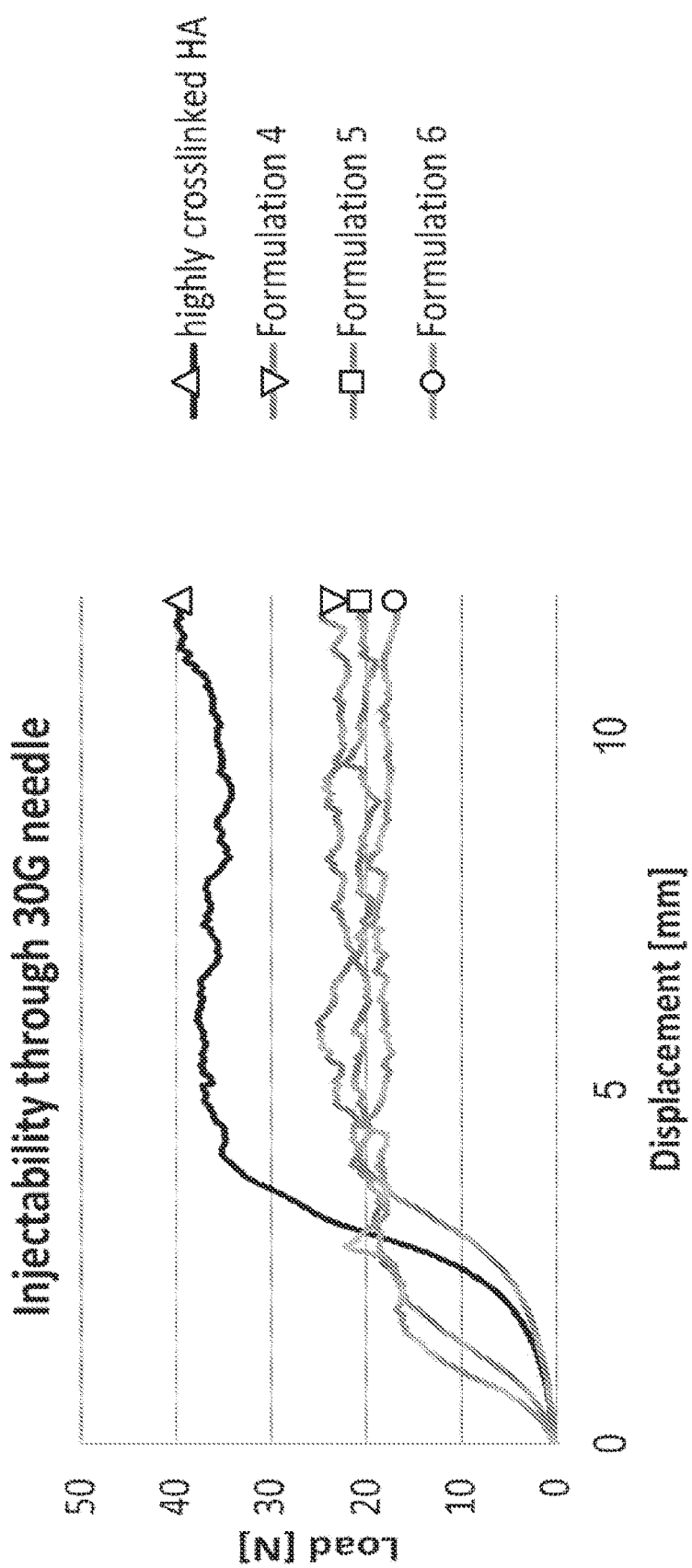
FIG. 55 shows a graph depicting injectability of selected double crosslinked formulations measured using a MULTI-TEST 1-i MECMESIN™ compression tester machine with 1 ml LUER-LOK™ syringes (BECTON-DICKINSON™) and 30 G needles used for all samples. Express force as a function of plunger displacement (12 mm/min) of representative double crosslinked formulations was compared to highly crosslinked HA. (Black ▲—Highly crosslinked HA; Grey ▼—Formulating 4; Grey □—Formulation 5; Grey ○—Formulation 6)

As shown in FIG. 55, the expression force required for the injection of Formulations 4, 5, and 6 through a 30 G needle was lower than the expression force required for the crosslinked HA alone, allowing easier usability for the physician and easier injection at fine lines and delicate areas of the patient. However, after in situ photocuring (following injection), the material stiffness can be adjusted to be significantly higher than crosslinked HA alone (see FIGS. 53 and 54).

Histology and Animal Studies

The average histology score for Formulation 4 at day 7 of subcutaneous injections was compared to highly crosslinked HA in Table 11.

TABLE 11

Day 7 Histology Scores.

| | Inflammation score | % Lymphocytes | % Macrophages | % Neutrophils | Necrosis score | Fibrosis Score |
|---|---|---|---|---|---|---|
| Formulation 4 | 1.5 | 42.5 | 50 | 7.5 | 0 | 1.5 |
| Commercially available material/ control | 1.333333 | 36.66667 | 53.33333 | 10 | 0 | 1.333 |

As shown in Table 11, Formulation 4 has a higher fibrosis score and a higher inflammation level than the highly crosslinked HA, indicating a more advanced process of tissue regeneration.

Figure 58:
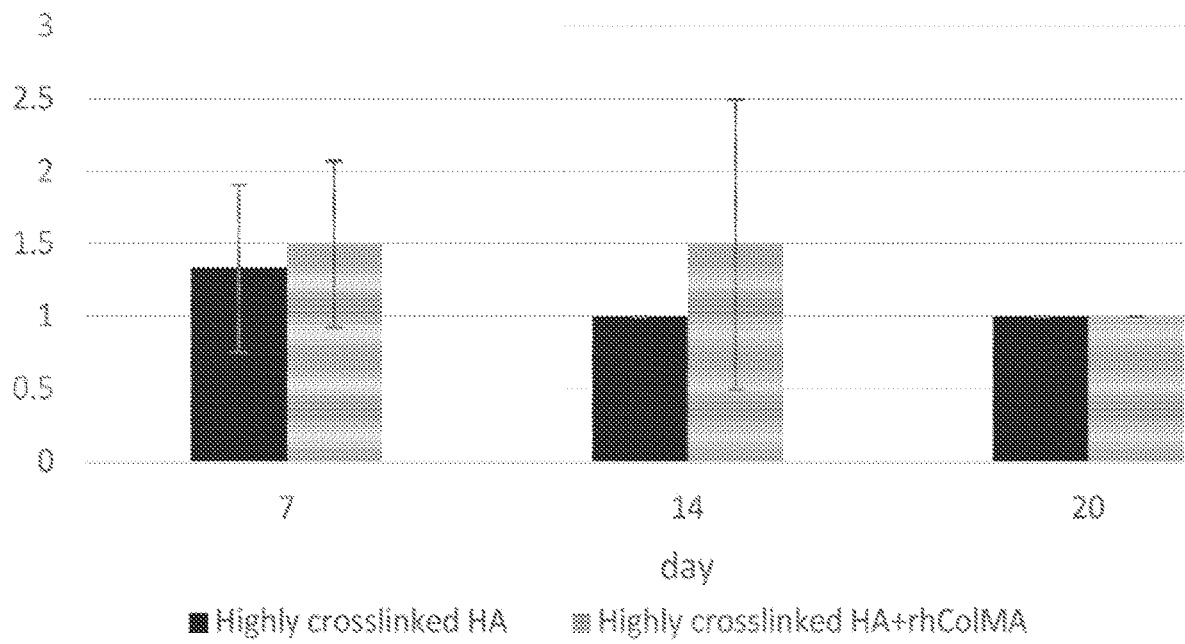
FIG. 58 presents photocurable histology scoring results of photocurable dermal fillers on day 7, day 14, and day 20. (Black—Control highly crosslinked HA; Grey—Formulation 4 highly crosslinked HA and rhColMA)
Figure 59:
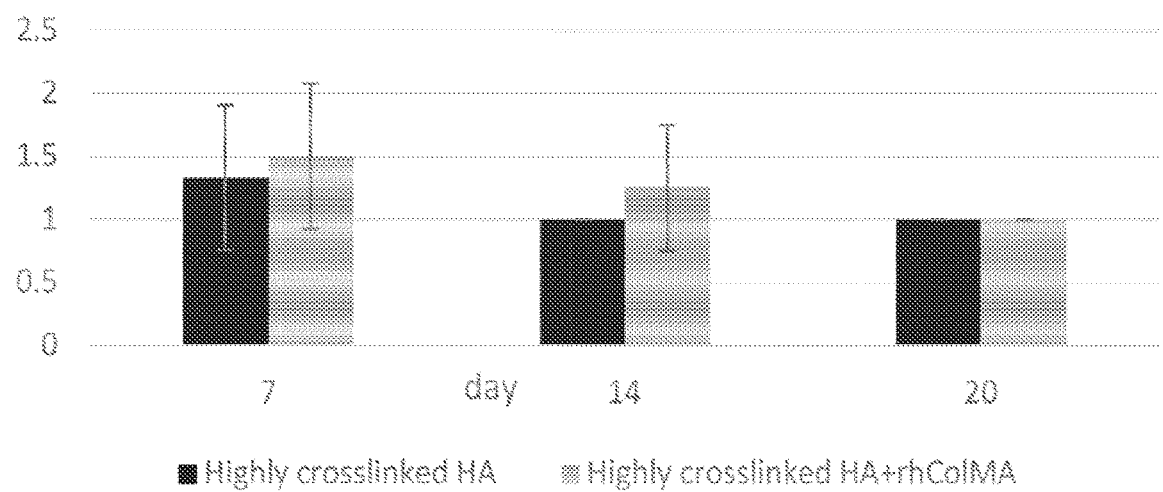
FIG. 59 presents fibrosis score results at day 7 and day 14 following injections of formulation 4 (Grey—highly crosslinked HA+rhColMA) vs. control (Black—highly crosslinked HA).

FIG. 58 and FIG. 59 show that Formula 4 has a higher inflammation score and fibrosis score than control dermal filler, indicating improved initiation of tissue regeneration process with the dermal filler of Formula 4.

Conclusion/Summary

The photo curable filler was developed to have a relative low stiffness before injection allowing easy injection through 27-32G needles but a significant improve in stiffness (tunable) following photocuring. Stiffness can be tuned by controlling the final ratio between rhCol and rhColMA. This technology allows the physician to sculpture the filler to the desired shape before fixing it with the photocuring illumination. The injected material strongly adheres to the sourroundy tissue. Preliminary in vivo results indicate initiation of regeneration process.

Example 25. In Vivo Animal Studies: Independent Injection of Dermal Filler Components Objective: To separately inject HA or its methacrylated derivative, and methacrylated rhCollagen into the subcutaneously at a semiliquid phase and crosslink them in situ (crosslinking is rhColMA to rhColMA), post injection, by white light illumination through the skin. This approach allows easier injection and in situ sculpturing of the material shape, just before fixing it by light polymerization. Using a subcutaneous rat model, the cell proliferation, tissue augmentation, and characteristics of matrix degradation overtime will be assessed.

Methods: In this model, sample formulation components (HA or its methacrylated derivative, and methacrylated rhCollagen and photoinitiator) for evaluation will be injected subcutaneously to the back of male Sprague Dawley rats and the injection sites followed for up to 20 days. Injections will be at about the same time (immediately one after the other), at the same location. Component solutions may be massaged in situ prior to or concurrent with or following crosslinking. The subcutaneous rat model is chosen as it is the simplest model to estimate biocompatibility, lifting effect and persistence. Moreover, Hillel at al. published a validation study for this specific model (Dermatol Surg 2012; 38:471-478).

Animals will be sedated with Ketamine/Xylasine prior to each treatment. The animal's back will be shaved, and the injection sites marked on the shaved skin. Each rat will be injected with 0.2 ml of the formulation using 27.5-32G needle at distanced locations on the dorsal plane, over all, 6 injections per rat.

The formulations will be crosslinked post injection by transdermal illumination of the injection site with a white light LED torch for 2 minutes.

All animals will be observed for morbidity and mortality twice daily throughout the entire study period. Every three days (time points 0, 1, 4, 7, 11, 14, 18, and 21 days post injections) the height, width, and length of each bleb will be measured with caliper, and the ellipsoid volume of each bleb $[(4/3)(\pi)(1/2 \text{ height})(1/2 \text{ length})(1/2 \text{ width})]$ calculated.

Animals will be sacrificed at time-points for example but not limited to 7, 14, and 21 days post-treatment.

At each scarification point, injections sites will be exposed and assessed macroscopically, and the blebs collected for histological assessment. Injections sites (including the blebs) will be excised with the overlying skin and, fixed in 4% formalin and embedded in paraffin.

Histology

Slides Preparation

Paraffin blocks will be sectioned at approximately 3-5 microns thickness, put on a glass slide, stained with Hematoxylin & Eosin (H&E) and Masson trichrome and covered by an automated machine. The histology evaluation of all the slides will be performed using a light microscope (Olympus BX60, serial NO. 7D04032).

Images will be taken at magnification of ×4. Image acquisition will be performed only on pathological changes and of representative animals.

Results:

Similar results to those obtained in Example 24 are expected, wherein the separate, independent injection of components of the photocurable dermal filler may provide increased ease of injection, for example due to decreased viscosity of the components compared with the formulation mix.

Although the dermal fillers, including cellular growth promoting scaffolds, and uses thereof have been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A polymerizable solution comprising:
a cross-linkable, plant-derived recombinant type 1 human collagen (rhcollagen);
a hyaluronic acid (HA), a modified HA derivative, a poly(vinyl alcohol) (PVA), a modified PVA derivative, a polyethylene glycol (PEG), a modified PEG derivative, oxidized cellulose (OC), a modified OC derivate, polymethylmethacrylate (PMMA) microspheres, modified PMMA microsphere derivatives, tricalcium phosphate (TCP), a modified TCP derivative, calcium hydroxylapatite (CaHA), a modified CaHA derivative, carboxymethylcellulose, a modified carboxymethylcellulose derivative, crystalline nanocellulose (CNC), a modified CNC derivative, or a combination thereof; and
a photoinitiator.

2. The polymerizable solution of claim 1, wherein the cross-linkable, plant-derived human collagen is methacrylated or thiolated plant-derived recombinant type 1 human collagen (rhcollagen).

3. The polymerizable solution of claim 1, wherein the modified derivative of hyaluronic acid (HA), poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, or crystalline nanocellulose (CNC) comprises a methacrylated or thiolated derivative.

4. The polymerizable solution of claim 1, wherein the hyaluronic acid (HA), poly(vinyl alcohol) (PVA), polyethylene glycol (PEG), oxidized cellulose (OC), polymethylmethacrylate (PMMA) microspheres, tricalcium phosphate (TCP), calcium hydroxylapatite (CaHA), carboxymethylcellulose, or crystalline nanocellulose (CNC) comprises a crosslinked hyaluronic acid (HA), crosslinked poly(vinyl alcohol) (PVA), crosslinked polyethylene glycol (PEG), crosslinked oxidized cellulose (OC), crosslinked polymethylmethacrylate (PMMA) microspheres, crosslinked tricalcium phosphate (TCP), crosslinked calcium hydroxylapatite (CaHA), crosslinked carboxymethylcellulose, or crosslinked crystalline nanocellulose (CNC).

5. The polymerizable solution of claim 1, comprising:
methacrylated or thiolated plant-derived recombinant type 1 human collagen (rhcollagen); a crosslinked hyaluronic acid (HA), crosslinked poly(vinyl alcohol) (PVA), crosslinked polyethylene glycol (PEG), crosslinked oxidized cellulose (OC), crosslinked polymethylmethacrylate (PMMA) microspheres, crosslinked tricalcium phosphate (TCP), crosslinked calcium hydroxylapatite (CaHA), crosslinked carboxymethylcellulose, or crosslinked crystalline nanocellulose (CNC); and
said photoinitiator.

6. The polymerizable solution of claim 1, comprising:
methacrylated plant-derived recombinant type 1 human collagen (rhcollagen);
a hyaluronic acid (HA), a crosslinked hyaluronic acid (HA), a methacrylated or thiolated hyaluronic acid (HA) or any combination of said hyaluronic acid (HA), said crosslinked hyaluronic acid (HA), and said methacrylated or thiolated hyaluronic acid (HA); and
a photoinitiator.

7. The polymerizable solution of claim 6, wherein a ratio of said hyaluronic acid (HA), said crosslinked hyaluronic acid (HA), said methacrylated or thiolated hyaluronic acid (HA) or said combination thereof to said methacrylated plant-derived recombinant type 1 human collagen (rhcollagen) ranges from 6:1 to 1:6.

8. The polymerizable solution of claim 7, wherein said ratio ranges from 4:1 to 1:4 or from 3:1 to 1:3, or from 3:1 to 2:1.

9. The polymerizable solution of claim 1, wherein the cross-linkable, plant-derived recombinant type 1 human collagen and the photoinitiator are included together and independently from said hyaluronic acid (HA), said modified HA derivative, said poly(vinyl alcohol) (PVA), said modified PVA derivative, said polyethylene glycol (PEG), said modified PEG derivative, said oxidized cellulose (OC), said modified OC derivate, said polymethylmethacrylate (PMMA) microspheres, said modified PMMA microsphere derivatives, said tricalcium phosphate (TCP), said modified TCP derivative, said calcium hydroxylapatite (CaHA), said modified CaHA derivative, said carboxymethylcellulose, said modified carboxymethylcellulose derivative, said crystalline nanocellulose (CNC), said modified CNC derivative, or said combination thereof.

10. The polymerizable solution of claim 1, wherein the cross-linkable, plant-derived recombinant type 1 human collagen, said hyaluronic acid (HA), said modified HA derivative, said poly(vinyl alcohol) (PVA), said modified PVA derivative, said polyethylene glycol (PEG), said modified PEG derivative, said oxidized cellulose (OC), said modified OC derivate, said polymethylmethacrylate (PMMA) microspheres, said modified PMMA microsphere derivatives, said tricalcium phosphate (TCP), said modified TCP derivative thereof, said calcium hydroxylapatite (CaHA), said modified CaHA derivative, said carboxymethylcellulose, said modified carboxymethylcellulose derivative, said crystalline nanocellulose (CNC), said modified CNC derivative, or said combination thereof, and said photoinitiator are included together.

11. The polymerizable solution of claim 1, further comprising a non-modified plant-derived recombinant type 1 human collagen.

12. The polymerizable solution of claim 1, wherein a concentration of said cross-linkable, plant-derived recombinant type 1 human collagen ranges from 1 to 12 mg/ml.

13. The polymerizable solution of claim 1, being an injectable solution at the temperature of use, and/or having a texture and viscosity which permits flow through a suitable delivery device.

14. The polymerizable solution of claim 1, being a photocurable solution.

15. The polymerizable solution of claim 1, wherein the photoinitiator induces polymerization of the polymerizable solution in response to visible light having a wavelength of 390-800 nm.

16. The polymerizable solution of claim 1, being a dermal filler.

17. The polymerizable solution of claim 1, being capable of augmenting a tissue in a subject.

18. The polymerizable solution of claim 17, wherein said tissue is skin tissue.

19. The polymerizable solution of claim 1, being capable of filling a tissue space under an epidermis.

20. A double crosslinked dermal filler comprising:
   (a) a plant-derived recombinant human type 1 collagen; and
   (b) a crosslinked hyaluronic acid;
wherein the plant-derived human collagen is crosslinked to the crosslinked hyaluronic acid.

21. The double crosslinked dermal filler of claim 20, further comprising a non-crosslinked hyaluronic acid.

22. The double crosslinked dermal filler of claim 20, wherein the crosslinker linking the crosslinked hyaluronic acid differs from the crosslinker linking the plant-derived recombinant human type 1 collagen with the crosslinked hyaluronic acid.

23. The double crosslinked dermal filler of claim 20, wherein a ratio of said crosslinked hyaluronic acid to said plant-derived recombinant human type-1 collagen ranges from 6:1 to 1:6.

24. The double crosslinked dermal filler of claim 20, wherein a concentration of said crosslinked hyaluronic acid ranges from 5 to 50 mg/ml.

25. The double crosslinked dermal filler of claim 23, wherein a concentration of said crosslinked hyaluronic acid ranges from 5 to 50 mg/ml.

26. The double crosslinked dermal filler of claim 20, wherein the crosslinker crosslinking said hyaluronic acid and the crosslinker crosslinking said plant-derived recombinant human type 1 collagen are each independently selected from 1, 4-butanediol diglycidyl ether (BDDE), 1-[3-(Dimethylamino)propyl]-3-ethylcarbodiimide methiodide (EDC), N,N'-dicyclohexylcarbodiimide (DCC), N,N'-diisopropylcarbodiimide (DIC), Divinyl Sulfone (DVS) and glutaraldehyde.

27. A method of preparing a double crosslinked dermal filler comprising a plant-derived recombinant human type-1 collagen crosslinked to a crosslinked hyaluronic acid, the method comprising:
   crosslinking hyaluronic acid;
   neutralization of the crosslinked hyaluronic acid;
   neutralization of the plant-derived human collagen;
   mixing the neutralized crosslinked hyaluronic acid with the neutralized plant-derived human collagen;
   adding lower molecular weight hyaluronic acid (MW HA);
   crosslinking the mix of crosslinked hyaluronic acid and plant-derived human collagen; and
   dialyzing double crosslinked hyaluronic acid-plant-derived human collagen dermal filler.

* * * * *